(12) United States Patent
Karlberg et al.

(10) Patent No.: US 12,129,472 B2
(45) Date of Patent: Oct. 29, 2024

(54) PLANTS WITH IMPROVED GROWTH

(71) Applicant: SweTree Technologies AB, Umeå (SE)

(72) Inventors: Anna Karlberg, Umeå (SE); David Jonsén, Umeå (SE); Linus Möller, Umeå (SE); Magnus Hertzberg, Umeå (SE); Pär Jonsson, Umeå (SE)

(73) Assignee: SweTREE Technologies AB, Umeå (SE)

( * ) Notice: Subject to any disclaimer, the term of this patent is extended or adjusted under 35 U.S.C. 154(b) by 518 days.

(21) Appl. No.: 16/769,393

(22) PCT Filed: Dec. 4, 2018

(86) PCT No.: PCT/SE2018/051245
§ 371 (c)(1),
(2) Date: Jun. 3, 2020

(87) PCT Pub. No.: WO2019/112509
PCT Pub. Date: Jun. 13, 2019

(65) Prior Publication Data
US 2021/0403932 A1    Dec. 30, 2021

(30) Foreign Application Priority Data
Dec. 4, 2017   (SE) .................................. 1751493-6

(51) Int. Cl.
*C12N 15/82* (2006.01)
(52) U.S. Cl.
CPC ..... *C12N 15/8226* (2013.01); *C12N 15/8227* (2013.01); *C12N 15/8229* (2013.01); *C12N 15/8261* (2013.01)
(58) Field of Classification Search
None
See application file for complete search history.

(56) References Cited

U.S. PATENT DOCUMENTS

| 2004/0019925 | A1 | 1/2004 | Heard et al. | |
| 2010/0162427 | A1* | 6/2010 | Riechmann | C07K 14/415 800/290 |

FOREIGN PATENT DOCUMENTS

| JP | 2016127811 A | 7/2016 |
| WO | WO-2002015675 A1 | 2/2002 |
| WO | WO-2004031349 A2 | 4/2004 |
| WO | WO-2004076638 A2 | 9/2004 |
| WO | WO-2004097024 A1 | 11/2004 |
| WO | WO-2005047516 A2 | 5/2005 |
| WO | WO-2006069201 A2 | 6/2006 |
| WO | WO-2006130156 A2 | 12/2006 |
| WO | WO-2009084999 A1 | 7/2009 |
| WO | WO-2011109661 A1 | 9/2011 |
| WO | WO-2012117330 A1 | 9/2012 |
| WO | WO-2014100289 A1 | 6/2014 |
| WO | WO-2014195287 A1 | 12/2014 |
| WO | WO-2016108750 A1 | 7/2016 |

OTHER PUBLICATIONS

Han, et al. (Plant Physiology 190.1 (2022): 421-440) . (Year: 2022).*
Supplementary Search Report from European Application No. 18885832.8 dated Aug. 3, 2021.
Anisimov et al., "Cloning of new rubisco promoters from *Brassica rapa* and determination of their activity in stably transformed *Brassica napus* and Nicotiana tabacum plants," Mol Breeding, 19:241-253 (2007).
Bakshi et al., "WRKY transcription factors—Jack of many trades in plants," Plant Signaling & Behavior 9, e27700, 18 pages (2014).
Björklund et al., "Ethylene is Limited by ACO Activity and is an Endogenous Stimulator of Cell Division in the Vascular Cambium of Populus in Response to Leaning Stress," Doctoral thesis 81, Faculty of Forest Sciences, Umeå, Sweden (2007).
Byrne et al., "Asymmetric leaves1 mediates leaf patterning and stem cell function in *Arabidopsis*," Nature, 408:967-971 (2000).
Coussens et al., "Brachypodium distachyon promoters as efficient bilding blocks for transgenic researc in maize," Journal of Experimental Botany, 63(11):4263-4273 (2012).
Czechowski et al., "Genome-Wide Identification and Testing of Superior Reference Genes for Transcript Normalization in *Arabidopsis*," Plant Physiology, 139:5-17 (2005).
Dewitte et al., "*Arabidopsis* CYCD3 D-type cyclins link cell proliferation and endocycles and are rate-limiting for cytokinin responses," PNAS 104(36):14537-14542 (2007).
Eulgem et al., "The WRKY superfamily of plant transcription factors," Trends in Plant Science, 5(5):199-206 (2000).
Farquhar et al., "Carbon Isotope Discrimination and Photosynthesis," Ann. Rev. Plant Physiol. 40:503-537 (1989).
Gilmartin et al., "Localization of a Phytochrome-Responsive Element within the Upstream Region of Pea rbcS-3A," Mol Cell Biol, 10(10):5565-5568 (1990).
Hajdukiewicz et al., "The small, versatile pPZP family of Agrobactierum binary vectors for plant transformation," Plant Mol. Biol. 25:989-994 (1994).
Ho et al., "Agrobacterium tumefaciens-mediated transformation of Eucalyptus camaldulensis and production of transgenic plants," Plant Cell Reports, 17:675-680 (1998).
Journot-Catalino et al., "The Transcription Factors WRKY11 and WRKY17 Act as Negative Regulators of Basal Resistance in *Arabidopsis thaliana*," The Plant Cell, 18:3289-3302 (2006).
Kim et al., "Extracellular ATP in Plants. Visualization, Localization, and Analysis of Physiological Significance in Growth and Signaling," Plant Physiology, 142:984-992 (2006).
Koyama et al., "Isolation and expression analysis of phosphate transporter genes from Eucalyptus camaldulensis," Plant Biotechnology 23:215-218 (2006).

(Continued)

*Primary Examiner* — Charles Logsdon
(74) *Attorney, Agent, or Firm* — MARSHALL, GERSTEIN & BORUN LLP

(57) ABSTRACT

The present invention relates to genetically modified plants comprising a heterologous nucleic acid construct comprising a promoter sequence operably linked to a coding sequence encoding a gene product. The invention further relates to methods for producing such plants.

20 Claims, 3 Drawing Sheets

Specification includes a Sequence Listing.

(56) References Cited

OTHER PUBLICATIONS

Larkin et al., "Clustal W and Clusta X version 2.0," Bioinformatics Applications Note, 23(21):2947-2948 (2007).
Li et al., "Functional Characterization of *Arabidopsis thaliana* WRKY39 in Heat Stress," Mol. Cells 29:475-483 (2010).
Liu et al., "Multiple bHLH Proteins from Heterodimers to Mediate CRY2-Dependent Regulation of Flowering-Time in *Arabidopsis*," PLoS Genet 9(10), 12 pages, e1003861 (2013).
Mitsuda et al., "NAC Transcription Factors, NST1 an NST3, Are Key Regulators of the Formation of Secondary Walls in Woody Tissues of *Arabidopsis*," The Plant Cell 19:270-280 (2007).
Mizukami et al., "Plant organ size control: Aintegumenta regulates growth and cell numbers during organogenesis," PNAS, 97(2):942-947 (2000).
Nilsson, "Molecular Regulation of Vascular Cambium Identity and Activity," Doctoral Thesis Faculty of Forest Sciences, Umeå (2010).
Noh et al., "The poplar basic helix-loop-helix transcription factor BEE3-Like gene affects biomass production by enhancing proliferation of xylem cells in poplar," Biochemical and Biophysical Research Communications 462:64-70 (2015).
Park et al., "WRKY group IID transcription factors interact with calmodulin," FEBS Letters 579:1545-1550 (2005).
Pires et al., "Original and Diversification of Basic-Helix-Loop-Helix Proteins in Plants," Mol. Biol. Evol. 27(4):862-847 (2010).
Rodrigues et al., "The tonoplast intrinsic aquaporin (TIP subfamily of Eucalyptus grandis: Characterization of EgTIP2, a root-specific and osmotic stress-responsive gene," Plant Science 213:106-113 (2013).
Schrader et al., "A High-Resolution Transcript Profile acorss the Wood-Forming Meristem of Poplar Identifies Potential Regulator sof Cambial Stem Cell Identity," The Plant Cell 16(9) 2278-2292 (2004).
Shi et al., "GhWRKY39, a member of the WRKY transcription factor family in cotton, has a positive role in disease resistance and salt stress tolerance," Plant Cell Tiss Organ Cult 118:17-32 (2014).
Tournier et al., An efficient procedure to stably introduce genes into an economically important pulp tree (Eucalyptus grandis x Eucalyptus urophylla), Transgenic Research 12(4):403-411 (2003).
Vicentini et al., "In silico evaluation of the Eucalyptus transcriptome," Genetics and Molecular Biology, 28(3 suppl):487-495 (2005).
Yokoyama et al., "The *Arabidopsis erecta* gene is expressed in the shoot apical meristem and organ primordia," The Plant Journal, 15(3):301-310 (1998).
Ülker et al., "WRKY transcription factors: from DNA binding towards biological function, Current Opinion in Plant Biology," 7:491-498 (2004).
Office Action from Canadian Application No. 3,083,782 dated Aug. 31, 2023.

\* cited by examiner

SEQUENCE LISTING

```
<160> NUMBER OF SEQ ID NOS: 131

<210> SEQ ID NO 1
<211> LENGTH: 144
<212> TYPE: PRT
<213> ORGANISM: Arabidopsis thaliana

<400> SEQUENCE: 1

Met Asp Tyr Arg Glu Ser Thr Gly Glu Ser Gln Ser Lys Tyr Lys Gly
1               5                   10                  15

Ile Arg Arg Lys Trp Gly Lys Trp Val Ser Glu Ile Arg Val Pro
            20                  25                  30

Gly Thr Arg Asp Arg Leu Trp Leu Gly Ser Phe Ser Thr Ala Glu Gly
        35                  40                  45

Ala Ala Val Ala His Asp Val Ala Phe Phe Cys Leu His Gln Pro Asp
    50                  55                  60

Ser Leu Glu Ser Leu Asn Phe Pro His Leu Leu Asn Pro Ser Leu Val
65                  70                  75                  80

Ser Arg Thr Ser Pro Arg Ser Ile Gln Gln Ala Ala Ser Asn Ala Gly
                85                  90                  95

Met Ala Ile Asp Ala Gly Ile Val His Ser Thr Ser Val Asn Ser Gly
            100                 105                 110

Cys Gly Asp Thr Thr Thr Tyr Tyr Glu Asn Gly Ala Asp Gln Val Glu
        115                 120                 125

Pro Leu Asn Ile Ser Val Tyr Asp Tyr Leu Gly Gly His Asp His Val
    130                 135                 140

<210> SEQ ID NO 2
<211> LENGTH: 361
<212> TYPE: PRT
<213> ORGANISM: Populus tremula x tremuloides

<400> SEQUENCE: 2

Met Ala Val Glu Leu Met Met Gly Tyr Ser Gly Asp Ser Phe Ala Thr
1               5                   10                  15

Lys Met Gln Glu Asn Asp Val Arg Glu Ala Ala Thr Ala Gly Ile Gln
            20                  25                  30

Ser Val Glu Glu Val Ile Lys Leu Leu Lys Gln Asn Gln Leu Glu Gln
        35                  40                  45

Gln Gln Lys Gln Gln Tyr Tyr Gln Glu Leu Ser Ala Ala Ser Ser Ser
    50                  55                  60
```

-continued

Ser Asn Leu Gly Thr Asp Asn Ile Met Ala Val Thr Asp Met Ala Val
65                  70                  75                  80

Asn Asn Phe Lys Lys Val Ile Ser Leu Leu Gly Arg Thr Thr Arg Thr
            85                  90                  95

Gly His Ala Arg Phe Arg Arg Ala Pro Val Ala Cys Pro Pro Gln Gln
            100                 105                 110

Arg Met Gln Glu Pro Glu Pro Glu Pro Gln Gln Gln Lys Gln Gln Val
            115                 120                 125

Gln Glu Pro Val Pro Tyr Val Arg Ala Ile Asn Ser Gln Pro Thr Glu
130                 135                 140

Gln Gly Ser Ala Phe Arg Val Tyr Gln Pro Thr Pro Ile His Arg Leu
145                 150                 155                 160

Pro Pro Leu Pro His Asn Gln Gln Gln Lys Thr Leu Val Val Thr Lys
                165                 170                 175

Asn Gly Leu Ser Asp Arg Asn Glu Met Ala Thr Thr Ile Asn Phe Ser
            180                 185                 190

Asn Ser Pro Thr Ile Ser Ala Pro Thr Ser Phe Leu Ser Ser Val Thr
            195                 200                 205

Gly Glu Thr Asp Ser Phe Gln Arg Ser Thr Leu Ser Gly Phe Gln Phe
210                 215                 220

Thr Gln Pro Ser Ala Gly Lys Pro Pro Leu Ser Ser Ser Ser Leu Lys
225                 230                 235                 240

Arg Lys Cys Asn Ser Met Asp Ala Ala Leu Lys Cys Gly Ser Ser
                245                 250                 255

Ser Ser Arg Cys His Cys Ser Lys Lys Arg Lys Ser Arg Ile Lys Arg
            260                 265                 270

Val Val Arg Val Pro Ala Ile Ser Ser Lys Met Ala Asp Ile Pro Pro
            275                 280                 285

Asp Asp Tyr Ser Trp Arg Lys Tyr Gly Gln Lys Pro Ile Lys Gly Ser
            290                 295                 300

Pro His Pro Arg Gly Tyr Tyr Lys Cys Ser Ser Val Arg Gly Cys Pro
305                 310                 315                 320

Ala Arg Lys His Val Glu Arg Ala Leu Asp Ser Met Met Leu Val
            325                 330                 335

Val Thr Tyr Glu Gly Glu His Asn His Ser His Pro Ile Asp Glu Ala
            340                 345                 350

Pro Gly Ala Leu Val Leu Glu Ser Ser
        355                 360

<210> SEQ ID NO 3
<211> LENGTH: 568
<212> TYPE: PRT
<213> ORGANISM: Populus tremula x tremuloides

<400> SEQUENCE: 3

Met Glu Arg Asp Lys Leu Phe Val Ser Glu Gly Ala Asn Thr Ala Ala
1               5                   10                  15

Thr Ile Trp Asn Ser Cys Ser Phe Gly Met Glu Ile Gln Ala Asn Glu
            20                  25                  30

Leu Ser Cys Gly Pro Glu Lys Leu Val Asn Cys Phe Leu Asn Pro Asn
        35                  40                  45

Trp Asp Asn Ser Leu Asp Gln Ser Asp Pro Phe Glu Ser Ala Leu Ser
    50                  55                  60

Ser Ile Val Ser Ser Pro Val Ala Ser Gly Ala Asn Ala Asn Ala Asn

```
            65                  70                  75                  80
Ala Val Pro Asn Ala Gly Val Gly Gly Asp Gly Phe Met Ile Arg Glu
                85                  90                  95
Leu Ile Gly Arg Leu Gly Asn Ile Cys Asn Ser Gly Asp Ile Ser Pro
            100                 105                 110
Gln Ser Phe Val Asn Asn Asn Asn Ser Thr Asn Thr Ser Cys Tyr
        115                 120                 125
Ser Thr Pro Leu Asn Ser Pro Pro Lys Leu Asn Leu Ser Met Met Asp
    130                 135                 140
Ser Gln Met Arg Gly Asn Leu Pro Ile Pro Gly Asn Ser Val Val Lys
145                 150                 155                 160
His Pro Gly Leu Ala Pro Phe Pro Ala Asp Phe Val Glu Arg Ala Ala
                165                 170                 175
Arg Phe Ser Cys Phe Gly Ser Asn Asn Leu Gly Gly Leu Asn Lys Gln
            180                 185                 190
Phe Gly Leu Asn Glu Ser Glu Leu Ile Asn Arg Leu Met Pro Arg Val
        195                 200                 205
Glu Pro Gly Lys Leu Ser Arg Val Ser Ser Asn Asn Ser Met Lys Val
    210                 215                 220
Thr Val Ser Gln Ala Asn Val Gln Glu Ser Asn Lys Ser Ser Pro Gln
225                 230                 235                 240
Asp Gly Ser Leu Asn Ser Asp Lys Lys Phe Ser Arg Gln Ser Arg Pro
                245                 250                 255
Ser Thr Ser Glu Asn Gly Asp Ser Arg Glu Glu Ser Ser Val Ser Glu
            260                 265                 270
Gln Val Pro Gly Gly Lys Leu Ser Met Lys Ser Gln Asn Asp Ala Asn
        275                 280                 285
Ser Arg Lys Arg Lys Ser Ile Pro Arg Gly Lys Ala Lys Glu Thr Pro
    290                 295                 300
Ser Ser Ser Pro Ser Ala Ser Asp Val Lys Val Ala Ala Glu Asn Asp
305                 310                 315                 320
Asp Ser Lys Ala Lys Arg Ser Lys Ser Asp Glu Thr Asn Gly Ser Asp
                325                 330                 335
Lys Asp Thr Ala Lys Glu Lys Glu Glu Asn Gly Asn Gln Lys Gln
            340                 345                 350
Asn Lys Asn Asn Ser Lys Pro Pro Glu Pro Lys Asp Tyr Ile His
        355                 360                 365
Val Arg Ala Arg Arg Gly Gln Ala Thr Asp Ser His Ser Leu Ala Glu
    370                 375                 380
Arg Val Arg Arg Glu Lys Ile Ser Glu Arg Met Lys Phe Leu Gln Asp
385                 390                 395                 400
Leu Val Pro Gly Cys Asn Lys Val Thr Gly Lys Ala Val Met Leu Asp
                405                 410                 415
Glu Ile Ile Asn Tyr Val Gln Ser Leu Gln Arg Gln Val Glu Phe Leu
            420                 425                 430
Ser Met Lys Leu Ser Ser Val Asn Pro Arg Met Glu Phe Asn Met Glu
        435                 440                 445
Thr Leu Leu Ser Lys Asp Ile Phe Gln Ser Arg Gly Ser Met Pro His
    450                 455                 460
Ser Leu Tyr Pro Ser Asp Ala Ser Thr Pro Ala Phe Pro Tyr Gly Tyr
465                 470                 475                 480
Gln Ser Gln Gln Gly Leu Ala Leu Gln Asn Gly Met Pro Ser Asn Ala
                485                 490                 495
```

```
Glu Thr Gln Phe Ser Met Asn Pro Leu Asn Ala Ala Leu Arg Arg Asn
            500                 505                 510

Pro Ser Met His Leu Pro Pro Leu Asp Gly Phe Gly Asp Pro Ala Val
            515                 520                 525

Leu Gln Ala Ser Ala Met Trp Glu Asp Leu Gln Ser Val Val Gln
    530                 535                 540

Met Gly Tyr Gly Gln Asn His Gln Glu Ser Phe Gln Gly Ser Val Pro
545                 550                 555                 560

Ser Thr His Met Lys Ile Glu Leu
                565

<210> SEQ ID NO 4
<211> LENGTH: 347
<212> TYPE: PRT
<213> ORGANISM: Populus tremula x tremuloides

<400> SEQUENCE: 4

Met Glu Gly Val Glu Ala Asn Arg Ala Ala Val Glu Ser Cys His
1               5                   10                  15

Arg Val Ile Thr Leu Leu Ser Gln Pro Gln Asp Gln Val Gln Tyr Arg
            20                  25                  30

Asn Leu Met Val Glu Thr Gly Glu Ala Val Phe Arg Phe Lys Lys Val
            35                  40                  45

Val Ser Leu Leu Asn Thr Gly Leu Gly His Ala Arg Val Arg Lys Leu
    50                  55                  60

Lys Lys Leu Pro Thr Pro Leu Ser Gln Ser Ile Leu Leu Asp Asn Pro
65                  70                  75                  80

Leu Ser Ser Thr Gly His Pro Ser Lys Thr Ser Gln Phe Leu Gln Ser
                85                  90                  95

Ser Ser Tyr Leu Glu Ser Gln Ser Ile Gln Glu Leu Gly Ser Ile Ala
            100                 105                 110

Lys Asn Cys Leu Ser Leu Gly Thr Pro Ser Leu Glu Leu Ser Ser Asn
            115                 120                 125

Gly Lys Asn Pro Leu Gln Leu Gly Gln Pro Thr Pro Ala Ala Pro Tyr
    130                 135                 140

Gln Phe Leu Gln Gln Gln Leu His Arg Leu Gln Leu Gln Gln Gln
145                 150                 155                 160

Gln Gln Met Lys Gln Gln Ala Glu Ile Met Phe Arg Lys Asn Asn Ser
                165                 170                 175

Gly Met Ser Leu Asn Phe Asp Ser Ser Ser Cys Thr Pro Thr Met Ser
            180                 185                 190

Ser Thr Arg Ser Phe Ile Ser Ser Leu Ser Ile Asp Gly Asn Val Ala
            195                 200                 205

Asn Leu Glu Gly Thr Ala Phe His Leu Thr Gly Ala Ala Arg Ser Ser
    210                 215                 220

Asp Gln Ser Ser Gln Gln His Lys Arg Lys Cys Ser Gly Arg Gly Glu
225                 230                 235                 240

Asp Gly Ser Met Lys Cys Gly Ser Ser Val Arg Cys His Cys Ser Lys
                245                 250                 255

Lys Arg Lys His Arg Val Lys Arg Ser Ile Lys Val Pro Ala Ile Ser
            260                 265                 270

Asn Lys Leu Ala Asp Ile Pro Pro Asp Asp Tyr Ser Trp Arg Lys Tyr
            275                 280                 285

Gly Gln Lys Pro Ile Lys Gly Ser Pro His Pro Arg Gly Tyr Tyr Lys
```

```
                290                 295                 300
Cys Ser Ser Met Arg Gly Cys Pro Ala Arg Lys His Val Glu Arg Cys
305                 310                 315                 320

Leu Glu Asp Pro Ser Met Leu Ile Val Thr Tyr Gly Glu His Asn
                325                 330                 335

His Pro Arg Ile Pro Ala Gln Ser Thr Asn Thr
            340                 345

<210> SEQ ID NO 5
<211> LENGTH: 301
<212> TYPE: PRT
<213> ORGANISM: Populus tremula x tremuloides

<400> SEQUENCE: 5

Met Ala Val Asp Leu Val Arg Tyr Ser Lys Met Glu Asp Gln Met Ala
1               5                   10                  15

Ile Gln Glu Ala Ala Ser Ala Gly Leu Glu Ser Met Glu His Leu Ile
                20                  25                  30

Phe Ala Leu Ser Asn Gln Thr Arg Gln Ser His Gln Leu Asp Cys Gly
            35                  40                  45

Glu Ile Thr Asn Phe Thr Val Ala Lys Phe Lys Gln Val Ile Ser Met
50                  55                  60

Leu Asn Arg Thr Gly His Ala Arg Phe Arg Arg Gly Pro Thr Ser Ser
65                  70                  75                  80

Pro Ser Ser Tyr Pro Val Pro Val Arg Pro Val Pro Gln Glu Pro Gln
                85                  90                  95

Lys Leu Asn Leu Asp Phe Val Asn Ser Lys Ser Pro Pro Lys Ala Glu
            100                 105                 110

Ser Lys Asn Asp Leu Ser Leu Gly Ser Gln Tyr Ser Lys Asp Ser Leu
        115                 120                 125

Ser Ser Gly Thr Thr Thr Ser Ser Phe Val Ser Val Thr Ala Asp
130                 135                 140

Gly Ser Val Ser Asn Gly Lys Gln Gly Gly Ser Ser Leu Phe Gly Thr
145                 150                 155                 160

Gln Ala Arg Ser Thr Gly Lys Pro Pro Leu Ser Ser Thr His Arg Lys
                165                 170                 175

Lys Cys His Asp His Ala Leu Ser Ala Arg Lys Ile Ser Ser Gly Gly
            180                 185                 190

Ser Cys His Cys Ser Lys Arg Arg Lys Ser Arg Val Lys Arg Thr Ile
        195                 200                 205

Arg Val Pro Ala Val Ser Ser Lys Leu Ala Asp Ile Pro Ala Asp Glu
210                 215                 220

Tyr Ser Trp Arg Lys Tyr Gly Gln Lys Pro Ile Lys Gly Ser Pro Tyr
225                 230                 235                 240

Pro Arg Gly Tyr Tyr Lys Cys Ser Ser Val Arg Gly Cys Pro Ala Lys
                245                 250                 255

Lys His Val Glu Arg Ala Val Asp Asp Ser Ala Met Leu Ile Val Thr
            260                 265                 270

Tyr Glu Gly Glu His Arg His Ser His Thr Pro Leu Pro Glu Asp Val
        275                 280                 285

Thr Ala Ser Ala Ala Met Arg His Val Phe His Ser Thr
290                 295                 300

<210> SEQ ID NO 6
<211> LENGTH: 1084
```

```
<212> TYPE: DNA
<213> ORGANISM: Eucalyptus grandis

<400> SEQUENCE: 6
cagaagccct tgcgttgact acagtctgca tttcagggca gttaagaaag agggaaagga      60
ggagagggag agatgtagaa agatggagag tccatcagaa acagaaactg actacagcca     120
tttatttata ggaagatgag gactctcgag actcgtggcg aagaacgagt catcaagcac     180
ggggcccttc gatgcggaat ttttttggag gtcctgaaga tgattattca tttccccacc     240
atgtctataa attcttcgaa tttgtggcaa ttcaagttgg ggaacaaaac acggccagac     300
ccaaagagga aaatgagttt acaacataat tcaaccgaca tgaaaaatta gttcttgcaa     360
atatgatgcc atatagatca ttcttcatag ttaagctact atgtggttgt aacatgata      420 ttcgtgttga tacttataaa gagaccaatc aaaatcgatc cttatcctta aaaagtcaat     480
atattttcgg ggaggcctat tggaatacta ataatcatgc tgcctaattt tgtcataaga     540
atgtgagatc tcgatataat caaaggtcgt gagatcatga cagatgtaga taggtaggtt     600
tcttaggagc aaagcaaaat atcggggaca ctgctggcca gtaaagccca tgatgcagat     660
aaaggaacga atccctccct ccatctttgg aagcccaacc cacctcagag gccaaaagct     720
acgttgacag gagaatggga gcagagagtc gcatcgttca acgacgtgtg gttggaccga     780
cgaaaacttc aaaagccagg gaaaaagaaa gagcgcctgt gatcctttac gtaaatacgc     840 ggggggggagt tctgtggtgc gtttcggttt tttttcaaca ccgaccctcc cagttgtctt     900
ccttcctgcc taagatcggt tttactttta gacgatcgat tagacgatcg atcgctctct     960
ctctctctct ctctctgtgg cctcacgcgc attttccatag gcaaccaaca acagcagcag    1020
aaagtagagt tcctgcggcg atatcgcgcg atccgagtcg cgagctgagg ccccgacccc    1080
gacg                                                                 1084

<210> SEQ ID NO 7
<211> LENGTH: 2000
<212> TYPE: DNA
<213> ORGANISM: Eucalyptus grandis

<400> SEQUENCE: 7
aaaaacacgg atatgataca aaatagagag agagagggat ctattattct cacttggatg      60
tattgtaaga aatcacaata aatctttcat tcttgctaga aggggaagtt gatacccca     120 atctaaactt gttcttttta gtccatctat tttggtcaat tgagtagctt ccctctacc     180 aaactctgaa atgttctaaa ataatttctc aaaaaaagat ttttttatca aaagaataga     240
ccttgaatat atattaagcc atgtcaaaat tgcaaatcac agcaattaca attaataatc     300
ctaaaacgaa aaatcaagct tgtaacgatg attgctacaa aaaaaattat gaattgcaat     360
ttttttgggg agttcactaa attatgtaac cttcaagaac tgagtaaatc taaaaaaatg     420
ttccaaaact ctagtagaat tacgatagta acttacactt gctaaataat ctaaagaccc     480
caaaagaaat aaagttattt tagtaagtga aacgcttcgg attctgatag tggaattccc     540
agctataaaa tctcaagcac atcccaaacc tatagtatta aaaaaattgc caaatcttcg     600
aacttggaga acttttttt ctagaaaccg atcaaattta attttagtag gcacatgcag      660
acatgtgcca tttcaccagt aaactaaaaa ccaagaaaag attaacacgg aatgacaaca     720
ttctataata aatttgagaa aatcgcagaa aatgtgcaac aaaatcgaga gatccaatcc     780
attcactaga aaaatgtaat atcgagcgca attaccaaaa acatcgagtt cccatacgcg     840
```

```
cgatcacaca agacatatag caaaaataaa gaaaagagat tatttccaaa aaaaataaat        900
tggatttata cacggcatct agaaagaggc cgactcttgg atacattacc aaagaagaaa        960
ttcactcgca agaccatcca tattctgtag aagattctag aaccaggagc tcgcgaaagg       1020
tagttgccaa cttgctcatg tcttgtctgt ccgccatcaa cctttcatcg gcttttgact       1080
tttcctcctg accaaaaaaa ccctaattca attcaaaatt ctcctccggc tgctgggttt       1140
aggtactcct aaattcggcg ggcaatgcct taagggccac aagttttcct tcagtctcgc       1200
acaattttt  tttttttta acaacacata aaataatagt aattttgcg ggcgtctaat         1260
ataataaaga atagatcaaa attgcttgat caaaatttac tttgcgctgg cgcaatatgc       1320
tcagtctttt gttcttgaat taatcacttc ttcgatatga ctgtcgctaa aagcgacata       1380
cgcgaaacaa attttggtac gtaagatcga tacaaattgt tcacaatttc ttagaatttc       1440
taatatttct tttattttt  gcaaaggggg aggcaaaaaa ttaaatgaga aggaaataat       1500
gttagacaag cggaaccatt gaaaacctcc tcctacccaa gcccaccggc tctcagatat       1560
gctccgaata ttcccgcttc tcgttttccc cacgctcgct tcacgcgcgt ggctcacaat       1620
cctaccctcc gcgccggcct ccctttcgaa ttccccgagc tcggcgcgtg cccgtgatgg       1680
gcacgacatt cccgaaccag cgggctccca acagagtccc gctttcaact aaatcagcgg       1740
ctcgaagcat cgttcttctc gctatcatct ttagggattt cgtttcgccc aaggcagaga       1800
gaaaaaagag agaggctgac tcgtcgactc acgtgacccg gcccgagcgg actcaccgtt       1860
ctgactcgct tatttaaagc gtcttactgt ccctcaccct gttgtctcaa accactctca       1920
actcactctc atctctacac tgcttttct cgtcttctct cgctagccat ttccagaacc        1980
ctcgtcgcgc gtcgcttgcc                                                  2000

<210> SEQ ID NO 8
<211> LENGTH: 2000
<212> TYPE: DNA
<213> ORGANISM: Eucalyptus grandis

<400> SEQUENCE: 8
aaatggatat gactacacaa ttattttcga gtgcatactt tgtccatcaa acaaaaatgc         60
ctgaaaattt ctttattaat gggctcgaca aggatgctaa ttgctagtga aattcggtga        120
tttgctgctg ctgctagaga catgttagac tcttgtccat gttcgtgcct cttgggcaat        180
tttgttgtct aattcgagag agatcacaaa aaaacatgga agtgtgaatc tcttctcgtc        240
tacttgatat gtagccaaat cacatgacct taagagccta tcttttttcat caattcgcca        300
atcatacgag ggaggttaga tgctgattcg cgagccgtaa aaagcccatt catcgtctaa        360
ctagccatgc ctaggtgaat gcaaccgcac aattagctcc aaaagcatat atcgttcgtc        420
gaacggaaat gtctaagaat ttatcgacac tacaaaaagg atcctgattg gatgtgttgg        480
actcgtgtct atgcgtgtcc cctttggaca acttggttgt ctaattcgag agaaaataca        540
agaagccatg aaagtgcaga tctcttgctt ttcctttag  agtacttgat atatggccaa       600
atcacatgat cctagaggcc atatctttca tcgtttcgcc aattatatga aggaggttag       660
gcactaattc acaagctgta aaagcaccag catgttaaac aagtaaacga aaacgtcat        720
acattcaaaa atgtatacac ataacgagta tcttggaata gaatactatg ttattatcca       780
gtttcgatac gacggagaat cgccaagtca tgatcttctc gcgattccat tgatcggaac       840
aaggttcgcc tatgctccga cagtaaatcc tagggagggc caccccccaca tttctaaatg     900
ctaacaagaa tcaagaacga gctcgagaca aaaagatgt cctgtaataa ccttagaagt        960
```

```
cctgcattga ttcgcacacg tcaggcaatt tttcattttg atggtaacc aatccatcga    1020 agcttggctc aatgcataca gaatagaaac aagtatgggg ggcatcgagt attaaatttg    1080
gaaatgatga gagatgggag aggccatggt gcgagaacgc agttaattct tgctctgcaa    1140
cacacagtga aagagagaga aataattcgt ccttttcgac ccctgaaatg gatcgccatt    1200
tacattttac ccccatctct gcaagaaaac agctccccc cagcaagaac cgagaagcga    1260
aagcgaccca ttattcatta cggcgtatgt aaccaagcat cccaacattc aagaagaga    1320 gagagaaacg gtagtagtgg ggtggggagg aggggggaa atgtagagag agaaatttca    1380
ccacccagag tgtcatagcg cgcagagaga gagagagtat agcgttgcag gcgttgttgc    1440
agaaccgtgg cagatggtct tttaaccttt tctctcgaaa taattcgctc cctctctctc    1500
tctacccacg tctatctctc tcctcattac ggttctattc tggggtggct ctttgcctgg    1560
gagcagtgag cattatatgc tcatcgaagg aggagaaaaa aatgagaacg gaaaagcaaa    1620
atgcagtgta ccccatcttt ctctgcaggc agagagagcc ctgtgtgtgc cagagcgatg    1680
tgatggaacg agtaaaagta agctaatctc agacttgagg ctgtcataac atctcagagg    1740
gagaagaaga agaagaagaa agcccaagaa tttacttctt ggtttttca aaatgactat    1800 caaagaccca acgaacatgc gcttctcttt cttcagctcc tccttcctat ctctgcaggc    1860
atcgtgtcgg tgagctcgga gtgggctccg accgggcaag ctttgcttcc gaagcattcg    1920
ttcgtaacag agtccaaagt tggctccttt gccgcgaatt ctggagtttg aaaagtgtgt    1980
ggttggctgg gggaacggcc                                               2000
```

<210> SEQ ID NO 9
<211> LENGTH: 2500
<212> TYPE: DNA
<213> ORGANISM: Eucalyptus grandis

<400> SEQUENCE: 9

```
ctcacaatcc atatgcatcg cgggccatta tatcttaacc gaattttagt gcgccctaaa     60
atgaaatcat gcagatattc attcgttaaa tcgcacgtct tttcgcaaga gcacgtcata    120
aataatgctc tagcggatgc aaaagcgtgt gctgttaatc tcgaatcaaa agctgtaaac    180
cacgttcgag gggctaaggc aatgttttc gcaggaagtc gcagacagga aagaagaga     240 tctaaaatta gatactcaag ctgtaaatag ggtagagaga gggggaggga gtactgtacg    300
taggaagtga ctggagggtg cacagtgtcc ctcccggtca tatctatctt aggccctgcg    360
cctctgaaaa aaaagctacc cagttttggt tatcttcttt gctgtcgcct tgggaaaact    420
cgttatttta ttattttaca aaaaaaataa agtattttt tggtacgtac catctgtttg    480
atatatactg tgctggattt ttttttttt ctgggtgtgg cggtcgatac tttggtggat    540
atcgtatgat ttctgttttt ttttttgtt tattcattt ctggtccatt ttcttttgag     600
ttgcttttat tataacagaa ctagtgataa tgatttctct gatttcattc ctgaaactac    660
attgtaaaat catgtagaac ttattagcag acaacattaa catttaaatc tggaaaaaaa    720
aatcataact tgtttcttaa aattagaaac aagctggaag gggccatacc cgcgtggatt    780
atctctccgg acattatcat aagagttgta tgcccgccaa cattgttcat tttgaactag    840
ccaattgtta ttgcctcatc ataatgttag caaaaatgga atcggagtta tcctgaatga    900
caacatgatc aaacctacac tttggataca cattcctgaa attctaccct tcaaacttg    960 tcacaacata accatttaaa ggagatgctc caaaagctta attcctccta ttttaaaaaa    1020
```

| | |
|---|---|
| aaagatcgtg ctttacatga gattcatctt gaaaatttat gtacaataaa caaaagacc | 1080 |
| acccaaaaaa gttagaatag aagattcatc cacaacgaga agtatgacaa gtgtacgagt | 1140 |
| cattgatttt gcttaggttg ggtaagaatc gggaattgaa tttcttggca aaacaaagat | 1200 |
| tctcaatgca attcaaacaa tgatcgcaaa agtctgtacg tatatataga gtttgtaaac | 1260 |
| gtcgatgatt tcaatattaa acaaatctca aatggcaaaa agatgaaagt cgctctaaat | 1320 |
| tagccctatg tgagcaatat ttgtggatga tcatttgccc cgtgacatta atatgtggcc | 1380 |
| tttttcctac tagacgctca aaatctaata aatatagact tttgaggcca catcaatagt | 1440 |
| cttcataatt tactaacata acagttttg ggctaccgtg agaataataa tttgatgcga | 1500 |
| gtcacaaatt attacgaggt acaaattatc gaaagaatgg acctcataat aatctacaat | 1560 |
| tatttgttat ttagttttt atgatctaaa acaaactatt attaaagaac atcatccaat | 1620 |
| tattactcat tttctttttt attggaaaga gtccataatt tcccaaataa ttataatgta | 1680 |
| atgtttactg tgacgaaaaa atcaaatgct acttattttt tggttggctg agagctggac | 1740 |
| cagaaagagg cagacgctgt accaatatat gaatgtcatt aatgtaaaat agtgcgttgg | 1800 |
| gattctatgg agggagggaa ggggaggatg tttgtagttt ccattaaata aatatagtgt | 1860 |
| ggaactttaa tggtatcagg acgacaacga gccaaagaat gtccggaggt cgctgtagga | 1920 |
| gcacgttttc tgggcttata taatgcgcgc gtccgggatt tgtgtgcttg tgttaagtgt | 1980 |
| cgagttttgt tggctgttgt ctcattaagc caaaaggcca atccataaga gaaggagga | 2040 |
| aaaaaaagg agaaaagcag agagagagag agagagagag agagggagta gggggatttc | 2100 |
| tcgcacattg ccttacacag atccccatgg cttttttatg cagggatact acccagcatt | 2160 |
| cgcttggagc tgagctcttt ttattctctt tgttttagat tgaagtgaag ggaccatttc | 2220 |
| tctctctctc tccccccta tatatgagag cttgagaggc tgtgggtgtg aagttgttgg | 2280 |
| gttatattct cggaactaga caacaacaac agggaaaaaa aaaaaaaaaa acccaagtgt | 2340 |
| gtgtgggtgt gtgtttttctc tctcagatgc aagaagattt cgaaatgatt acttcccttc | 2400 |
| ttgccaatga ttgaagcctc gagctcgtgc ttgcctcgca ccacaatgag acatgcttaa | 2460 |
| cgaagtaccg acttttttaac tgaacgagga ggaggagaag | 2500 |

<210> SEQ ID NO 10
<211> LENGTH: 2700
<212> TYPE: DNA
<213> ORGANISM: Eucalyptus grandis

<400> SEQUENCE: 10

| | |
|---|---|
| aatgcaaaat ggccgaaaaa gagaggagag aaaagaaaaa actcagtccc gtctctcctc | 60 |
| cgcacgatcc ccatcccat ccgacgcgcc tgatctctcc ccagcgagat cagaagacgc | 120 |
| tttttacacc gaaacggatc gttctgatac ggggacggg gggcaggacc gagcccaagt | 180 |
| ccccggcacg gcaaaagcga atcgcgagca aagctcggtg cgtactgcag agaattcggg | 240 |
| gcacggagcg gtgtaaaata tgcaggggag aaatcgcgaa ataataaccg gaagcagggg | 300 |
| agcttacgat atcaaattcc ctcgtacacg tcagccgccg tggggaccac ctccttcttt | 360 |
| tgtcctcttg ctcctgctgc cctcgcatgc tcctgctctc tactctctct ctctctctat | 420 |
| actctccatc cgtgctttgc tctctcttgt cacttcctgt caaagttgct tgctttctct | 480 |
| ctctagctta gcttggagct tacctactgt actctgcttt tccccccct ctctctctct | 540 |
| ctctcgctct gaacgttttt cagtcatcga gccgagctga actcctctct ctctctctct | 600 |
| ctgggtgacc cttcttccct tttctctgcg cttccgtcga agtgaaagag ggcgccgagg | 660 |

```
ttgtcgtccg agatgcgtcg gagaaggacc tctctcctga tttcatgaga ccgaccagtg    720
agtaagctcg ctccgatgac tggagcttcc tctgacctcc ctttctttct ttttcgggtg    780
ctgagcttgt ccagcgtctt ggccgtcgtc aatttttacgc tttcgtgtga gctttgcttg    840
ctgtctttgt gggtgccgtg cgggactcga ttcgtctggt aatcgcgaat gcaggatcga    900
tgctgacttt tgagctcccg aaggacggac cctttttatct ttactagcag aagaccttaa    960
aaagtggagg ttctgatttc tttttcatat ttttctttgg ctcacggtct caaatgagtg   1020
atcggtttcg gttcttggaa agatggcatt tcttttttctt gaaagaacag catctggtga   1080
atattttatt gttatctcat gcctagaaag gttccttttta ttttttatttt cttttttggtt   1140 ctgggaaagg gttccagatt ccattatatc tcatcactcg gttgcatatt caattgggct   1200
ctttggtttc cctcggggttg catctgtctt gtaccctgaa gaatttggca tccgccgttc   1260
ttaatgcaga ttcgttcact ttttggagct tctgtttggt ctctcttttct gcatgacatt   1320 cttgcattgg ttggtccccg tggactactc acaattggaa ggttcagatg cttttctggg   1380
tgcataattt ctatcagatg tttgtagaga tggactcctt tggggggtca tcctcctaca   1440
tctactttgg gggctctagt atgctgtatt ctgtatggtt ttaagcttta ctggaatttt   1500
aacatccttt cctcttgtgg tgtttggttg atgagatgcg gatgatagaa ttccgaactc   1560
atcatttaga ctttcatttg tcgatttaaa gactgataat cagaaaggag aattcaacgc   1620
aatttcacgt tcaattaact tcttgctcca cttaaattgc gggtgcagtt caggggccgg   1680
tttggattct ctccttcaat agatttagat gggtaatctc tttataatgt tttggagatt   1740
ctggaacaag catctaggag tcaatgcaca aattgcaaca ctcagcagca tcaatcatag   1800
tgttcaccat ttgttggaaa ctgtagattt gacgatagat tattgatagg gggttttctg   1860
gattttctgt atagttagat ttgcttggaa gggacttgtg gatgatctag gcggaataa   1920 attggtatta gatttcaatc tctttttgtc tgagctcaaa ttccttgttt caatgcattt   1980
taactatagt tatggtacta gatttctttc tttccttggc tgaatgtatg tgaatattgc   2040
ttccttcatg aaaattgttg aaccagagaa atgcatggaa acatagtgct gcttgcttcg   2100
ggaattgaac aatatagctg gaccagtttg gtcgtgtagt gactggaagt ttgcctaggg   2160
taatatcatt ttgcttacaa aaccttaaca aaagaatgtg ggactcttca ttctgttctt   2220
ggtgattgtt ctttcagaca tagatttcgc ttttcagttg ttatatttct tggattaggt   2280
ataattagag aatttgaaca tcagcctgct catgtccttt ccttgaaaat gacatatcca   2340
cccagatacc ctatgaattt atggaggata agtgacgacc tcggctgtaa atgttgttac   2400
acaactgttt tctctttatg atgctaggga gagattgccg cttgtttttt cttgcttgcc   2460
tcactaattg gccattgtct tttatagttt cccctaggtc tgctttcatt ccttggata   2520 aacctgtctc ctccttggga ttcttttctt ttctcagacc agttaactca gctaaaatgt   2580
tgtgtattat attgtgatgt gagaaattac ttctaatttg tattatcacc atcttcttct   2640
gtagccacac tatgaaagat ctaagtttga ggcaatggga agtggtgtct acacctggca   2700
```

<210> SEQ ID NO 11
<211> LENGTH: 2500
<212> TYPE: DNA
<213> ORGANISM: Eucalyptus grandis

<400> SEQUENCE: 11

```
ataaaaaact cctaagcata ggtgcttcga gcatcctaaa tgcgagttct cttattgcaa     60
```

```
gagattgaaa actctcaagc atgagaaatt gagattccca acaagattc aatgaaaact      120
ctcataaaag taagagcaat cgaagaaagc caaccataat tgtatagttt ttacctaaat      180
tttaggttga agaagagcgc aatttgagtc gatgtggaaa attgatctcc aaaagatgtc      240
ttcttggatt tggaatatga gataaaactg gacatgccac attactaagt gcaactttag      300
atggagtgat aacggaatga gaatcaagta aaaattagtg gtgttttatg agacaaaaaa      360
agtttaggtt agaataagga cttgacataa agtttaaggt aggattgtga ttagaccaaa      420
agttgagcat ttttaatgaa aaaagaaaa gattagggta gaattggaac ttaactgaaa       480
tttgaggaat ttttagggta ttagggtcac ataaaacaca tgataattat atcctagaaa      540
aagtacttca atttttagct tgcatatcat cttttattta gccaattagt gatgtaataa      600
gtaaattatc actcgtatgc caaaaaatat caattataat atatcatctt cacagagaaa      660
atgtaataat gattttatttt ctctttaata ggatcagatt agtaataaac tcagtcatta     720
aatgcggcat gtatataaaa ttttgtagtt atagtggtcc tataaagata tgcaattttt      780
tttttctcat ttataacgca gttgatttga taaactcgtg ataatgaa gcttagatta      840
tatattagta atgtctaatt tctgttgcgt atttttttcat ccctcatccc acatcataaa    900
atttcagtct tctatgttac caacaaaggg tgtaaaagaa ctcatcgaca tcgagttaaa     960
aggttgttta ctaacgtttg catagcaatt tcttttttatt tttgaaagca aacaaaaaca    1020
attattgaaa acattgttt gggtggtac aaaaaaaaat taattatgta aaaataaaag      1080
aaaaaaaatg acacaaatgg ttactcttgc caagcctcga tcttttgacc ttaaacaatg    1140
caaagccttt actactgggc tactatgtta ggtggtgcat tttagataga aggatatcac    1200
aagatatttg ttattccatg tccttcagac agcaattcac acttactgat ttgagatttt    1260
ttgtatgcac aacgttctta tgttctgtga ccatatttac tattgtcata gtgttgtaac    1320
tagattatac aattcacttg gttttcttct tttatgtcga gcgtgctaat acacaagttc    1380
ccttacttga ttaaaagagc atacataaga tcttgaagac tgcggagaca taaagatttt    1440
aactttgagg gtggttaaag agattacatg gaatatttta aatttaaata actatcgata    1500
ctcacatggt aggttaggaa agacaaataa cttttctaaat aagatagtgg caagcgattt   1560
tattcaacaa gtatcaaatg caaagtcctc accgaatctg gggtttataa tagttgagtc    1620
atcttggttt gtccatataa ggattctagt cctttaccta ataggttttt tcaaggttta    1680
tgtgatgtga tgggcttgcc catcttgttg aaaacatcaa gattttttgct agtaagcgag    1740
acagacttta caatagtctc tatataactg gatcgattaa gacccgacta aactaaatga    1800
tatataaacg atatatcgga aacctaaagt ccaactcaac aattgacgta gatatcaacg    1860
tatgatctac tccattaatc tgatcgtctc tagacaagtg actgggtagt atgtgaaaag    1920
agatattatc caatcgatgc actttggatt aagggtttta aacttacaca ttgattaaaa    1980
tattaagaaa atttcgtgaa tttgatttat aatatgatac gatagactct ttattaaata    2040
ctaacatgac acatttactc tccactcatg atttatatca tgctattttg taagtcaatt    2100
atataaaatc tagagaggcc atgcctcagc tcttgccttt ggtctaaccc agccttgacc    2160
ccacaaaaaa aaaagagcaa aaatctttcc gaggaaaaat tgcacaaatt ctacattaaa    2220
cttttttgca gatatgaaca aatatttttt ttttctcgaa aatcttccaa gacaaaaggc    2280
gaggcccctt catctccttc ctcacgcaat cgcttggagc gccctctctc cctcactccc    2340
tccctcctct ctctctctct ctctctctct ctctctctcc atcccacatt cttgaaagag    2400
acacatcaga agcgcaggca tgaatctggg caccggctcg ttctcttttcc tgctccatct   2460
```

```
ataatgagca aagccttcgc tctcttctcc gcagaagggc                    2500

<210> SEQ ID NO 12
<211> LENGTH: 2101
<212> TYPE: DNA
<213> ORGANISM: Eucalyptus grandis

<400> SEQUENCE: 12
caacctcgtg gtaatgcaac gaaactagcc caaatatatg ttgatagcca atttggagta      60
actctaattt tgtttgcgtt ggtataagat gcaacaaggt acataaaatc caattccatt     120
gaccctgaat tgtgtgaggt cttctcatgc tggaaagcac tgaaaattac aaattcaccc     180
ccacccagag tcaatacgta gacatacata tgattttacg caatcattga agatcaaagt     240
ggaataaaat aatatttgga gggtgatagt gccactgcca tggtggtgcg gtgctttaac     300
cctggagctc tctacacaat tctctctctc tctctctttc ggattatgaa aatgaaagtg     360
gggttacgta ttgctggttt tgaactgttt gggaaattga agcaagctgt tcccaaagaa     420
aaaagcacgc catttattgg caaaataata ttaaacatat atctggggca ttcagataga     480
gttttctcaa cactttgcct attttaaata tttattattt tccaattgta tattccactt     540
ccattgccta aagacgacgg cattcagttt tcccccttc tttattcatt tatttccccc      600
cccccccct tttcccgtca ttggactgcg tagaaaagag gcaatttcga gtatagggat      660
tggagggatc tttctttcgt ttttttcttt tttttgctt gaattatttt tactattttt      720
tttaattatt tgcttcattc cctcgcacct cttcaacttt atggaagaaa aaggttgata     780
gaggccaccg aaaagcatgg acaccttatc atgaaagcga gaaaaacacg acccgatttg     840
acgggccaac acacacccac aacacaaaat accaaaaacc actcgagcgc ctcgcaaaaa     900
attcacacgc ttgttccatc atcacattca catctccatc tccaccttct attccctctt     960
ggctattctc tccacccct ttttcctcgg tctctgttga cgagcatgat ggagaaatac     1020
agagagtttt gtcatgtttt tgaagaagag attggctcct tctgctggct tgcaatgaag     1080
aagtggagag ctgctgaatg gctccatatc cttccaatct tccaaaattc cacttgatta     1140
ggatggacaa tagtctgtca aaaagggaaa ataaacttat cctgggaaaa tcatcgtttc     1200
aatcttggcc cttaaagtt gaatatcaag attattcgcg ttatttacaa tttggagaag     1260
taaactgagt caatttgctc caactcgaca tgattgtagt ccataaacct ttaaagggga     1320
aaaatgacat attgcaattg ttttgctggt gagaaatcat gatataaaga ggataaaatt     1380
gagttaggca attgagagca taccaatcca tgcaatcaaa agcactttat tgaaaaaaaa     1440
tcaaataaag atatgataat aattcatttt tctcaataat ggaaaaatac cttatcaatc     1500
tcatgaatga gataaacatg agttaaggat ctaggtggat gcatctatat taaactcttt     1560
acggtaggtg gtgtagaaaa ctatgatccc ttttatgagc ctaatccaca cacaaatatg     1620
ttttttaatc actagccaaa ctctacaaat taaataccat aagaaaaatt aaacaataag     1680
aaaggcataa tttaaagtat tataaatttc catgctagtg catttaatgc aactgaaaga     1740
gcacctcaaa gcaaaatggc aatcataaac agtttctcct ttttccttt tgctccagtg     1800
caactttagc ttttttcatcg tgtgggtaat caatctccaa gtcaacctcg cctcatcatt     1860
tggtcttggg ttcttctgaa caacccacca tgcacctcat ttcccacttt cccactttcg     1920
ctctctctct cgctctctct ctctctttct ctctctccct ccctctctcc ctccctcttt     1980
ttcgttttgt ttttgttttt accttttcaa caggagtgtg tcattcccta tataattgcc     2040
```

```
tctctctttt agccggatct tcccctcatg ggaagcagaa gcatctcgtt tcaggcaaag    2100
c                                                                    2101

<210> SEQ ID NO 13
<211> LENGTH: 1487
<212> TYPE: DNA
<213> ORGANISM: Populus tremula x tremuloides

<400> SEQUENCE: 13
tctgcttatg aatggcatgg acaacaagct ctgcattttc gcccatttgc accacaaaat     60
cgttgtgtga agattttga agggcaccag cacaacttg aaaagaactt gtgaaaagat     120
agctggtcac cagatggaag caaggttact agtgcagatc gcatggctta tatatgaatc    180
tgtcaatgag tgtgtcttcc acctactgaa cctatcttg gatcatgcag cagcgacaaa    240
cagatttatc ttggggaaat ctgattacta ttttgtcagt ttgcttaaaa cgagttgtta    300
gtaacagtga ggatattttg gggcttgctt gtgagtaccc aacagaaaga ttaaacaggt    360
tgtaatgata ctatgttaca ttttacttaa ctttctcata tcctgctgac atgtttgcag    420 ttctttttg cttgttggcg atcctttca actgaagtat gtacgcatga atcaattagc     480
tcaaaatgta tgttcgagca atatgcctgg tgaatgtttg ttagatacga aattaagtta    540
ctgaacttgt actctttgat tttgaaacaa gtttccgact atgttcattg tcctagcacg    600
gtgatattgg tacgtcgaat tttcaactat ttttgtcttg ttttcaacta tttctgtctt    660
gattttcaaa gtcttctga aaataaaaaa cccaaaaata tgttttcagt gtcttgttag    720
ctaaatctgt tgtacaacca agcctccccg acttgctttg tgaaaagaa agatgggagc    780 tgggggtttt gtgttgatta tacaaaacct tacgagataa ctgatataca agcaaaaaca    840
ccctcatatt attgaatctg cgacttctac agttcatttc tgaggaagaa ttaggtgact    900
actttctgga ctagatattt ccgtgttcaa tgcgtcgcaa caattgattt gttggctgga    960
ttatgaacat gataatcaca ctatagaaag acgacgatta tatttcaagc tatggacaat   1020
gatgttacct gctcgaagat caatacgctt gaaggccaag atatgatcac aggtatgcag   1080
gcagtccaga tggctcttgg gatatgagct tcaagattgt tcttgaaaag aaccaaataa   1140
attgtaaaat tctctgggaa tattttttg taaaattatc agcattgcta ttttttttt    1200 caaattcatt taaatattgc tattgggtta gtagttcagc gcaattaact tagctggcag   1260
tctggcatta gcttcaaatc atatcacaac gttaaaagta gccgttgcaa ctagtcagcc   1320
cactagcatt tgctggtgac caatcagatc ataaaaggaa aactagccgt tggcaaaccc   1380
tctttcaacg gtcatctccc tgcttcatga tatatatgct tagatatccc agtatcccct   1440
tcaacaaatt atctcaatct tcaaaaccca gtccccagtt acagcag                1487

<210> SEQ ID NO 14
<211> LENGTH: 1780
<212> TYPE: DNA
<213> ORGANISM: Populus tremula x tremuloides

<400> SEQUENCE: 14
gatgcaaaag ctggaatgag aatgcgctaa atgcgaaaag acagagagag cgaataaatc     60
gtgctaaaaa aggagtgggg tgggtaacgg gttgagctag aagaagaaaa gagacaagtg    120
cactttagga gggggcaac cagagcgtag atgataatgg ttcatgtgga aacaacacac     180
atgagcagtt ggtgagaact tgaatgaacc ctaacagccc aaccaaaccc ggagccaccc    240
ttaccgaacc accacttcta aaagtacacc atgccttttt cttgagcttg gttgcacagg    300
```

```
gtgccaggtg gggttgtttc gttttgggta atcatgcgat agtttaaata cctttgcgat      360
aatcatatca atggtgactt ttaagcacat gttaggtgct cggttcttat ctaaacatgg      420
acatggcaac aagagttaat gctaaaataa tatacgtaca ttacctgtga atgaatcgtc      480
gctgtcttct gatcatggct tcaaataata tgcagataaa caagtgtcga tttttcagtg      540
aagattttat gaaagtgccc gttctcctta agattacctg tgaatgaatc atccctgtca      600
ggctgatcct gggtggtttt tccccatgat gttcggaaga tataattata taaatgatgg      660
aatttacatg aaataagttt cagtacattc ttagcagaaa agcaatatcg acgaagacaa      720
atgatgctgt ttaagacaaa ctggggtaat atcaatttac tagtaagaga tttgtctgct      780
tttcttaatt ctcaagaaac tttcactaaa atgcacagcc atgttaaaca atttacattc      840
aacttaaaaa ctaaaattgt aggatgggta gctatccaag aattacgctt tttgtaaact      900
taattttgat gggcatgtag ttaacaagta tttttcatcg atcaattcaa gagccatgtc      960
tgcatcataa ttgtgggagt ggaggaggct tttgttgcta gggaaggaat gccttcttag     1020
ttcatggctt tggacttcgg acaaggagcg catagaatgg ggttaccatt tttgaaaaaa     1080
attacatttg aaccctccaa ctattatcat gtatgtttaa tctacaatcc tcgtccgcta     1140
gaagaagttt gggttcaaag tcatccgctc aatgtaaacc atggagagac agggactaat     1200
tgaaaatagt atgttagttg gagggtctgc atgtattatg tccaaacatt ctcttattat     1260
tcctgtatca tctctgagaa attcatccga aaataataaa acaaaatggc cttttttaaa     1320
ataagaagct gatgcatagg ataccaaaag cgccttgtcc attaggagcg tcagactttg     1380
aaaataagac caataattcc ctgtaagcta tcatctcatc ttttatttty tttgaacttg     1440
tagacgtagg ctttaagcgt tccatgatgt tcagtcacat gttgctgtct acttgattat     1500
ggaatttaat tcattcggct cataagaaga taaaaggatt atgacgttga agaactctgg     1560
tcactcctta cttacggtca cataaaaacg atgcatcttt ccccaccaac catcttcaag     1620
tgaacccact ttcccttgca ttaggtaagg agtatgggtt aagtcatctt catgaaatta     1680
gtcccctagt ggagctaatt ctactcactc catatttact cattccacta tataacgccc     1740
tcaacgacca tcctcaaagc aacccaaaca ccttcttctc                           1780
```

<210> SEQ ID NO 15
<211> LENGTH: 2001
<212> TYPE: DNA
<213> ORGANISM: Eucalyptus grandis

<400> SEQUENCE: 15

```
tcaggctctg tggcgggcca acgaccaatt ctaggttggt cagttattgc tctggacaat       60
ataataggcg cagatccatg gttcatggtc agacatgtcg agcgcatcca tgcacgacat      120
gccgtcccta tgtttagcca ccgcaaagaa catcaataac aattcgtctc gtgactggtg      180
aaggaactat ccagctttcg tctctttgaa tgcgaattgc gattgcgtgt tgttaccccg      240
tccttccttc acgtccttct agattaaact ctccttggtt cttcgtacgc aagttccgca      300
tacaataata agaatccccc ccaaacgaaa ggagattcat gaaaaggtac gagcagcaaa      360
gtttctctct acccttttaa aaaaatcagg atgtagaagg gtcacaactc atcattcctc      420
atatagaccc tttctagaaa gcaagtgggt ggtgtatgta cacgtctt tgagacagat       480 tcccacgtaa aagagcgagc gagcagttgg ccaaatcaac cggacccttc acacaattat      540
gctctccacc aaacccccaag tcatcaccaa cccccctctc ctccatctct cgtccgatcc      600
```

```
catcgaaagt gaccatcatt attcatcagt gtgttctcac tttctcagag cttggccatg      660
tgggcgttac cccgttttgt cccgtaattc cgcttctcgg ttcgatcccc gcaccgcccc      720
attgcaggta aaaatcgatg tccgtgacga ccccttttta tctcctttta ggtggatggt      780
tgcgatcgtg gtttggtgga aaaggggat caaatcatgc tacatgatcc tgctgttgac       840
atgtggtagt aatgtcttcc cccatttgtc tgaactctga tgtcaagatc gtgtaattct      900
atgcttcaaa ctgaagcgat gagaccctgt gcgtctccca cttatcatgc ctctccagaa      960
ggattgatcc gcttgtcgcc acttacctac tttggttttg atttcagtt tccaacttat      1020 tggagcgtag cgcgtaattc cccaagcaat tgatgacaat ttaagcaact tcctgaactt     1080
tgaaaccatg cgagtactgc aagcatgtca ttactgtagc tcactaatca aagatataag     1140
ccaagaaaat ctcggttaaa ccactcgatc tattgttaag gacggccatt tccccgacat     1200
tttaagatgt gggatatgtt aaagagtact gtagttatta ggacttatcg aaggtatttg     1260
tgtccaaaaa tgaggaattc gtgtctactt ttgagattgg tagttctctt ttaatgggca     1320
ttgatatatc cggacataa ttagcatcgg tttcattaac ctcgatcagt aatggtgcaa      1380
tgacatcgca tccctcttat gtgaggagtc ccgtttccaa gggctcaaca gctcaccagt     1440
ttaatcaatc caacattccc aaaaataata gtggtaattc aaacaaagaa aggtcaccaa     1500
ttcatttacc ttgaatgtta ctttgaggct ttgagtagaa tttaagtact cgtacaacat     1560
aacgactagg ttgtaattgg tgagctttac tagcgtcaaa ttgctctcat ggcaatgacg     1620
aatgggttgg ttcttatccg tcaagaaaat tagtgacatg attaacttta aagctttgtg     1680
aacattctct ggactatgat ggttatcggt aaatctttta gccgatcgaa atggaccgga     1740
catcatcata caagggaca aagaggcta aagaaagaga tgagacctat ctgttttttg       1800
ggcctagggg cattacttc gaaaactgcg ccatcatgat gtgattaagt agaccaaaca      1860
ttaccaactc cggcggcccc aattccttcg taccatcttt ccttcgtacc atcttgtttt     1920
atataagatc aaaaacccgg acggcattcc atcgaaactc aacgattact ctctctctct     1980
ctcaaaagac ataaacataa g                                               2001

<210> SEQ ID NO 16
<211> LENGTH: 600
<212> TYPE: DNA
<213> ORGANISM: Eucalyptus grandis

<400> SEQUENCE: 16
cgacgcaggt cagacgactg agtactgaaa gcattggcct atccgtcctc attgaaccaa       60
acaatcaact gatgggtcgg gccgctccga gattaagact atttgtcaga gaattttttcc    120 caattggtgg tccattttcg tccttacct tattcaaatg gaagtctcga gatattcatg      180
taaaatcaac gaaaataat tttctaaaat gaaagaaac aagaggaaaa tttcgtgtga       240
catataagca gacgggcccc tgtcccctg tcgcactcaa aacacaagat gacaaactct      300
tctcgattag cacccattct ttagaggcgg ttttgtgtcc accgcgtctc ttatccggat     360
aaaatggctc gagtgcttaa tccgtctaag cccacaattt ttttttccca ttttctcatt    420
taatttacaa tttttttcct ttttttccta attcgagtgg aatttacatt ttagaattta    480
gaggtcgagt ggagctataa atagaggggc acggtttgca atgtaccctc aagcaactag    540
gagaaagtga taagccttgt gaggtgttga agacagcttt gccccaaggg gagatcagtg    600

<210> SEQ ID NO 17
<211> LENGTH: 1800
```

<212> TYPE: DNA
<213> ORGANISM: Eucalyptus grandis

<400> SEQUENCE: 17

```
atttgtcaga aagactaaat tggtaaatct tcataggggtt taagactaaa ttggtcaaat      60
tgaaaagttt aaaactgaat cagtacccgt ataataggct taattatttt ttgataatta     120
tcttgtcata tcaatcccct aatatcttga ggcaattaag gctttactca caagatcaaa     180
gacaactgag gctttctgaa taggaaaatt gttcaaaaaa ccataaattt attgtgcaat     240
ggtcaattta attctaaata tttcaatttt gtaatttagt tttaaacctt tgacaacat      300
gataattcaa tcataaactt tttgattgtg ccaatttaat tataaacttt taacggattg     360
tcaatttagt cattttggct aattttggct agatatcgtt gatatgatgg cctagtcaac     420
gctaactgtc ctatgtaaca tagtagacgt ttatgcatac attaattttt aaaaaataaa     480
tttaattttt ctattttttt tttatatttt cttttttccac tttttcaaag gctaatgga     540
gttactagcc attgaggaag ggcagtgaag cccttgctag tggtaggtga gggccacaac     600
ctcgccattc cttgttgtgg tggcgatagc ctaggcaagg gctcatggca cccttgccag     660
ccatagtgag ggcttacgag cccttgccat acctagccag ccatgacacc ctcgctagat     720
tcagcgaggg ccgtgacctt gtggtcgaga aggcttcgca atccttgcct agggcccaac     780
gagggtcgcc gattcttggc tagtgaccct ttgtaaaaag aggggaaaaa agaaaaaga     840
ttactaaaaa ctttgaataa ttttttaaac attaaaaatt gttcacgtca gtaacgtcca     900
atcaaaatta attggaatga ccaaatagac aatccgttaa aggatttagg acttatttgg     960
caaattatta aaattttagg ataaaattgg cataattaaa tgggttagga ttggattagt    1020
gaattattta aaaatttaag attaaattga taaattttaa aaggtttaga attaaattga    1080
ctgtcatata ataaattaat aatttttggg atatcttttc cctttcagat ccataaagcg    1140
tggtcacaaa ttttgaactt tttgcaatcg atgtcgatcc aactcggatc cgtttaaaac    1200
cgacgcaggt cagacgactg agtactgaaa gcattggcct atccgtcctc attgaaccaa    1260
acaatcaact gatgggtcgg gccgctccga gattaagact atttgtcaga gaattttttcc    1320
caattggtgg tccattttcg tcctttacct tattcaaatg gaagtctcga gatattcatg    1380
taaaatcaac gaaaataat tttctaaaat gaaagaaac aagaggaaaa tttcgtgtga    1440
catataagca gacgggcccc ctgtcccctg tcgcactcaa aacacaagat gacaaactct    1500
tctcgattag cacccattct ttagaggcgg ttttgtgtcc accgcgtctc ttatccggat    1560
aaaatggctc gagtgcttaa tccgtctaag cccacaattt ttttttccca ttttctcatt    1620
taatttacaa tttttttcct ttttccccta attcgagtgg aatttacatt ttagaattta    1680
gaggtcgagt ggagctataa atagaggggc acggtttgca atgtaccctc aagcaactag    1740
gagaaagtga taagccttgt gaggtgttga agacagcttt gccccaaggg gagatcagtg    1800
```

<210> SEQ ID NO 18
<211> LENGTH: 2000
<212> TYPE: DNA
<213> ORGANISM: Eucalyptus grandis

<400> SEQUENCE: 18

```
ggtcacctcc tcccgcttgg gaggagaccc ttcatttcct tgtaccacgc ccttgtgttt      60
caaatgggaa ggcgtcgcaa ggatccaagc ggggttaccc cttgtggcca ggcccctagt     120
aggggatcca ttttactga gggggatccc ctccctctat cttgtctttc caagatgtca     180
```

```
aaaccttttta aggtcttgct tatgaccaaa ttgtcaccac tcttatcccg gtctagagga      240
ctaacttaga tataacagaa ctgcaaacat gaattcaacg tagatattaa tcaagcaaga      300
ggctgttcct tacatttgaa taatataaga tacagctgta tttagatttg tgtgaaagaa      360
ttataattaa aatatatcga gcgccggcac cacctacaat gtggcatgtg atggtcattg      420
ccgttcgcat cattcggcaa ggatacttat aaaaaaccag tgtttccaat caggtgttta      480
cacgccagtt tttgtccttt atacgaaaga gcatcgggca acttgtgtga ctagtgatgt      540
accgtaataa cgatcgcgtc aacgaggaca gagatcagca aaaccaaggt gtgcgagaga      600
gagttaagca atttcactgt attcacattc aagttcgcaa atgaaggttt gactttatg       660 ggaatatgcc gtggagatgc tgaagctcac atggctcttc tcggtgtcag tagactttaa      720
atacaacccc cgtccaacat ttatctacga ctctctctct ctctctctct ctctcttctc      780
tcggggtgag cagagtttaa atacaacccc atccatcccc tcgttctctc catccctct       840 ttctctccgt cccaacccaa ggttggcgac attttcttac aactctccct ctccatcccc      900 tcttctctc cgtcccaacc caaggttggc gacattttca tacaactctc tctctctctc      960
catcccctat ttctctccgt cccaacccaa ggtcggcgac attttcatac aactctctct    1020
ctctctctct ctctctctct ctctgccctc cattgttgcc gcgagagact gaggttagtg    1080
ttcattgctc ttttattgtt gcactcgttt gtggtgtgtc ttttgcattt gcagacgacg    1140
agaaggggct taagaaattt ggttcgtcac gcttgacagt tgaaaaagc aatcttgtat     1200 ttagccatgt tttggttacg tagaatttta gcggactctc ttgtctaagg agaatgataa    1260
cccgcacact gtcatagata tagcaacggg attgaattac tttgttgtta agcattattc    1320
ttgtcctata ttcagtagag ctatgttggt acccgaaaca ggaggtgacg tgacaatttc    1380
aaatggcgtc tgaaattttg tagacaatta catcatctgt aaatgtctct attggtttct    1440
atggttgaag ttcataattt gttttttctag aattgatgtc gttttaagaa ttcttatcaa    1500
ctttgatctc tcttgaagat aaaacgaaga atgatatgac gcctttatga agtgagatac    1560
ttaaaggagt aatgagtcga ccggttgcca ttgaagttgc atcatcaaac aataattggc    1620
ataattagat taattgacca tctcgaaaga agtacaacag acagcctcac atcataaatt    1680
aaaagttttg ttctgtaccc gccaatcgaa atacgattta tacatccaat gatgtggtgt    1740
tagaatcttg acatgttctt gtgcttaaaa atctataaaa tctaatgtaa tatcataaac    1800 taaaaattt gaactagggc acgtaaaaac aattttcttt accccgtatt tttacttaag     1860
atcattgttg gttttattg tctctctttt ccctagatat atatatactt ccataatcac     1920
ttaaatataa tttgattatc tctttcatgg gcaggaaaat tgttgaacta gttggaaggc    1980
attgaactcc agcttcgatc                                                 2000
```

<210> SEQ ID NO 19
<211> LENGTH: 2000
<212> TYPE: DNA
<213> ORGANISM: Eucalyptus grandis

<400> SEQUENCE: 19

```
caccacaatg agcaaataaa aacaaaaaaa atgagagaaa taagacacca aatgaggtga       60
aaaaaatact tccaaattag atggagggag gaggagaaaa gaaaaccaaa gcccaaaaaa      120
gaaaagtaaa gcaaagcaag cttttttgaa gggattttt tgggagagag acggttacca      180
atagaaagat taggattttt tgttagttag agagttcctc gttagtttg agataaataa       240 acgaaaggaa tcccaacgtg aataacaaac attcccctt ttaggcagtg atagagcacg      300
```

```
tagacagata aaatgcactc taattttttcg ctactggctt tgaatgtgag ggataaaagt    360
gcttaccact tgggatttat ttgcacgaat ctaactctca aattccacaa gttgagggag    420
aaattgaagc ggcccaaccc gatggtagtc ttctctcttt cgtctccctt agaacggttg    480
ggctgcccat ggagataaag cacagacaca tcctcctctt ctaggcctaa ctttttgata    540
ctcaccggcg atttaacagc agccatggat ctctctctct cctccgacat gggagaaagc    600
acggccgagc cagctaacga aaattccgag gccgtatctc gctaaaggct cgggctggcc    660
ggaactagca ctcggcctga agtccttgt ccgatcatcc tcatgcttaa aaatctttag    720
gttttccatg tagaaccaaa tgggcctaga cggcccagta gataggttag gctcaaacag    780
gaatcgctag cccaactcac ccaactttgc ccgatcggac ttgggtaggc ccaaacaagc    840
gcgaggcatt tgccggctga tcatgtttat tcttcgctaa tgaaaaatat ttagctctca    900
agggaccgtc aattcaggat cgtgaagtta cgtgcgctag taaagttcat cgactagtag    960
tagatgcgga tgacaagtaa atctacacaa gcgagacata ggcaagtcgt ttcaacctcc   1020
tatcccattc ataattaatg aaatgagatc ttctaaaacg agtcatcgca gtctgttctt   1080
ctatctacta accatatgat gtttgcttta ataggcaagt cattccctca ctctgcatga   1140
ctttcataaa ttttttcaccg tctctgtgtt acatttcttt atcatagagc attaagacta   1200
gatactgaga taggcaaact agataccttc attatgcccc cgaagatgaa gccgagataa   1260
agaaattaac ttgacatgaa tcgggatggc aaacctctaa gaacagtggg ggcaaggttg   1320
ggcaactcgc ccggcccgct ctacttcatt ccattccatt ccattccatt accattccat   1380
taccattacc attaccattc ccattcccca tatcttcatg aaaggttggt ggacaatagt   1440
ggtgcttatc tcgatcgtac cttccgcta ttttattcat gcaaatagcc cttcggcgcg   1500
tccattctca tgtcacgagg aaaatgacat aaggacatga ttagggtcga tggtcctttg   1560
cttccgcgaa ttattccctc taaaaccgca tttaataatc tcccggaaga gcgacaggga   1620
ctcgcttgtc tcgttgcacg taaattacta gttaagctgg ttgtccttat gcccataatc   1680
gcccattatt acacatttaa gaattcatcg gcggttggtc ggcgcccaac caccgcgctc   1740
cactgcatcc ccggtcccaa tgggcggtgc cggctgtgcc ctcctcgtcc atctctagct   1800
aatatatact cgaattagcc tgataaaaga ttaaggagat ggattaaaat aagaaagcca   1860
ctattcgaaa ggatgccttt agggcgagta tatgcgcg tcttgttcgc cggacttgac   1920
gcacaagctc actgcgaagc atagctaagc gagttctctt tctaaaagtg gttgattcta   1980
gttctttcga tcgagcaaac                                                2000

<210> SEQ ID NO 20
<211> LENGTH: 942
<212> TYPE: DNA
<213> ORGANISM: Cauliflower Mosaic Virus

<400> SEQUENCE: 20
gatctccttt gccccggaga tcaccatgga cgactttctc tatctctacg atctaggaag     60
aaagttcgac ggagaaggtg acgataccat gttcaccacc gataatgaga agattagcct    120
cttcaatttc agaagaatg ctgacccaca gatggttaga gaggcctacg cggcaggtct    180
catcaagacg atctacccga gtaataatct ccaggagatc aaatacctcc caagaaggt    240
taaagatgca gtcaaaagat tcaggactaa ctgcatcaag aacacagaga agatatatt    300
tctcaagatc agaagtacta ttccagtatg gacgattcaa ggcttgcttc ataaaccaag    360
```

```
gcaagtaata gagattggag tctctaagaa agtagttcct actgaatcaa aggccatgga        420
gtcaaaaatt cagatcgagg atctaacaga actcgccgtg aagactggcg aacagttcat        480
acagagtctt ttacgactca atgacaagaa gaaaatcttc gtcaacatgg tggagcacga        540
cactctcgtc tactccaaga atatcaaaga tacagtctca gaagaccaaa gggctattga        600 gactttcaa caaagggtaa tatcgggaaa cctcctcgga ttccattgcc cagctatctg         660
tcacttcatc aaaaggacag tagaaaagga aggtggcacc tacaaatgcc atcattgcga        720
taaaggaaag gctatcgttc aagatgcccc tgccgacagt ggtcccaaag atggaccccc        780
acccacgagg agcatcgtgg aaaaagaaga cgttccaacc acgtcttcaa agcaagtgga        840
ttgatgtgat atctccactg acgtaaggga tgacgcacaa tcccactatc cttcgcaaga        900
cccttcctct atataaggaa gttcatttca tttggagagg ac                          942

<210> SEQ ID NO 21
<211> LENGTH: 435
<212> TYPE: DNA
<213> ORGANISM: Arabidopsis thaliana

<400> SEQUENCE: 21
atggattaca gagaatccac cggtgaaagt cagtcaaagt acaaaggaat ccgtcgtcgg         60
aaatggggca atgggtatc agagattaga gttccgggaa ctcgtgaccg tctctggtta        120
ggttcattct caacagcaga aggtgccgcc gtagcacacg acgttgcttt cttctgttta        180
caccaacctg attctttaga atctctcaat ttccctcatt tgcttaatcc ttcactcgtt        240
tccagaactt ctccgagatc tatccagcaa gctgcttcta acgccggcat ggccattgac        300
gccggaatcg tccacagtac cagcgtgaac tctggatgcg agatacgac gacgtattac        360 gagaatggag ctgatcaagt ggagccgttg aatatttcag tgtatgatta tctgggcggc        420
cacgatcacg tttga                                                        435

<210> SEQ ID NO 22
<211> LENGTH: 1086
<212> TYPE: DNA
<213> ORGANISM: Populus trichocarpa

<400> SEQUENCE: 22
atggctgtgg agcttatgat gggtattct ggcgatagtt ttgctacaaa aatgcaagag          60
aatgatgtga gagaagccgc aactgctggg atacaaagcg ttgaggaagt cataaaactg        120
ctcaaacaaa atcaactgga acagcaacaa aaacaacaat actaccagga ttgtctgca        180 gcctcctcaa gttccaatct tggcacggat aatatcatgg ctgttactga tatggccgtg        240
aacaatttca aaaggttat ttctttactg ggtcgtacca caagaactgg ccatgctcga        300
tttagaagag ctcctgttgc ctgccctcct caacaacgaa tgcaagaacc agaaccagaa        360
ccgcaacagc aaaaacagca agttcaagag ccagtaccat atgttcgagc aattaattcg        420
cagccaacag agcaaggctc tgcttttaga gtttatcaac cgaccccaat tcatcgtctc        480 cctccttgc ctcacaatca gcaacaaaag acactggtgg ttacgaaaaa tggattatca        540
gatcggaatg aaatggctac tacgatcaat ttctccaatt cgccaacaat atctgctcct        600
acttctttct tgtcttctgt aacaggggaa actgatagct tccagcgttc tacgctttct        660 ggtttcagt ttacccaacc ttctgctggt aaaccccctt tgtcctcttc ttctcttaag        720
agaaagtgta actccatgga tgatgctgct ctcaagtgtg gctcctcttc tagtcgctgc        780
cactgctcca agaaaaggaa atcaagaatt aaaagggtgg ttagagttcc tgcaattagt        840
```

```
agtaagatgg ctgatatccc acctgatgat tattcctgga gaaagtatgg tcaaaagccc      900
atcaaaggct ctcctcatcc caggggatac tacaagtgca gtagcgtgag aggatgtccg      960
gcacgcaaac acgtggagag agctctagat gactcgatga tgcttgttgt gacctatgaa     1020
ggggaacaca accactctca tccaatcgat gaagcacccg gtgctcttgt ccttgaatca     1080
tcttaa                                                                 1086

<210> SEQ ID NO 23
<211> LENGTH: 1707
<212> TYPE: DNA
<213> ORGANISM: Populus trichocarpa

<400> SEQUENCE: 23
atggaaagag ataagttgtt tgtgagcgag ggagcgaaca cagcagcaac catttggaat       60
tcttgcagtt ttggaatgga aatacaagcc aatgagctga gttgtggtcc agagaaactt      120
gtcaattgct ttctcaatcc caattgggac aactcattgg atcagagcga tcccttgag       180 tctgctttga gctccattgt atcctcacct gttgcatccg gtgccaatgc aaacgccaac      240
gccgttccta atgctggcgt tggtggtgac ggttttatga ttagagaact cattggaaga      300
ctaggaaaca tttgcaattc tggagacatt tcaccacaat cttttgttaa caataataac      360
aatagcacta cacttcttg ctatagtacc cctttgaatt ccctccaaa gctgaatctt       420 tcgatgatgg attcacaaat gagaggaaat ctgccaattc ctgggaacag cgtagtaaag      480
catccaggtt tagcaccatt tccagctgat tttgtagaga gggctgcacg attttcttgc      540
tttgggagca acaatcttgg aggcctcaat aaacaattcg gattgaatga atccgaattg      600
attaataggt tgatgccacg agtagaacct ggtaagctct cgagagtttc gagtaacaat      660
tcaatgaagg tcactgtatc gcaagcaaat gttcaagaaa gcaacaagag ctcaccccag      720
gatgggagtt tgaattctga taaaaaattc agtaggcagt caaggccttc aacatcagag      780
aatggagatt ccagggagga atcttcagtg tctgagcaag tcccaggtgg gaaattgagc      840
atgaaatccc agaatgacgc caattccagg aaaagaaaat caattcccag aggaaaagcc      900
aaagaaactc cctcttcatc tccatctgct tctgatgtca aggttgcagc agagaatgat      960
gactcgaagg caaaagaag caaatcggat gaaactaatg gcagtgacaa ggatacagca     1020
aaggaaaagg aagaagaaaa tggaaatcag aaacagaaca aaaataattc aaagccgcca     1080
gagccaccaa aggattatat ccatgtcaga gccagaaggg gtcaggctac agatagccac     1140
agtcttgctg aaagagttag aagagagaaa atcagtgaaa gatgaagtt cctccaggat     1200 cttgttcccg gatgcaataa ggttactggt aaagcagtga tgcttgacga gattataaac     1260
tatgtacagt cattgcagcg ccaggttgag tttctgtcca tgaagctgtc atctgtgaat     1320
ccgagaatgg agttcaacat ggaaactctg ttgtccaagg atattttcca atcccgtgga     1380
tccatgcctc atagtcttta tccatcagat gcctccacgc cggcattccc ttatggatac     1440
caatcccagc aagggctggc cctgcaaaat ggcatgccaa gcaatgcaga aacccagttc     1500
tccatgaacc cattaaacgc tgcgttgcgg cgaaacccga gcatgcatct gccaccccct     1560
gatggttttg gtgatcctgc tgttcttcag gcctcagcca tgtgggaaga cgaccttcaa     1620
agtgttgtgc agatgggata tggtcagaat catcaggaga gctttcaagg ctcagtgccc     1680
tcaactcaca tgaaaattga gctgtaa                                         1707

<210> SEQ ID NO 24
```

<211> LENGTH: 1044
<212> TYPE: DNA
<213> ORGANISM: Populus trichocarpa

<400> SEQUENCE: 24

| | | | | | |
|---|---|---|---|---|---|
| atggagggggg | ttgaagaagc | taaccgggca | gctgtggaga | gctgccatag | agttataact | 60 |
| ttgctatccc | aaccccaaga | tcaggttcaa | tataggaatt | taatggtgga | aactggagag | 120 |
| gctgtgttta | ggttcaagaa | agtagtttcc | cttttaaata | ctggtttagg | tcatgcaaga | 180 |
| gttcgaaaac | ttaagaagtt | accgacccct | ttatcccaaa | gcatccttt | agacaaccca | 240 |
| ctgagcagta | caggccaccc | atccaaaaca | tcccagtttc | tccagtccag | tagttacctg | 300 |
| gaaagccaat | caattcaaga | attgggctca | attgctaaaa | attgtctatc | tctgggaacc | 360 |
| ccatccctgg | aattgagttc | aaatgggaaa | accctcttc | agcttggaca | acccacgcca | 420 |
| gcagcgccct | atcagttcct | tcagcaacag | caactgcata | ggctacagct | tcaacagcag | 480 |
| cagcaaatga | agcagcaagc | tgagataatg | tttagaaaaa | acaatagtgg | gatgagcttg | 540 |
| aatttcgata | gttctagctg | cactcctaca | atgtcatcca | ccagatcttt | tatatcgtcc | 600 |
| ttgagtattg | acggtaatgt | ggctaatttg | gaaggaactg | cattccattt | aacggggcg | 660 |
| gctcgctcct | cagatcagag | ttcacagcaa | cacaagagga | aatgttccgg | aaggggagaa | 720 |
| gatgggagta | tgaaatgtgg | aagcagcgtt | agatgtcatt | gctcaaagaa | gaggaaacat | 780 |
| agggtgaaga | ggtcgatcaa | ggttcctgct | attagcaaca | agcttgctga | tatccctcct | 840 |
| gatgattact | catggagaaa | gtatgggcaa | aagccaatca | agggttctcc | tcatcctagg | 900 |
| ggatattaca | aatgtagcag | tatgagaggt | tgtcctgcaa | ggaagcatgt | ggagaggtgc | 960 |
| ttggaagatc | cgtccatgct | tattgttacc | tatgagggtg | aacataacca | cccaaggatt | 1020 |
| ccagcacaat | ccacaaacac | gtaa | | | | 1044 |

<210> SEQ ID NO 25
<211> LENGTH: 906
<212> TYPE: DNA
<213> ORGANISM: Populus trichocarpa

<400> SEQUENCE: 25

| | | | | | |
|---|---|---|---|---|---|
| atggctgtgg | atctagttag | gtattcaaag | atggaagatc | agatggctat | acaagaagct | 60 |
| gcatcagctg | ggctcgagag | catggagcac | ttgatctttg | cactctctaa | ccaaactcga | 120 |
| caaagccacc | aacttgactg | cggagaaatc | acaaacttca | ccgttgccaa | gttcaagcaa | 180 |
| gtcatctcca | tgttgaaccg | gaccggtcat | gcccgttttc | gccgtggacc | aacttcttct | 240 |
| ccttcttcct | acccggttcc | cgtccgacct | gtccctcaag | aacctcaaaa | actgaacctt | 300 |
| gattttgtta | acagtaagag | ccccctaaa | gctgagtcga | aaaatgacct | gtctttgggt | 360 |
| agtcagtatt | caaaggatag | ccttagctct | ggcaccacta | cctcatcctt | cgtgtcttct | 420 |
| gttacagctg | atgggagtgt | ctctaatggg | aaacaaggtg | gctcttctct | tttcggaact | 480 |
| caagctcgat | ctaccggaaa | gccacctctc | tcatcgaccc | accgcaagaa | atgccacgat | 540 |
| catgcccttt | ccgccagaaa | gatctcctcc | ggtggcagct | gtcattgctc | caaaagaagg | 600 |
| aaatcaaggg | ttaagaggac | aataagggta | ccagccgtga | gttccaagct | tgccgatata | 660 |
| ccagcagatg | agtactcatg | gagaaaatat | ggtcaaaagc | caatcaaggg | ctcaccatac | 720 |
| ccaagagggt | attacaagtg | tagtagtgtg | agggatgtc | ccgcaaagaa | gcatgtggag | 780 |
| cgtgccgtag | atgactcggc | catgcttatt | gtgacttacg | aggggagca | ccgtcactca | 840 |
| catactccgt | tgccggaaga | cgtcacggct | agtgctgcaa | tgcgacacgt | gtttcactca | 900 | acatga 906

<210> SEQ ID NO 26
<211> LENGTH: 1802
<212> TYPE: DNA
<213> ORGANISM: Populus trichocarpa

<400> SEQUENCE: 26

```
gcgagcctgt caaacaaac cattgacacc aatcttggat agaataaatg tgggaagagg     60
aaattgaaaa aaagagagaa gaaattggca ccgtggactg ctaataggtc tgcatctgaa    120
acaatggatt gcctacccca attagttttt gttcatcatg tactgtgttc tcaaatcaag    180
atcatacttg ggaaagtaca attgacggtt tggaattaac ggtgcagtgt tgatctcatg    240
ttcttaaaat tcactcagtc atttcaaaca tctaacatga tcacacctat gaactgtcaa    300
caacgaaaag ttgataaaag taattttgcc tttcaattct cttttgaaaa tttgccaggg    360
aatgctattt tgagccgttg gcgtttgaga aggttgaaat tgcctatctt caaaagatgc    420
tggacccgtt ttctatttaa aaaaacggtt cgaatttaga gagaaacggc tcttttggag    480
tcacattaat gtattttag aagttgggta aaagttaatt tttaaaaata tttttttattt    540
aaaaatatat taatttttta aaaaacataa ttaaatcaca gtcataaacg cgtccgtagt    600
gagtataatc tgcagggcgg cattttttat aataaaggta atttaaatca ggtcttcttt    660
ccggtgactt aacactgatt ttactccgac tccaacttaa ttccgtagat aattatgtaa    720
aataaataaa tgacgcttaa agttaagctt tgtcccctaa actccttaat ttaatttaat    780
ttctccttct tcttattaac tcgactgagt tatcgatact acgtgcaata tattatctcc    840
actaatggat attatttatg tagaaccaaa aaataaaaaa ataaacaatt acttttgata    900
ttaattaaat tccaatatca ggaattgagt aaatagatat tatttacttt tgagattatg    960
atttttttt aaatcatcga tgaggtattt aatcaggaaa gatttaaagc gaaatccgaa   1020
gcaaacatct ttcaactccc tgaaacgatt ttgttgctgt atttattgtt attattataa   1080
ctattcatga attaaaaaaa aaaaaagtct cttgtgagtc ccaaacaaaa tatatgtgcc   1140
cattaagtta aagaaattaa actaaaggac aaaacacacc tttgaatttg agtaaataga   1200
tattattttt taaatatttt tttatttaaa aatacaataa aataaatttt ttatatttta   1260
aaatttattt ttgatattac taacaaaata ataaaaaaat taatttaaaa ctaaaaatat   1320
ttacaataac attattgaaa cacaatgtgc atggtgtaga atatgtagat gtagtttaat   1380
attacgacag tatttgtttt ttaaagtgtt tttatttta aaatatatta aaataatata   1440
tattttatta ttttaaaatt tatttttttaa aaaaataaa aaaatttaa ataaaaaat    1500
aaaaaattt aaattttttg aaagcaaaat taaatctcgt aggcactaga aaacgtcgta   1560
aaatatattt ttaactggaa tctagcacag cagcagcaac ctccctagtt ctcaaagtgt   1620
ctttccattt gaaaaaccat taaataaatc gtttctcctc ctcctcctcc tcctacccat   1680
cccaacacac acacaaaaag aagaaaaaat tcaaacttca aactcaagct cagatcccat   1740
cctctctcaa acgccacctt ttcctccaga tccagcctcg atctaccaaa tcaccgtcac   1800
cg                                                                 1802
```

<210> SEQ ID NO 27
<211> LENGTH: 2000
<212> TYPE: DNA
<213> ORGANISM: Populus trichocarpa

<400> SEQUENCE: 27

```
gtgttttccc atatgatttt ttatgatttt tttcaaaatt atctttgtcg atttttgttt     60
aatattgagt tggttaagaa ttataattat aatgaagcta atcatatgg gaaaagcgtt    120
gcagattttc tcacaaaaca ctatgaattg ctacagtatt tctctaaatg gttttttatt    180
ttattttatc ggggaaagca ttgtagtttt cctcacaaaa cattatcaat tgctacagtg    240
ttttttttca taggtatttt cattccaaaa ttatctttgt tgatttttt ttaatattaa    300
gttggtaaag aatttagctt tataattctt tttgctttt attaacagaa aatctaaatc    360
atgtggtgaa aacactgtgt ctttcctccc aaaacactgt gaattgctac agatcatttt    420
gttaagtctc taagtttttt atcaccaata taactttatt tccatcataa aatattaatt    480
ctatcatact tttaatttt attattttatc taatactgat acataattat aacattatta    540
atacttgtgt ttataaattc atggcaacat gcgcgcatgc catctcatga taataaaata    600
caggagttct taaggtacat tggttttgcc acttgcatga cgttgggttt ctgctcagaa    660
cgctggctga cctgttgcca agaatctttg tgagcatgcc atggcccaaa ttgaatataa    720
cccgagttat atatatatat atatatat atgggtttga ccaataaaca atttcttcgc    780
aaatgtttaa aagaattata attatctcct tttaggatct ctgttatgct agtttgaaaa    840
tgtaattgtg attatttttt aaaaaaattt tatttaaaaa tatattaaaa taatattttt    900
ttttattttt ttaaaattat ttttgacatc agcacatcaa aatgatttga aaacattaaa    960
aaaatattaa tttgaaataa aaaaataaaa aaatttattt ttttttttaaa atgcttttac   1020
aatacaaaaa caaatcaaat ctaaacacta atactttcat taaattggta taagtcacgg   1080
caactttcac tcaatagatc tttcatgttt ttatatataa aaaaatttag acactaatac   1140
taacttgatt ttataattaa gttatttctt atattaattt caacttaaaa ctgttttaat   1200
tcgtcgtcaa tgacttctgt taaaatcatc caacaagaat tattattatt attattatta   1260
tttaaaataa tgttgtttct gttttaaaaa gtataatttt ggtaaaaaaa atataaaagt   1320
tttaaaaaat tcacataaaa gttcttaatt atactctttt aatttaaaag tgaaattaaa   1380
aaaaaatcat ttgacaataa aatcgaaagg tgggtatttt tgagatctac ttttcaagtt   1440
tctagcaacg gaaaaccgtg aaacttgtgt ggcagcaaat tcaggcttga cctcgcaggc   1500
tgctgatgtc agcagagagc tcatgcaatt agtccacgac aagagccttc cgttgctggg   1560
cccaacaact ttgagcccat cggacatact ccgaatattc ccacttccag aacattaaga   1620
ctcccacggt cattaaggaa agtgcgctat accttcctct tacgcctctc cctcatagat   1680
aaacaaccag tcaaccaccc aagactgaat ccaaatgcca caaaatcgcg tgaatttcct   1740
ttttaaaatc agcggctaat acaacggctt tcaaaattc caatcagcgg cttaaaacca   1800
agctaattgt ttctttcgtt ttgcccaaga aaaaaaaaac cgctcacgtg acctaacccc   1860
accacgcacc tactcttctt tatatgaccc tcaattagca gccactctcc tcactaaaat   1920
tatctctgtt taagcttatc cctcaaatct cccctcttaa ttctaaatct ctcctctgtg   1980
tcccgttact atcaacaaca                                                2000
```

<210> SEQ ID NO 28
<211> LENGTH: 2000
<212> TYPE: DNA
<213> ORGANISM: Populus trichocarpa

<400> SEQUENCE: 28

```
agttcgcgtc tcattacaag cgtggggtga agatgatcaa ttacatgtaa ctttggttct     60
```

```
tgagagcaag attcttgctg gatcaagttg taaacttttc ttcaaacttc aaattagtaa      120
tctaagagac aattccacat caaatagtaa ttaacaggac atggatcaaa tgttaaggaa      180
aaaataatta aaagggttat cctaaacttt taaagggggtt gatgcaaatt ttaaaggaaa     240
aaaatggtcg ttggtgccaa actagaggtg catttagtgc acccttcgcg gggggctcca      300
aaatctttca aacactatca tagaaggcga tgtttggtga ttaaatgtcc ccacacttgt      360
cgtccacttg ttagggcatg caaaaaaatt ttaaaattat tttttaaaat acaaaaatac      420
ccctgagtta tcttgatatt aaaaaactat gatgaaaaga caaaaaaaaa acttgaaaaa      480
tagttttgtt aatttcaaac ccaagtataa ttaagtaatt taacttcaat agaaaattaa      540
aaaagacata aaatcctctg ggtttaagcc ctttttttt tgttccggga tatttaaata       600
acttaactgt tttttttttt taaaagacta atctaccata aaataatttg aaaatgacgt      660
tgaagaggat atgtatttt ttgtttcgac agtaagaata ttataccgag ctagcttgtg       720
cgtcaacaga aattcaaatt tttttagaat gattttaaaa atatattctt cacattgaca      780
tgataaatta aaaataataa taattactaa tactaagatt tagatttaaa aaaaataaaa      840
gaactttctt aattaccgaa caatttcata ggaggtaatg gtttacagtt tacaatacgg      900
cgatgatttg gtttcaagga cagtcaaaat cggaaattgc cccctgacga ccccagggga     960
agaaaacaat aattacatga aaagatgagt ggtcaccacc actaccacca ccttgtaaaa    1020
atgtatgacg acccaaaaca aaaacgccaa ctacaccatt aacaccacaa acccatttt     1080 aggcaactaa tccttgcacc aggaagaggg agatgtattt tcatgcctct tctaaataca    1140
atcatggtaa ttacattaca ttaccttacc catcccccctc tctctgtgca ttaccgtaag   1200
gttataaaga cagctcaatg caaaaacaaa gagagagagg gggagaaaac gacttgttat    1260
tattcactag aatggcattg gttacaatca gaaaatcata caccacaccc aataacccaa    1320 ttgagtttata gaagagagag agaaagggac tctgagagag ttgcaggttt tatagcagag   1380
gtctctgaca gtaagagagt atatattta actttatcta tcaaataatt ctctcttact     1440
ctctctctct atataggagc tagctgcttg ttctctttat gtttctctct ttcacacttg    1500 tatcttttg gtactgatga atactcaatg agtctactgt ttttcttaga gagatagaga    1560
gacttgtgtg ttgccagaac gatgtgatgg aacgatataa agccaagcca agccagactg    1620
agagctagtc atgttataac tacattacat aagcccaaa agcaaaaact tattcaaaaa     1680
gaaaatcata accccatttg cataaaccct tctctttctc tgaaaaccctt gtattttcat   1740 ttcattgtcg gcgacttctt ctcaatgaga gcttaaaagg gttcttctt tctccaagtt     1800 ttaagtgacg ggaatggtta ttttggctgc ctagagtggt taagtttgga ggagggggt     1860 ttttgaacga tggttgttct caagtgagca aattttggat tctcttttt ggaagagcag     1920 tgaagtgatg gcatttcgtt tggaacttgt cctttttgct cttcttctct ctttggttgt    1980
tgattctgtg cattctgatg                                                2000
```

```
<210> SEQ ID NO 29
<211> LENGTH: 2500
<212> TYPE: DNA
<213> ORGANISM: Populus trichocarpa

<400> SEQUENCE: 29
aacatcttgg atttgtttac tcatcaattg gcccccttatg tgggaactga taaaaaaact     60
atcaatttct aaaacttatt tttgacactt tcatgtcatt gcatgacaca caaccaaaac    120
```

```
actcatgggt taagatgcaa gataaatcta cttgttatca cgaacatttc tacccagcta      180
gactttcaac aactcacaag ttagatgcaa cttctcaccc aaaccgtatt ggtaacccaa      240
ggtcaaaata agaccttacc accccaaca agtcttggta actatgacaa cacacttgat       300
cccatcacca tttccactgg ccgctcccaa cgcccatagc ccattgcact acccataaga     360
gcctgggtag aatgacctcc aagtgagtat tctgcctcca tactcgtcaa gtccctccag     420
gggtcgctcg cgctattgtg atacccgtgc acatagccag gactccatat tgctccccta    480
actaccgtag gatggacctt ggttaccaat ctcgttgttt catgccaaac tttttaggcc     540
atactcgtca agaccatgaa tgatgaaatt gatgctattg aaaaaaaaca acacttgaaa    600
atcaatgaag cttctaaaaa gacaaaaaac cattgatgta aaatggattt ttaaaacaaa    660
attgaagggg aatgataggt tgacaagtat aaaacatgct tggtaactaa aggtaacaag   720
caagagtacg atgtcgatta ctaagaagtt tttgttttag ttgccgggta tgatacaata    780 atatttttc tttggtaact caaaatccat ggtttatgtt gaatgtaaaa ccaatatttt       840
tacatgaaga ccttggttat aagagagttc ttcatcatta aactgattgt tcaagaacat     900
cgatataaag gagaaatagt tagatattag ttgaaatcct attccaagta gaaattcttg   960
atagaaaagg atttgtgtct aaaatcctta ttgaattagt taattataaa tcttattgga    1020
ttatgattgt tagaggttgc atcctataaa tataaaactt ttaccagatt ttctgtcctt     1080
ctgtagtggt tgaaaatgt tgcagggcca tgacgcacgc tattttttgaa agaaaaatat  1140 acaggagaaa tagacatgtt gaaaacaaag aaaattcgag gcacacgcac ttggtttta     1200 tagttttgta ctgggcacat gggttaaaat ctttcaggcc taaccatact tggtttattt    1260
tatttattta tttatttggc tctaatttgt ttttacattt tacaataaaa tcaactgtaa    1320
ataaatttat tcagacattc tcttttctag aaaaaataac gtgtcttaat actcgaatat    1380
cccttcttaa aactcacatg tacatccaat ttattttat tatatgagaa aaaaatagta    1440
ttatgttcca agcttacact tgaaaaaaaa caacgaaaag gataccgttt gattacgaac   1500
gcagcatcgg aaaataaaat aagaatttcg actttatcct cccggagggg cctttgatca   1560
tcattcccgg aatcttttaa atatatcaca gacccacttc cccacctttt gccgtggaag  1620
caggtgctca ctccacaccg aatgacccaa agtcgttaaa aaagcaaatg gagtctctgt   1680
tctttttcgc atttatattc aaatccgaaa agaaaaaggt ttaattttac accacgcgct   1740
ctatatagcg tggcacgtga caatcgcgtt ttgtttttt tacatcatct taagtgattt    1800
tcttttcctt ttcaatgaaa atatttaccc tttcttcatt tgtaatttca agagattata  1860
tattgcctgc actttaacat gacgtcaatg aaaccgttaa tccctttcaa aataaattcc   1920
gacatctgtt tttttatcca aagcattctg tatgtatctt ttaaattttt gaaaaaaatg   1980
gttttttata ccaacagctc ccttttttttt aatattttat ttattctggt cggaactaat  2040
ttctctgatt gaacttccct tttaactttt tttttgtaat tataaattaa ctttattaag  2100
ctaaaaaaca aatattttag aggtaattat gagtacgata gcgttgttat ttttaaagta    2160
tttttactta taaattcatt taaataatac ttttatttt ttaaaattta tttttgatat    2220
taacatatca aaaataattt ataaataaaa aattaattt taaataaaaa aattaaaatt    2280
ttatcgaaac tcacaccagc accgaacggg ccgaagttgc tcacttcacc taatgttttta  2340 tagataaaca aaaagtcacg ctagcaattc acagggaaca gtcaccacca atatcatgct   2400
gccagatgaa taaagcagaa agtcaaaaat ggtcacatcg atgacccgca taagaagctt   2460
tcaatccaaa tgaacggtgg gtgatggggc tgtgagagca                          2500
```

<210> SEQ ID NO 30
<211> LENGTH: 2700
<212> TYPE: DNA
<213> ORGANISM: Populus trichocarpa

<400> SEQUENCE: 30

| | | | | | |
|---|---|---|---|---|---|
| aacatgcctg | taataataat | aatttaaaaa | aattgatatt | acggaagttt | tgctattgtg | 60 |
| cgctgaaacg | gtggtcttaa | tacaagctac | aagcggactc | ctcgttgact | taggttttga | 120 |
| tttatagtat | taagtcaagc | aatagattaa | ttaggattat | tattattatt | agcatgggct | 180 |
| tatgtttaga | gtaattgtgt | taagagcaac | agggaccacg | tacgtgcctg | atagtgtcac | 240 |
| gcttcccaat | aacatgaaac | cgccgtagcc | ctcaatcact | ctgactgcag | gtggcatatg | 300 |
| caacctttat | aaaaatcgag | agaaaagttg | acttgttaaa | gtcagagata | tccatggctg | 360 |
| tgattttgcc | cttcaatacc | cttaaataac | aggcttgttg | tatctgctat | gttttttttt | 420 |
| tttttttaaa | aaaatggatt | cacgtcatgt | gtgtttaaac | aggagagcgc | atgattacag | 480 |
| gaggaggagt | gataatcaac | ccacaaaact | agaaagcagc | aaaacgacgg | aatgtggcgc | 540 |
| atttgaagcg | ctgaaatcga | gcgtacaccg | ttgcctcttt | tttttttttt | ttgtctatat | 600 |
| ctcttcctct | gtaaacccca | ttaatttaat | gcgcctctca | cttcccactc | tgtagacact | 660 |
| gctacctact | ctctctactc | tcttagctct | gtctttctct | gcaaacactg | tgctgtcagt | 720 |
| tgctgttgtg | gagatatata | atggtggtgg | ctgtgatgga | ggaggtgcac | cggagtagct | 780 |
| gaccctagga | cattccttat | tatataaaaa | aaaaaggaaa | atcttgtttt | tgcccttttgt | 840 |
| cattcgcgtg | cccccttttt | aagcctagtg | tcagtcgtca | gatctctctc | tttctacatg | 900 |
| tttaagtttg | ttagtgtttt | tctcgaaaaa | ttaattttct | ttgcagtctc | aagtctaatc | 960 |
| tctcatttct | gtctttgctc | tctcgtattc | tgttccgttc | ctgctcgttc | ctctctctct | 1020 |
| agctaggcag | gcatctttct | ccctctcctc | cagggtttgt | tttagcccct | ttcaattccc | 1080 |
| attttatata | aattaacagt | attacattcg | agatgcgtcg | aaaagaagt | tcggtttcaa | 1140 |
| ccacttgaag | aagaatgtac | gtgaccatgt | tcctctttaa | tatagttttt | cttttcctgc | 1200 |
| tatcccttgc | ttcttccttc | caaataagag | gtttggttgc | tggattgttt | tttctgtat | 1260 |
| gtatatatat | atatatctct | ggatctaatg | actgcagctt | ttgctttctc | gtttattatt | 1320 |
| agagtagtaa | aaaaaccgaa | gtaacggtaa | agattttcac | acaaaaattg | ttttgtcagc | 1380 |
| ccggtaataa | agtatagttg | cttgttgtgt | tttttttttt | ttttttgag | attgtgttgt | 1440 |
| ttcgatgaag | agtgctattg | ttaatatttt | ataacattgt | tgcagtagct | taaacgatta | 1500 |
| tcttttttc | agatgcctct | gatttgtggc | taatatataa | gttgttttct | tagattttc | 1560 |
| agaaatattg | atatttgaaa | cacaaccatt | agatttggag | gacgttgata | gaaatttggt | 1620 |
| ttttttttt | cttaagctgc | aggtctatgt | atagttttgt | attttccgtt | gtggcttgaa | 1680 |
| aaaataaata | aataaaagtt | atgatatcaa | gaacaatgga | tcatacggtt | aacaagtttc | 1740 |
| gcttttttgca | ccttatttgt | tggtaattga | ttatgggatg | ctcacgacca | ttattagtat | 1800 |
| tttgtgcagc | aaacaaatcc | acaaagatgc | atttgtcata | atatgccctt | tttttatgc | 1860 |
| tgaagtttat | gattgcttga | ggaattctgg | tagatataag | tgaagtttca | ctgaattctt | 1920 |
| ttgggtttac | aaatcattgc | tatacacgtt | tttgggagtt | acatatgata | tggtagggga | 1980 |
| aacaaggatt | tgatgagatt | gtgtatttgg | atgaatttct | caagtattag | accacaccac | 2040 |
| atgctgtttc | gttgctgatg | cctatggccc | aataccaatg | gtgaattatt | ggtgctgagc | 2100 |

| | |
|---|---|
| atttctaaaa gtggagctac ttggtgaatt attgcttgac atcatttgct gtttgggctg | 2160 |
| gaattctatc atcataaccc agtaaattgc tcaatctgtt atcggttgta attgcttact | 2220 |
| tgtgcctgac ttatgacatg ataagaaatt catcttgctt attccgtgat tgtttgttgc | 2280 |
| caatgataga agcaatgtgt tgttgtgtg ttttaggatt attttatttt ttattaattc | 2340 |
| tatgtctttt tatggatact gctactaaac ttgttcaggt gtgtatatat atcatacaca | 2400 |
| tgaaggcgag cttttcatta ctccgtttgt acattcttga tgcaggttat ggcccttgtt | 2460 |
| cgcgggtcca aggttgataa ttttgttggg atccttatgt taatttctgc agtgcggacc | 2520 |
| tacttattta gatgttatat attcatcttg ggctaaaccc tgcttttctt ttgatgtgga | 2580 |
| atagtagagt aattatttac atgttttgcc aaggtgaagg agattgatgc catgttctgc | 2640 |
| tatgtttcag atacattatg aagagttcaa ggcaatggaa agtggtgtct acacctagaa | 2700 |

<210> SEQ ID NO 31
<211> LENGTH: 2500
<212> TYPE: DNA
<213> ORGANISM: Populus trichocarpa

<400> SEQUENCE: 31

| | |
|---|---|
| ctctataatt gtagaaatct tagattattg aacctgaata ccatcaacaa acacaataaa | 60 |
| ccaagaaaaa ttacaatact agtaaagaac ttaaactttt tgcgtttgac atataattgt | 120 |
| tctttcctta aagtgccaaa aatagccctt aaatcctcag aatataacta aaatcagga | 180 |
| tgtcgttaaa ataaaccaca acaaattgc ctataaatgg tctcaatttc taactcataa | 240 |
| acctcatgaa agtgctgaga gtattgcaca tatcatatag cataaccatc cattcatata | 300 |
| aaccatattg tgttttaaag gctatctttt actcatcctc gacttgattt tgatataatg | 360 |
| gtggtcattc ttgagatcaa tcttggaaaa cacctttgaa cctgccagtt agtcaaacat | 420 |
| gtcatctagt tatgatattg agtactagta ttttattgtg acctgttaat ggctcaaccc | 480 |
| catactcata tacgtcatga accattattt ttagggaata agagagctaa aactttacat | 540 |
| gagctcatac tttcttaaat atactccttt tttagcaact tcaccatttg tttcaacaaa | 600 |
| ttttcttctt ttttaaggct agtctataag ttagtatatt caatagacta aaacttagta | 660 |
| ctagatcaat atggtgttgt atctttctca tgaaaggtaa tttctagggc aactcttttg | 720 |
| acatcaaatc tagaaatttt gttagcatac catgcatttta attgtaaatg tcattaacat | 780 |
| tgtcctcttt cccaactgca tttcaacttg tagtatcaac ttctctcaac ctcgttcaac | 840 |
| caatttatga attcctctat ttgtaaaatt cctactaact caaggatttt gatatgaaat | 900 |
| ccaaaatcct tcaatatgtt ctctttttga tcaagaggtt gtctcctctg attctgcctt | 960 |
| tggtctttag tgttggctag ggacccatgg ttgttcttct agtcttggtc tcccaggtcc | 1020 |
| ctcttctcta acctgccgtt caactctgca atctgcctcc gtatgtcctc aatgatgacc | 1080 |
| ttctaaatgt ttgtctctaa tgaggtaacc tcctaatccc ctccttgatc atgccacact | 1140 |
| tcgtaacctc atcctttcat ggttattaat agcaaacaac aaataaataa gtatccacaa | 1200 |
| gattgtaaca caacaaacaa tgaacctgag atcattaggc tctgatacca attaatacta | 1260 |
| gcaaaatcac aatagacaac aacaagcata aaaaaaatag aattttttgat gagtgaaaag | 1320 |
| gctgcagata taagccttaa attcataatt tattattcta aaataaagtc taataatatc | 1380 |
| tacctcctaa gaggttatat aagatattta aatatgtcag aaaacccttat ctctattagg | 1440 |
| atacaaatca aaatttgaaa aagaaaaatt aacataaaat ccaaaataaa ataataaatc | 1500 |
| caaaaaaatc aagaaaaaat tacaaaattg gcccaaataa catcttctag atctaatttt | 1560 |

```
gggagatcca ttagtttgat gaacgacaaa tcattttttt atatgaacat ggccgttaga    1620
attatctaat caaatttaaa atcgattcaa cgatcagatc ttctgttatg atttgtttta    1680
gttattattt tggtctgaca taaccaagct ttttttttga cctagacttt tctcaattat    1740
ccataaaaac atttattaga tcatccatat agtttgtttg ggacaaaacc tcattcaaat    1800
gctcaaaatt tcagctttta caatctcgac tacattgtct cattacatat atgtttagat    1860
gaagttttat tatatatata tttttttttt gcatgtacat cattttcaat ttaagaaact    1920
cctttgtcat tgtgattaca atttaatttt atatacaaat tatgatgatt tatttctttt    1980
aatttcaaag ttttttgttt tatatttaaa tttttaaata tagtcgaatc gccgatgaca    2040
atacataata agtgtacttt ctcctctcat cttgcaaaaa ctagccacat cggatatagg    2100
ccacccaatc tgataatggg gttgggtaag ggttaggttt tccattgatt ttaatattta    2160 ttgaccttt aattatataa acatttgtta aaaaaaatga agaaatttag ttgtactaat    2220
aataacgaaa atacaaaaat aatattggta gcgaagtaat agaggaaagg taataagaaa    2280
ttaataacga aaaaaaaaaa aaggacaggc gtgaagggt tctcagataa aatccttccc    2340
ttccctactg tatttgtctc tctctattac tccatctctc ggtagggcct aaaaagagag    2400
aaagatatgc aatatataca aagagaagct tgagagattt taccttcctt ttcattttca    2460
tggttttcta taatgagaag aggattgaat ctcttcttct                          2500

<210> SEQ ID NO 32
<211> LENGTH: 2101
<212> TYPE: DNA
<213> ORGANISM: Populus trichocarpa

<400> SEQUENCE: 32
gcggtcggga gagagggaga aagggtcatg tcagccaggc agccaaatct ttatacttga      60
attcttgttt accggaaata ttgtatgtaa tgaattttat ccacaaggaa attttttta     120 tgggaattat agccttttag atgcatgaaa gttaccctag agtcatgccc taagaatttt    180
ttgttacatc gatcacatgc actgagaatg ttttccactg ctatcatgtg ggaaatgact    240
ttcagtccct cactctatgg tctatgccta tgaatgtctc ttgtctaact gcttccagaa    300
aagaggtggt ttttgagga aaaaatacgt cctccgagct gcatattcca ccttaatatc    360
ctcacaaaat cagtgcaaat tcacaataga tcatgactca tcaccacacg actaggtcaa    420
gataagaagt tgtggggatg ttttccaaa ccaatacaaa tgtgtttgaa agttttgaag    480
aaatagcatc gaggataaaa ggattttgaa aaatagcaca ataaacaaaa aaactacaat    540
aaaaatgagg tatttaaaca aaacgtagtt gagaattgtg atatttaaat gaagatacct    600
ttatactaaa tgctatttaa aaaagaaaaa aaaccagta gttctgtga tttaaaaaaa     660 aatcgcatgc aagaatcaca gattttctag ctgtgcttct tttcaaaaaa acgttttat     720 acgtactagc tagtcaaatt tttaaaaaag ctctgctaat ttcttataat aaaattgaag    780
gtttcaccac acaattattg aaaacaaatt tagtgcataa acgacatatt tgaagtcaat    840
tttttagcaa ttactaccag aatcttgtcc attagaggaa aaacatgctc agctcagtcg    900
aggtttcctt tcaacagtac tcaataaact ctggtctgtc cacactgccc cctaagaaa    960 atcacagcta cgaagggcaa tcatataaga aaaatttacc atttggcaaa tgtttgcgat    1020
aatgattcat gacaatgata attctgatta atcaagcaca tctgctgttt atgtctgatc    1080
acaatttctt tgcccaccca atcacacgtg ctatatggaa tcacttattg acagttcaaa    1140
```

-continued

| | |
|---|---|
| gtgcatgatg cccgtgattg cagtcagtcg aaatccttct gcaatcctcc agtttcactg | 1200 |
| agaaactaat cataatgcac atgaccagaa ctattattct ctccaaatgt tattatacgt | 1260 |
| gcttatcatc aactaatcag tggtctgtca gataatacat aaatatttag ctatggctt | 1320 |
| gtttacgcag ttcatatctc cgagtgttat ttatagtctc gcttcgcttg aaaaattatt | 1380 |
| aaaaaaaaat tatctttttc aattcatacg gagttgaaaa tgccgcagta ccaaacaaac | 1440 |
| aaacacggaa caggacatga aaggggggga taaatgggtg gggtttggtg gttttttatag | 1500 |
| tttatactat gtgggaaatt ggagctacag atcccagaga agaggaattg gatttggata | 1560 |
| tggcatgcac tactgaaata aatatatatt agggttattt atgttttaat ttttcaacgt | 1620 |
| tctctaccag ttaaaagacg acggcattca ccaatattta tccgtatctt gaaaagcaaa | 1680 |
| gaagttccat tttcaagttt agggattgga ggaatctttt tcatcctctc cctccctctc | 1740 |
| tccctctctt tactttatac tgtaatgaaa agcttgaga gagaaccaga gaggccaccg | 1800 |
| aaaagcatgg acaccttatc atgaaagcaa gaaaaaaacg aaccgatttg acgggccaac | 1860 |
| ccacacgcat aaacacacag ttactcactc actaacacac ccacacgctc gatcgatcac | 1920 |
| acatttgtgt cactcactgt gtgttaattt ttgggtgtct ttccttttgt taaaaatatg | 1980 |
| gaaatcataa gtcaacctcc cctcatgatt tggtcttggt ttcttctaag caccacctca | 2040 |
| tatcccactt tctttagcac cctctatata attaccactc cctttcattc agtccttcac | 2100 |
| c | 2101 |

<210> SEQ ID NO 33
<211> LENGTH: 1801
<212> TYPE: DNA
<213> ORGANISM: Eucalyptus grandis

<400> SEQUENCE: 33

| | |
|---|---|
| tggtgcgccg ggaccatcta atattttctc gggactgaaa cggtagaatt gtcaactttt | 60 |
| tctcaacctt tatgcgactg tgattggtta gccatttaaa aaggataata gaatttaaaa | 120 |
| gaaaaaagtt caaagagaaa aagagaaaaa ttggagattt ttaaaagaaa aattgcagtt | 180 |
| gcgatttgtt attctctgga aaaaaaatat aatttaaacg aaaaaagagt aaaaaagaaa | 240 |
| aaaagaaaa attggggatt tttactaatg gacggtggat tgggagctga ttatggaatc | 300 |
| tacgcgaacg atttattata ttaaatattc agaaattcgc atgcgtggga catctaggcc | 360 |
| aagtgatttc aagcgcgaga tccacacgtg tcagctctag agtaatactg cggtaaaaaa | 420 |
| gtcaacctttt gaaccatcga gctttcgaga ggagaaaaaa attattgagc ttaatggcgt | 480 |
| cgagcaccgg acgtgaacca gaagttaaat ttcgtcgtat aatgatttat aacgagggtt | 540 |
| aatatcttta aaaatcttaa attattatta catgatacct taattccaaa ctaattttca | 600 |
| cctcataaat gatcctaaat cagtgcttcc atggcacttt tatctcaaat tgattctcat | 660 |
| atcacaaaaa tttccaaacc ggtatctaat gtcacattca cttgtattaa taattttcat | 720 |
| ctcactgaaa atatcaaact aagaccctaa ccaagtctgc cttccagtag tattgtgcac | 780 |
| aatatcccat tagaaatgac aactataaga tagatcgacg tataaaatgc taacgaatag | 840 |
| caaattcggg tcgaggagtg ctagttgggg aattttgtt gaatgagaag tagttcatta | 900 |
| acaaaaaatt ggatgaaaat tgaattgagt taaaggttta atacctcaaa aaatctaaaa | 960 |
| ctataccaat tgtaacacaa atagcgaaaa acttttttct tgtcactaaa aaacctcaaa | 1020 |
| cttacccatt gtaacacaat ttccaagctt tttttgagtt ataaaaaacc caaaccccat | 1080 |
| atcaatatga taaatatatc ttaaatagaa ctaaaataga gaatatatat gtcacacata | 1140 |

| | |
|---|---|
| tataggttta aatttttttg tgataaaaaa atattttatt tatgtcatgg taaacttaat | 1200 |
| ttggagcttt ttgttatatt taccttaaga taaatatgct taattgatat caacttgtaa | 1260 |
| ttttcagtag taattaattg ttataataac atgggaggtt agaaagtcga tgacaagacg | 1320 |
| atagcgagag ggtgaggtga acaggctgaa taatgatggt cattagggtt gagataatta | 1380 |
| ttatagatta tgatgattgg gcaaaagaaa acaaaaaag aaaaagacaa aagacaaag | 1440 |
| gaggacaaac tagccgttcc agtcccgcag cgaatccaat taaaattaaa gcaaaagcgg | 1500 |
| acggtgggac cgccgcgagc acgacgggtg tgctggacct cttttttatt attataaatt | 1560 |
| gtcattatta tattttgtt tttcaacgg tcagatttt gctccacagt gccgaatgtg | 1620 |
| accgtttgag catgtcattc ggccggatat aagaaccatc tctccgtctt ccatcccaa | 1680 |
| ttcactcctc aaactcctcc tctcttctct tcttcagcat catcatctag ccagcttcga | 1740 |
| aagagctttc cttgaattac tcagatttt gccaagcgaa atcaagggaa gaaaaagaaa | 1800 |
| t | 1801 |

<210> SEQ ID NO 34
<211> LENGTH: 600
<212> TYPE: DNA
<213> ORGANISM: Populus trichocarpa

<400> SEQUENCE: 34

| | |
|---|---|
| ttttaatgca cttgatgaca tattttcaag ctattaaaat ttaaaaaata accgctatct | 60 |
| tcctttccgg caccgtccga gcccacaaca ctacaattcg ttgcctgcca cttcatccaa | 120 |
| atgtgatgtg aacttaaatg agtagagccc atatgtatga gcttaactaa gatcatctgg | 180 |
| tcaatagccg agcaccacaa gggtggtcag gtgcatctta aggggcttg aaagagagag | 240 |
| tagaagccga agctcgactc ggcgataacc tcaaatgaac tagtatcaca catccatgtc | 300 |
| ctcccgagga tgagataagg tcctggagct tcttccacgt ggcaaatcca ttgtggtgcc | 360 |
| taacgataag gctagcattc caagaatttc caccctcatg tggatagaat ggtgtcatgt | 420 |
| catcacttat catatccaac ggtcacattt tgctcattat caaccacgat agcttgtgtc | 480 |
| cataggatat gagatagaca agttgaggca ttatatatac ggtgtggcag gagtacttca | 540 |
| atcttacaat actagcaaaa ccacatatag agggtgtaat agctaagtag cctgtaagag | 600 |

<210> SEQ ID NO 35
<211> LENGTH: 1800
<212> TYPE: DNA
<213> ORGANISM: Populus trichocarpa

<400> SEQUENCE: 35

| | |
|---|---|
| taaaacttga tctctaataa atttaatatt aaaagataaa ttaaaaaaaa aactaaatta | 60 |
| aaaaaatata tcaagttatc aaattaataa cttgaattat aagattacat gattctatcc | 120 |
| aaaacaaatt aaaataaaat ataatgcaaa acataactct tgctttatcc attaccatga | 180 |
| catcatatgt gacaattctc cattatctag taaatctaat aatgaattat aaattttaa | 240 |
| aaaactaaat tataaaaaat aaaaaaaatt aataaattca atatttcaac aaaccttgtt | 300 |
| ttatgaggat atatatat atttgttaaa tcaaacatgt acaattcat aaaacaaagg | 360 |
| acataatcaa taagagctag cagggaagaa acggagagga gttgtggtgg tagcattgag | 420 |
| tgagaaaaa ataataatgg tctgttatgg tatgagccca catgctcttt acagatggcc | 480 |
| atgagaagct tctattggcc aattgaaagt ttgaaacatc tagaccattt cctttgtttt | 540 |

-continued

```
cccctgaata tgtagcattg ggtttcataa atacactgga ccggaccatc aaagccttgt    600
ctggtggact aaattgcatc atttaaacat ttaaagggcc tgatgcataa ttttgactgt    660
gacacttaac aggcctacac ggtccaaact cgagggacct gaacatctat ggggccttca    720
gctagtttag ggtttcattt tcgataatgg aagctccatc ccttttctaa taattcaagt    780
ttaaagtttc tcctaaaagc tccactgtgc aattgaagat tgagtgtaaa agacgctcca    840
agagtcattt tcgatcacat tgacatgcca atcgaaagtg ttcttttta ttattattat     900 taatgtgaat gtctggacta atttgcgcgt attttgatta attctacgag ccatgaagtt    960
aacgaccatg taaacttcca atgaccctga actttatgag attcgaattg gtaacttcta   1020
gaaaacaaac ttaaaacctg atcagataag ctacacctct cgagattgtg ttcttcttct   1080
aagcagtggg tgccaaaaaa atcaaccccat gcatgcaatc tggtatcaat ttcttagaaa   1140
aaattgattt tgaaaaaga aggttacaca taatttaggg gcatggttca ctttcattct    1200
ttttaatgca cttgatgaca tattttcaag ctattaaaat ttaaaaaata accgctatct    1260 tccttttccgg caccgtccga gcccacaaca ctacaattcg ttgcctgcca cttcatccaa   1320
atgtgatgtg aacttaaatg agtagagccc atatgtatga gcttaactaa gatcatctgg   1380
tcaatagccg agcaccacaa gggtggtcag gtgcatctta aaggggcttg aaagagagag   1440
tagaagccga agctcgactc ggcgataacc tcaaatgaac tagtatcaca catccatgtc   1500
ctcccgagga tgagataagg tcctggagct tcttccacgt ggcaaatcca ttgtggtgcc   1560
taacgataag gctagcattc caagaatttc caccctcatg tggatagaat ggtgtcatgt   1620
catcacttat catatccaac ggtcacattt tgctcattat caaccacgat agcttgtgtc   1680
cataggatat gagatagaca agttgaggca ttatatatac ggtgtggcag gagtacttca   1740
atcttacaat actagcaaaa ccacatatag agggtgtaat agctaagtag cctgtaagag   1800
```

<210> SEQ ID NO 36
<211> LENGTH: 2000
<212> TYPE: DNA
<213> ORGANISM: Populus trichocarpa

<400> SEQUENCE: 36

```
gtcaaacaaa ctaaaagcaa ggtgacccat gttattttaa aattgaccac aaaaatctca     60
tataaagcga attaaaaaaa taatagaata gtaaagtata aaaaaaggct ttaaaaaagc    120
aaaaaaacac ggaaacctgt gtccatgtca acttcgttaa tcaaagtcaa tctcttaaat    180
ctataaatca ttaaattcta cacctggact aaactaagaa acctaacccg atcaccctgc    240
gacccaagat atgagatgag gattacccga caaaaagaa agttgaacaa atcacaaagc     300
tcatagccta ataattcaat gtcaaatgat aaaaataaaa aaaattctga aaaggatttt    360
aaaaaatacc aaactcaaac taagtaaatc gttgaaacta gtgaactagg tcataaaaat    420
gagacaaccc tgtaaaagaa agaaataatc aaaaagcaaa atcctcaatt ataaaaaatt    480
aaaaaaataa acaataagga ccaaatatga tattaaaaat aattgaaaaa aactaattag    540
ggacaaaact gaaaacaaaa taatgaaga aaatgataga aaggagtaa tgaaaaaaat     600 aagtaccaaa attttaaaaa aatgaattaa aattttaaag gacaaaatca aaaaaataaa    660
ataaatgcaa aggatgaaaa aacaacaatt gaaagaataa ggaccagatt gtaaataaaa    720
aaattaaatt aaatgcagag agggattaaa ttgaaaaaaa taaatttcta aaagcattaa    780
aatcaaagca aatagaaatc aaaagaatga ggttcgaatc caaaacaaat tcaaaatgaa    840
ggacaactaa attttttcaag gcttggcatg aaaaccaaga ccgagagaga aacaaagggc    900
```

```
aagagaaaaa accccatcgc caccaaaccg ctgcccgtcg tggagcacgc gccactccag    960
cggctgcgcc acatccttgc atattgattg agatggcgat ctgttttatt ggccatcgtc   1020
cttggccaca cgcaccttca gaatagcatg aaggattctg acacgttgat gcgtgtgtgg   1080
catacgttat catattttac tgattttatta atattttaat aagaaaaatt acaaaaaga   1140 gcccaatgac ataccattat tacaaagaaa tcatgatgca aagattgaaa caccctcgga   1200
agctatgctt taaatatgga aagtcaaagg tcaataacgt aattttttctg tacaaaaata   1260 atagtcaaag gtcaataacg taattttttt gtataaaaat aatacaaaga caaataaatc   1320
ccttattgca aggtcatttt gtttgagcac ccaagggtat aatcatttta ctgtgtaaat   1380
taaaaaaaaa tcttagtagg agaccatttt tatcagattt caagggtata taaaaatata   1440
ttttcactgt gcattataat ttagaatgaa atctttgccc ctgatgaatt ctgaaatacc   1500
atttgaatct catggacaat attattttac cccagtatca tagataaaaa attataatta   1560
cactgcttga atttacggtg attctcctta tatgctacag tgttttcttt cgcaaggagc   1620
ccttaacccg agtccctagt cgaactaaaa gattatcgcc atggccattt aatctacgct   1680 ttttttttt tttcttatga acttacaatt aatttatttt tcaattttttt tttggtataa   1740 aagaactatt tctcgtaaag aatctcgtta aattcgttgg gaaccgaaga ggttttattt   1800
tctaaaatct cggagaatcc agagacagaa ggagtagatc tttggtggac attgaactcc   1860
gactcttccc gggacacata aaccgtatcc tgctaggact attacgcttg attccccatt   1920
ctataaatat atcaaactcg gtttagaaaa ggagctctca gcaaaaagtt tcagatcagg   1980
aaggcagggg aacctcaacc                                              2000

<210> SEQ ID NO 37
<211> LENGTH: 2000
<212> TYPE: DNA
<213> ORGANISM: Populus trichocarpa

<400> SEQUENCE: 37
aaaaaaatta attttttta aaatattttt aaacaaaaa ataaccagt tttaaataaa     60 gatgagatgg caagcttttc cactagtcac ccaaatacgg cttcaaagtt caaataggta    120
tacatttttt tcctttttttt cggtgggact ttaaataccg accacaattt attttaatgt   180
tgtcctgaaa ccttatgtag attaatatac gtttaatgaa acagatccac atcatgatca   240 ataataatt gccgactcac tcaacataga aaactccaca tctctcttct tgatactgtt    300
ctcatcattg aaggattcgt gtcttgaaaa acagtccatt atcatcatta atttgaatgt   360
ttttcgtaaa ttttatctgt tagacgtctg ctatatatat ataatttata tatatatata   420
tatatatata tatatatata attttctttt aaaattacaa ttaattgtta gagacttaga   480
ggacgtaaat acctagtgtt taattatcaa gtgcaaatgt aaatttgtaa tatatcactt   540
tcgtgtttcc atttcgatt atagtaatta aatcagaaat tgaagcagaa agaaatatgg    600
tttgatcaaa ttaattagct tctcaagact gagaattaat ttcacaagaa ccttatcgat   660
actctaaagg aagattgtaa ctcattgact tggatgctat tgccagctct tgaaatggac   720
gtccccgtca caatcatgac gggattatcg actatatata tatatatata tacctaattc   780
taattctcta aacaaagcta attattatct atacatttga agtggaaaac acgatttata   840 taaaacaaa aaccacctca agtttatttt atttttttca actccttttt attatttggg    900
acctttcaac tccttttat tatttgggtc ccttttttcat tcaattttat ttattgtatc    960
```

```
gttttgcttt tcatttaaca attgtagtgc agtttcataa aattgatgct ccataaacca      1020
tgaaataatg tttgaaatta caaatatgta aaacaatgta aggtgaaaga aatattaaaa      1080
aaataataat ggaaaaacaa tatagaaaaa agacaatcca ctaagagttg caataattac      1140
ccataatgta ttatttttat ttttttgtcg cttgattctt ttatttttaa tttaatcatt      1200
tcatattaaa tttatttgtg attgaatttg atgttttgtt ttgattgact ctaacatagg      1260
gctctcacaa tattaaaaat aaattttgat gttgtgttga attaaaaatt ttgagatcca      1320
atttgaaatt aaaacaaata ttcaatttgt ttttttaaa taacattttt attttagctt       1380
cccaactcaa ttttttaattg taattaatag atttattatt atttattaac atatataatt    1440
ttttatttat tctattaaat atatgcatgt ataaactttt cagttcgcaa taaaaatatt     1500
taacattgtg gaaaatcaaa ctagcttgat tcatgagaaa tgcccccccct tttttttatcg   1560
tttgatacga ggaaaatgac ataggagggc attaatcatt tccaagttgt agcttacttt    1620
ggtgcaaatg aattattcta tcaaaacatg cttatcctca caagttataa gatgttggct   1680
ttgtgtcttt gtttccgtaa ctaacattta gcagggttta ttttagttgt cttatgctca    1740
taattaatgt ataattatta ctaatcaaat aaaaggcggt tggtcggctt ccaatcatat    1800
agtgctcctc cattcatatg ggtcccatgg tcggtgccgg ctatgatgct tattgcaaaa   1860
ttagcatcgc agagcgccag tggtgctata atataaacca cgcccatgaa atcaatgcag   1920
cccatagaaa cacatacaag aacttgagct agctagcagt aattaagctt aattggccca    1980
ggactactga tcaagcaaga                                                 2000

<210> SEQ ID NO 38
<211> LENGTH: 2500
<212> TYPE: DNA
<213> ORGANISM: Populus trichocarpa

<400> SEQUENCE: 38 tttttttgact cgataaataa taaatataaa ctcgatttaa tttgatgagt actcactatc      60
atctttagcc acggtgaatc cagcttgcca cttgtttgat ttaaataaaa cagtaacaag     120
attcgttgct ccacgtgcaa atgctaaatc gaaccagcta gatttcatcg accttgtaaa    180
tccaatgcac gtggctcacc catggcggga aaacacaact ccggtggtga ataataatag    240
cacgggaaga aaagcagtgg aaaaaaatgg tcactgaagc ctatatttct tctttttttc    300
ttgctcttcg agcaactagg atattaattt ttattaatct ttgaaaaaat aataataata    360
aatatcttat aaagcttaaa gatcgtgaaa tattgttaaa aaaaatcact ataattgatg    420
taatgcttat ctaacccttg aaaaaataac aatgatgttg atactcttat tatcatagtt    480
ttaaaactcg gtctagcagg ttaatcctga atccgacaga tccggggtta aaatcgagcc    540
gagttgagaa aaaatagag aaagaaaaaa cccggtgtga cccggtcaaa aatccggata    600
caacctgttg acttttgttt ttttatttaa ctaaaaaatt gacccggacg acctggtcaa    660
aaccagaacc cgaaccttga accgggccgg attttaaaaa atatggttct tgtattagtt   720
ttctcctcct ttaatatttt taatttcttt tagtgataaa gattcagaca acataggatg    780
acgattatcc ttttatatat atatatatat atatatctga catttttaca tgagaaaaat    840
aacttaaagt atagggactt aaaaatgcca ttaaactaac ggaaaacagc aggagagtgg    900
atcgagagac aagttttatt acagtgctct tttcaatcga attcgtttag aatttcaagc    960
tgtgtatcat aaaaatttaa gattttattt tatttaagat taattttta tattattaaa    1020
tcgttttaat atattaatat aaaaatacat tattaaaaac taaaaatata ttattttaat   1080
```

```
atatttttaa acaaaaaaac attttaaaaa ccacctttac aaccttacca aaaactcata  1140
aaagcaacct cggcgcgtgc acagtctacc gttacagatt ctgacagtct ccgttcgaat  1200
acggtcaacg cttttgacgc tttccagaac cacacttaca tctgcgcgtg tcaagcacat  1260
acacggatct gtgagaactt gtaaagcacg cgttttcttg aaaggcgacg ttagaaatcg  1320
gttttggtat ggtcatcata tgcttactcg caggttatct cttttagttt ttagattttt  1380
attttatttt ttctcgggaa atatcggtga cgcccgccct tcgagtggcg gttagttttt  1440
cctatcccct tgatttataa tttgtaactt ttattatcat tgttggattt atcttattat  1500
aaataaaaaa aataatgata ttgataatat tataattcaa gtttcagtat atttattata  1560 ttttttatttt ctctactttt ttgtatattt aatattttta aagtatatta ttattctaaa  1620
tatcaacaaa ttataaaaat catgttttt aattatgata tatataaact gtgttatttt  1680
atcaatactt ttaaaatata tgttaaaaat aaaaaataac cctctttcca ttaactatcc  1740
atacgaaagg gaaaaaaaaa tctatcaagg atttaggatt taattctaaa aacaagttat  1800
gaataattat ttttttcatt ttacaacctt tgttgtttaa ttattcttc aaaatatatt  1860 aacaattata aaaaaaaact aaaaaagaag tgattttttag tgtatttctc cacacaaaat  1920
attatttatt ataataatgt ttttatttttt ttatcatttg atatttttt atttagtatt  1980 ttttttaatt tcatcattta atattaaatt tattttttat tgagttatttt tattttcatg  2040 acatgaatta tgagttttgc atattatatt aactaactca gttttttttaa ttaattttta  2100 ttttttttatt ttattttttta atattaattt gattaataaa aaatctaaat aataataaat  2160
ttttacttgt ataatactat ttgctaaaat attatgtttt tttcaaataa ataaatttaa  2220 cgaaaatca agaaaataat agcaaggtaa taacggaaag cgcagtgaga aaagaaaag  2280 aaagaaaag ggcaaaaaaa gacaggcgtg aagagttctc agataaaacc ccttcactcg  2340
cttactctat ttgtctctct ccattacagt agggcctcat agagagagaa agatatgcaa  2400
tatatgcaaa gagaagcttg agagattttt atctcccttt ttcattttttg atggtgttct  2460 ataatgagaa gaggattaaa tctcttcttc tctgaagaag                         2500
```

<210> SEQ ID NO 39
<211> LENGTH: 2101
<212> TYPE: DNA
<213> ORGANISM: Populus trichocarpa

<400> SEQUENCE: 39

```
atgctcaacc tttttaattt tttaaaaaaa atctctttca ctactttct tgttttatat   60 aattcaagaa ttggttgcta tacgaagatc caagttgttg atgataaaaa gaaaggaaag  120
aaaagaaatc caagttgtcg gttctttaaa ttgtgcaagg aaagcaagag cagataagct  180
taaatgttaa gaggaaagcc aaaggtctgc atgtcgtctg tgtataaacc cgtcaagagt  240
ttagaatgag ttgttcagca acccaaatcc atatgtcagg ccaaaaacat tgttagctga  300
aggatcttat tgtactacat tgcaaatatg tggtcgagag agagaggttc acatcaactc  360
ggtcgccaaa tctttatctt agaagccttt gtttaccgga aaaacaaaa tatagtgaat  420 tttgtccata ggtaaaaatc atatggataa atagccagc tagatgcatg aaagttacac  480
tagagtcata gcctgaagaa ttttttgttac attagttaat caaatgtact cgtaatgttt  540
ttaacagctt attaatttaa catgtttttt aaaatccttt ttaaaatttg ttttatataa  600
aaagaatatt aaattaatat ttttcactgt tatcacgtgg aaaatggctt tatccctcat  660
```

```
tttaaacatg ttttttaata tgcttttttaa attagttttt tattaaaaaa atattaaatt    720
gatttttaa  gatgttttt  gatttgttaa tataaaaaat atatttttaat acattttat     780
ttcacattaa tatcccccac aaaatctgtg aaaattaata atggacgact ccccaaccaa     840
gtcaagacac gaggtctctc cacacaatta ctggaaacaa atttaatgcg tttaggacat     900
gtatttgaag tgcaatcgct tccaagaacg taaccttgtc cataagagga aaaacatgct     960
cagctcagtc gagattccta taaatagtca atgaactctg gtctgtccac attggcaccc    1020
ttaattacta aaccactaga gaaagttaca gccacacaag ggcaatcata tatatataat    1080
aattaagaac ataaatttac catttggcaa atgtttttt  atagtgattg atgataatcc    1140
agattaatca agcacgtctg ctgttaatgt ctcccaattc atttaccaaa tcacacgtgc    1200
tacgcagaat cacttattga cagtccaaag tgcatgatgg ccgtgattgc agtcagtgag    1260
atccttctgc gatgctctag tttcactcaa caactaatta taacgcacag aatcagaatt    1320
attattcacc ccaatgttat aatacgtact tatcatcaac taatcagtgg tttatgagat    1380
aatacattat atagttagtg taataagaca cgataaggta ctgccataga attaagaaaa    1440
aggggaataa gaggtggggt tcggaggttt ttataattta gagaggttat tctacgtggg    1500
aaactggagc tagctacagc tctcgaagaa gaggagttgg atttggatat ggtatgctgc    1560
tactacattc aaatagatat attgtgatta tatatgcttt gttttttcaa cattctctac    1620
cacttcgaga cgacggcatt cactcgctgg cttctctcag tcaccaatat ttttccgtat    1680
cctgaaaagc aaagaagttc cattttcaag ttttgggatt ggaggaatct ttttcattct    1740
ctccctctct actttatact ataataacaa aaaaaaaagc ttgagagaga accgaagagg    1800
ccaccgaaaa acatgggaca ccttatcatg aaagcaagaa aaaaacgac ccgattagac     1860
gggccaaccc acacgcatat acacacagtt actcacacac ccacacgctc gatcgatcac    1920
acatggtctc tctccctctg tgttaaattt gtgtgtgcct cgttctttct tttaaaaatg    1980
gaaatcataa gtcaacctcc cctaatgatt tggtcttggg ttcttctaag caccacctca    2040
tatcccactt tctttagcat cctctatata attaccactc cctatcattc agtccttcgc    2100
c                                                                    2101
```

<210> SEQ ID NO 40
<211> LENGTH: 600
<212> TYPE: DNA
<213> ORGANISM: Populus trichocarpa

<400> SEQUENCE: 40

```
aaatctagtg aatccagcca aacctaattg gttaactcta aattttttta ttttaaatat     60
gaaacaatat tattttaaa  aaatcttatt gacccaaatt gacattaact ttttttttat    120
atatatatat atatgaagta aactaagctc taaaatcact gtgtcaatgg caagctgcca    180
agaaccacag aagtggtcat aaatatctta aattaaggga gctgaaagag agagtggaat    240
taatcgaaag gctgcctcag caagaaccat aaagccataa attaactagc atcacacatc    300
catgacgtcc tccatgggat gagataaggt catcgagctt cttccacgtg gaaacctctt    360
tgtggtgcta acgatgaggc tagcatcaaa agaattccca ccttcatgtg gacagaatag    420
tgtaatgtca tcacttatcg tatcgaacgg tcaaattccg ctcattatca actccactga    480
tttgtgaccg taggatacga gggggacaag ttgaagcact atatatagga agtgacagta    540
aagcgagttc agaatatcac atttataggg agcactgcat agcttacaag cttgtaagag    600
```

<210> SEQ ID NO 41
<211> LENGTH: 1800
<212> TYPE: DNA
<213> ORGANISM: Populus trichocarpa

<400> SEQUENCE: 41

| | | | | | |
|---|---|---|---|---|---|
| cattcaaata | aataagagat | tttaggaggg | aatcatatca | gcatccaacc | tatccatcaa | 60 |
| ttttaatcgg | atcccagaac | tacaaattaa | ttttcccaat | tgaattccta | aaggattgga | 120 |
| catttctcaa | ttgagtattc | caacaactat | atttattggc | attttccgtt | atttcatgca | 180 |
| ataaatagca | tgaaactatt | ttgaaaacaa | tttgacattt | ttctattaaa | aagctacaat | 240 |
| gatgtcaaat | gaaacaagaa | tttcctaaca | cgtgagaatt | ttttttataa | atttaatcat | 300 |
| tagaagttca | taacacattg | gagtcgaaaa | caaaattctt | acaaaatctt | caccatctaa | 360 |
| gttgtccata | gcaaattaca | ttttttacaa | gagcgatagc | gtttgaaaac | gcggataac | 420 |
| tcgctttcta | aaaagtttta | attttgttt | tttgctaaaa | attaaatttt | ttttatgtt | 480 |
| ttgaattgtt | ttgatacgct | gatcttaaaa | ataattttt | taaataaaa | aaaattattt | 540 |
| taatgtattt | caacatgaaa | aatactttaa | aaagtaatca | caatattctc | tcaaacaggt | 600 |
| ccaaaataaa | aaaagaaaa | aaaaaagaa | gagggagttg | ctgggctgtt | tagtaatgtg | 660 |
| taacggaggt | gagattataa | tgggcggaaa | tggttttagc | ccgacttctc | tttagaaata | 720 |
| gccatgggcc | catggcattc | ttctttgggc | taatttaaat | tgctagacca | ttttctttt | 780 |
| ttttccctaa | gaaagtactg | gaccagacca | ttaagaaccc | tgtccactcc | ttgttacttt | 840 |
| ggccattttc | aatgcatact | gagctggatt | tgatcgttag | aggacctaaa | gcattgctta | 900 |
| cttgtgacca | cgtattgctt | taaattttga | ggttttgagg | gtgttgtttt | ttaaattatt | 960 |
| attttttatt | tagagttgta | ttaaaataat | attttttat | ttattaagat | ttattcttga | 1020 |
| catcaaaata | ataataaaaa | atataaaaaa | ataatttaa | ataaaaaaaa | gtaaattttc | 1080 |
| aatgatcttt | attggatcg | caattccaaa | ccaatactaa | aaaccagatt | gttgagcttt | 1140 |
| catgaatgtt | ttggttttac | tttccataat | gaaattgctc | caactaaaaa | aaaaaaggta | 1200 |
| aaatctagtg | aatccagcca | aacctaattg | gttaactcta | aattttttta | ttttaaatat | 1260 |
| gaaacaatat | tattttaaa | aaatcttatt | gacccaaatt | gacattaact | ttttttttat | 1320 |
| atatatatat | atatgaagta | aactaagctc | taaaatcact | gtgtcaatgg | caagctgcca | 1380 |
| agaaccacag | aagtggtcat | aaatatctta | aattaaggga | gctgaaagag | agagtggaat | 1440 |
| taatcgaaag | gctgcctcag | caagaaccat | aaagccataa | attaactagc | atcacacatc | 1500 |
| catgacgtcc | tccatgggat | gagataaggt | catcgagctt | cttccacgtg | gaaacctctt | 1560 |
| tgtggtgcta | acgatgaggc | tagcatcaaa | agaattccca | ccttcatgtg | gacagaatag | 1620 |
| tgtaatgtca | tcacttatcg | tatcgaacgg | tcaaattccg | ctcattatca | actccactga | 1680 |
| tttgtgaccg | taggatacga | gggggacaag | ttgaagcact | atatatagga | agtgacagta | 1740 |
| aagcgagttc | agaatatcac | atttataggg | agcactgcat | agcttacaag | cttgtaagag | 1800 |

<210> SEQ ID NO 42
<211> LENGTH: 2000
<212> TYPE: DNA
<213> ORGANISM: Populus trichocarpa

<400> SEQUENCE: 42

| | | | | | |
|---|---|---|---|---|---|
| tgggaagggt | tgtcgggact | ctcgtgaggg | tacgacaaaa | ataataacaa | aatgataaaa | 60 |
| gatggaaaca | aaaagctttt | aaaaaaacaa | aagcaccatg | gaaacttgtg | tccctatcag | 120 |

```
cttcattaat cggagtcaat ctcttaaact tgtaaaccgt taaattctac actcggacta    180
aacttagaaa cttaacccga ccaacctacg acctgagata tgaaatgggg ataactcgac    240
aaaaaaaaaa gctaaacaaa tcacaaagct catagcccaa taattcaaag tcaaatgaaa    300
aaaattaaat aaaaacaaat taataagtca atgtcaaatg ataaaaataa acaaaaaaaa    360
ccgaattcta aaaaggattt taaaaaatat cgaactcaaa ctaggtaaat cattgaaact    420
ggtgaactga gtcatgagaa cgggacaacc atgtaaaaga aagaaataat caaaagaaa     480 aatcctcaat ttaaaaaaaa attaaagat  aaccaatgag gaccaaatct tgcacaaaaa    540
ataattgaaa gaaagtaatt agggacaaaa ttgaaaataa aataaatgaa gaaaaggaaa    600
aaaaatgagt aatgaaaaaa tgaggaccaa aatttgaaaa aaatgaatta aaattgtaaa    660
ggacaaaatc aaaaaaataa aataaatgaa aaggatgaaa aaacaacaat taaaagatta    720
aggaccagat tgtaaacaaa aaacaaaata aattaaatgc aaagaaggat gaaactgaga    780
aaaataaatt tcaagaagca ttaaaatcaa agcaaataga atctaaaga atgaggaccg     840 aacccaaaac aaattcaaaa tggaggacaa ctaaattttt taagatctag catgaaaacc    900
aagatctaag agagagaaac gaagggcagg agaaaaaacc cattgccgcc accaatcgtg    960
gagcacgcgc cactccagca gctgcgccac atccttgtgt atcagttgag acggagatcg   1020
gttttattgg ccatcgtact tggccacacg cgccttcgga atagcgttga ggaccctgac   1080
acactgatgc atgcatgata cacgtcagca tattttactg atttattaat attttaataa   1140
gtaaaattac aaaaaaaatc caaggacata ccattattac aaagaaacca tggtgcaaag   1200
actaatatgc cctcagaagt taagctttaa atccggaaag tcaaaggtca acaatgtaaa   1260
ttttagtata aaaataatgc aaagacaaat aaacccctcc ttgcaaggct atttttgtg    1320 agcactcaga gctataaatg ttattttact gtgtaagtta aaaaaaaata caaaaaaaaa   1380
ctaattatta ttagatttta agagcaaaat agtattttt  accgtgcatt atagtttgga   1440
atgcaatcta tgcccctgat caattctaaa ataacattta aatctcatta aaaaatataa   1500
agataattat taagaataat gaagagcaaa accataatta cactgcttga atacgtaatt   1560
aatcacctca tgatacagcg aaaaactaca ctgaggccat ttaattttt  tttgtgagcc   1620 cttcacccga gtccctagtc gaactaaaag attatcgcca tggccattta atctacgctt   1680 tttatttat  ttttccttgag aacttacaat taatttattt ttcatttttt ttttgtataa   1740
aagaactatt tctcgtaaag aatctcgtta aattcgttgg gaaccgaaga ggttttattt   1800
tctaaaatct cggagaatcc agagacagaa ggagtagatc tttggtggac attgaactcc   1860
gactcttccc gggacacata aaccgtatcc tgctaggact attacgcttg attccccatt   1920 ctataaaatat atcaaactct gtttagaaaa ggagctctca gcaaaaagtt tcagatcagg   1980
aaggcagggg aacctcaacc                                               2000
```

<210> SEQ ID NO 43
<211> LENGTH: 2000
<212> TYPE: DNA
<213> ORGANISM: Populus trichocarpa

<400> SEQUENCE: 43

```
aatttttta tataattttt tatttgatta tataataaaa atgatgtttg taaaatcaaa     60
aaccaactaa atatcagagt gttttattca agattctgat aaacctatga atatcaaata   120
taataatttt atgtttccca ataaaaaatc aataaaatat taagaataa gattgaaaag    180 aattaagcaa gaaaaatcaa taaaaatcca attatgaatg atcaaattga aaaaaaaaca   240
```

```
attcaaaaaa ataaataaaa gaaggcaaaa ataaaaagag ccaattgtga aggatcaaat        300
tgaaaaaaaa ggcccatgag tgcaagcttg aggctgttaa attttttttc ttttattgtc        360
cacctatggt tttttgaaaa aaaatagca ggcaacttgt tgccttctct atccagattt        420
tgattgtcgg ccataggtgt taaacaccat aaaaatttat ttaaaccata attttggccc        480
caaaacactt gataaacatc ttgaagactt aaataaactt gtttatacct ttaataatt        540 caaaaatgat aaacaaacaa aaaatcaagt cgaaatcaaa atactttctg agatcagatt        600
tactttttta agaaaactat aggtgaaaga acaccttact agaactcttt ccggcatata        660
aaactcgtac aaaccaatat cgactatttt ggtagcataa ttcgttgtca accaatattt        720
tttctccact agcagaattt aatttaatga ctttctctct tccatcttga actagaaaat        780
ggacaaaaaa aatttgttcc acaattgagt ttttgaaata tttagggacc gagaagttat        840
catttaaaaa gtaagaaggt caaagtttac tttttatccc ttttgataa caccacatgt         900 ttcctccttg ttttacttat caatctcatt tgttttaatc ttgtctctca ttaacaattt        960
ttgataaatc atccacgaaa attgggcatt gaaggacaca attgaataga aaaaaattga       1020
ataaacaatt atagaattgt gaattgcaac actaaaaaac tcatgcattt tagagttttt       1080
gttaataaat aactaatata aaattaatat ataaaattaa tataatattt taattttttt       1140
aaaatgaatc ttaaacttaa ttatcaagtt taatatgata taataatttt aataatggtc       1200
tataatttta atttcaatat tactcattcc cacttactaa aatagtaaac ttaagcaaaa       1260
gttgtaatta gtcatcatga ccgtgaagac tcataatata taaatataaa taaaaaatta       1320
ctaaaaaaat tcaatttaat atattttttaa gttaaaaata ttttaaaaa atatctagaa       1380 gcaaaaccag aaattatacc gaacaactca gatgacattg ctagctctag aaagagttac       1440
ccatcacaat catgatggaa ttatcaacca tgtaccatat ttaaaaaaaa aaaaaaaaac       1500
acaccaactc tttgaacaaa gctaattatt tcatatatga taaaacgccc taattttttat       1560 catttgatac ggggaaatga cacgtggaca tcgatcatta ccatattaat tattggtgct       1620
gaattgatca tatcccatca aaacatgctt tgtttccttt cttaacacac acacataaat       1680
aacaagtaaa ttagttgtct tgtgttcata attagtgatg acatattagt tattactaat       1740
caaataaaag gcggttggtc ggcttccatt ctttagggc tcttccattc atatgggtcc       1800
cacggtcggc gccggctatg atgcttactg caaatttagc atagcaaatc accagtagga       1860
gcgtgtattt aaaccacgcc catgagacca acgcattgca gcccatcgag aaacacacac       1920
aagaactcga gcgagctata ttgatagttc taataattaa ttaagtttaa ttagtctaat       1980
aattagtgaa acaagaaaga                                                    2000

<210> SEQ ID NO 44
<211> LENGTH: 1757
<212> TYPE: DNA
<213> ORGANISM: Populus trichocarpa

<400> SEQUENCE: 44
ttcgcaattc aaagccttt tttttttaat gattttgata catgaaaatt aatttaaaaa         60
acattatttt aaaaaaaaaa atatttcacc atattactga aaatacactt attctagtta        120
ggctattaat caaatagatt aagttttaa tttgctaaaa cttgttaagt ttagttaatt        180
ttttaataat ctaaatgaca tgataaagtc aaataaaaag gtttaagacc taaattataa        240
gtttaacgag ttgagttaat ttatttcaat ccaaaacaat gttatatttt tttaaaaatt        300
```

```
gaaacaatat gattttgaaa tatatatata tatatatata tatatatata tatatatttt    360 ataatttat  agtcaaatca aatttcatcc agaaatttaa cttctataaa attaattata    420
tttaactaaa ttaattttca ctttatttaa tataaaaccc gattcaaatc aggttttaaa    480
acaccttaat tgaaaatatt caaagattat taactattgt aggaaaaatc attacttttc    540
tttgtctctt ttatttcaca cttggctcga gatttacttg aaataatatg caacaattta    600
gaatttcatg tggtgggata gatgttttgc aagcttgaag catgtctttg tgcatataga    660
tttcatgtta tagactttag aatttcattt taacagcaat ctacctaaca attattttta    720
tataagaagt gatgcccatg tctggattat ttttacttt ttatgtataa gaaaatatt     780 ttaaaaatat tttaattatt ttctccattt aaactggcca acaatttca tagttggtgg     840 gatgctagca agcacgaagg atggcttgtc tgtgactaat gttagcttaa tatcttgtaa    900
agatgagatt caaccagcaa gaatatatct catgtttata gacttaatta ataatttc     960 tatataatag taattgaaca aataaagata ataatgttat tttcattttt cttgtataaa   1020
aaagtagcat gtattgattt tttatgctga taatcattat gttatttgtc cattaaccca   1080
tctagatatt ctagacgtga ttgagaccct aacccttttt aaattaaata taatcaacaa   1140
tatattaaag attaaaaaaa aaattgtacg gataggtagt taaatatata tatatata     1200 tatatatata tatatata tatatatata tttcagaaaa atgaagaata ttccaaggac    1260
attgaagggc atccggtcat ggtttcagaa gacatcgctg gatttcttgc tagttaatta   1320
gctctgaaaa aacttaggaa tatcccagaa cattaaattt gaccctcagt agaatgatta   1380
gcatggagag gtaagttaca tattgatctc tttccttgag gcaacagaga gagggacata   1440
tttgttttct aatataattt aatttgtatc ttcgttatga gcaagagtgt atgaaagctt   1500
aaccatactt gttttcagtc ataattattt tttaaaaaat ttatttagtt ttctaaatta   1560
gattaattat aattccaaat gggtatatcc tcaatattcc ctttctaatt tcttgttatt   1620
ctcccatggc ttagtgttca tcgagctcga cgtgcattat tttttctta tcatattgct    1680 taaaatacca attatataac catgaaatcc taggcaagaa aattaaccac tcccgccaaa   1740
agaacgaaaa gaaagac                                                  1757
```

<210> SEQ ID NO 45

<400> SEQUENCE: 45

000

<210> SEQ ID NO 46

<400> SEQUENCE: 46

000

<210> SEQ ID NO 47

<400> SEQUENCE: 47

000

<210> SEQ ID NO 48

<400> SEQUENCE: 48

000

<210> SEQ ID NO 49

<400> SEQUENCE: 49

000

<210> SEQ ID NO 50
<211> LENGTH: 186
<212> TYPE: PRT
<213> ORGANISM: Populus trichocarpa

<400> SEQUENCE: 50

```
Met Ser Gly Ser Ser Gly Gly Ser Ser Ser Ser Ser Arg Ile
1               5                   10                  15

Ile Asp Gln Glu Ser Gly Ala Ser Ala Ser Gln Arg Lys Phe Lys Gly
            20                  25                  30

Ala Arg Arg Lys Trp Gly Lys Trp Val Ser Glu Ile Arg Ile Pro
        35                  40                  45

Gly Lys Gln Glu Arg Leu Trp Leu Gly Ser Tyr Ser Thr Pro Glu Ala
    50                  55                  60

Ala Ala Val Ala His Asp Ile Ala Ser Tyr Cys Leu Arg Gly Pro Ser
65                  70                  75                  80

Ser Leu Glu Ser Leu Asn Phe Pro Leu Met Leu Pro Ala Ser Val Arg
                85                  90                  95

Glu Asp Met Ser Pro Lys Ser Ile Gln Lys Ala Ala Ser Asp Ala Gly
            100                 105                 110

Met Ala Ile Asp Ala Gln Met Ile Leu Asn Arg Ser Leu Gln Asn Glu
        115                 120                 125

Val Lys Val Gly Pro Glu Asn Val Ala Ile Asn His Gly Pro Gln Thr
    130                 135                 140

Gln Leu Trp Glu Pro Ala Ala Gly Gly Gly Asp Ser Ser Asn Arg
145                 150                 155                 160

Cys Glu Asn Trp His Glu Asn Asn Ile Gly Thr Arg Val Gly Asp Asp
                165                 170                 175

Leu Asn Ile Ser Ile Glu Asp Tyr Leu Met
            180                 185
```

<210> SEQ ID NO 51
<211> LENGTH: 561
<212> TYPE: DNA
<213> ORGANISM: Populus trichocarpa

<400> SEQUENCE: 51

| | | | | | |
|---|---|---|---|---|---|
| atgagtggta | gcagcggcgg | cagcagcagc | agcagcagca | gcaggataat | agatcaagaa | 60 |
| agtggagcaa | gtcatctca | aaggaaattc | aagggagcaa | gaaggcgaaa | atggggcaag | 120 |
| tgggtgtctg | aaataaggat | tcctgggaag | caagaacgac | tttggttagg | ttcttattct | 180 |
| acacccgagg | cagctgcggt | ggctcatgac | atagcttctt | attgtttacg | tgggccttct | 240 |
| tcgttagaga | gtctgaattt | cccctaatg | ttgcctgcaa | gtgtaaggga | agacatgtca | 300 |
| cccaagtcca | tacagaaagc | tgcgtcggat | gctgggatgg | caatcgatgc | tcagatgata | 360 |
| ctgaacaggt | cgctccaaaa | cgaggtcaag | gttggacctg | agaatgttgc | gattaatcat | 420 |
| gggccacaga | cacagttatg | ggaacctgca | gcaggtggtg | gtggtgatag | tagtaatcgt | 480 |
| tgcgagaact | ggcatgaaaa | caatatcgga | acgagagtag | ggacgatttt | aaacatctcc | 540 |
| attgaagatt | atctcatgta | g | | | | 561 |

<210> SEQ ID NO 52
<211> LENGTH: 168
<212> TYPE: PRT
<213> ORGANISM: Populus trichocarpa

<400> SEQUENCE: 52

```
Met Ser Gly Ser Ser Ser Arg Thr Asp Gln Glu Ser Gly Ala Ser
1               5                   10                  15

Ala Ala Arg Lys Lys Phe Lys Gly Val Arg Arg Lys Trp Gly Lys
                20                  25                  30

Trp Val Ser Glu Ile Arg Ile Pro Gly Lys Gln Asp Arg Leu Trp Leu
            35                  40                  45

Gly Ser Tyr Ser Thr Pro Glu Ala Ala Val Ala His Asp Ile Ala
        50                  55                  60

Ser Tyr Cys Leu Arg Gly Pro Ser Ser Ile Glu Ser Leu Asn Phe Pro
65                  70                  75                  80

Leu Met Leu Pro Ala Ser Val Arg Glu Asp Met Ser Pro Lys Ser Ile
                85                  90                  95

Gln Lys Ala Ala Ser Asp Ala Gly Met Ala Ile Asp Ala Gln Met Ile
                100                 105                 110

Leu Asn Arg Val Pro Glu Asn Glu Val Lys Phe Trp Thr Ala Ser Gly
            115                 120                 125

Gly Val Asn His Gly Leu Glu Ile Glu Leu Cys Glu Pro Ala Gly Gly
    130                 135                 140

Asp His Gly Gly Asn Trp His Gly Asn Asn Thr Gly Met Arg Glu Gly
145                 150                 155                 160

Asp Ile Ser Ile Glu Asp Tyr Leu
                165
```

<210> SEQ ID NO 53
<211> LENGTH: 507
<212> TYPE: DNA
<213> ORGANISM: Populus trichocarpa

<400> SEQUENCE: 53

```
atgagcggta gtagcagcag cagaacagat caagaaagtg gagcaagtgc agctcggaag    60
aaattcaagg gagtgaggag gcggaaatgg ggcaagtggg tgtctgaaat aaggattcct   120
ggcaagcaag atcgactttg gttaggttct tattcaacac ccgaggcagc tgcggtggct   180
catgacatag cctcttattg tttacgcgga ccttcttcga tagagagtct caatttccct   240
ctaatgttgc ctgcaagtgt aagggaagac atgtcaccta gtccataca gaaagctgct   300
tcagatgctg gcatggcaat tgatgctcaa atgatactga acagggtacc agaaaatgag   360
gtcaagttct ggactgcaag tggtgggtt aatcatgggc tggagataga gttatgcgaa   420
cctgcaggtg gcgatcatgg tggtaattgg catggaaaca atactggaat gagagaaggg   480
gacatctcca ttgaagatta tctctag                                       507
```

<210> SEQ ID NO 54
<211> LENGTH: 155
<212> TYPE: PRT
<213> ORGANISM: Eucalyptus grandis

<400> SEQUENCE: 54

```
Met Ser Ser Ser Ser Glu Glu Pro Arg Asn Ala Lys Tyr Ala Gly
1               5                   10                  15

Val Arg Arg Arg Lys Trp Gly Lys Trp Val Ser Glu Ile Arg Val Pro
                20                  25                  30
```

Gly Thr Gln Glu Arg Leu Trp Leu Gly Ser Tyr Thr Ser Pro Glu Gly
            35                  40                  45

Ala Ala Val Ala His Asp Val Ala Ser Tyr Cys Leu Arg Gly Pro Ser
 50                  55                  60

Cys Leu Asp Lys Leu Asn Phe Pro Ser Leu Pro Pro Ser Ala Arg
 65                  70                  75                  80

Pro Gly Val Ser Pro Arg Ser Ala Gln Arg Ala Ala Ser Asp Ala Gly
                85                  90                  95

Met Ala Val Asp Ala Arg Tyr Ile Ala Arg Arg Ser Asp Glu Glu Ala
                100                 105                 110

Asp Arg Thr Ser Pro Gly His Arg Pro Glu Val Gly Trp Glu Cys Ala
                115                 120                 125

Gln Gly Asn Glu Ala Ser Ser Gly Thr Arg Gly Gly Arg Gly Gly Gly
            130                 135                 140

Asp Gly Leu Ser Ile Ser Val Asp Asp Tyr Leu
145                 150                 155

<210> SEQ ID NO 55
<211> LENGTH: 468
<212> TYPE: DNA
<213> ORGANISM: Eucalyptus grandis

<400> SEQUENCE: 55
atgagcagct cgtcgtccga ggagcccagg aacgccaagt acgccggggt ccgccggagg      60
aagtggggca gtgggtgtc ggagatccgg gtccccggca cgcaggagcg gctctggctc     120
ggctcctaca cctcccccga gggcgccgcc gtcgccacg acgtcgcctc ctactgcctc     180 cgcgggcct cctgcctcga caagctcaac ttccctcgc tgctgccgcc cagcgcgcgg     240
cccggcgtgt cgccgaggtc ggcgcagagg gccgcctcgg acgccggcat ggcggtcgac     300
gcgcggtaca tcgccaggag gtcggacgag aagcggaca ggacgagccc cggccaccga     360
ccagaggtcg gttgggagtg tgcgcaaggg aatgaggctt cttccgggac gcggggaggg     420
agaggaggag gtgatggttt gagcattcg gtggatgact acctgtga                  468

<210> SEQ ID NO 56
<211> LENGTH: 388
<212> TYPE: PRT
<213> ORGANISM: Populus trichocarpa

<400> SEQUENCE: 56

Met Pro Leu Ala Phe Glu Arg Gly Lys Val Asn Gln Ser Ile Glu Arg
 1               5                  10                  15

Lys Arg Asp Ser Val Leu Asp Gly Val Lys Asp Met Ala Val Glu Leu
                20                  25                  30

Met Met Gly Tyr Ser Gly Asp Ser Phe Ala Thr Lys Met Gln Glu Asn
            35                  40                  45

Asp Val Arg Glu Ala Ala Thr Ala Gly Ile Gln Ser Val Glu Glu Val
 50                  55                  60

Ile Lys Leu Leu Lys Gln Asn Gln Leu Glu Gln Gln Lys Gln
 65                  70                  75                  80

Tyr Tyr Gln Glu Leu Ser Ala Ala Ser Ser Ser Asn Leu Gly Thr
                85                  90                  95

Asp Asn Ile Met Ala Val Thr Asp Met Ala Val Asn Asn Phe Lys Lys
                100                 105                 110

Val Ile Ser Leu Leu Gly Arg Thr Thr Arg Thr Gly His Ala Arg Phe

```
            115                 120                 125
Arg Arg Ala Pro Val Ala Cys Pro Gln Gln Ile Gln Glu Pro
        130                 135                 140
Glu Pro Gly Pro Gln Gln Lys Gln Val Gln Glu Pro Val Pro
145                 150                 155                 160
Tyr Val Arg Ala Ile Asn Ser Gln Pro Thr Glu Gln Gly Ser Ala Phe
                    165                 170                 175
Arg Val Tyr Gln Pro Thr Pro Ile His Arg Leu Pro Pro Leu Pro His
                180                 185                 190
Asn Gln Gln Gln Lys Thr Leu Leu Val Thr Lys Asn Gly Leu Ser Asp
                195                 200                 205
Arg Asn Glu Met Ala Thr Thr Ile Asn Phe Ala Asn Ser Pro Thr Ile
210                 215                 220
Ser Ala Pro Ser Phe Leu Ser Ser Leu Thr Gly Glu Thr Asp Ser Phe
225                 230                 235                 240
Gln Cys Ser Lys Ser Ser Gly Phe Gln Phe Thr Gln Pro Ser Ala Gly
                    245                 250                 255
Lys Pro Pro Leu Ser Ser Ser Leu Lys Arg Lys Cys Asn Ser Met
                260                 265                 270
Asp Asp Ala Ala Leu Lys Cys Gly Ser Ser Ser Arg Cys His Cys
                275                 280                 285
Ser Lys Lys Ser Arg Lys Ser Arg Ile Lys Arg Val Val Arg Val Pro
290                 295                 300
Ala Ile Ser Ser Lys Met Ala Asp Ile Pro Pro Asp Asp Tyr Ser Trp
305                 310                 315                 320
Arg Lys Tyr Gly Gln Lys Pro Ile Lys Gly Ser Pro His Pro Arg Gly
                    325                 330                 335
Tyr Tyr Lys Cys Ser Ser Val Arg Gly Cys Pro Ala Arg Lys His Val
                340                 345                 350
Glu Arg Ala Leu Asp Asp Ser Met Met Leu Ile Val Thr Tyr Glu Gly
                355                 360                 365
Glu His Asn His Ser His Pro Ile Asp Glu Ala Pro Gly Ala Leu Val
                370                 375                 380
Leu Glu Ser Ser
385

<210> SEQ ID NO 57
<211> LENGTH: 1167
<212> TYPE: DNA
<213> ORGANISM: Populus trichocarpa

<400> SEQUENCE: 57
atgcctttgg catttgagag aggaaaggtc aatcaatcca tagagagaaa gagagattca      60
gtcttggatg gtgtaaaaga catggctgtg gagcttatga tggggtattc tggtgatagt     120
tttgctacaa aaatgcaaga gaatgatgtg agagaagccg caactgctgg gatacaaagc     180
gttgaggaag tcataaaact gctcaaacaa atcaactgg aacagcaaca aaaacaacaa      240
tactaccaag agttgtctgc agcctcttca agttccaatc ttggcacgga taatatcatg     300
gctgttactg atatggccgt gaacaatttc aaaaaggtta tttctttact gggtcgcacc     360
acaagaactg gccatgctcg atttagaaga gctcctgttg cctgccctcc tcaacaacaa     420
atacaagaac cagaaccagg accgcaacag caaaaacagc aagttcaaga gccagtacca     480
tatgttcgag caattaattc gcagccaaca gagcaaggct ctgcttttag agtttatcaa     540
```

```
ccgaccccaa ttcatcgtct ccctcctttg cctcacaatc agcaacaaaa gacactgctg    600
gttacgaaaa atggattatc agatcggaat gaaatggcta ctacgatcaa tttcgctaat    660
tcgccaacaa tatctgctcc ttctttcttg tcttctttaa caggggaaac tgatagcttc    720
cagtgttcta agtcttctgg gtttcagttt acccaacctt ctgctggtaa acctcctttg    780
tcctcttctt ctcttaagag aaagtgcaac tccatggatg atgctgctct caagtgtggc    840
tcttcttcta gtcgctgcca ctgctccaag aaaagcagga atcaagaat taaaagggtg    900 gttagagttc ctgcaattag tagtaagatg gcagatatcc cacctgatga ttattcctgg    960
agaaagtatg gccaaaagcc catcaaaggc tctcctcatc ccaggggata ctacaagtgc   1020
agtagcgtga gaggatgtcc ggcacgcaaa cacgtggaga gagctctaga tgactcgatg   1080
atgcttattg tgacctatga agggaacac aaccactctc atccaatcga tgaagcacct   1140
ggtgctcttg tccttgaatc atcttaa                                       1167
```

<210> SEQ ID NO 58
<211> LENGTH: 358
<212> TYPE: PRT
<213> ORGANISM: Populus trichocarpa

<400> SEQUENCE: 58

```
Met Ala Val Glu Leu Met Met Gly Tyr Ser Gly Asp Cys Phe Ala Thr
1               5                   10                  15

Lys Met Gln Glu Asn Ala Val Arg Glu Ala Ala Ala Ser Gly Ile Gln
            20                  25                  30

Ser Val Glu Glu Val Ile Lys Leu Leu Lys Gln Asn Gln Leu Glu Gln
        35                  40                  45

Gln His Tyr Gln Glu Leu Ser Ala Ala Ser Ser Ser Ser Asn Leu Gly
    50                  55                  60

Thr Asp Asn Ile Met Thr Val Thr Asp Met Ala Val Asn Asn Phe Lys
65                  70                  75                  80

Lys Val Ile Ser Leu Leu Gly Arg Thr Thr Arg Thr Gly His Ala Arg
                85                  90                  95

Phe Arg Arg Ala Pro Asp Thr Pro Thr Gln Gln Gln Ile Arg Glu
            100                 105                 110

Glu Pro Glu Ser Gln Gln Glu Lys Arg Gln Val Gln Glu Pro Gly Pro
        115                 120                 125

Ser Val Arg Ala Ile Asn Ser Gln Pro Thr Glu Gln Ala Ser Ala Phe
    130                 135                 140

Arg Val Tyr Gln Pro Thr Pro Ile His Arg Leu Pro Pro Leu Pro His
145                 150                 155                 160

Asn Gln Gln Gln Lys Ser Pro Leu Leu Val Thr Lys Lys Gly Leu Ser
                165                 170                 175

Asp Arg Asn Glu Ile Pro Thr Thr Ile Asn Phe Ser Asn Ser Pro Ser
            180                 185                 190

Ile Ser Ser Ala Thr Ser Phe Met Ser Ser Leu Thr Gly Glu Thr Asp
        195                 200                 205

Gly Phe Gln Arg Ser Met Pro Ser Arg Phe His Phe Thr Gln Pro Ser
    210                 215                 220

Ala Gly Lys Pro Pro Leu Ser Ser Ser Leu Lys Arg Lys Cys Asn
225                 230                 235                 240

Ser Met Asp Asp Ala Ala Leu Lys Cys Gly Ser Ser Ser Gly Arg Cys
                245                 250                 255

His Cys Ser Lys Lys Ser Arg Lys Ser Arg Ala Lys Arg Val Val Arg
```

```
            260                 265                 270
Val Pro Ala Ile Ser Asn Lys Met Ala Asp Ile Pro Pro Asp Asp Tyr
        275                 280                 285

Ser Trp Arg Lys Tyr Gly Gln Lys Pro Ile Lys Gly Ser Pro His Pro
        290                 295                 300

Arg Gly Tyr Tyr Lys Cys Ser Ser Val Arg Gly Cys Pro Ala Arg Lys
305                 310                 315                 320

His Val Glu Arg Ala Leu Asp Asp Ser Met Met Leu Ile Val Thr Tyr
            325                 330                 335

Glu Gly Glu His Asn His Ser His Pro Phe Asp Asp Ala Pro Ala Ala
            340                 345                 350

Leu Val Pro Glu Ser Ser
        355

<210> SEQ ID NO 59
<211> LENGTH: 1077
<212> TYPE: DNA
<213> ORGANISM: Populus trichocarpa

<400> SEQUENCE: 59
atggctgtgg agcttatgat ggggtattct ggtgattgtt ttgctacaaa aatgcaagag      60
aatgccgtga gggaagcggc agcttctggg atacaaagcg tcgaggaagt cataaaattg     120
ctcaaacaaa atcaacttga acagcaacac taccaagagt tatctgcagc ctcttcaagt     180
tccaatcttg gcacggataa tatcatgact gttactgata tggcggtgaa caacttcaaa     240
aaggtcatct ctttactggg tcgcaccaca agaactggcc acgctcgatt tagaagagct     300
cctgataccc cccctactca acaacaaata cgagaagaac cagaatcgca caagaaaaa      360 cggcaagttc aagagcctgg accatctgtt cgagcaatta ttcgcagcc aacagagcaa      420 gcctctgctt ttagagttta tcaaccgacc ccaattcatc gtctccctcc tttacctcac     480
aatcagcagc aaaagagccc tcttctggtt acaaaaaaag ggttgtcaga tcggaatgaa     540
attcctacca caatcaattt ctctaattcg ccatcaattt cttctgccac ttctttcatg     600
tcttctctta caggggaaac tgatggcttc agcgttcta tgccttctag gtttcatttt      660
acccaacctt ctgctggtaa accccctttg tcctcttctt ctcttaagag aaagtgcaac     720
tccatggatg atgctgctct caagtgtggc tcttcttctg gtcgctgcca ttgctccaag     780
aaaagcagaa aatcaagggc taaaagagtg gtcagagttc ctgcaattag caataagatg     840
gctgatattc cacctgatga ttattcctgg agaaagtatg gtcaaaagcc catcaaaggc     900
tctcctcatc caaggggata ttacaagtgc agcagcgtga gaggatgtcc agcacgcaaa     960
catgtggaga gagctctaga tgactccatg atgcttattg tgacctatga aggggaacac    1020
aatcactctc atccattcga tgatgcacct gctgctctcg tccctgaatc atcttaa       1077

<210> SEQ ID NO 60
<211> LENGTH: 437
<212> TYPE: PRT
<213> ORGANISM: Eucalyptus grandis

<400> SEQUENCE: 60

Met Pro Arg Gly Gly Lys Ala Arg Gly Gln Ile Tyr Leu Tyr Val Leu
1               5                   10                  15

Arg Pro Leu Ser Ser Arg Leu Leu Pro Leu Leu Leu Ile Asp Pro Pro
            20                  25                  30

Arg Ala Arg Leu Leu Leu His Met Cys Ser Phe Ser Ser Arg Ser Arg
```

```
                35                  40                  45
Glu Arg Gly Met Ala Val Glu Leu Met Met Gly Tyr Gly Ser Gly Gly
 50                  55                  60

Asp Gly Gly Val Gly Phe Ala Val Lys Lys Glu Thr Ala Leu Arg
 65                  70                  75                  80

Glu Ala Ala Ser Ala Gly Ile Gln Ser Val Glu Asn Leu Ile Lys Met
                 85                  90                  95

Leu Ser Ser Ser Pro Ser Ser Pro Ser Gly Gly Val Gly Gly Gly
                100                 105                 110

Arg Arg Ala Gly Gln Asp Ser Pro Ser Pro Ser Ser Ser Ser Gly
                115                 120                 125

Gly Pro Ser Pro Ala Val Asp Ile Glu Ala Ala Thr Asp Ala Ala Val
130                 135                 140

Asn Lys Phe Arg Lys Val Ile Ser Leu Leu Asp Arg Ala Arg Thr Gly
145                 150                 155                 160

His Ala Arg Phe Arg Arg Ala Pro Val Ala Asp Pro Leu Pro Glu Asn
                165                 170                 175

Arg Glu Ala Phe Thr Pro Val Arg Pro Ala Glu Asn Pro Val Gly Ser
                180                 185                 190

Ala Arg Leu Gln Ser Ala Glu Pro Val Ser Ala Phe Lys Val Tyr Cys
                195                 200                 205

Pro Thr Pro Ile Gln Arg Leu Pro Pro Leu Pro His Asn His His
210                 215                 220

His His Asn His Asn His His His His His Gln Val Gln Asn
225                 230                 235                 240

Pro Ile Pro Val Val Pro Lys Val Glu Arg Lys Glu Ser Ala Thr Pro
                245                 250                 255

Thr Thr Ile Asn Phe Ser Thr Ser Pro Pro Ile Ser Ala Ala Asn Ser
                260                 265                 270

Ser Phe Leu Ser Ser Leu Thr Gly Glu Thr Asp Ser Val Gln Arg Ser
                275                 280                 285

Phe Ser Ser Ala Gly Phe Gln Met Thr His His Leu Ser Gln Val Ser
                290                 295                 300

Ser Ala Asp Lys Pro Pro Leu Ser Tyr Ser Leu Lys Arg Lys Cys Ser
305                 310                 315                 320

Ser Met Asp Asp Ala Ala Leu Lys Cys Gly Ser Ser Gly Lys Cys
                325                 330                 335

His Cys Ser Lys Lys Arg Lys Ser Arg Leu Lys Arg Val Val Arg Val
                340                 345                 350

Pro Ala Val Ser Ser Lys Met Ala Asp Ile Pro Pro Asp Asp Phe Ser
                355                 360                 365

Trp Arg Lys Tyr Gly Gln Lys Pro Ile Lys Gly Ser Pro His Pro Arg
                370                 375                 380

Gly Tyr Tyr Lys Cys Ser Ser Val Arg Gly Cys Pro Ala Arg Lys His
385                 390                 395                 400

Val Glu Arg Ala Leu Asp Asp Pro Gly Met Leu Ile Val Thr Tyr Glu
                405                 410                 415

Gly Glu His Asn His Ser Gln Ser Val Ala Asp Val Lys Ala Pro Leu
                420                 425                 430

Val Leu Glu Ser Ser
                435

<210> SEQ ID NO 61
```

-continued

```
<211> LENGTH: 1314
<212> TYPE: DNA
<213> ORGANISM: Eucalyptus grandis

<400> SEQUENCE: 61
atgccaagag gaggaaaggc gaggggggcag atctatctct atgtcctgcg acccctttcc      60
tctcgtcttc ttcccttct tcttatagac cccccaggg ctcggcttct tcttcatatg       120
tgttccttct ctagccgctc cagggagaga ggtatggccg tggagctgat gatgggttac      180
gggagcggcg gcgacggcgg cgttggcttc gcggtgaaga aggaggagac cgccctccgg      240
gaggccgcct ccgccggcat acagagcgtc gagaatctca tcaagatgct gtcttcctcg      300
ccttcctccc cctccggcgg cggcgtgggc ggcgggcggc gggccgggca ggactcgccg      360
tcgccgtcgt cgtcctcttc cggggggccg agccccgccg tggacatcga gccgccacg      420 gacgccgccg tcaacaagtt caggaaggtc atctcgctgc tcgacagggc gaggaccggc      480
cacgcccgct tcaggagagc ccctgtcgcc gacccctcc ctgagaaccg ggaagcgttt       540
actccggtcc gaccggcgga gaacccggtc gggagcgccc ggttgcagag cgccgagccg      600
gtctcggctt tcaaggtcta ctgcccgacg ccgatccagc ggctgccgcc cctgcctcac      660
aaccaccacc accaccacaa ccacaaccac caccaccacc accaccaggt ccaacagaac      720
cccatcccgg tggttccgaa ggtggagaga aaggagtccg cgacgccgac gactataaat      780
ttctccacct cgccgccgat ctcggctgcg aactcctcgt tcctgtcctc actgaccggg      840
gagacggaca gcgtgcagag atccttctcc tctgcagggt ttcagatgac gcaccatcta      900
tcgcaggttt cgtcggcgga caagcctccc ttgtcgtact cactgaagag gaagtgcagt      960
tccatggacg acgcggctct gaagtgcggg tcgtcctccg gcaagtgcca ttgctcgaag     1020
aagaggaaat cgagattgaa gagagtggtt agagtcccag cggtcagttc gaaaatggcg     1080
gacatcccac cagatgattt ctcatggagg aagtatggac agaagcccat caaaggctcc     1140
cctcatccaa ggggctatta caagtgcagc agcgtaagag gatgcccggc gaggaagcac     1200
gtggagcggg ccctggacga cccgggcatg ctcatcgtga cctacgaggg cgaacacaac     1260
cactcccagt ccgtcgccga cgtgaaggcg ccgctggtcc tggaatcttc ctag           1314
```

```
<210> SEQ ID NO 62
<211> LENGTH: 353
<212> TYPE: PRT
<213> ORGANISM: Arabidopsis thaliana

<400> SEQUENCE: 62

Met Thr Val Glu Leu Met Met Ser Ser Tyr Ser Gly Gly Gly Gly Gly
1               5                   10                  15

Gly Asp Gly Phe Pro Ala Ile Ala Ala Ala Lys Met Glu Asp Thr
            20                  25                  30

Ala Leu Arg Glu Ala Ala Ser Ala Gly Ile His Gly Val Glu Glu Phe
        35                  40                  45

Leu Lys Leu Ile Gly Gln Ser Gln Gln Pro Thr Glu Lys Ser Gln Thr
    50                  55                  60

Glu Ile Thr Ala Val Thr Asp Val Ala Val Asn Ser Phe Lys Lys Val
65                  70                  75                  80

Ile Ser Leu Leu Gly Arg Ser Arg Thr Gly His Ala Arg Phe Arg Arg
                85                  90                  95

Ala Pro Ala Ser Thr Gln Thr Pro Phe Lys Gln Thr Pro Val Val Glu
            100                 105                 110
```

```
Glu Glu Val Glu Val Glu Lys Lys Pro Glu Thr Ser Val Leu
            115                 120                 125
Thr Lys Gln Lys Thr Gln Tyr His Gly Gly Ser Ala Phe Arg
        130                 135                 140
Val Tyr Cys Pro Thr Pro Ile His Arg Arg Pro Pro Leu Ser His Asn
145                 150                 155                 160
Asn Asn Asn Asn Gln Asn Gln Thr Lys Asn Gly Ser Ser Ser Ser
                165                 170                 175
Pro Pro Met Leu Ala Asn Gly Ala Pro Ser Thr Ile Asn Phe Ala Pro
            180                 185                 190
Ser Pro Pro Val Ser Ala Thr Asn Ser Phe Met Ser Ser His Arg Cys
        195                 200                 205
Asp Thr Asp Ser Thr His Met Ser Ser Gly Phe Glu Phe Thr Asn Pro
            210                 215                 220
Ser Gln Leu Ser Gly Ser Arg Gly Lys Pro Pro Leu Ser Ser Ala Ser
225                 230                 235                 240
Leu Lys Arg Arg Cys Asn Ser Ser Pro Ser Ser Arg Cys His Cys Ser
                245                 250                 255
Lys Lys Arg Lys Ser Arg Val Lys Arg Val Ile Arg Val Pro Ala Val
            260                 265                 270
Ser Ser Lys Met Ala Asp Ile Pro Ser Asp Glu Phe Ser Trp Arg Lys
        275                 280                 285
Tyr Gly Gln Lys Pro Ile Lys Gly Ser Pro His Pro Arg Gly Tyr Tyr
            290                 295                 300
Lys Cys Ser Ser Val Arg Gly Cys Pro Ala Arg Lys His Val Glu Arg
305                 310                 315                 320
Ala Leu Asp Asp Ala Met Met Leu Ile Val Thr Tyr Glu Gly Asp His
                325                 330                 335
Asn His Ala Leu Val Leu Glu Thr Thr Thr Met Asn His Asp Lys Thr
            340                 345                 350
Leu

<210> SEQ ID NO 63
<211> LENGTH: 1062
<212> TYPE: DNA
<213> ORGANISM: Arabidopsis thaliana

<400> SEQUENCE: 63
atgactgttg agctgatgat gagcagctac agcggcggcg gaggaggagg tgatggtttt      60
cctgcaatcg ccgcggcggc gaaaatggaa gataccgctt tgagagaagc tgcttctgca     120
gggattcacg gtgtggagga gtttcttaaa ctgatcggtc aaagtcaaca accaacggag     180
aagagtcaga cggagataac cgcggtgact gacgtcgccg ttaacagctt caagaaggtc     240
atttctctac tcggtagatc tagaaccgga cacgctagat tcagacgagc tcccgcgtca     300
acgcaaacgc cgtttaagca aacgccggtg gttgaggagg aggtggaggt ggaggagaag     360
aagccagaaa caagctccgt gttaacaaaa cagaaaacag agcaatatca cggtggtgga     420
tctgcgttta gagtttattg tccaacacca attcatcgtc gtcctcctct atcacacaat     480
aacaacaaca atcagaatca aacaaagaac ggttcgtctt cttcatctcc tccgatgctc     540
gcaaacggag caccgtcaac gataaacttt gcgccgtcac caccagtctc agcgacgaac     600
tcattcatgt cttctcatag atgtgacacc gatagtactc acatgtcatc aggattcgag     660
ttcactaacc catctcagct ctctggttcg agaggtaaac ctcctttatc atcagcttcg     720
```

-continued

```
ttgaagagaa gatgtaattc atctccctca agccgttgcc attgctccaa gaaaaggaaa    780
tcaagagtaa aaagagtgat tagagttcca gcagtaagta gcaaaatggc tgatatacca    840
tcagatgagt tttcatggag aaaatatggt caaaaaccaa tcaaggctc  tcctcatcct    900 cggggatatt acaagtgcag cagtgtaaga ggttgtccgg cgcgtaagca tgtggagcgt    960
gcactagatg atgcgatgat gctaatcgtg acgtacgaag gagaccacaa ccatgctttg   1020
gttctcgaga cgacgacgat gaatcatgac aaaactcttt ag                     1062
```

```
<210> SEQ ID NO 64
<211> LENGTH: 572
<212> TYPE: PRT
<213> ORGANISM: Populus trichocarpa

<400> SEQUENCE: 64
```

```
Met Glu Arg Asp Lys Leu Phe Val Ser Glu Gly Ala Asn Thr Ala Ala
1               5                   10                  15

Thr Ile Trp Asn Ser Cys Ser Phe Gly Met Glu Met Gln Ala Asn Glu
            20                  25                  30

Leu Ser Cys Gly Pro Glu Lys Leu Ala Asn Cys Phe Leu Asn Pro Asn
        35                  40                  45

Trp Asp Asn Ser Leu Asp Gln Ser Asp Pro Phe Glu Ser Ala Leu Ser
    50                  55                  60

Ser Ile Val Ser Pro Val Ala Ser Gly Ala Asn Ala Asn Ala Asn
65                  70                  75                  80

Ala Ile Pro Asn Ala Gly Val Gly Gly Asp Ser Leu Met Ile Arg Glu
                85                  90                  95

Leu Ile Gly Arg Leu Gly Asn Ile Cys Asn Ser Gly Asp Ile Ser Leu
            100                 105                 110

Gln Ser Phe Val Asn Asn Asn Asn Ser Thr Asn Thr Ser Cys Tyr
        115                 120                 125

Ser Thr Pro Met Asn Ser Pro Pro Lys Leu Asn Leu Ser Met Met Asp
    130                 135                 140

Ser Gln Met Arg Gly Asn Leu Pro Ile Pro Gly Asn Ser Val Val Lys
145                 150                 155                 160

His Pro Gly Leu Ala Pro Phe Pro Ala Asp Phe Val Glu Arg Ala Ala
                165                 170                 175

Arg Tyr Ser Cys Phe Gly Ser Asn Asn Pro Gly Ile Asn Lys Gln
            180                 185                 190

Phe Gly Leu Asn Glu Ser Glu Leu Ile Asn Arg Leu Met Pro Arg Val
        195                 200                 205

Glu Pro Gly Lys Leu Ser Arg Val Ser Ser Asn Asn Ser Met Lys Val
    210                 215                 220

Thr Val Ser Gln Ala Asn Val Gln Glu Ser Asn Lys Ser Ser Pro Gln
225                 230                 235                 240

Asp Gly Ser Leu Asn Ser Glu Lys Lys Phe Ser Arg Gln Ser Arg Pro
                245                 250                 255

Thr Thr Ser Glu Asn Gly Asp Ser Arg Glu Glu Ser Ser Leu Ser Glu
            260                 265                 270

Gln Val Pro Gly Gly Lys Leu Ser Met Lys Ser Gln Asn Asp Ala Asn
        275                 280                 285

Ser Arg Lys Arg Lys Ser Ile Pro Arg Gly Lys Ala Lys Glu Thr Pro
    290                 295                 300

Ser Ser Ser Pro Ser Ala Ser Asp Val Lys Val Ala Ala Glu Asn Asp
305                 310                 315                 320
```

Glu Ser Lys Ala Lys Arg Ser Lys Ser Asp Glu Thr Asn Gly Ser Asp
                325                 330                 335

Lys Asp Thr Ala Lys Glu Lys Glu Glu Asn Gly Asn Gln Lys Gln
                340                 345                 350

Asn Lys Asn Asn Ser Lys Pro Pro Glu Pro Pro Lys Asp Tyr Ile His
                355                 360                 365

Val Arg Ala Arg Arg Gly Gln Ala Thr Asp Ser His Ser Leu Ala Glu
    370                 375                 380

Arg Val Arg Arg Glu Lys Ile Ser Glu Arg Met Lys Phe Leu Gln Asp
385                 390                 395                 400

Leu Val Pro Gly Cys Asn Lys Val Thr Gly Lys Ala Val Met Leu Asp
                405                 410                 415

Glu Ile Ile Asn Tyr Val Gln Ser Leu Gln Arg Gln Val Glu Phe Leu
                420                 425                 430

Ser Met Lys Leu Ser Ser Val Asn Pro Arg Met Glu Ile Asn Met Glu
                435                 440                 445

Thr Leu Leu Ser Lys Asp Ile Phe Gln Ser Arg Gly Ser Met Pro His
    450                 455                 460

Ser Leu Tyr Pro Leu Asp Ala Ser Thr Pro Val Phe Pro Tyr Gly Tyr
465                 470                 475                 480

Gln Ser Gln Gln Gly Leu Ala Leu Gln Asn Gly Met Pro Ser Asn Ala
                485                 490                 495

Glu Thr Gln Phe Ser Met Asn Pro Leu Asn Ala Ala Leu Arg Arg Asn
                500                 505                 510

Pro Ser Met His Leu Pro His Leu Asp Gly Phe Gly Asp Pro Ala Ala
                515                 520                 525

Leu Gln Leu Glu Phe Tyr Ser Ser Gly Leu Ser His Val Gly Arg Arg
    530                 535                 540

Pro Ser Lys Cys Cys Ala Asp Gly Ile Trp Ser Glu Ser Ser Gly Glu
545                 550                 555                 560

Leu Ser Arg Leu Ser Ala Leu Asn Ser His Glu Asn
                565                 570

<210> SEQ ID NO 65
<211> LENGTH: 1719
<212> TYPE: DNA
<213> ORGANISM: Populus trichocarpa

<400> SEQUENCE: 65
atggaaagag ataagttgtt tgtgagcgag ggagccaaca cagcagcaac catttggaat      60
tcttgcagtt ttggaatgga atgcaagcc aatgagctga gttgcggtcc agagaaactt     120
gccaattgct ttctcaatcc caattgggac aactcattgg atcagagcga tcccttgag     180 tctgctttga gctccattgt ctcatcacct gttgcatccg gtgccaacgc aaacgccaac    240
gccattccta tgctggcgt tggtggtgac agtcttatga ttagaaact tattggaaga     300 ctaggaaaca tttgcaattc tggagacatt tcactacaat cttttgttaa caataataac    360
aatagcacta acacttcttg ctatagtacc ccaatgaatt cccctccaaa gctgaatctc    420
tcgatgatgg attcacaaat gagaggaaat ctgccaattc tggaaacag cgtagtaaag    480 catccaggtt tagcaccatt tccagctgat tttgtagaga gggctgcacg atattcttgc    540
tttggtagca acaatcctgg aggcatcaat aaacaattcg gattgaatga atccgaattg    600
attaataggt tgatgccacg agtagaacct ggtaagctct cgagagtttc gagtaacaat    660

```
tcaatgaagg tcactgtatc gcaagcaaat gttcaagaaa gcaacaagag ctcaccccag    720
gatgggagtt tgaattctga aaagaaattc agtaggcagt caaggcctac aacatcagag    780
aatggagatt ccagggaaga atcttcattg tctgagcagg tcccaggtgg aaattgagc    840
atgaaatccc agaatgacgc caattccagg aaaagaaaat caattcccag aggaaaagcc    900
aaagaaactc cctcttcatc tccatctgct tctgatgtca aggttgcagc agagaatgat    960
gaatcgaagg caaaagaag caatcggat gaaactaatg gcagtgacaa ggatacagca   1020
aaggaaaagg aagaagaaaa tggaaatcag aaacagaaca aaaataattc aaagccgcca   1080
gagccaccaa aggattatat ccatgtcaga gccagaaggg gtcaggctac agatagccac   1140
agtcttgctg aaagagttag aagagagaaa atcagtgaaa gaatgaagtt cctccaggat   1200
cttgttcccg gatgcaataa ggttactggg aaagcagtga tgcttgacga gattataaac   1260
tatgtacagt cattgcagcg ccaggttgag tttctgtcaa tgaagttgtc atctgtgaat   1320
ccgaggatgg agatcaacat ggaaactttg ttgtccaagg atattttcca atcccgtgga   1380
tctatgccac atagtcttta tccattagat gcctccacgc cggtattccc ttatggttac   1440
caatcccagc aagggttagc cctgcaaaat ggcatgccaa gcaatgccga aacccagttc   1500
tctatgaacc cattaaatgc tgcgttgcgg cgaaacccga gcatgcattt gccacacctt   1560
gatggtttcg gtgatcctgc tgctcttcag ctagaatttt attcttcagg cctcagccat   1620
gtgggaagac gaccttcaaa gtgttgtgca gatgggatat ggtcagaatc atcaggagag   1680
ctttcaaggc tcagtgccct caactcacat gaaaattga                          1719
```

<210> SEQ ID NO 66
<211> LENGTH: 567
<212> TYPE: PRT
<213> ORGANISM: Populus trichocarpa

<400> SEQUENCE: 66

Met Glu Lys Asp Lys Leu Phe Met Ser Glu Gly Ala Ser Thr Ala Ala
1               5                   10                  15

Pro Ile Trp Asn Ser Cys Ser Phe Gly Met Glu Met Gln Thr Asp Glu
            20                  25                  30

Leu Asn Cys Ser Ser Gly Gln Leu Ala Asn Cys Phe Leu Asn Pro Asn
        35                  40                  45

Trp Asp Asn Leu Leu Asp Gln Ser Asp Pro Phe Glu Ser Ala Leu Ser
    50                  55                  60

Ser Ile Val Ser Ser Pro Val Ala Ser Val Asn Ala Asn Val Ile
65                  70                  75                  80

Ser Asn Ala Gly Val Gly Gly Asp Ser Val Leu Ile Arg Glu Leu Ile
            85                  90                  95

Gly Arg Leu Gly Asn Ile Cys Asn Ser Gly Glu Met Ser Pro Gln Ser
        100                 105                 110

Tyr Ile Asn Asn Asn Asn Ser Thr Asn Thr Ser Cys Tyr Ser Thr
        115                 120                 125

Pro Leu Asn Ser Pro Lys Leu Ser Ile Ser Met Met Asp Ser Gln
130                 135                 140

Met Arg Gly Asn Leu Pro Ile Leu Gly Asn Ser Leu Val Asn His Pro
145                 150                 155                 160

Ser Leu Ala Pro Phe Pro Ala Asp Pro Gly Phe Val Glu Arg Ala Ala
            165                 170                 175

Arg Tyr Ser Cys Phe Gly Ser Asn Asn Leu Gly Gly Leu Asn Gly Gln
        180                 185                 190

Phe Gly Leu Asn Glu Ser Glu Leu Ile Asn Arg Met Met Pro Arg Val
            195                 200                 205

Glu Pro Gly Lys Leu Ser Arg Val Ser Ser Asn Ser Met Lys Val
210                 215                 220

Ala Gly Ser Gln Ala Asn Val Gln Glu Ser Asn Lys Ser Ser Pro Gln
225                 230                 235                 240

Asp Gly Asn Leu Asn Ser Asp Lys Lys Phe Ser Arg Leu Ser Arg Pro
            245                 250                 255

Ser Thr Pro Glu Asn Gly Asp Ser Arg Glu Glu Ser Ser Val Ser Glu
        260                 265                 270

Gln Ile Pro Gly Gly Glu Leu Ser Met Lys Ser Gln Thr Asp Ala Asn
            275                 280                 285

Ser Arg Lys Arg Lys Ser Ile Pro Arg Gly Lys Ala Lys Glu Thr Pro
290                 295                 300

Ser Pro Ser Pro Ser Ala Ser Asp Val Lys Val Ala Ala Glu Asn Asp
305                 310                 315                 320

Glu Ser Ser Ala Lys Lys Ser Lys Ser Glu Asp Thr Asn Gly Ser Asp
            325                 330                 335

Lys Asp Ser Ala Lys Ala Met Glu Glu Glu Asn Gly Asn His Lys Gln
        340                 345                 350

Lys Lys Asp Asn Ser Asn Pro Pro Glu Pro Pro Lys Asp Tyr Ile His
            355                 360                 365

Val Arg Ala Arg Arg Gly Gln Ala Thr Asp Ser His Ser Leu Ala Glu
        370                 375                 380

Arg Val Arg Arg Glu Lys Ile Ser Glu Arg Met Lys Phe Leu Gln Asp
385                 390                 395                 400

Leu Val Pro Gly Cys Asn Lys Val Thr Gly Lys Ala Val Met Leu Asp
            405                 410                 415

Glu Ile Ile Asn Tyr Val Gln Ser Leu Gln Arg Gln Val Glu Phe Leu
        420                 425                 430

Ser Met Lys Met Ala Thr Val Asn Pro Lys Met Glu Ile Asn Met Glu
            435                 440                 445

Thr Phe Leu Ser Lys Asp Ile Phe Gln Ser Arg Gly Ser Met Pro His
        450                 455                 460

Gly Leu Tyr Pro Leu Asp Ser Ser Thr Pro Ala Phe Pro Tyr Gly Tyr
465                 470                 475                 480

Gln Ser Gln Gln Gly Leu Ala Leu Gln Asp Gly Met Ser Arg Asn Ala
            485                 490                 495

Glu Ser Gln Phe Ser Met Asn Pro Leu Asn Ala Ala Leu Arg Arg Ser
        500                 505                 510

Ser Ser Met Gln Leu Pro Ala Leu Asp Gly Phe Gly Asp Ala Ser His
            515                 520                 525

Gln Ala Ser Ala Met Trp Gln Asp Asp Leu Gln Ser Val Val Gln Met
530                 535                 540

Gly Tyr Gly Gln Asn Gln Gln Asp Phe Gln Gly Ser Val Pro Pro
545                 550                 555                 560

Thr Gln Met Lys Ile Glu Leu
                565

<210> SEQ ID NO 67
<211> LENGTH: 1704
<212> TYPE: DNA
<213> ORGANISM: Populus trichocarpa -continued

<400> SEQUENCE: 67

```
atggaaaaag acaagttgtt tatgagcgag ggagccagca cagcagctcc catttggaat      60
tcttgcagtt ttggaatgga aatgcaaacc gatgagctga attgcagttc agggcaactt     120
gccaattgct ttctcaatcc caattgggac aacttattgg atcagagcga tcccttttgag    180
tctgctttga gctccattgt ctcatctcca gtggcatcca gtgtcaatgc caacgttatt     240
tctaatgctg gcgttggtgg tgacagtgtt ttgatcagag aacttattgg aagactagga     300
aacatttgca attccggcga gatgtctcca caatcctaca ttaacaacaa taacaacagc     360
accaacactt cttgttatag taccccattg aattcccctc caaagctgag tatttcaatg     420
atggattcac agatgagagg aaatctgcca attcttggaa acagcttagt aaaccatcca     480
agtttagcac catttcctgc tgaccctgga tttgtagaga gggctgctcg atattcttgc     540
tttggaagca acaatcttgg aggcctaaat ggacaattcg gattgaatga atcagaattg     600
atcaatagga tgatgccccg agtagaacct ggtaagctgt cgagagtttc gagtaacaat     660
tcaatgaagg tcgctggatc gcaagcaaat gttcaagaaa gcaataagag ctcacccccag   720
gatgggaatt tgaattctga taagaaattc agtcggttgt caagaccttc aacaccagag     780
aatggagatt ccagggagga atcttcagtg tccgagcaga tcccgggtgg ggaattgagc    840
atgaaatccc agactgatgc caattccagg aaaagaaaat caattcccag aggaaaagcc    900
aaagaaactc cctctcccctc tccctctgct tctgatgtca aggttgcagc agagaatgat   960
gaatcgagtg caaaaaaaag caaatcagag gacactaatg ggagtgacaa ggattcagca   1020
aaggccatgg aagaagaaaa tggaaatcac aaacagaaaa aagacaattc aaacccgcca   1080
gagccaccaa aggactatat ccatgtcaga gccagaaggg gtcaggctac agatagccac   1140
agtcttgctg aaagagttag gagagaaaaa atcagcgaaa gaatgaagtt tcttcaggat   1200
cttgttcctg gatgcaataa ggttactggg aaagcagtga tgcttgatga gattataaac   1260
tatgtgcagt cattacagcg ccaggttgag tttctgtcaa tgaagatggc aactgtgaac   1320
ccgaagatgg aaattaacat ggaaactttc ttgtccaagg atattttcca atcccgtgga   1380
tccatgccac atggtctttta tccattagat tcctccacgc cggcattccc ttatggttac   1440
caatcccagc aagggttagc cctacaagat ggcatgtcca ggaatgcaga atcccagttc   1500
tctatgaacc cattaaatgc tgcattgcgg cgaagctcga gtatgcagtt gcctgccctt   1560
gatggctttg gtgatgcttc tcatcaggcc tcagcaatgt ggcaagatga tcttcaaagt   1620
gttgtgcaga tgggatatgg tcagaatcag cagcaggact ttcaaggctc agtgccacca   1680
actcagatga aaattgagct atga                                           1704
```

<210> SEQ ID NO 68
<211> LENGTH: 531
<212> TYPE: PRT
<213> ORGANISM: Eucalyptus grandis

<400> SEQUENCE: 68

```
Met Glu Gly Ser Ser Thr Pro Leu Thr Gln Asn Ser Ser Thr Phe Gly
1               5                   10                  15

Ile Gly Ile His Pro Asn Asp Gln Leu Pro Asn Cys Phe Leu Val Ala
            20                  25                  30

Gly Trp Glu Asp Ser Leu Asp Gln Gly Asp Pro Phe Glu Ser Ala Leu
        35                  40                  45

Ser Ser Ile Val Ser Ser Pro Val Ala Pro His Ala Gly Glu Gly Glu
    50                  55                  60
```

```
Ala Gly Met Ile Arg Glu Leu Ile Gly Arg Leu Gly Ser Ile Cys Asp
 65                  70                  75                  80

Ser Gly Gln Ala Ser Pro Gly Ser Tyr Asn His Ser Thr Thr Asn Thr
                 85                  90                  95

Pro Cys Tyr Ser Thr Pro Leu Asn Ser Pro Pro Glu Leu Ser Leu Ser
            100                 105                 110

Met Ala Asp Gln Leu Ala His Gly Gly Phe Pro Ala Pro Gly Ser His
        115                 120                 125

Phe Pro Gly His Pro Ser Phe Val Ser Val Met Ala Asp Pro Gly Phe
    130                 135                 140

Ala Glu Arg Ala Ala Arg Leu Ser Cys Phe Gly Pro Arg Asn Val Asn
145                 150                 155                 160

Ala Ala Asn Leu Asn Gly Gly Leu Gly Leu Asn Ala Ser Glu Phe Leu
                165                 170                 175

Gly Lys Gln Ala Asn Lys Leu Asp Ser Gly Arg Phe Cys Arg Val Pro
            180                 185                 190

Ser Ser Gln Ser Leu Arg Ala Asn Val Gly Ser Gln Ile Cys Ala Gln
        195                 200                 205

Gly Asn Glu Arg Ser Phe Leu Gln Pro Gly Val Ser Ile Ser Thr Pro
    210                 215                 220

Glu Asn Gly Glu Met Gly Glu Ser Arg Glu Gly Ser Ile Ser Glu
225                 230                 235                 240

Gln Val Thr His Gly Glu Met Arg Ala Asn Gly Gln Ile Asp Val Asn
                245                 250                 255

Ser Arg Lys Arg Lys Pro Ile Leu Lys Ala Lys Gly Arg Asn Ser Ala
            260                 265                 270

Val Ser Pro Gln Ser Ala Lys Asp Ser Glu Val Pro Met Glu Asn Glu
        275                 280                 285

Glu Pro Ile Thr Lys Lys Ile Lys Pro Ala Glu Thr Asp Gly Asn Glu
    290                 295                 300

Lys Asp Ala Ala Lys Gly Asp Gln Lys Gln Ser Lys Glu Asn Ser Lys
305                 310                 315                 320

Met Ala Glu Pro Gln Lys Asp Tyr Ile His Val Arg Ala Arg Arg Gly
                325                 330                 335

Gln Ala Thr Asp Ser His Ser Leu Ala Glu Arg Val Arg Arg Glu Lys
            340                 345                 350

Ile Ser Leu Arg Met Lys Ala Leu Gln Asp Leu Val Pro Asn Cys Asn
        355                 360                 365

Lys Val Thr Gly Lys Ala Met Met Leu Asp Glu Ile Ile Asn Tyr Val
    370                 375                 380

Gln Ser Leu Gln Arg Gln Val Glu Leu Leu Ser Met Lys Leu Ser Thr
385                 390                 395                 400

Leu Asn Pro Thr Val Asp Phe Asn Leu Glu Ala Phe Leu Ser Lys Asp
                405                 410                 415

Ile Leu His Pro Gln Gly Pro Leu Pro Asn Ser Leu Tyr Pro Val Asp
            420                 425                 430

Ser Ser Gly Ser Met Leu Tyr Gly Tyr Gln Pro Pro Gln Gly Leu Met
        435                 440                 445

Pro Met Pro Ser Val Val Ser Ser Asn Met Asp Ala Gln Phe Pro Val
    450                 455                 460

Asn Phe Leu Asn Ser Gly Ile His Arg Asp Ala Ser Leu Asn Leu Pro
465                 470                 475                 480
```

Leu Cys Val Asp Asn Tyr Gly Glu Ala Ser Ala Pro Ala Pro Ala Leu
            485                 490                 495

Trp Glu Asp Asp Leu Gln Ser Val Val Gln Met Gly Leu Gly Gln Ile
        500                 505                 510

Glu Pro Gln Arg Val Glu Gln Gly Ser Leu Ala Thr Ser Gln Met Lys
        515                 520                 525

Val Glu Leu
    530

<210> SEQ ID NO 69
<211> LENGTH: 1596
<212> TYPE: DNA
<213> ORGANISM: Eucalyptus grandis

<400> SEQUENCE: 69

| | | | | | | |
|---|---|---|---|---|---|---|
| atggaaggaa | gctccactcc | attgactcag | aattcatcca | cctttggcat | tggcattcac | 60 |
| cccaacgacc | agctcccaa | ctgcttcctc | gtcgccggct | gggaggactc | cctggatcag | 120 |
| ggcgatccct | ttgagtccgc | cctgagctcc | attgtgtcgt | ccccggtcgc | gccccacgct | 180 |
| ggcgagggcg | aggcgggcat | gatccgggag | ctaatcggga | ggctcggcag | catctgcgat | 240 |
| tccggccagg | cctccccggg | gtcctacaac | cacagcacca | ccaacactcc | ctgttacagc | 300 |
| accctctga | attcgccgcc | cgagctcagc | ctctcgatgg | cagatcagct | cgcccacggg | 360 |
| ggcttcccgg | ccccggcag | ccattttccg | ggccacccga | gttcgtgtc | ggtcatggcg | 420 |
| gatcccgggt | cgccgagag | ggcggcgagg | ctctcttgct | tcggccctag | gaatgtgaat | 480 |
| gccgccaatc | taaacggtgg | cctcgggttg | aatgcatcgg | aattcctggg | gaaacaggcg | 540 |
| aataagctcg | attcggggag | attttgcagg | gttccaagca | gtcagtcact | gagggctaat | 600 |
| gtcggatctc | aaatctgtgc | acaagggaat | gagagaagct | tcctccagcc | agggtctct | 660 |
| atttcgaccc | ctgaaaatgg | agaaatgggg | gaatcccgcg | aggggtcttc | gatctccgag | 720 |
| caggtcacgc | atgggagat | gcgtgccaat | ggacaaatcg | acgtgaattc | aagaaagagg | 780 |
| aaaccgatcc | tgaaagcaaa | agggcgaaac | tcggctgttt | ctccacaatc | tgctaaagat | 840 |
| tctgaggttc | ccatggagaa | tgaagaaccg | ataaccaaga | aaatcaaacc | cgccgagact | 900 |
| gacggcaatg | agaaagatgc | agcaaagggg | gaccagaaac | agagcaagga | gaattcgaag | 960 |
| atggcggagc | gcagaagga | ctatatccat | gtgagagcaa | gaaggggtca | ggccactgac | 1020 |
| agccatagcc | ttgctgaaag | agtcaggaga | gagaagataa | gtctgaggat | gaaggctctc | 1080 |
| caggatctcg | tgcctaactg | caacaaggtc | actgggaaag | ctatgatgct | cgatgagatc | 1140 |
| attaactacg | tccagtcctt | gcaacgtcag | gttgagcttc | tctccatgaa | gctgtcgact | 1200 |
| ctgaacccca | cagtggattt | caatctggaa | gctttcctgt | caaaagatat | cttgcaccct | 1260 |
| caaggaccct | taccgaattc | tctctatcca | gttgattcgt | cggggtccat | gttgtatggt | 1320 |
| tatcagcccc | cgcaaggact | aatgccgatg | ccaagcgtcg | tttccagcaa | tatggatgcc | 1380 |
| caatttccag | tgaactttt | gaattccgga | attcacagag | atgccagctt | gaacttgcct | 1440 |
| ctttgtgtgg | acaattacgg | cgaagcttct | gctccggccc | cagctctatg | ggaggatgac | 1500 |
| ctccaaagtg | tagtccaaat | gggtctcggc | cagattgagc | cccagagagt | agaacaaggc | 1560 |
| tccctggcga | cttctcagat | gaaagttgag | ttgtag | | | 1596 |

<210> SEQ ID NO 70
<211> LENGTH: 498
<212> TYPE: PRT
<213> ORGANISM: Arabidopsis thaliana

```
<400> SEQUENCE: 70

Met Asp Asn Glu Leu Phe Met Asn Thr Glu Phe Pro Pro Pro Glu
1               5                   10                  15

Met Ala Thr His Phe Glu His Gln Gln Ser Ser Ser Ala Met Met
                20                  25                  30

Leu Asn Trp Ala Leu Met Asp Pro Asn Pro His Gln Asp Ser Ser Phe
            35                  40                  45

Leu Trp Glu Lys Ser Thr Glu Gln Gln Gln Gln Ser Ile Phe Asp
    50                  55                  60

Ser Ala Leu Ser Ser Leu Val Ser Ser Pro Thr Pro Ser Asn Ser Asn
65                  70                  75                  80

Phe Ser Gly Gly Gly Asp Gly Phe Leu Ile Arg Glu Leu Ile Gly
                85                  90                  95

Lys Leu Gly Asn Ile Gly Asn Asn Asn Asn Ser Gly Glu Ile Tyr
                100                 105                 110

Gly Thr Pro Met Ser Arg Ser Ala Ser Cys Tyr Ala Thr Pro Met Ser
                115                 120                 125

Ser Pro Pro Pro Pro Thr Asn Ser Asn Ser Gln Met Met Asn Arg
    130                 135                 140

Thr Thr Pro Leu Thr Glu Phe Ser Ala Asp Pro Gly Phe Ala Glu Arg
145                 150                 155                 160

Ala Ala Arg Phe Ser Cys Phe Gly Ser Arg Ser Phe Asn Gly Arg Thr
                165                 170                 175

Asn Thr Asn Leu Pro Ile Asn Asn Gly Asn Asn Met Val Asn Asn Ser
                180                 185                 190

Gly Lys Leu Thr Arg Val Ser Ser Thr Pro Ala Leu Lys Ala Leu Val
                195                 200                 205

Ser Pro Glu Val Thr Pro Gly Gly Glu Phe Ser Arg Lys Arg Lys Ser
    210                 215                 220

Val Pro Lys Gly Lys Ser Lys Glu Asn Pro Ile Ser Thr Ala Ser Pro
225                 230                 235                 240

Ser Pro Ser Phe Ser Lys Thr Ala Glu Lys Asn Gly Gly Lys Gly Gly
                245                 250                 255

Ser Lys Ser Ser Glu Glu Lys Gly Gly Lys Arg Arg Arg Glu Glu Glu
                260                 265                 270

Asp Asp Glu Glu Glu Glu Gly Glu Gly Glu Gly Asn Lys Ser Asn Asn
                275                 280                 285

Thr Lys Pro Pro Glu Pro Pro Lys Asp Tyr Ile His Val Arg Ala Arg
    290                 295                 300

Arg Gly Gln Ala Thr Asp Ser His Ser Leu Ala Glu Arg Val Arg Arg
305                 310                 315                 320

Glu Lys Ile Gly Glu Arg Met Lys Leu Leu Gln Asp Leu Val Pro Gly
                325                 330                 335

Cys Asn Lys Val Thr Gly Lys Ala Leu Met Leu Asp Glu Ile Ile Asn
                340                 345                 350

Tyr Val Gln Ser Leu Gln Arg Gln Val Glu Phe Leu Ser Met Lys Leu
                355                 360                 365

Ser Ser Val Asn Asp Thr Arg Leu Asp Phe Asn Val Asp Ala Leu Val
    370                 375                 380

Ser Lys Asp Val Met Ile Pro Ser Ser Asn Asn Arg Leu His Glu Glu
385                 390                 395                 400

Gly Leu Gln Ser Lys Ser Ser Ser His His His Gln Gln Gln Leu Asn
```

```
                    405                 410                 415
Ile Tyr Asn Asn Asn Ser Gln Leu Leu Pro Asn Ile Ser Ser Asn Asn
                420                 425                 430

Met Met Leu Gln Ser Pro Met Asn Ser Leu Glu Thr Ser Thr Leu Ala
            435                 440                 445

Arg Ser Phe Thr His Leu Pro Thr Leu Thr Gln Phe Thr Asp Ser Ile
        450                 455                 460

Ser Gln Tyr Gln Met Phe Ser Glu Glu Asp Leu Gln Ser Ile Val Gly
465                 470                 475                 480

Met Gly Val Ala Glu Asn Pro Asn Asn Glu Ser Gln His Met Lys Ile
                485                 490                 495

Glu Leu

<210> SEQ ID NO 71
<211> LENGTH: 1497
<212> TYPE: DNA
<213> ORGANISM: Arabidopsis thaliana

<400> SEQUENCE: 71
atggacaacg agctgtttat gaacacagag tttccaccac cgccggagat ggcgacgcat      60
ttcgaacacc aacagtcttc ttcatcggcc atgatgctta attgggcttt aatggatcca     120
aatccgcatc aagattcttc cttttttatgg gaaaagtcaa cggaacaaca acaacaacaa    180
agcatctttg actctgcttt aagctcatta gtctcatcac cgacgccgtc aaattccaac    240
ttctccggcg gtggcggtga cggttttctc atcagagaac tcatcggaaa gcttggaaac    300
atcggtaata ataataacaa ctccggtgag atctacggaa ctccgatgtc tcgctccgcc    360
tcatgttacg caactccgat gagctctcca ccgccaccga cgaattcgaa ttctcagatg    420
atgatgaaca gaacgacgcc gttgacggaa ttctcagcag atccgggttt tgcggagaga    480
gcagctagat ctctcttgttt tggtagtcgg agctttaacg gaagaaccaa tacaaatctt    540
ccgattaaca acggtaataa catggtcaac aactccggga agctgacacg tgtctccagc    600
acaccagctc ttaaggctct tgtttcaccg gaagtcacac ccggcggcga attttcccgg    660
aagagaaaat ctgtgcctaa aggaaaatcc aaagaaaacc ccatttctac agcttctcca    720
tctcctagtt tctcaaagac ggcggaaaag aatggtggaa aaggaggaag taaaagttca    780
gaagaaaaag gaggaaaaag gagaagagaa gaagaagatg atgaagaaga agaaggagaa    840
ggtgaaggga caaaaagcaa taacacaaaa ccacctgagc ctcctaaaga ttacattcat    900
gttcgagctc gacgaggcca agcaaccgat agtcacagcc tcgccgaacg agttcggagg    960
gagaaaattg gtgaaaggat gaagcttctt caagatcttg tgcctggatg caataaggtt   1020
actggaaaag cactgatgct tgatgaaatt ataaactacg tacaatcatt gcaaagacaa   1080
gttgagttct tgtcaatgaa gttatcatca gtgaacgaca ccaggctgga ttttaacgtg   1140
gacgctcttg tgtcaaagga tgttatgatt ccatcaagta caaccgatt gcatgaagaa   1200 ggactccaat caaagtcttc aagtcatcat catcaacaac aacttaatat ttataacaat   1260
aattcacaat tacttcccaa tatttcttcc aataacatga tgctccagtc tcctatgaac   1320
tctttggaaa cctctaccct tagccagaag cttcactcact taccaacact tacccaattt   1380
actgactcaa tttctcagta tcaaatgttt agcgaagaag atttacaaag catagtagga   1440
atgggagtgg cagaaaaccc caacaatgaa tctcaacaca tgaaaattga gctttga      1497

<210> SEQ ID NO 72
```

```
<211> LENGTH: 456
<212> TYPE: PRT
<213> ORGANISM: Arabidopsis thaliana

<400> SEQUENCE: 72

Met Glu Asn Glu Leu Phe Met Asn Ala Gly Val Ser His Pro Pro Val
1               5                   10                  15

Met Thr Ser Pro Ser Ser Ser Ala Met Leu Lys Trp Val Ser Met
            20                  25                  30

Glu Thr Gln Pro Val Asp Pro Ser Leu Ser Arg Asn Leu Phe Trp Glu
            35                  40                  45

Lys Ser Thr Glu Gln Ser Ile Phe Asp Ser Ala Leu Ser Ser Leu Val
50                  55                  60

Ser Ser Pro Thr Pro Ser Asn Ser Asn Phe Ser Val Gly Gly Val Gly
65                  70                  75                  80

Gly Glu Asn Val Ile Met Arg Glu Leu Ile Gly Lys Leu Gly Asn Ile
                85                  90                  95

Gly Asp Ile Tyr Gly Ile Thr Ala Ser Asn Gly Asn Ser Cys Tyr Ala
            100                 105                 110

Thr Pro Met Ser Ser Pro Pro Gly Ser Met Met Glu Thr Lys Thr
            115                 120                 125

Thr Thr Pro Met Ala Glu Leu Ser Gly Asp Pro Gly Phe Ala Glu Arg
130                 135                 140

Ala Ala Arg Phe Ser Cys Phe Gly Ser Arg Ser Phe Asn Ser Arg Thr
145                 150                 155                 160

Asn Ser Pro Phe Pro Ile Asn Asn Glu Pro Pro Ile Thr Thr Asn Glu
                165                 170                 175

Lys Met Pro Arg Val Ser Ser Ser Pro Val Phe Lys Pro Leu Ala Ser
            180                 185                 190

His Val Pro Ala Gly Glu Ser Ser Gly Glu Leu Ser Arg Lys Arg Lys
            195                 200                 205

Thr Lys Ser Lys Gln Asn Ser Pro Ser Ala Val Ser Ser Ser Lys Glu
            210                 215                 220

Ile Glu Glu Lys Glu Asp Ser Asp Pro Lys Arg Cys Lys Lys Ser Glu
225                 230                 235                 240

Glu Asn Gly Asp Lys Thr Lys Ser Ile Asp Pro Tyr Lys Asp Tyr Ile
                245                 250                 255

His Val Arg Ala Arg Arg Gly Gln Ala Thr Asp Ser His Ser Leu Ala
            260                 265                 270

Glu Arg Val Arg Arg Glu Lys Ile Ser Glu Arg Met Lys Leu Leu Gln
            275                 280                 285

Asp Leu Val Pro Gly Cys Asn Lys Val Thr Gly Lys Ala Leu Met Leu
            290                 295                 300

Asp Glu Ile Ile Asn Tyr Val Gln Ser Leu Gln Arg Gln Val Glu Phe
305                 310                 315                 320

Leu Ser Met Lys Leu Ser Ser Val Asn Thr Arg Leu Asp Phe Asn Met
                325                 330                 335

Asp Ala Leu Leu Ser Lys Asp Ile Phe Pro Ser Ser Asn Asn Leu Met
            340                 345                 350

His His Gln Gln Val Leu Gln Leu Asp Ser Ser Ala Glu Thr Leu Leu
            355                 360                 365

Gly Asp His His Asn Lys Asn Leu Gln Leu Asn Pro Asp Ile Ser Ser
370                 375                 380

Asn Asn Val Ile Asn Pro Leu Glu Thr Ser Glu Thr Arg Ser Phe Ile
```

385             390             395             400
Ser His Leu Pro Thr Leu Ala His Phe Thr Asp Ser Ile Ser Gln Tyr
                405                     410                     415

Ser Thr Phe Ser Glu Asp Asp Leu His Ser Ile Ile His Met Gly Phe
                420                     425                     430

Ala Gln Asn Arg Leu Gln Glu Leu Asn Gln Gly Ser Ser Asn Gln Val
                435                     440                     445

Pro Ser His Met Lys Ala Glu Leu
        450                 455

<210> SEQ ID NO 73
<211> LENGTH: 1371
<212> TYPE: DNA
<213> ORGANISM: Arabidopsis thaliana

<400> SEQUENCE: 73
atggagaacg agctgtttat gaatgcagga gtttcgcatc cgccggtgat gacgtcaccg      60
tcttcttcgt cggcgatgct taagtgggtt tcaatgagga ctcagccagt ggatccaagt     120
ctcagtcgca atctgttttg ggaaaagtca acggaacaga gcatttttga ttcggctctg     180
agctcactcg tctcttctcc tacgccgtca aattcaaact tttcggttgg cggagtaggt     240
ggagaaaatg tcattatgag agagctcatc gggaaactgg gtaatatcgg cgatatctat     300
ggaattacgg cgagcaatgg aaactcgtgt acgcaactc cgatgagctc tccaccgcct      360
ggaagtatga tggagacgaa acgacgacg ccgatggcag aactgtccgg cgacccggga      420
ttcgctgaga gagcggcgag gttctcgtgt tttggtagcc ggagttttaa cagcagaaca     480
aactcgccgt ttccgattaa taacgaacca cccatcacaa ccaatgagaa atgccacgt      540 gtatcaagca gccagttttt taagcctctt gcgtctcatg ttcccgccgg cgaatcgtcc     600
ggtgaacttt cccggaaaag aaaaactaaa tccaagcaga attctccttc tgcagtttca     660
tcatcaaagg agattgaaga aggaagat tctgatccaa agagatgcaa aaatcagaa        720 gaaaatggag acaaaactaa atcaattgat ccttacaaag attacattca tgttagagct     780
cgacgaggcc aagccaccga tagtcacagt ctcgccgaac gagttcgaag agagaaaata     840
agcgaaagaa tgaagctgct tcaagatctt gtccctggat gcaacaaggt tactggaaaa     900
gcactgatgt tggatgaaat tataaactat gtccaatcat tgcaacgaca gttgagttc     960 ttgtcgatga agttatcgtc agtgaacacc aggctggact ttaacatgga cgctctcttg    1020
tctaaggata tatttccttc aagcaacaat ctaatgcatc atcaacaagt acttcaatta    1080
gattcttcag cagaaacgtt attgggtgat catcacaaca aaaatttgca attgaaccct    1140
gatatttctt ctaataacgt aataaaccct ttggaaactt ctgaaactag aagcttcatt    1200
tctcacttac caacacttgc tcatttcact gactctattt ctcagtattc aacatttcc     1260 gaagatgatt tacatagcat tattcatatg ggttttgcgc aaaaccgtct ccaagaattg    1320
aaccaaggtt catcaaacca gtaccatcg cacatgaaag ctgaactttg a              1371

<210> SEQ ID NO 74
<211> LENGTH: 301
<212> TYPE: PRT
<213> ORGANISM: Populus trichocarpa

<400> SEQUENCE: 74

Met Ala Val Asp Leu Val Arg Tyr Ser Lys Met Glu Asp Gln Met Ala
1               5                   10                  15

| | | | | | | | | | | | |
|---|---|---|---|---|---|---|---|---|---|---|---|
|Ile|Gln|Glu|Ala|Ala|Ser|Ala|Gly|Leu|Glu|Ser|Met|Glu|His|Leu|Ile|
| | | |20| | | |25| | | |30| | | | |

```
Ile Gln Glu Ala Ala Ser Ala Gly Leu Glu Ser Met Glu His Leu Ile
             20                  25                  30

Phe Ala Phe Ser Asn Gln Thr Arg Gln Ser His Gln Leu Asp Cys Gly
         35                  40                  45

Glu Ile Thr Asn Phe Thr Val Ala Lys Phe Lys Gln Val Ile Ser Met
 50                  55                  60

Leu Asn Arg Thr Gly His Ala Arg Phe Arg Arg Gly Pro Thr Ser Ser
 65                  70                  75                  80

Pro Ser Ser Tyr Pro Val Pro Val Arg Pro Val Pro Gln Glu Pro Gln
             85                  90                  95

Lys Leu Asn Leu Asp Phe Val Asn Ser Asn Ser Pro Pro Lys Ala Glu
            100                 105                 110

Ser Lys Asn Asp Leu Ser Leu Gly Ser Gln Tyr Ser Lys Asp Ser Leu
        115                 120                 125

Ser Ser Gly Thr Thr Thr Ser Ser Phe Val Ser Ser Val Thr Ala Asp
    130                 135                 140

Gly Ser Val Ser Asn Gly Lys Gln Gly Gly Ser Ser Leu Phe Gly Thr
145                 150                 155                 160

Gln Ala Arg Ser Thr Gly Lys Pro Pro Leu Ser Ser Thr His Arg Lys
                165                 170                 175

Lys Cys His Asp His Ala Leu Ser Ala Arg Lys Ile Ser Ser Gly Gly
            180                 185                 190

Ser Cys His Cys Ser Lys Arg Lys Ser Arg Val Lys Arg Thr Ile
        195                 200                 205

Arg Val Pro Ala Val Ser Ser Lys Ile Ala Asp Ile Pro Ala Asp Glu
210                 215                 220

Tyr Ser Trp Arg Lys Tyr Gly Gln Lys Pro Ile Lys Gly Ser Pro Tyr
225                 230                 235                 240

Pro Arg Gly Tyr Tyr Lys Cys Ser Ser Val Arg Gly Cys Pro Ala Arg
                245                 250                 255

Lys His Val Glu Arg Ala Val Asp Asp Ser Ala Met Leu Ile Val Thr
            260                 265                 270

Tyr Glu Gly Glu His Arg His Ser His Thr Pro Leu Pro Gly Asp Val
        275                 280                 285

Thr Ala Ser Ala Ala Met Arg His Val Phe His Ser Thr
    290                 295                 300
```

<210> SEQ ID NO 75
<211> LENGTH: 906
<212> TYPE: DNA
<213> ORGANISM: Populus trichocarpa

<400> SEQUENCE: 75

| | |
|---|---|
|atggctgtgg atctagttag gtattcaaag atggaagatc agatggctat acaagaagct|60|
|gcatcagctg ggctcgagag catggagcac ttgatctttg cattctctaa ccaaactcga|120|
|caaagccacc aacttgactg cggagaaatc acaaacttca ccgttgctaa gttcaagcaa|180|
|gtcatctcca tgttgaaccg gaccggtcat gcccgttttc gccgtggacc aacttcttct|240|
|ccttcttcct acccggttcc cgtccgacct gtccctcaag agcctcaaaa actgaacctt|300|
|gattttgtta acagtaatag ccccctaaa gctgagtcga aaaatgacct gtctttgggt|360|
|agtcagtatt caaggatag ccttagctct ggcaccacta cctcatcctt cgtgtcttct|420|
|gttacagctg atggagtgt ctctaatggg aaacaaggtg gctcttctct tttcggaact|480|
|caagcgcgat ctaccggaaa accacctctc tcatcgaccc accgcaagaa atgccacgat|540|

```
catgccctct ccgccagaaa gatctcctcc ggtggaagct gtcattgctc caaaagaagg    600
aaatcaaggg ttaagaggac aataagggta ccagccgtga gttccaagat tgccgatata    660
ccagcagatg agtactcatg agaaaaatat ggtcaaaagc caatcaaggg ctcaccatac    720
ccaagagggt attacaagtg tagcagtgtt agaggatgtc cagcaaggaa gcatgtggag    780
cgtgccgtag atgactcggc catgcttatc gtgacttacg aggggagca ccgtcactca     840 catactccgt tgccgggaga cgtcaccgcg agtgctgcaa tgcgacacgt gtttcactca    900
acatga                                                               906
```

<210> SEQ ID NO 76
<211> LENGTH: 300
<212> TYPE: PRT
<213> ORGANISM: Populus trichocarpa

<400> SEQUENCE: 76

```
Met Ala Val Asp Leu Val Gly Tyr Ser Lys Met Glu Asp Gln Met Ala
1               5                   10                  15

Ile Gln Glu Ala Ala Ser Ala Gly Ile Lys Ser Met Glu His Leu Ile
            20                  25                  30

Phe Ala Leu Ser Asn Gln Thr Gln Gln Ser His Gln Leu Asp Cys Arg
        35                  40                  45

Glu Ile Thr Ser Phe Thr Val Ala Lys Phe Lys Gln Val Ile Ser Ile
    50                  55                  60

Leu Asn Arg Thr Gly His Ala Arg Phe Arg Arg Gly Pro Thr Ser Ser
65                  70                  75                  80

Asn Pro Val Ser Val Arg Pro Val Val Gln Glu Pro Gln Lys Leu Asn
                85                  90                  95

Leu Asp Phe Phe Lys Ser Asn Asn Thr Phe Lys Ser Glu Thr Lys Asn
            100                 105                 110

Asp Leu Ser Phe Gly Ser Gln Tyr Ser Lys Asp Cys Phe Ser Ser Gly
        115                 120                 125

Thr Thr Thr Ser Ser Phe Leu Ser Ser Val Thr Ala Asp Gly Ser Val
    130                 135                 140

Ser Asp Gly Lys Gln Gly Gly Ser Ser Ser Leu Phe Gly Thr His Pro
145                 150                 155                 160

Arg Pro Thr Gly Lys Pro Pro Leu Ser Ser Ile His Arg Lys Lys Cys
                165                 170                 175

His Asp His Thr Leu Ser Thr Ser Lys Ile Ser Ser Ser Gly Gly Ser
            180                 185                 190

Cys His Cys Ser Lys Arg Arg Lys Ser Arg Val Lys Arg Thr Ile Arg
        195                 200                 205

Val Pro Ala Ile Ser Ser Lys Val Ala Asp Ile Pro Ala Asp Glu Phe
    210                 215                 220

Ser Trp Arg Lys Tyr Gly Gln Lys Pro Ile Lys Gly Ser Pro Tyr Pro
225                 230                 235                 240

Arg Gly Tyr Tyr Lys Cys Ser Ser Val Arg Gly Cys Pro Ala Arg Lys
                245                 250                 255

His Val Glu Arg Ala Val Asp Asp Pro Ala Met Leu Ile Val Thr Tyr
            260                 265                 270

Glu Gly Glu His Arg His Ser His Ala Pro Leu Pro Glu Asn Val Thr
        275                 280                 285

Ala Asn Ala Ala Met Arg His Val Phe Gln Ser Thr
    290                 295                 300
```

<210> SEQ ID NO 77
<211> LENGTH: 903
<212> TYPE: DNA
<213> ORGANISM: Populus trichocarpa

<400> SEQUENCE: 77

```
atggctgttg atctagttgg gtactcaaag atggaagatc agatggctat tcaagaagct      60
gcatcagctg ggattaagag catggagcac ttgatctttg cactctctaa ccaaacccaa     120
caaagtcacc aacttgactg cagagaaatc actagcttca ccgttgctaa gttcaagcaa     180
gtcatctcca tcctgaaccg gaccggtcat gcccgtttcc gccgtggacc cacttcttcc     240
aacccggttt ccgtccgacc tgtcgtccaa gaacctcaaa actaaatct tgatttcttt      300
aagagtaaca ataccttta atctgagacc aaaaacgact tgtcattcgg cagtcagtat      360
tccaaggatt gttttagctc tggcacgact acttcgtcct tcctgtcttc tgttacagct     420
gatgggagtg tctctgatgg gaaacaaggt ggctcgtctt ctcttttcgg aactcatcct     480
cgacctaccg gaaaaccacc tctctcatct atccatcgca agaaatgcca tgatcatacc     540
ctctccacca gcaagatctc ctcctccggt ggcagctgcc attgctccaa agaaggaaa     600
tcaagggtga agaggacaat aagagtccca gcaataagtt ccaaagttgc tgatatacca    660
gcagatgagt tctcatggag aaaatatggt caaaagccaa tcaagggttc accttaccca     720
agagggtact acaagtgtag tagtgtgagg ggatgtccag caaggaagca cgtggagcgt     780
gccgtagatg atccggccat gcttattgta acatacgaag gggagcaccg tcactcacat     840
gctcccctac cagaaaatgt cacagccaac gctgccatgc acacgtgtt ccagtcaaca      900
tga                                                                    903
```

<210> SEQ ID NO 78
<211> LENGTH: 343
<212> TYPE: PRT
<213> ORGANISM: Eucalyptus grandis

<400> SEQUENCE: 78

Met Ala Ile Glu Leu His Leu Gly Phe Ser Lys Met Glu Asp His Thr
1               5                   10                  15

Ala Ile Gln Glu Ala Ala Ser Gln Gly Leu Lys Thr Met Glu His Leu
            20                  25                  30

Ile Gly Val Leu Ser Arg Gln Asn Leu His His Pro Gly Ala Val Asp
        35                  40                  45

Cys Thr Asp Leu Thr Asp Arg Thr Val Ser Lys Phe Arg Lys Val Ile
    50                  55                  60

Ser Leu Leu Asp Arg Thr Gly His Ala Arg Phe Arg Arg Ala Pro Leu
65                  70                  75                  80

Pro Ser Ser Ser Ser Ser Ser Lys Ser Ala Pro Val Ala Ser Pro
                85                  90                  95

Val Pro Pro Ala Val Gln Ser Arg Ser Gln Pro Leu Ala Pro Thr Pro
            100                 105                 110

Ile Gln Ala Pro Thr Ser Ser Gln Pro Ser Pro Ala Ser Phe Leu His
        115                 120                 125

Ala Gln Pro Lys Gln Ser Leu Thr Leu Asp Phe Thr Arg Pro Ser Ile
    130                 135                 140

Leu Gly Pro Asn Ser Lys Gly Val Ser Glu Ile Glu Phe Ala Lys Asp
145                 150                 155                 160

```
Ser Phe Ser Val Ser Ser Asn Ser Ser Phe Met Ser Ser Ala Ile Thr
            165                 170                 175

Gly Asp Gly Ser Val Ser Asn Gly Lys Leu Gly Thr Ser Met Phe Ile
        180                 185                 190

Ala Pro Ala Ser Gly Pro Ala Ser Ser Ala Gly Lys Pro Pro Ile Ser
    195                 200                 205

Ser Val Pro Tyr Lys Lys Arg Cys His Glu His Asp Pro Ser Asp Asn
210                 215                 220

Ile Ser Gly Lys His Ser Gly Ser Ser Gly Lys Cys His Cys Ser
225                 230                 235                 240

Lys Arg Arg Lys Asn Arg Val Lys Lys Val Thr Arg Val Pro Ala Ile
                245                 250                 255

Ser Asn Lys Ile Ala Asp Ile Pro Ala Asp Glu Phe Ser Trp Arg Lys
            260                 265                 270

Tyr Gly Gln Lys Pro Ile Lys Gly Ser Pro Phe Pro Arg Gly Tyr Tyr
        275                 280                 285

Lys Cys Ser Thr Met Arg Gly Cys Pro Ala Arg Lys His Val Glu Arg
    290                 295                 300

Ala Pro Asp Asp Pro Thr Met Leu Ile Val Thr Tyr Glu Gly Glu His
305                 310                 315                 320

Arg His Ser Gln Ser Ala Ser Gln Glu Ile Val Pro Ala Gly Ala Met
                325                 330                 335

Asn Leu Val Phe Lys Ser Thr
            340

<210> SEQ ID NO 79
<211> LENGTH: 1032
<212> TYPE: DNA
<213> ORGANISM: Eucalyptus grandis

<400> SEQUENCE: 79
atggcgatcg agctgcatct tggcttctcc aagatggagg atcacacggc gatacaggag      60
gccgcgtctc aggggctgaa gaccatggag cacctgatcg gcgtcctctc ccgccagaac     120
ctccaccacc ccggcgccgt cgactgcacc gacctcaccg accggaccgt ctccaagttc     180
aggaaggtca tctccctcct ggaccgcacc ggccacgccc gcttccggcg ggccccgctc     240
ccctcctcct cctcttcctc ctccaagtct gcccccgtcg cttcccctgt cccccccggcg    300 gttcagtctc ggagccagcc tctagcgccg acgcccatcc aggccccgac gagctcgcag     360
ccgtctccgg ccagcttcct ccacgcgcag cccaagcaga gcttgaccct cgacttcacc     420
cggccgagca tcctgggccc caactccaaa ggcgtttccg agatcgagtt cgcgaaggac     480
agcttcagcg tgtcgtccaa ctcttccttc atgtcttcgg cgatcaccgg cgacggaagc     540
gtttcgaacg ggaagctggg gacgtcgatg ttcatagctc cggcgtccgg cccggcttcg     600
tccgccggaa agccaccgat ctcgagcgtg ccgtacaaga gcggtgccga cgagcacgac     660
ccctccgata acatctccgg caagcactcc ggctccggca gcggcaagtg ccactgctcc     720
aaaagaagga aaaaccgagt gaagaaggtg acgagagtgc cggcgatcag caacaagatc     780
gcggacatcc cggccgacga gttctcgtgg aggaagtacg gacagaagcc gatcaaaggg     840
tctcccttcc cacgaggtta ctacaagtgc agtacaatga gagggtgccc cgcgaggaaa     900
cacgtggaga gggcccccga cgatccaacg atgctgatcg tgacgtacga gggggagcat     960
cgtcactccc agtccgcgtc gcaggagatt gtgcccgccg gtgcgatgaa cctggtattc    1020
aagtcaacct ga                                                        1032
```

<210> SEQ ID NO 80
<211> LENGTH: 325
<212> TYPE: PRT
<213> ORGANISM: Arabidopsis thaliana

<400> SEQUENCE: 80

Met Ala Val Asp Leu Met Arg Phe Pro Lys Ile Asp Asp Gln Thr Ala
1               5                   10                  15

Ile Gln Glu Ala Ala Ser Gln Gly Leu Gln Ser Met Glu His Leu Ile
            20                  25                  30

Arg Val Leu Ser Asn Arg Pro Glu Gln Gln His Asn Val Asp Cys Ser
        35                  40                  45

Glu Ile Thr Asp Phe Thr Val Ser Lys Phe Lys Thr Val Ile Ser Leu
    50                  55                  60

Leu Asn Arg Thr Gly His Ala Arg Phe Arg Arg Gly Pro Val His Ser
65                  70                  75                  80

Thr Ser Ser Ala Ala Ser Gln Lys Leu Gln Ser Gln Ile Val Lys Asn
                85                  90                  95

Thr Gln Pro Glu Ala Pro Ile Val Arg Thr Thr Thr Asn His Pro Gln
            100                 105                 110

Ile Val Pro Pro Ser Ser Val Thr Leu Asp Phe Ser Lys Pro Ser
            115                 120                 125

Ile Phe Gly Thr Lys Ala Lys Ser Ala Glu Leu Glu Phe Ser Lys Glu
    130                 135                 140

Asn Phe Ser Val Ser Leu Asn Ser Ser Phe Met Ser Ser Ala Ile Thr
145                 150                 155                 160

Gly Asp Gly Ser Val Ser Asn Gly Lys Ile Phe Leu Ala Ser Ala Pro
                165                 170                 175

Leu Gln Pro Val Asn Ser Ser Gly Lys Pro Pro Leu Ala Gly His Pro
            180                 185                 190

Tyr Arg Lys Arg Cys Leu Glu His Glu His Ser Glu Ser Phe Ser Gly
            195                 200                 205

Lys Val Ser Gly Ser Ala Tyr Gly Lys Cys His Cys Lys Lys Ser Arg
210                 215                 220

Lys Asn Arg Met Lys Arg Thr Val Arg Val Pro Ala Ile Ser Ala Lys
225                 230                 235                 240

Ile Ala Asp Ile Pro Pro Asp Glu Tyr Ser Trp Arg Lys Tyr Gly Gln
                245                 250                 255

Lys Pro Ile Lys Gly Ser Pro His Pro Arg Gly Tyr Tyr Lys Cys Ser
            260                 265                 270

Thr Phe Arg Gly Cys Pro Ala Arg Lys His Val Glu Arg Ala Leu Asp
            275                 280                 285

Asp Pro Ala Met Leu Ile Val Thr Tyr Glu Gly Glu His Arg His Asn
    290                 295                 300

Gln Ser Ala Met Gln Glu Asn Ile Ser Ser Ser Gly Ile Asn Asp Leu
305                 310                 315                 320

Val Phe Ala Ser Ala
                325

<210> SEQ ID NO 81
<211> LENGTH: 978
<212> TYPE: DNA
<213> ORGANISM: Arabidopsis thaliana

<400> SEQUENCE: 81

-continued

```
atggccgtcg atctaatgcg tttccctaag atagatgatc aaacggctat tcaggaagct      60
gcatcgcaag gtttacaaag tatggaacat ctgatccgtg tcctctctaa ccgtcccgaa     120
caacaacaca acgttgactg ctccgagatc actgacttca ccgtttctaa attcaaaacc     180
gtcatttctc tccttaaccg tactggtcac gctcggttca cgcgcggacc ggttcactcc     240
acttcctctg ccgcatctca gaaactacag agtcagatcg ttaaaaatac tcaacctgag     300
gctccgatag tgagaacaac tacgaatcac cctcaaatcg ttcctccacc gtctagtgta     360
acactcgatt tctctaaacc aagcatcttc ggcaccaaag ctaagagcgc cgagctggaa     420
ttctccaaag aaaacttcag tgtttcttta aactcctcat tcatgtcgtc ggcgataacc     480
ggagacggca gcgtctccaa tggaaaaatc ttccttgctt ctgctccgtt gcagcctgtt     540
aactcttccg gaaaccacc gttggctggt catccttaca gaaagagatg tctcgagcat     600
gagcactcag agagtttctc cggaaaagtc tccggctccg cctacggaaa gtgccattgc     660
aagaaaagca ggaaaaatcg gatgaagaga accgtgagag taccggcgat aagtgcaaag     720
atcgccgata ttccaccgga cgaatattcg tggaggaagt acggacaaaa accgatcaag     780
ggctcaccac acccacgtgg ttactacaag tgcagtacat tcagaggatg tccagcgagg     840
aaacacgtgg aacgagcatt agatgatcca gcgatgctta ttgtgacata cgaaggagag     900
caccgtcata accaatccgc gatgcaggag aatatttctt cttcaggcat taatgattta     960
gtgtttgcct cggcttga                                                  978
```

<210> SEQ ID NO 82
<211> LENGTH: 321
<212> TYPE: PRT
<213> ORGANISM: Arabidopsis thaliana

<400> SEQUENCE: 82

```
Met Thr Val Asp Ile Met Arg Leu Pro Lys Met Glu Asp Gln Thr Ala
1               5                   10                  15

Ile Gln Glu Ala Ala Ser Gln Gly Leu Lys Ser Met Glu His Leu Ile
            20                  25                  30

Arg Val Leu Ser Asn Arg Pro Glu Glu Arg Asn Val Asp Cys Ser Glu
        35                  40                  45

Ile Thr Asp Phe Thr Val Ser Lys Phe Lys Lys Val Ile Ser Leu Leu
    50                  55                  60

Asn Arg Ser Gly His Ala Arg Phe Arg Arg Gly Pro Val His Ser Pro
65                  70                  75                  80

Pro Ser Ser Ser Val Pro Pro Val Lys Val Thr Thr Pro Ala Pro
                85                  90                  95

Thr Gln Ile Ser Ala Pro Ala Pro Val Ser Phe Val Gln Ala Asn Gln
            100                 105                 110

Gln Ser Val Thr Leu Asp Phe Thr Arg Pro Ser Val Phe Gly Ala Lys
        115                 120                 125

Thr Lys Ser Ser Glu Val Val Glu Phe Ala Lys Glu Ser Phe Ser Val
    130                 135                 140

Ser Ser Asn Ser Ser Phe Met Ser Ser Ala Ile Thr Gly Asp Gly Ser
145                 150                 155                 160

Val Ser Lys Gly Ser Ser Ile Phe Leu Ala Pro Ala Pro Ala Val Pro
                165                 170                 175

Val Thr Ser Ser Gly Lys Pro Pro Leu Ser Gly Leu Pro Tyr Arg Lys
            180                 185                 190
```

```
Arg Cys Phe Glu His Asp His Ser Glu Gly Phe Ser Gly Lys Ile Ser
            195                 200                 205

Gly Ser Gly Asn Gly Lys Cys His Cys Lys Lys Ser Arg Lys Asn Arg
    210                 215                 220

Met Lys Arg Thr Val Arg Val Pro Ala Val Ser Ala Lys Ile Ala Asp
225                 230                 235                 240

Ile Pro Pro Asp Glu Tyr Ser Trp Arg Lys Tyr Gly Gln Lys Pro Ile
                245                 250                 255

Lys Gly Ser Pro His Pro Arg Gly Tyr Tyr Lys Cys Ser Thr Phe Arg
                260                 265                 270

Gly Cys Pro Ala Arg Lys His Val Glu Arg Ala Leu Asp Asp Ser Thr
            275                 280                 285

Met Leu Ile Val Thr Tyr Glu Gly Glu His Arg His Gln Ser Thr
        290                 295                 300

Met Gln Glu His Val Thr Pro Ser Val Ser Gly Leu Val Phe Gly Ser
305                 310                 315                 320

Ala
```

<210> SEQ ID NO 83
<211> LENGTH: 966
<212> TYPE: DNA
<213> ORGANISM: Arabidopsis thaliana

<400> SEQUENCE: 83

```
atgaccgttg atattatgcg tttacctaag atggaagatc aaacggctat acaagaagct    60
gcatcacaag gcttaaaaag catggaacac ttgattcgtg tcctctctaa ccgtcccgaa   120
gaacgtaacg ttgattgctc tgagatcact gatttcacag tttctaagtt caagaaagtt   180
atctctcttc ttaaccgttc cggtcacgcc cggtttagac gtggtccggt tcattcccct   240
ccttcctcct ccgttcctcc accggtgaaa gtgacaactc cggctcccac tcagatctct   300
gctccagcac cggttagctt cgttcaggca aatcaacaaa gcgtgacgtt agatttcact   360
agaccgagcg tttttggcgc taaaaccaag agctcggagg ttgttgagtt tgctaaagag   420
agctttagcg tatcttctaa ctcttctttc atgtcttctg cgatcaccgg tgatggaagt   480
gtctctaaag gctcttcgat cttttcttgct ccggctccag cggtgccagt gacttcctcc   540
gggaaaccgc cgctttctgg tcttccttac aggaagagat gctttgaaca tgaccactct   600
gaaggctttt ccggcaagat ctctggctcc ggcaacggca agtgccattg caagaaaagc   660
cgaaaaaatc ggatgaagag aaccgtgaga gtaccggcgg taagtgcaaa gatcgccgat   720
ataccaccag acgaatattc atggagaaag tatggacaaa aaccgatcaa aggctcacca   780
catccacggg gttattacaa gtgtagtaca tttagaggat gtccagcgag gaaacacgtg   840
gaaagagctt tggatgattc aacgatgttg attgtgacgt acgaaggaga gcaccgtcat   900
caccagtcca cgatgcagga gcatgtaact cctagcgtga gtggtttggt gtttggttcg   960
gcttga                                                               966
```

<210> SEQ ID NO 84
<211> LENGTH: 347
<212> TYPE: PRT
<213> ORGANISM: Populus trichocarpa

<400> SEQUENCE: 84

```
Met Glu Gly Val Glu Glu Ala Asn Arg Ala Ala Val Glu Ser Cys His
1               5                   10                  15
```

```
Arg Val Ile Ser Leu Leu Ser Gln Pro Gln Asp Gln Val Gln Tyr Arg
            20                  25                  30
Asn Leu Met Val Glu Thr Gly Glu Ala Val Phe Arg Phe Lys Lys Val
        35                  40                  45
Val Ser Leu Leu Asn Thr Gly Leu Gly His Ala Arg Val Arg Lys Leu
 50                  55                  60
Lys Lys Leu Pro Thr Pro Leu Ser Gln Ser Ile Leu Leu Asp Asn Pro
 65                  70                  75                  80
Leu Ser Ser Thr Asp His Pro Ser Lys Thr Pro Gln Phe Leu Gln Ser
                85                  90                  95
Ser Ser Tyr Leu Glu Ser Gln Pro Ile Gln Glu Leu Gly Ser Ile Ala
            100                 105                 110
Lys Asn Cys Leu Ser Leu Gly Thr Pro Ser Leu Glu Leu Ser Ser Asn
        115                 120                 125
Gly Lys Asn Pro Leu Gln Leu Gly Gln Pro Thr Pro Ala Ala His Tyr
130                 135                 140
Gln Phe Leu Gln Gln Gln Leu His Arg Leu Gln Leu Gln Gln Gln
145                 150                 155                 160
Gln Gln Met Lys Gln Gln Ala Glu Met Met Phe Arg Lys Ser Asn Ser
                165                 170                 175
Gly Ile Ser Leu Asn Phe Asp Ser Ser Ser Cys Thr Pro Thr Met Ser
            180                 185                 190
Ser Thr Arg Ser Phe Ile Ser Ser Leu Ser Ile Asp Gly Asn Val Ala
        195                 200                 205
Asn Leu Glu Gly Ser Ala Phe His Leu Thr Gly Ala Ala Arg Ser Ser
210                 215                 220
Asp Gln Ser Ser Gln Gln His Lys Arg Lys Cys Ser Gly Arg Gly Glu
225                 230                 235                 240
Asp Gly Ser Met Lys Cys Gly Ser Ser Val Arg Cys His Cys Ser Lys
                245                 250                 255
Lys Arg Lys His Arg Val Lys Arg Ser Ile Lys Val Pro Ala Ile Ser
            260                 265                 270
Asn Lys Leu Ala Asp Ile Pro Pro Asp Asp Tyr Ser Trp Arg Lys Tyr
        275                 280                 285
Gly Gln Lys Pro Ile Lys Gly Ser Pro His Pro Arg Gly Tyr Tyr Lys
290                 295                 300
Cys Ser Ser Met Arg Gly Cys Pro Ala Arg Lys His Val Glu Arg Cys
305                 310                 315                 320
Leu Glu Asp Pro Ser Met Leu Ile Val Thr Tyr Glu Gly Glu His Asn
                325                 330                 335
His Pro Arg Ile Pro Ala Gln Ser Thr Asn Thr
            340                 345
```

<210> SEQ ID NO 85
<211> LENGTH: 1044
<212> TYPE: DNA
<213> ORGANISM: Populus trichocarpa

<400> SEQUENCE: 85

```
atggagggggttgaagaagctaaccgggcagctgtggagagctgccatagagttataagt    60 ttgctatcccaaccccaagatcaggttcaatataggaatttaatggtggaaactggagag   120 gctgtgtttaggttcaagaaagtagtttcccttttaaatactggtttaggtcatgcaaga   180 gttcgaaaacttaagaagttaccgaccccttt atcccaaagcatcctcttagacaaccca   240
```

```
ctgagcagta cagaccaccc atccaaaaca ccccagtttc tccagtccag tagttacctg    300
gaaagccaac caattcaaga attgggctca attgctaaaa attgtctatc tttgggaacc    360
ccatccctgg aattgagttc aaatgggaaa aaccctcttc agcttggcca acccacgcca    420
gcagcgcact atcagttcct tcagcaacag caactgcata ggctacagct tcaacagcag    480
cagcaaatga agcagcaagc tgagatgatg tttagaaaaa gcaatagtgg gattagcttg    540
aatttcgata gttctagctg cactcctaca atgtcatcta ccagatcttt tatatcgtcc    600
ttgagtattg atggtaatgt ggctaatttg gaaggaagtg cattccattt aacgggggcg    660
gctcgctcct cagatcagag ttcacagcaa cacaagagga atgttctgg aagggagaa    720 gatggaagta tgaaatgtgg aagcagcgtt agatgtcatt gctcaaagaa gaggaaacat    780
agggtgaaga ggtcgatcaa ggttcctgct attagcaaca agcttgctga tatccctcct    840
gatgattact catggagaaa gtatgggcaa aagccaatca agggttctcc tcatcctagg    900
ggatattaca aatgtagcag tatgagaggt tgtcctgcaa ggaagcatgt ggagaggtgc    960
ttggaagatc cgtccatgct tatttgttacc tatgaaggtg aacataacca cccaaggatt   1020
ccagcacaat ccacaaacac gtaa                                           1044

<210> SEQ ID NO 86
<211> LENGTH: 351
<212> TYPE: PRT
<213> ORGANISM: Populus trichocarpa

<400> SEQUENCE: 86

Met Glu Gly Val Glu Glu Ala Asn Arg Ala Ala Val Glu Ser Cys His
1               5                   10                  15

Arg Val Ile Ser Leu Leu Ser Gln Pro Gln Asp Gln Val Gln Tyr Arg
                20                  25                  30

Asn Leu Met Val Glu Thr Gly Glu Ala Val Phe Arg Phe Lys Lys Val
            35                  40                  45

Val Ser Leu Leu Asn Thr Gly Leu Gly His Ala Arg Val Arg Lys Leu
        50                  55                  60

Lys Lys Leu Pro Thr Pro Leu Ser Gln Ser Ile Leu Leu Asp Asn Ser
65                  70                  75                  80

Leu Asn Arg Thr Gly His Ser Ser Lys Thr Pro Gln Phe Leu Gln Ser
                85                  90                  95

Ser Ser Tyr Leu Glu Ser His Pro Ile Gln Glu Leu Gly Ser Ser Ala
                100                 105                 110

Lys Asn Cys Leu Ser Leu Gly Thr Pro Ser Leu Glu Leu Ser Ser Thr
            115                 120                 125

Gly Lys Asn Pro Leu Gln Leu Gly Gln Pro Thr Ser Ala Ala Asn Tyr
        130                 135                 140

Gln Phe Leu Gln Leu Gln Gln Gln Leu His Arg Leu Gln Leu Gln
145                 150                 155                 160

Gln Gln Gln Gln Gln Met Lys Gln Gln Ala Glu Met Met Phe Arg
                165                 170                 175

Lys Ser Asn Ser Gly Ile Ser Leu Asn Phe Asp Ser Ser Cys Thr
            180                 185                 190

Pro Thr Leu Ser Ser Thr Arg Ser Phe Ile Ser Ser Leu Ser Ile Asp
        195                 200                 205

Gly Ser Val Ala Asn Leu Glu Gly Ser Ala Phe His Leu Met Gly Pro
    210                 215                 220

Ala Arg Ser Ser Asp Gln Ser Ser Gln Gln His Lys Arg Lys Cys Ser
```

```
                225                 230                 235                 240
Gly Arg Gly Glu Asp Gly Ser Val Lys Cys Gly Ser Ser Gly Arg Cys
                245                 250                 255

His Cys Ser Lys Lys Arg Lys His Arg Val Lys Arg Ser Ile Lys Val
            260                 265                 270

Pro Ala Ile Ser Asn Lys Leu Ala Asp Ile Pro Asp Asp Tyr Ser
        275                 280                 285

Trp Arg Lys Tyr Gly Gln Lys Pro Ile Lys Gly Ser Pro His Pro Arg
    290                 295                 300

Gly Tyr Tyr Lys Cys Ser Ser Met Arg Gly Cys Pro Ala Arg Lys His
305                 310                 315                 320

Val Glu Arg Cys Leu Glu Asp Pro Ser Met Leu Ile Val Thr Tyr Glu
                325                 330                 335

Gly Glu His Asn His Pro Arg Ile Pro Ala Gln Ser Ala Asn Thr
            340                 345                 350

<210> SEQ ID NO 87
<211> LENGTH: 1056
<212> TYPE: DNA
<213> ORGANISM: Populus trichocarpa

<400> SEQUENCE: 87 atggagggggg ttgaagaagc aacagagca gctgtggaga gctgccatag agttataagt      60
ttgttgtctc aacctcaaga tcaggttcaa tataggaatt taatggtgga aactggcgag    120
gctgtgttta ggttcaagaa agttgttcct ctttaaata ctggtttagg tcatgcaaga    180
gttcggaaac ttaagaagtt accgaccct ttatcccaaa gcatcctttt agataactca    240
cttaatagaa caggccactc atccaaaaca cctcagtttc tccagtctag cagttacctg    300
gaaagccatc cgattcaaga attgggctca agtgctaaga actgtctttc tctgggaacc    360
ccatctttgg aattgagttc aaccgggaaa aaccctcttc agcttgggca acccacttca    420
gcagctaatt atcagttcct tcagcttcaa cagcagcagc tgcacaggct acagcttcag    480
cagcagcagc agcagcaaat gaagcagcaa gctgagatga tgtttagaaa aagcaatagt    540
ggaattagct tgaattttga tagttctagc tgcacaccta cactgtcatc caccagatct    600
tttatatctt ccttgagtat agatggtagt gtggctaatt ggaaggaag tgcattccat    660 ttaatgggc cggctcgctc ctcggatcag agttcacagc aacacaagag gaaatgttct    720 gggagggggag aagatggaag tgtgaaatgt ggaagcagtg gtagatgtca ttgctcgaag    780
aagaggaaac atagggtaaa gaggtcgatc aaggtacctg ctattagcaa caagcttgct    840
gatatccccc ctgatgatta ttcctggaga agtatggac aaaagcccat caagggctct    900
cctcatccca gggatatta caagtgtagc agtatgagag gttgtcctgc aaggaagcat    960
gtggagaggt gcttggaaga tccgtccatg cttattgtta cctatgaagg tgaacataac   1020
cacccgagga ttccagcaca atctgcaaac acataa                             1056

<210> SEQ ID NO 88
<211> LENGTH: 343
<212> TYPE: PRT
<213> ORGANISM: Eucalyptus grandis

<400> SEQUENCE: 88

Met Glu Glu Val Glu Glu Ala Asn Arg Ala Ala Val Glu Ser Ser His
1               5                   10                  15

Arg Val Leu Ser Leu Leu Ser Gln Pro Gln Asp Gln Val Gln Cys Arg
```

```
                    20                  25                  30
Asn Leu Met Leu Glu Thr Gly Asp Ala Val Phe Arg Phe Lys Arg Val
             35                  40                  45

Val Ser Leu Leu Asn Thr Cys Leu Gly His Ala Arg Val Arg Lys Leu
     50                  55                  60

Lys Lys Leu Pro Thr Pro Leu Pro Gln Lys Ala Leu Leu Asp Asn Pro
 65                  70                  75                  80

Ile Val Arg Thr Asp Gln Ser Ser Lys Ser Leu Gln Leu Leu Pro Pro
                 85                  90                  95

Asn Tyr Pro Glu Asn Ala Ile Gln Glu Leu Asn Thr His His Lys Ala
                100                 105                 110

Ser Leu Ser Leu Gly Asn Pro Asn Leu Glu Leu Ser Ser Asn Gly Lys
            115                 120                 125

Ser Pro Leu His Leu Ala Gln Gln Ala Pro Ser Ala His Tyr His Phe
        130                 135                 140

Leu Gln Gln Gln Gln Gln Gln Lys Leu Gln Phe Gln Gln Met
145                 150                 155                 160

Lys His Gln Ala Glu Met Met Tyr His Arg Ser Asn Ser Gly Ile Ser
                165                 170                 175

Leu Asn Phe Asp Ser Ser Ser Cys Thr Pro Thr Met Ser Ser Thr Arg
            180                 185                 190

Ser Phe Ile Ser Ser Leu Ser Ile Asp Gly Ser Val Ala Asn Leu Asp
        195                 200                 205

Ala Asn Ala Phe His Leu Ile Gly Ala Ala Arg Ser Ser Asp Gln Asn
    210                 215                 220

Ser Gln His Lys Arg Lys Cys Ser Gly Arg Gly Glu Asp Gly Ser Met
225                 230                 235                 240

Lys Cys Gly Ser Ser Ser Arg Cys His Cys Ser Lys Lys Arg Lys His
                245                 250                 255

Arg Val Lys Arg Ser Ile Lys Val Pro Ala Ile Ser Asn Lys Leu Ala
            260                 265                 270

Asp Ile Pro Pro Asp Asp Tyr Ser Trp Arg Lys Tyr Gly Gln Lys Pro
        275                 280                 285

Ile Lys Gly Ser Pro His Pro Arg Gly Tyr Tyr Lys Cys Ser Ser Met
    290                 295                 300

Arg Gly Cys Pro Ala Arg Lys His Val Glu Arg Cys Leu Glu Asp Pro
305                 310                 315                 320

Ser Met Leu Ile Val Thr Tyr Glu Gly Asp His Asn His Pro Arg Val
                325                 330                 335

Pro Ser Gln Ser Ala Asn Thr
            340
```

<210> SEQ ID NO 89
<211> LENGTH: 1032
<212> TYPE: DNA
<213> ORGANISM: Eucalyptus grandis

<400> SEQUENCE: 89

```
atggaggagg ttgaagaagc gaacagagca gctgtggaga gctcccacag ggttctgagc      60
ctcttgtcgc agccgcaaga tcaggttcag tgtagaaatc tgatgcttga gactggtgat     120
gctgtattca ggttcaagag agtggttttct cttctcaata cttgcttggg tcatgctaga    180
gttaggaagt taagaaaact accgaccccct tgccccaaa aggcccctctt ggacaaccct    240 attgttagaa ctgaccaatc ttcaaagagt ctccaactcc tccctcctaa ttaccctgaa     300
```

```
aatgcaattc aggaactcaa tacacatcac aaagcctctc tttctttagg taacccgaac    360
ttggagttga gctccaatgg caaaagccct cttcatttag cccagcaagc gccatcagca    420
cactatcact ttctccagca gcagcagcag cagcagaagt tacagttcca gcaacaaatg    480
aaacaccaag ctgagatgat gtaccatagg agcaatagtg cataagctt  gaatttcgat    540 agctctagct gcacgcccac catgtcgtct acgaggtctt tcatttcttc actgagtata    600
gatgggagcg tggctaactt ggatgcgaat gctttccatt tgatcggggc ggctcgctca    660
tctgatcaga actcgcagca taagaggaag tgctctggca gaggagagga tgggagcatg    720
aaatgcggta gcagtagtag atgtcattgc tctaagaaga ggaaacatag ggtgaagagg    780
tcgattaagg tacctgctat aagcaacaag cttgcggata ttcctcccga tgattattcg    840
tggaggaagt acgggcagaa gccaatcaag ggttctcctc atcctagggg atactacaaa    900
tgtagcagca tgagaggttg ccctgcaagg aagcatgtgg aaaggtgctt ggaggacccg    960
tctatgctca ttgtcaccta cgaaggtgac cataaccacc ccagggtgcc atcacaatct   1020
gccaatacat ga                                                       1032

<210> SEQ ID NO 90
<211> LENGTH: 380
<212> TYPE: PRT
<213> ORGANISM: Arabidopsis thaliana

<400> SEQUENCE: 90

Met Glu Glu Ile Glu Gly Thr Asn Arg Ala Ala Val Glu Ser Cys His
1               5                   10                  15

Arg Val Leu Asn Leu Leu His Arg Ser Gln Gln Gln Asp His Val Gly
                20                  25                  30

Phe Glu Lys Asn Leu Val Ser Glu Thr Arg Glu Ala Val Ile Arg Phe
            35                  40                  45

Lys Arg Val Gly Ser Leu Leu Ser Ser Ser Val Gly His Ala Arg Phe
        50                  55                  60

Arg Arg Ala Lys Lys Leu Gln Ser His Val Ser Gln Ser Leu Leu Leu
65                  70                  75                  80

Asp Pro Cys Gln Gln Arg Thr Thr Glu Val Pro Ser Ser Ser Ser Gln
                85                  90                  95

Lys Thr Pro Val Leu Arg Ser Gly Phe Gln Glu Leu Ser Leu Arg Gln
            100                 105                 110

Pro Ser Asp Ser Leu Thr Leu Gly Thr Arg Ser Phe Ser Leu Asn Ser
        115                 120                 125

Asn Ala Lys Ala Pro Leu Leu Gln Leu Asn Gln Gln Thr Met Pro Pro
    130                 135                 140

Ser Asn Tyr Pro Thr Leu Phe Pro Val Gln Gln Gln Gln Gln Gln Gln
145                 150                 155                 160

Gln Gln Gln Gln Gln Gln Glu Gln Gln Gln Gln Gln Gln Gln Gln Gln
                165                 170                 175

Gln Gln Phe His Glu Arg Leu Gln Ala His His Leu His Gln Gln Gln
            180                 185                 190

Gln Leu Gln Lys His Gln Ala Glu Leu Met Leu Arg Lys Cys Asn Gly
        195                 200                 205

Gly Ile Ser Leu Ser Phe Asp Asn Ser Ser Cys Thr Pro Thr Met Ser
    210                 215                 220

Ser Thr Arg Ser Phe Val Ser Ser Leu Ser Ile Asp Gly Ser Val Ala
225                 230                 235                 240
```

```
Asn Ile Glu Gly Lys Asn Ser Phe His Phe Gly Val Pro Ser Ser Thr
            245                 250                 255

Asp Gln Asn Ser Leu His Ser Lys Arg Lys Cys Pro Leu Lys Gly Asp
        260                 265                 270

Glu His Gly Ser Leu Lys Cys Gly Ser Ser Arg Cys His Cys Ala
        275                 280                 285

Lys Lys Arg Lys His Arg Val Arg Arg Ser Ile Arg Val Pro Ala Ile
        290                 295                 300

Ser Asn Lys Val Ala Asp Ile Pro Pro Asp Asp Tyr Ser Trp Arg Lys
305                 310                 315                 320

Tyr Gly Gln Lys Pro Ile Lys Gly Ser Pro Tyr Pro Arg Gly Tyr Tyr
                325                 330                 335

Lys Cys Ser Ser Met Arg Gly Cys Pro Ala Arg Lys His Val Glu Arg
            340                 345                 350

Cys Leu Glu Asp Pro Ala Met Leu Ile Val Thr Tyr Glu Ala Glu His
        355                 360                 365

Asn His Pro Lys Leu Pro Ser Gln Ala Ile Thr Thr
        370                 375                 380

<210> SEQ ID NO 91
<211> LENGTH: 1143
<212> TYPE: DNA
<213> ORGANISM: Arabidopsis thaliana

<400> SEQUENCE: 91
atggaggaga tagaaggaac aaacagagca gctgttgaga gttgtcatag agttcttaat      60
cttttacata gatcacagca acaagatcat gttggttttg aaaagaattt agtatctgaa     120
actagagaag ctgtgattag gttcaagaga gttgggagtt tgttaagcag tagtgttggt     180
catgctaggt ttagaagagc taagaaactt cagagtcatg tctctcaaag tctcttactt     240
gatccatgtc aacaaaggac aacagaagtt ccatcatcat cttctcagaa acaccggta      300 ctccggtctg gtttccagga attgagcttg agacaaccct cagattcact cactttaggg    360
actcgctctt ttagtttaaa ctcaaatgct aaagctcctc tccttcagct taatcagcag    420
acaatgcctc cttcgaatta tcctactttg tttccagtac aacaacaaca acaacaacaa    480
caacaacaac aacagcagga gcagcagcag cagcagcagc agcaacagca acagtttcat    540
gaacggttac aagctcacca tcttcatcag aacagcagc tacagaaaca tcaagctgag     600
cttatgctta ggaaatgcaa tggtgggata agtttgagtt cgataactc tagttgtact     660 ccaactatgt catccactag gtcctttgtt tcttcactta gcatagatgg tagtgttgct    720
aatatagagg gaaagaactc cttccatttt ggggttccta gttcaactga tcagaattca    780
ctacattcta agaggaaatg cccctttgaaa ggagatgaac atggaagctt aaaatgcggg    840
agctctagcc gatgccactg cgctaagaag aggaaacatc gggttaggag atcgattaga    900
gtaccggcta aagtaacaa ggttgcagat atccctcctg atgattattc atggcgaaaa    960
tatggtcaga agcccatcaa gggctctcct tatcccagag atattacaa atgtagtagc     1020 atgagaggtt gtccagcgag gaagcatgtt gagagatgtt tggaagatcc ggcaatgctt    1080
attgttactt atgaagcaga gcataaccac ccgaaattgc catctcaagc tataacaact    1140
taa                                                                   1143

<210> SEQ ID NO 92
```

```
<400> SEQUENCE: 92

000

<210> SEQ ID NO 93

<400> SEQUENCE: 93

000

<210> SEQ ID NO 94

<400> SEQUENCE: 94

000

<210> SEQ ID NO 95

<400> SEQUENCE: 95

000

<210> SEQ ID NO 96

<400> SEQUENCE: 96

000

<210> SEQ ID NO 97

<400> SEQUENCE: 97

000

<210> SEQ ID NO 98

<400> SEQUENCE: 98

000

<210> SEQ ID NO 99

<400> SEQUENCE: 99

000

<210> SEQ ID NO 100
<211> LENGTH: 178
<212> TYPE: PRT
<213> ORGANISM: Zea mays

<400> SEQUENCE: 100

Met Arg Arg Ala Glu Pro Val Gly Glu Gln Ala Asp Ala Glu Arg Arg
1               5                   10                  15

Met Ser Gly Tyr Lys Gly Val Arg Arg Arg Arg Trp Gly Lys Trp Val
            20                  25                  30

Ser Glu Ile Arg Val Pro Gly Ser Arg Glu Arg Leu Trp Leu Gly Ser
        35                  40                  45

Tyr Ala Thr Pro Glu Ala Ala Val Ala His Asp Thr Ala Val Tyr
    50                  55                  60

Phe Leu Arg Gly Gly Gly Ala Gly Asp Val Ala Ala Leu Asn Phe
65                  70                  75                  80

Pro Glu Arg Ala Ala Ala Tyr Gly Ala Gly Arg Leu Ser Pro
                85                  90                  95
```

```
Arg Ser Val Gln Arg Val Ala Ser Asp Ala Gly Met Ala Ala Asp Ala
              100                 105                 110

Gln Leu Val Ala Ala Arg Glu Asp Thr Arg Ala Leu Arg Ala Gly Ile
            115                 120                 125

Gly Gly Gly Ala Ser Ala Arg Pro Arg Asp Arg Asp Ala Gly Asp Ala
        130                 135                 140

Cys Ala Gly Arg Ala His Asn Ala Ser Leu His Ser Thr Gly Ala Gly
145                 150                 155                 160

Arg Glu Gln Pro Val Ser Gly Glu Ile Ser Val Asp Asp Met Asp Ile
                165                 170                 175

Leu Leu

<210> SEQ ID NO 101
<211> LENGTH: 537
<212> TYPE: DNA
<213> ORGANISM: Zea mays

<400> SEQUENCE: 101
atgaggcgcg cggagccggt cggcgagcag gcggacgcgg agcggcgcat gagcgggtac      60
aagggcgtgc ggcggcgccg gtggggggaag tgggtgtcgg agatccgggt gcccggctcg    120
cgggagcgcc tgtggctcgg ctcctacgcc acgcccgagg ccgccgccgt cgcgcacgac    180
acggccgtct acttcctccg cggcggcggc ggcgcgggcg acgtcgcggc gctcaacttc    240
cccgagcgcg cggcggccgc gtacggcgca ggggccgcc tgtcgccccg gtccgtgcag    300
cgcgtggcgt ccgacgccgg catggccgcc gacgcgcagc tcgtcgcggc gcgggaggac    360
acccgcgcgc ttcgcgccgg cattggcggt ggcgccagcg cgcgcccgcg cgatcgggat    420
gctggtgacg cctgcgcggg ccgtgcgcac aacgctagcc ttcacagtac gggcgccgga    480
agggagcagc ctgtctccgg ggagattagc gtggatgaca tggatatttt gctgtag       537

<210> SEQ ID NO 102
<211> LENGTH: 186
<212> TYPE: PRT
<213> ORGANISM: Zea mays

<400> SEQUENCE: 102

Met Ser Arg Ala Ala Thr Asn Ser Gly Ala Glu Arg Arg Cys Arg Tyr
1               5                   10                  15

Arg Gly Val Arg Arg Ala Trp Gly Lys Trp Val Ser Glu Ile Arg
            20                  25                  30

Val Pro Gly Thr Arg Glu Arg Leu Trp Leu Gly Ser Tyr Ala Ala Pro
        35                  40                  45

Glu Ala Ala Ala Val Ala His Asp Ala Ala Ala Cys Leu Leu Arg Gly
    50                  55                  60

Cys Ala Gly Arg Arg Leu Asn Phe Pro Gly Arg Ala Ala Cys Tyr Tyr
65                  70                  75                  80

Ala Cys Gly Gly Gln Gln Pro Leu Ser Pro Arg Ser Val Gln Arg Val
                85                  90                  95

Ala Ser Asp Ala Gly Met Ala Ala Asp Ala Gln Ile Val Asp Ala Arg
            100                 105                 110

Ala Ala Leu Ala Ser Pro Pro Val Val Gln Pro Ala Ala Leu Ala
        115                 120                 125

Gly Ile Ile Gly Gly Ala Ala Arg Glu Gly Gly Gly Val Arg Gly
    130                 135                 140

Pro Ala Cys Ala Pro Ala Pro Pro Ser Asn Gly Ala Gly Ser Ser Ser
```

```
                    145                 150                 155                 160
Thr Tyr Trp Ser Thr Pro Ser Ser Glu Pro Pro Leu Val Tyr Gly Asp
                165                 170                 175

Ile Ser Val Asp Asp Ile Glu Ile Leu Ile
            180                 185

<210> SEQ ID NO 103
<211> LENGTH: 561
<212> TYPE: DNA
<213> ORGANISM: Zea mays

<400> SEQUENCE: 103
atgagccgcg cagcgaccaa cagcggcgcg gagcggcggt gccggtacag gggcgtgcgg       60
cggcgggcct gggggaagtg ggtgtcggag atccgggtgc cgggcacgcg ggagcggctg      120
tggctgggat cctacgcggc gcccgaggcc gccgccgtcg cgcacgacgc cgccgcgtgc      180
ctcctccgcg gctgcgcggg ccgccgcctc aacttcccgg gccgcgccgc ctgctactac      240
gcctgcggcg ggcagcagcc gctgtcgccg cgctccgtgc agcgcgtcgc gtccgacgcc      300
ggcatggccg ccgacgcgca gatcgtcgac gcgcgggcgg ccctcgcctc gccgccgccc      360
gttgtccagc cgccgctctc gctggcatt attggcggcg ccgcgcgaga aggcggcgga      420
ggcgtgcgag gccccgcgtg cgcgccggcg ccgccaagca acggcgctgg cagcagcagt      480
acgtattggt ccacgccgag cagtgagccg ccgcttgttt acggggacat tagcgtagac      540
gacatagaga tcttgatttg a                                                561

<210> SEQ ID NO 104
<211> LENGTH: 316
<212> TYPE: PRT
<213> ORGANISM: Zea mays

<400> SEQUENCE: 104

Met Ala Val Asp Leu Met Gly Cys Tyr Ala Pro Arg Arg Ala Asn Asp
1               5                   10                  15

Gln Leu Ala Ile Gln Glu Ala Ala Ala Gly Leu Arg Ser Leu Glu
            20                  25                  30

Leu Leu Val Ser Ser Leu Ser Thr Gln Ala Ala Ala Pro His Arg Ala
            35                  40                  45

Ala Ala His Gln Leu Gln Lys Pro Pro Ser Gln Pro Pro Ile Gly Glu
        50                  55                  60

Ile Ala Asp Gln Ala Val Ser Arg Phe Arg Lys Val Ile Ser Ile Leu
65                  70                  75                  80

Asp Arg Thr Gly His Ala Arg Phe Arg Arg Gly Pro Val Val Glu Ala
                85                  90                  95

Pro Pro Val Pro Pro Pro Ala Val Ser Ala Pro Ala Leu Pro Val
            100                 105                 110

Ala His Val Val Ala Pro Val Gly Ala Ala Gln Pro Gln Ser Leu Thr
        115                 120                 125

Leu Asp Phe Thr Lys Pro Asn Leu Ala Val Ser Gly Ala Thr Ser
    130                 135                 140

Val Thr Ser Thr Ser Phe Phe Ser Ser Val Thr Ala Gly Glu Gly Ser
145                 150                 155                 160

Val Ser Lys Gly Arg Ser Leu Val Ser Ser Gly Lys Pro Pro Leu Ser
                165                 170                 175

Gly His Lys Arg Lys Pro Cys Ala Gly Ala His Ser Glu Ala Thr Thr
            180                 185                 190
```

```
Asn Gly Ser Arg Cys His Cys Ser Lys Arg Lys Asn Arg Val Lys
        195                 200                 205

Arg Thr Ile Arg Val Pro Ala Ile Ser Ala Lys Ile Ala Asp Ile Pro
    210                 215                 220

Pro Asp Glu Tyr Ser Trp Arg Lys Tyr Gly Gln Lys Pro Ile Lys Gly
225                 230                 235                 240

Ser Pro Tyr Pro Arg Gly Tyr Tyr Lys Cys Ser Thr Val Arg Gly Cys
                245                 250                 255

Pro Ala Arg Lys His Val Glu Arg Ala Thr Asp Asp Pro Ala Met Leu
                260                 265                 270

Val Val Thr Tyr Glu Gly Glu His Arg His Thr Pro Gly Ala Pro Ala
            275                 280                 285

Pro Ala Pro Ser Pro Leu Ala Ala Ala Ser Pro Val Pro Ala Ser Ala
        290                 295                 300

Ala Ala Ala Val Ser Ala Gly Asn Asn Gly Leu Val
305                 310                 315

<210> SEQ ID NO 105
<211> LENGTH: 951
<212> TYPE: DNA
<213> ORGANISM: Zea mays

<400> SEQUENCE: 105
atggccgtgg acctgatggg gtgctacgcc ccgcgccgcg ccaacgacca gctcgccatc      60
caggaggcgg cggcggcggg gctccgcagc ctggagctcc tcgtgtcgtc gctgtccacg     120
caggccgccg cgccgcacag ggccgcggct caccagctgc agaagccgcc ttcgcagccg     180
ccgatcggcg agatcgccga ccaggccgtc tccaggttcc gcaaggtcat ctccatcctg     240
gaccgcaccg gccacgcccg cttccggcgc gggcccgtgg tcgaggcgcc gccaccggtg     300
cctcctccgg ccgtctccgc tcccgctctc cccgtggcgc acgtggtggc tcccgtcggc     360
gcggcgcagc cccagagcct gaccctggac ttcacgaagc cgaacctggc cgtgtcgggc     420
ggcgccacgt ccgtcaccct cacgtccttc ttctcctcgg tcacggccgg cgagggcagc     480
gtgtccaagg gccgcagcct ggtgtcctcc ggcaagccgc cgctgtccgg ccacaagcgg     540
aagccctgcg ccggcgcgca ctccgaggcc accaccaacg cagccgctg ccactgctcc      600 aagagaagga aaaccgcgt gaagaggacc atcagagtgc cggcgatcag cgccaagatc      660
gcggacatcc cgccggacga gtactcgtgg aggaagtacg ccagaagcc catcaagggc      720 tcccctac cacggggcta ctacaagtgc agcaccgtgc gcgggtgccc ggcgaggaag      780
cacgtggagc gcgccaccga cgacccggcc atgctggtgg tgacgtacga gggcgagcac     840
cgccacacgc cgggcgcgcc cgcgcccgcg cccagccccc tggcggccgc gtcgccggtg     900
cccgcctccg ccgccgccgc cgtctccgcc ggcaacaacg gcttgtctag                951

<210> SEQ ID NO 106
<211> LENGTH: 331
<212> TYPE: PRT
<213> ORGANISM: Zea mays

<400> SEQUENCE: 106

Met Thr Thr Leu Asp Leu Met Gly Gly Tyr Gly Arg Val Asp Glu Gln
1               5                  10                  15

Val Ala Ile Gln Glu Ala Ala Thr Ala Gly Leu Arg Gly Met Glu Arg
            20                  25                  30
```

Leu Ile Leu Gln Leu Ser Gln Ala Gly Thr Gly Glu Arg Ser Leu Ser
 35                  40                  45

Pro Pro Ala Val Gln Ala Gln Arg Gln Gln Lys Gln Leu Glu Gln
 50                  55                  60

Ile Gln Gln Gln Val Asp Cys Arg Glu Leu Thr Asp Met Thr Val Ser
65                  70                  75                  80

Lys Phe Lys Lys Val Ile Ser Ile Leu Asn Arg Thr Gly His Ala Arg
                85                  90                  95

Phe Arg Arg Gly Pro Val Ala Ala Arg Ser Gln Ser Gln Ser Gln Gly
            100                 105                 110

Pro Ala Ser Pro Glu Pro Ala Gln Ser Ala Pro Ala Ala Arg
        115                 120                 125

Pro Leu Thr Leu Asp Phe Thr Lys Ser Val Ser Gly Tyr Ser Arg Asp
    130                 135                 140

Ser Gly Phe Ser Val Ser Gly Ala Ser Ser Phe Leu Ser Ser Val
145                 150                 155                 160

Thr Thr Gly Asp Gly Ser Val Ser Asn Gly Arg Ala Gly Gly Ser Ser
                165                 170                 175

Phe Leu Met Phe Pro Pro Ala Pro Gly Ala Ala Ser Cys Ala Lys Pro
            180                 185                 190

Pro Pro Ala Gly Ala Ala Gln Lys Arg Lys Cys His Asp His Ala His
        195                 200                 205

Ser Glu Asn Val Ala Gly Gly Lys Tyr Gly Ala Asn Gly Gly Arg Cys
    210                 215                 220

His Cys Ser Lys Arg Arg Lys His Arg Val Lys Arg Thr Ile Arg Val
225                 230                 235                 240

Pro Ala Ile Ser Pro Lys Val Ala Asp Ile Pro Ala Asp Glu Tyr Ser
                245                 250                 255

Trp Arg Lys Tyr Gly Gln Lys Pro Ile Lys Gly Ser Pro Tyr Pro Arg
            260                 265                 270

Gly Tyr Tyr Lys Cys Ser Thr Val Arg Gly Cys Pro Ala Arg Lys His
        275                 280                 285

Val Glu Arg Asp Pro Ala Asp Pro Ser Met Leu Ile Val Thr Tyr Glu
    290                 295                 300

Gly Glu His Arg His Ser Pro Ala Ser Gly Gln Asp Pro Pro Pro
305                 310                 315                 320

Ser Leu Ala Pro Leu Pro Glu Leu Pro Ser His
                325                 330

<210> SEQ ID NO 107
<211> LENGTH: 996
<212> TYPE: DNA
<213> ORGANISM: Zea mays

<400> SEQUENCE: 107
atgacgaccc tcgatctgat gggagggtac gggcgggtgg acgagcaggt ggccatccag    60
gaggccgcca cggcggggct gcgcgggatg gagcgtctca tcttgcagct ctcccaggct   120
ggcaccgggg agcggtcgtt gtccccaccg gcggtacagg cgcagcgcca gcagcagaag   180
cagctggagc agatccagca gcaggttgac tgccgggagc tcacggacat gacggtgtcc   240
aagttcaaga aggtgatctc catcctgaac cgcacggggc acgcgcggtt ccggcgtggc   300
cccgtggcgg cgcggtcgca gtcgcagtcg cagggacctg cctcccccga gcccgcgcaa   360
tcggcgccgg ctcccgccgc gaggcccctg acgctggact tcaccaagtc ggtgtccggt   420

-continued

```
tacagcaggg actccgggtt cagcgtgtcc ggcgcgagct cgtcgttcct gtcgtcggtg    480
acgaccgggg acgggagcgt gtcgaacggg cgcgcgggag gctcgtcgtt cctcatgttc    540
ccaccggcgc ccggcgcggc cagctgcgcg aagccgccgc ccgccggtgc ggcgcagaag    600
cgcaagtgcc acgaccacgc gcactcggag aacgtcgccg gcggcaagta cggggctaac    660
ggcgggcgct gccactgctc gaagcgcagg aagcaccgtg tgaagcgcac gatccgcgtg    720
ccggcgatca gccccaaagt ggcggacatc cccgccgacg agtactcgtg gcgcaagtac    780
ggccagaaac ccatcaaggg gtcgccctac ccacgcggct actacaagtg cagcacggtg    840
cgcggctgcc ccgccggaa gcatgtggag cgcgaccccg ccgacccgtc gatgctgatc    900
gtcacctacg agggcgagca ccgccacagc cccgcctccg gccaggaccc gccgccgccg    960
tcgctcgcgc cgctgccgga gctgcccagc cattga    996
```

```
<210> SEQ ID NO 108
<211> LENGTH: 350
<212> TYPE: PRT
<213> ORGANISM: Zea mays

<400> SEQUENCE: 108
```

Met Asp Ser Asp Tyr Ile Ala Ser Leu Leu Met Gly Ser Ser Ala Pro
1               5                   10                  15

Ala Leu Ser Phe Ala Ala Leu Asp Ala Gly Phe Leu Asp Thr Leu Arg
            20                  25                  30

Gly Gly Gly Gly Gly Gly Leu Phe Gly Val Pro Ala Glu Ala Gly Cys
        35                  40                  45

Gly Gly Gly Ser Pro Glu Gly Ser Ser Val Ser Asp Pro Ala Trp Ala
    50                  55                  60

Arg Ala Arg Asp Tyr Gly Asn Ala Arg Lys Arg Lys Ala Pro Pro Thr
65                  70                  75                  80

Gly Ser Ala Gly Gly Lys Glu Ala Cys Leu Ser Lys Val Ala Glu Ala
                85                  90                  95

Lys Gly Pro Asp Gly Lys Arg Cys Arg Val Val Gly Ala Ser Asp Ser
            100                 105                 110

Pro Val Lys Pro Lys Glu Glu Glu Glu Ala Ala Ala Ser Asp Ala
            115                 120                 125

Leu Val Glu Val Lys Ala Gln Lys Lys Gly Lys Gly Lys Ser Ser Lys
    130                 135                 140

Pro Ala Val Glu Pro Pro Lys Asp Tyr Val His Val Arg Ala Arg Arg
145                 150                 155                 160

Gly Gln Ala Thr Asp Ser His Ser Leu Ala Glu Arg Val Arg Arg Glu
                165                 170                 175

Lys Ile Ser Gln Arg Met Lys Phe Leu Gln Asp Leu Val Pro Gly Cys
            180                 185                 190

Asn Lys Val Val Gly Lys Ala Leu Met Leu Asp Glu Ile Ile Asn Tyr
        195                 200                 205

Val Gln Ser Leu Gln Gln Gln Val Glu Phe Leu Ser Met Lys Leu Ala
    210                 215                 220

Thr Val Asn Pro Glu Leu Asp Phe Ser Asn Leu Ser Thr Leu Leu His
225                 230                 235                 240

Lys Asp Met Tyr Gln Gln Pro Cys Gly Gly Pro Ser Ala Ser Ser Val
                245                 250                 255

Phe Pro Leu Glu Ser Ala Gly Ala Ala Phe Pro Phe Cys Glu Gln Ala
            260                 265                 270

```
Asp Leu Phe His Ser Phe Gly Ser Gly Gly Ser Gly Ser Gly
            275                 280             285

Met Glu Asp Gln Cys Ser Leu Ser Leu Leu Leu Asp Thr Ala Leu Pro
        290                 295                 300

His Ala Ala Ser Pro Gln Phe Ala Phe Gln Lys Gln Gln Arg Asp Leu
305                 310                 315                 320

Trp Glu Asp Gly Leu Gln His Ala Leu Pro Thr Pro Thr Thr Gly Ser
                325                 330                 335

Glu Gln Arg Gln Glu Glu Asp Gly Leu Leu Val Pro Asp Leu
            340                 345                 350
```

<210> SEQ ID NO 109
<211> LENGTH: 1053
<212> TYPE: DNA
<213> ORGANISM: Zea mays

<400> SEQUENCE: 109

```
atggacagcg actacattgc cagcctgctc atgggctcat ccgcccctgc actcagcttc    60
gccgcgctgg acgccgggtt cctcgacacg ctacgcggcg gcggcggcgg gggcctcttc   120
ggggtgcccg cggaggcagg gtgtggcggc gggtctccgg aggggtcgtc ggtgtccgac   180
ccagcgtggg cgcgcgctag ggactacggc aatgccagga acgcaaggc gccgcccacg   240
gggtccgccg gtggcaagga ggcctgcttg agcaaggttg cggaggccaa ggtccggac   300
gggaagaggt gcagagtagt gggtgccagc gacagtccgg tgaagccgaa ggaagaggag   360
gaggaggcgg cggcgagcga cgccttggtt gaagtcaaag cgcagaagaa gggcaagggg   420
aagagctcga agccggcagt cgaaccgccc aaagactacg tccatgtccg ggcgcggcgg   480
gggcaggcga ctgacagcca cagccttgca gagagggtta aagagagaa gattagccag   540
aggatgaaat ttctacagga cctagtgcca ggatgcaaca aggtggtcgg caaggcactc   600
atgctcgatg agatcataaa ctacgtccag tcgctgcagc agcaagttga gttcctgtcc   660
atgaagctcg ccactgtgaa cccagagctt gatttcagca acctatcgac actcctgcac   720
aaagacatgt accaacagcc atgtggtggc ccttcggcaa gttcggtctt tccactggaa   780
agcgccggcg cagcttttcc attctgcgag caggcggatc ttttccacag ctttggctcg   840
ggtggtagcg gtagcggtag tggtatggag gatcagtgct ctctaagcct gctgctagac   900
acggctctgc cccacgcggc cagcccacag tttgcttttc aaaagcagca aagggacttg   960
tgggaggatg gcctacagca tgctttgcct accctacta ccggtagcga gcaaaggcag  1020
gaggaggatg gctttttagt acccgacctt tga                              1053
```

<210> SEQ ID NO 110
<211> LENGTH: 460
<212> TYPE: PRT
<213> ORGANISM: Zea mays

<400> SEQUENCE: 110

```
Met Asp Cys Gly Pro Pro Asp Gln Leu Pro Ser Ser Ala Pro Ala
1               5                  10                  15

Cys Phe Leu Asn Leu Asn Trp Asp Gln Ser Met Ala Ala Thr Ala
            20                  25                  30

Gly Asp His Leu Asp Leu Val Ser Ser Pro Ala Ser Asn Ser Thr Ala
            35                  40                  45

Ala Asp Gly Leu Ala Leu His Gly Ile Ser Pro Gln Pro Gln Tyr Gly
        50                  55                  60
```

```
Gly Thr Pro Leu Ser Ser Pro Arg Lys Leu Asn Leu Ser Met Met Gly
 65                  70                  75                  80

Gln Phe His His Tyr Pro Pro Met Gly His Leu Asp Gln Phe Leu Ala
                 85                  90                  95

Asp Pro Gly Phe Ala Ala Arg Ala Ala Arg Leu Ser Gly Phe Asp Gly
            100                 105                 110

Arg Pro Gly Gly Ser Gly Tyr Gly Gly Ala Val Pro Gly Gln Phe Gly
        115                 120                 125

Leu Pro Asp Ala Gly Pro Ile Gly Gly Ala Leu Arg Glu Leu Glu Leu
    130                 135                 140

Gly Asn Gly Arg Asp Glu Ser Ser Val Ser Asp Pro Ala Ser Ala Ser
145                 150                 155                 160

Ala Glu Met Ala Leu Lys Ala Pro Ser Asp Gly Asn Ala Lys Lys Arg
                165                 170                 175

Lys Ala Ser Gly Lys Gly Lys Gly Lys Asp Gly Pro Gly Ser Thr Ala
            180                 185                 190

Ala Thr Lys Glu Glu Ser Ser Gly Lys Arg Cys Lys Ser Ala Glu Glu
        195                 200                 205

Ser Asn Gly Ala Glu Glu Asn Ser Gly Lys Lys Ala Ala Ala Gln
    210                 215                 220

Ser Asn Ser Asp Asn Gly Gly Lys Lys Gln Gly Lys Asp Gly Ala Ser
225                 230                 235                 240

Lys Pro Pro Glu Pro Lys Asp Tyr Ile His Val Arg Ala Arg Arg
                245                 250                 255

Gly Glu Ala Thr Asp Ser His Ser Leu Ala Glu Arg Val Arg Arg Glu
        260                 265                 270

Lys Ile Ser Gln Arg Met Lys Leu Leu Gln Asp Leu Val Pro Gly Cys
    275                 280                 285

Asn Lys Val Val Gly Lys Ala Val Met Leu Asp Glu Ile Ile Asn Tyr
    290                 295                 300

Val Gln Ser Leu Gln Arg Gln Val Glu Phe Leu Ser Met Lys Leu Ala
305                 310                 315                 320

Thr Val Asn Pro Gln Leu Asp Phe Asn Asn Leu Pro Asn Leu Leu Pro
                325                 330                 335

Lys Asp Met His Gln Ser Cys Gly Pro Leu Gln Asn Ser His Phe Pro
            340                 345                 350

Leu Glu Thr Ser Gly Ala Pro Leu Pro Tyr Leu Asn Gln Gly Asn Pro
        355                 360                 365

Leu Ile Gly Cys Gly Leu Pro Asn Gly Met Asp Asn Ser Gln Ser Ser
    370                 375                 380

Met His Pro Leu Asp Pro Ala Phe Cys Arg Pro Met Ser Ser Gln Gln
385                 390                 395                 400

His Pro Phe Leu Asn Gly Val Ser Asp Ala Ala Ser Lys Val Gly Thr
                405                 410                 415

Phe Trp Gln Asp Asp Leu Gln Ser Val Val His Met Asp Met Gly Gln
            420                 425                 430

Gln Ser Gln Gln Glu Met Ala Pro Thr Ser Ser Asn Ser Tyr Asn Asp
        435                 440                 445

Gly Ser Leu Gln Thr Val His Met Lys Met Glu Leu
    450                 455                 460

<210> SEQ ID NO 111
<211> LENGTH: 1383
<212> TYPE: DNA
```

<213> ORGANISM: Zea mays

<400> SEQUENCE: 111

```
atggactgcg ggccgcccga ccagctgccg ccgtcgtcgg cgccggcgtg cttcctcaac      60
ctcaactggg accagtccat ggccgccgcc acggctggcg accacctcga cctggtctcc     120
tccccggcgt ccaactcgac ggcggctgac ggcctcgctc tccacgggat ctcgccgcag     180
ccgcagtacg gaggcactcc gctcagctcg ccccgcaagc tgaacctctc catgatgggc     240
cagttccacc actacccgcc gatgggccat ctagaccagt tcctcgccga cccaggcttc     300
gccgcgcgcg cggcgaggct ctccggcttc gacggccgcc ccgtgggag tggctacggc      360
ggcgccgtcc cgggacagtt tggcctcccc gacgccggcc ccatcggcgg cgcattgagg     420
gagctggagc tcgggaacgg ccgggacgag tcatcggtgt ccgatccggc gtccgccagc     480
gccgagatgg cgctcaaggc gccttccgat ggcaatgcga agaaacggaa ggctagcggg     540
aaggggaaag gcaaggacgg ccccgggtcc accgccgcca ccaaggagga gtccagtggg     600
aaacggtgca atcggcgga ggagagcaat ggcgcggagg agaactccgg caagggtaag      660
gccgccgcgc agagcaacag cgacaacggt gggaagaagc aggggaagga cggcgcgtcc     720
aagcctccgg agccgcccaa ggactacatc acgtccggg cgaggcgcgg cgaggcgaca      780
gacagccaca gcctcgctga gagggtgaga agggagaaga tcagccagcg gatgaagctt     840
ctgcaggatc tcgtcccggg ctgcaacaag gtggtcggca aggcggtgat gctggatgaa     900
atcataaact acgtgcagtc cttgcaacgg caagtcgagt tcctgtccat gaaactggcc     960
accgtgaatc cccagctgga cttcaacaac ctgcctaacc tccttcctaa agatatgcac    1020
cagtcctgcg gccgctgca gaactcgcat ttcccgctgg agacctcagg cgcgccgctg     1080
ccataccctca accaggggaa ccctctaata ggctgcggcc tacccaacgg catggacaac    1140
agccagagct ccatgcaccc gctcgacccg gcgttttgcc ggccgatgag ctcgcagcag    1200
cacccttttcc tcaacggtgt cagcgacgca gcgtccaagg tcgggacttt ctggcaagat    1260
gaccttcaga gcgtagtcca catggatatg gggcagcaga ccagcagga gatggctccc     1320
acctcctcca cagctacaa cgacggttcg ttgcaaacag tgcacatgaa aatggagctt     1380
tga                                                                  1383
```

<210> SEQ ID NO 112
<211> LENGTH: 404
<212> TYPE: PRT
<213> ORGANISM: Zea mays

<400> SEQUENCE: 112

```
Met Lys Glu Gly Arg Pro Gly Ala Gly Asp Tyr Ile Ala Ser Leu Leu
1               5                   10                  15

Ser Ser Ser Pro Arg Leu Asp Phe Gly Gly Glu Glu Glu Glu Asp Cys
            20                  25                  30

Leu Asp Arg Phe Cys Gly Asp Pro Gly Phe Ala Ala Arg Ala Ala Arg
        35                  40                  45

Leu Ser Ser Phe Ser Gly Gln Arg Phe Ala Val Thr Ala Gly Leu Phe
    50                  55                  60

Gly Leu Pro Pro Pro Leu Pro Ala Ala Ser Gly Gly Glu Phe Ala
65                  70                  75                  80

Gly Ser Arg Glu Ala Ser Ser Val Ser Asp Pro Ala Ser Ala Met Lys
                85                  90                  95

Asp Ala Asn Ala Lys Lys Arg Lys Ala Pro Ala Ala Ala Ala Ala Lys
```

```
              100                 105                 110
Gly Lys Gly Arg Glu Pro Ser Ala Gln Ala Gln Ala Gly Glu Pro Lys
            115                 120                 125
Gly Pro Asp Ala Lys Arg Cys Cys Lys Ala Glu Gly Glu Gly Gly Glu
        130                 135                 140
Glu Gly Ser Pro Val Lys Leu Pro Lys Pro Glu Gln Ala Gly Ser Asp
145                 150                 155                 160
Ser Ser Val Glu Asp Gly Gly Ala Gln Asn Gln Lys Pro Pro Pro Pro
                165                 170                 175
Val Lys Gly Lys Asn Ala Lys Pro Val Glu Pro Pro Arg Asp Tyr Val
            180                 185                 190
His Val Arg Ala Arg Arg Gly Gln Ala Thr Asp Ser His Ser Leu Ala
        195                 200                 205
Glu Arg Val Arg Arg Glu Arg Ile Ser Gln Arg Met Lys Val Leu Gln
210                 215                 220
Asp Leu Val Pro Gly Cys Asn Lys Val Ile Gly Lys Ala Leu Met Leu
225                 230                 235                 240
Asp Glu Ile Ile Asn Tyr Val Gln Ser Leu Gln Arg Gln Val Glu Phe
                245                 250                 255
Leu Ser Met Lys Leu Ala Thr Val Asn Pro Leu Asp Leu Ser Asn Leu
            260                 265                 270
Pro Thr Leu Leu Gln Lys Asp Met Phe Gln Ala Cys Gly Ala Ser Ala
        275                 280                 285
Ser Ser Val Phe Ser Leu Glu Ser Cys Ser Pro Gly Phe Pro Phe Gly
    290                 295                 300
Gly Gln Gly Asp Val Phe Gln Ser Phe Val Pro Asn Gly Leu Glu Asn
305                 310                 315                 320
Pro Cys Gly Gly Leu Asn Pro Leu Asp Leu Ala Leu Ser Gln Ala Thr
                325                 330                 335
Gly Gly Gln Phe Gly Phe Gln Asp Gly Thr Ala Gly Thr Asn Leu Gln
            340                 345                 350
Gln Arg Asn Tyr Trp Glu Glu Glu Glu Asp Leu Gln Ser Val Phe
        355                 360                 365
His Ile Asp Asp Asn Gly Gln Ser Gln Glu His Gly Ala Ser Ala Ser
    370                 375                 380
Ala Gln Ser Phe His Gly Gln Leu Gln Pro Gln Glu Gly His Met Lys
385                 390                 395                 400
Met Glu Phe Phe

<210> SEQ ID NO 113
<211> LENGTH: 1215
<212> TYPE: DNA
<213> ORGANISM: Zea mays

<400> SEQUENCE: 113
atgaaagagg gcagacccgg cgccggcgac tacattgcca gcctgctaag ctcgtcgccg      60
aggctcgact tcgcgggga ggaggaggag gactgcctgg acaggttctg cggcgacccg     120
gggttcgcgg ctcgcgcggc gcggctgtcc agcttcagcg gcagcgctt cgccgtcacc     180 gcgggcctct tcgggctgcc cccgccgctg cccgccgcga gcggcggcgg cgagttcgcc     240
gggtcccggg aggcgtcgtc ggtgtcggac ccggcgtcgg cgatgaagga cgccaatgcc     300
aagaagcgga aggcgcccgc ggcggcggcg gccaagggca aggcaggga gccatctgcg     360 caggcacagg caggggagcc gaagggtccg gacgccaaga ggtgctgcaa ggcggaggga     420
```

```
ggcgaggggg aggaggggag ccccgtgaag ctgcccaagc cggagcaggc cggcagcgac      480
agctccgtcg aggacggcgg cgcgcagaac cagaagccgc cgccgccggt gaagggaaag      540
aatgccaagc cggtggagcc tcccagggac tacgtccatg tccgggccag gagagggcag      600
gctaccgaca gccacagcct cgcagagagg gtgagaaggg agaggatcag ccagaggatg      660
aaggtccttc aggacctggt gccaggatgc aacaaggtga tcggcaaggc gctgatgctc      720
gacgagatca taaactacgt gcagtcgctg caacggcagg tcgagttcct ctccatgaag      780
ctcgcaaccg tcaacccact ggacctgagc aacctgccca cgctcctaca aaagatatg       840 ttccaggcct gcggcgcttc ggcgagctcg gtcttctcgc tggagagctg cagcccgggg      900
ttcccgttcg gcgggcaagg ggacgtgttc cagtccttcg tcccgaacgg cctggagaac      960
ccgtgcggcg gcctgaaccc gctggacctg gctctgtccc aggctaccgg cgggcagttc     1020
ggtttccagg acggaacggc cggcacaaac ctgcagcaaa ggaactactg ggaggaggag     1080
gaggaggacc tgcagagcgt gttccacatc gacgacaacg gcagagccac ggagcacggg     1140
gcctcagctt cagcacaaag cttccatggt cagcttcaac cacaagaggg ccacatgaag     1200
atggagttct tctga                                                     1215
```

<210> SEQ ID NO 114
<211> LENGTH: 397
<212> TYPE: PRT
<213> ORGANISM: Zea mays

<400> SEQUENCE: 114

```
Met Glu Gly Met Glu Glu Ala Asn Arg Thr Ala Val Glu Ser Cys His
1               5                   10                  15

Arg Val Leu Ala Leu Leu Ser Asn Pro His Gly Gln Leu Val Pro Ser
            20                  25                  30

Lys Glu Leu Val Ala Ala Thr Gly Glu Ala Val Ala Lys Phe Gly Ser
        35                  40                  45

Leu Thr Ala Lys Leu Ser Asn Ser Asn Gly Asp Gly Leu Leu Gln Gly
    50                  55                  60

His Ala Arg Val Arg Lys Val Lys Lys Pro Leu His Ile Phe Asp Ser
65                  70                  75                  80

Asn Leu Phe Leu Glu Ser Ser Ala Val Ala Ala Ala Ala Pro Ala
                85                  90                  95

Lys Thr Pro Ser Pro Ser Pro Ile Leu Gly Leu Gln Leu Phe Pro Arg
            100                 105                 110

Tyr His Gln Phe Glu Gly Ser Ser Lys Asp Pro Val Arg Ile Pro
        115                 120                 125

Thr Gln Phe Pro Lys Arg Leu Leu Leu Glu Lys Pro Thr Ala Gly Met
    130                 135                 140

Glu Gly Ser Thr Ser Gln Ser Pro Ile Val Gln Met Val Gln Pro
145                 150                 155                 160

Val Ser Val Ala Pro Pro Ala Gly Thr Pro Thr Pro Ala Leu Pro Pro
                165                 170                 175

Ala His Leu His Phe Ile Gln Gln Gln Ser Tyr Gln Arg Phe Gln
            180                 185                 190

Leu Met Gln Gln Met Lys Ile Gln Ser Glu Met Met Lys Arg Ser Asn
        195                 200                 205

Leu Gly Asp Gln Gly Gly Ser Leu Ser Gly Gly Gly Gly Gly Arg
    210                 215                 220
```

```
Lys Gly Val Asn Leu Lys Phe Asp Ser Ser Asn Cys Thr Ala Ser Ser
225                 230                 235                 240

Ser Arg Ser Phe Leu Ser Ser Leu Ser Met Glu Gly Ser Leu Ala Ser
            245                 250                 255

Leu Asp Gly Ser Arg Thr Ser Arg Pro Phe Gln Leu Leu Ser Gly Ser
        260                 265                 270

Gln Thr Ala Ser Thr Pro Glu Leu Gly Leu Val Gln Arg Arg Arg Cys
    275                 280                 285

Ala Gly Arg Glu Asp Gly Thr Gly Arg Cys Ala Thr Gly Ser Arg Cys
290                 295                 300

His Cys Ser Lys Lys Arg Lys Leu Arg Ile Arg Ser Ile Lys Val
305                 310                 315                 320

Pro Ala Ile Ser Asn Lys Val Ala Asp Ile Pro Ala Asp Glu Phe Ser
                325                 330                 335

Trp Arg Lys Tyr Gly Gln Lys Pro Ile Lys Gly Ser Pro His Pro Arg
            340                 345                 350

Gly Tyr Tyr Lys Cys Ser Ser Val Arg Gly Cys Pro Ala Arg Lys His
        355                 360                 365

Val Glu Arg Cys Val Asp Asp Pro Ser Met Leu Ile Val Thr Tyr Glu
370                 375                 380

Gly Asp His Asn His Asn Arg Val Leu Ala Gln Pro Ala
385                 390                 395
```

<210> SEQ ID NO 115
<211> LENGTH: 1194
<212> TYPE: DNA
<213> ORGANISM: Zea mays

<400> SEQUENCE: 115

```
atggagggga tggaggaggc aacaggacg gcagtggaga gctgccaccg ggtgctggcg      60
ctcctctcca acccgcacgg ccagctcgtc cccagcaagg agctcgtggc cgccaccggg    120
gaggccgtcg ccaagttcgg ctcactgacg gccaagctct ccaactccaa cggcgatggc    180
ctactgcagg ccacgctag ggtcaggaag gtcaagaagc cctgcacat cttcgacagc     240 aacctcttcc tcgagagctc tgcggtggcc gccgccgctg ctccggccaa gacgcccagc    300
ccgagcccga tccttggcct ccagctgttc ccgaggtacc accagtttga gggctcgtcg    360
tctaaggatc ctgtcaggat ccctacccag ttccccaaga ggttgctgct agagaagccg    420
actgccggta tggagggggtc gacgtcgcag tcccctccga tcgtccagat ggtccagccg    480
gtgtccgttc gcccccccgc agggacgccc accccggcat tgccccccgc tcaccttcat    540
ttcatccagc agcagcaaag ctaccagagg tttcagctca tgcagcagat gaagatccag    600
agcgagatga tgaagaggag caatcttggt gatcagggtg gtagcttaag tggcggcggc    660
ggcggcggtc gtaagggtgt gaatctcaag tttgacagct ctaattgcac ggcgtcatcg    720
tctcgctcgt tcctttcgtc tctgagcatg aagggagtc ttgcgagttt ggatggaagc    780
cggaccagca ggccgttcca gctacttagt ggctctcaga cagctagcac gccggagctg    840
ggcctggtgc aaaggagaag gtgcgctggc agggaggatg ggactggtcg gtgtgcaacc    900
gggagccggt gccattgttc aaagaaaagg aagctaagga taaggaggtc catcaaagtc    960
cctgcaataa gcaacaaggt tgcagacatc ccagctgatg aattctcatg gaggaagtat   1020
gggcagaagc caattaaggg atccccacat cctaggggtt attacaagtg tagcagtgtg   1080
agaggctgcc ccgcgaggaa gcatgtcgag aggtgcgtgg acgaccctc gatgctgatt   1140
```
gttacctatg aaggtgacca caaccacaac cgagttctag cccagccagc ctga         1194

<210> SEQ ID NO 116
<211> LENGTH: 374
<212> TYPE: PRT
<213> ORGANISM: Zea mays

<400> SEQUENCE: 116

| | | | | | | | | | | | | | | | |
|---|---|---|---|---|---|---|---|---|---|---|---|---|---|---|---|
| Met | Glu | Glu | Val | Glu | Val | Ala | Asn | Arg | Ala | Ala | Val | Glu | Ser | Cys | His |
| 1 | | | | 5 | | | | | 10 | | | | | 15 | |
| Arg | Val | Leu | Ala | Leu | Leu | Ser | Gln | Gln | Arg | Asp | Pro | Ala | Leu | Leu | Lys |
| | | | 20 | | | | | 25 | | | | | 30 | | |
| Ser | Val | Ala | Ser | Glu | Thr | Ala | Glu | Cys | Ala | Lys | Phe | Arg | Lys | Val | |
| | | 35 | | | | | 40 | | | | | 45 | | | |
| Ala | Ala | Leu | Leu | Gly | Ser | Gly | Val | Gly | His | Ala | Arg | Gly | Arg | Phe | Ser |
| | 50 | | | | | 55 | | | | | 60 | | | | |
| Arg | Arg | Val | Arg | Pro | Leu | Gly | Leu | Val | Gly | His | Lys | Ser | Pro | Val | Gly |
| 65 | | | | | 70 | | | | | 75 | | | | | 80 |
| Ser | Gly | Gly | Asn | Asn | Pro | Val | Glu | Met | Leu | Pro | Ser | Ala | Ala | Ala | Val |
| | | | | 85 | | | | | 90 | | | | | 95 | |
| Thr | Ser | Pro | Ser | Pro | Ser | Thr | Ser | Tyr | Pro | Pro | Gln | Met | Arg | Ala | Arg |
| | | | 100 | | | | | 105 | | | | | 110 | | |
| Leu | Asn | Gly | Val | Pro | Asp | Pro | Arg | Gly | Leu | Asp | Met | Ala | Cys | Ser | Ser |
| | | | 115 | | | | | 120 | | | | | 125 | | |
| Ser | Ser | Lys | Ser | Gly | Gly | Val | Gly | Gly | Gly | Gly | Ala | His | Pro | Phe | Gly |
| | 130 | | | | | 135 | | | | | 140 | | | | |
| Gly | Ala | Pro | Lys | Leu | Val | Gln | Pro | Leu | Ser | Val | Gln | Phe | Gln | Ile | Gly |
| 145 | | | | | 150 | | | | | 155 | | | | | 160 |
| Asn | Val | Ala | His | Arg | Tyr | Pro | Phe | His | Gln | Gln | Pro | Pro | Ser | Arg | Gln |
| | | | | 165 | | | | | 170 | | | | | 175 | |
| Lys | Leu | Gln | Ala | Ala | Glu | Met | Phe | Arg | Arg | Ser | Ser | Ser | Gly | Thr | Ile |
| | | | 180 | | | | | 185 | | | | | 190 | | |
| Ser | Leu | Lys | Phe | Asp | Ser | Pro | Ile | Pro | Ser | Gly | Gly | Gly | Gly | Ala | Ala |
| | | 195 | | | | | 200 | | | | | 205 | | | |
| Gly | Thr | Val | Ser | Phe | Val | Ser | Ser | Leu | Ser | Met | Asp | Gly | Ser | Val | Gly |
| | 210 | | | | | 215 | | | | | 220 | | | | |
| Val | Ala | Ser | Leu | Asp | Gly | Lys | Arg | Pro | Phe | His | Leu | Val | Gly | Thr | Pro |
| 225 | | | | | 230 | | | | | 235 | | | | | 240 |
| Val | Ala | Ala | Ser | Asp | Thr | Ala | Ala | Asp | Ala | His | Arg | Ala | Pro | Lys | Arg |
| | | | | 245 | | | | | 250 | | | | | 255 | |
| Arg | Cys | Thr | Cys | Arg | Gly | Gly | Glu | Glu | Asp | Gly | Arg | Gly | Asn | Lys | Cys |
| | | | 260 | | | | | 265 | | | | | 270 | | |
| Gly | Thr | Ser | Gly | Arg | Cys | His | Cys | Ser | Lys | Arg | Lys | Leu | Arg | Ile | |
| | | 275 | | | | | 280 | | | | | 285 | | | |
| Lys | Arg | Ser | Ile | Lys | Val | Pro | Ala | Ile | Ser | Asn | Lys | Val | Ala | Asp | Ile |
| | 290 | | | | | 295 | | | | | 300 | | | | |
| Pro | Pro | Asp | Glu | Tyr | Ser | Trp | Arg | Lys | Tyr | Gln | Lys | Pro | Ile | Lys | |
| 305 | | | | | 310 | | | | | 315 | | | | | 320 |
| Gly | Ser | Pro | His | Pro | Arg | Gly | Tyr | Tyr | Lys | Cys | Ser | Ser | Val | Arg | Gly |
| | | | | 325 | | | | | 330 | | | | | 335 | |
| Cys | Pro | Ala | Arg | Lys | His | Val | Glu | Arg | Cys | Val | Asp | Asp | Pro | Ala | Met |
| | | | 340 | | | | | 345 | | | | | 350 | | |
| Leu | Ile | Val | Thr | Tyr | Glu | Gly | Glu | His | Gly | His | Thr | Gln | Leu | Pro | Ala |
| | | | 355 | | | | | 360 | | | | | 365 | | |

Gln Pro Ser Thr Gln Thr
    370

<210> SEQ ID NO 117
<211> LENGTH: 1125
<212> TYPE: DNA
<213> ORGANISM: Zea mays

<400> SEQUENCE: 117

| atggaggagg tggaggtggc caaccgggcc gcggtggaga gctgccaccg tgtgctggcc | 60 |
| ctgctctcgc agcagcggga cccggccctg ctcaagagtg tagcgtcaga cggccgaa | 120 |
| gcctgcgcca agttcaggaa ggtagccgcc ctcctcggca gcggtgtcgg ccacgctaga | 180 |
| ggcaggttct ccagacgagt ccggcctctg gggctcgttg ccacaagag ccccgtgggg | 240 |
| agcggcggca acaacccggt ggagatgctg cccagcgccg ccgccgttac gtccccgtct | 300 |
| ccgtcaacca gctacccgcc gcaaatgcgc gctcggctga acggcgtgcc agacccacga | 360 |
| gggctggaca tggcctgctc cagcagcagc aagagcggcg gcgttggcgg aggcggcgct | 420 |
| catccattcg gcggagcgcc gaagctggtg cagccgctgt ccgtgcagtt ccagatcggg | 480 |
| aacgtcgcgc acaggtaccc gttccaccag cagccgccgt cgcggcagaa gctgcaggcc | 540 |
| gccgagatgt tcaggaggag cagcagcggg acgatcagcc tcaagttcga tagcccaatc | 600 |
| cctagcggtg gcgtggcgc cgctggcacc gtgtcgttcg tgtcgtcctt gagcatggac | 660 |
| gggagcgtgg gcgtggcaag cttggacggg aagcggccgt tccatctggt cggcaccccg | 720 |
| gtggcggcga gcgacacggc ggcagacgcc caccgcgcgc ccaaacgccg gtgcacgtgt | 780 |
| agaggaggcg aggaggatgg agaggcaac aagtgcggca cctccggcag gtgccattgc | 840 |
| tcaaagagaa ggaagctgcg gatcaagagg tcgatcaaag tgccagccat cagcaacaag | 900 |
| gtcgccgaca tacctcccga cgagtactcg tggcgcaagt acgggcagaa gccgatcaag | 960 |
| ggctccccgc acccgagggg ctactacaag tgcagcagcg tcaggggctg cccggcgagg | 1020 |
| aagcacgtcg agcggtgcgt ggacgaccca gcgatgctga tcgtgacgta cgaaggcgag | 1080 |
| cacggccaca cccagctgcc ggcgcagcct tccacccaga cgtag | 1125 |

<210> SEQ ID NO 118
<211> LENGTH: 367
<212> TYPE: PRT
<213> ORGANISM: Zea mays

<400> SEQUENCE: 118

Met Glu Glu Val Glu Val Ala Asn Met Ala Ala Val Glu Ser Cys His
1               5                   10                  15

Arg Val Leu Ala Leu Leu Ser Gln Gln Gln Asp Pro Ala Leu Leu Lys
            20                  25                  30

Ser Val Ala Ser Glu Thr Ala Glu Ala Cys Ala Lys Phe Arg Lys Val
        35                  40                  45

Ala Ala Leu Leu Gly Ser Ala Ser Gly Gly Gly Cys Gly His Ala
    50                  55                  60

Arg Gly Arg Phe Ser Arg Arg Val Arg Pro Leu Gly Leu Val Asn Gln
65                  70                  75                  80

Lys Ser Pro Leu Gly Ile Ala Thr Gly Ser Gly Asn Pro Leu Glu Met
                85                  90                  95

Met Pro Ser Thr Ala Ala Ala Gly Ser Pro Ser Pro Gln Ser
            100                 105                 110

Thr Ser Tyr Ala Gln Met Arg Ala Arg Leu Ser Ser Ala Pro Glu Ser

|   |   |   | 115 |   |   |   | 120 |   |   |   | 125 |   |   |
|---|---|---|-----|---|---|---|-----|---|---|---|-----|---|---|

Ser Arg Gly Leu Asp Leu Ala Cys Ser Ser Arg Cys Ser Pro His
    130                  135               140

Pro Phe Gly Ala Pro Lys Leu Val Gln Pro Leu Ser Val Gln Phe Gln
145               150               155              160

Ile Gly Ser Val Ala His Arg Tyr Pro Phe His Gln Gln Gln Ser Arg
             165              170             175

Gln Lys Leu Gln Ala Glu Met Phe Arg Arg Ser Asn Ser Gly Ile Ser
        180               185              190

Leu Lys Phe Asp Ser Pro Ser Pro Ser Gly Ala Ala Gly Thr Met
           195              200             205

Ser Ser Ala Arg Ser Phe Met Ser Ser Leu Ser Ile Asp Arg Ser Met
    210                215              220

Ala Ser Leu Asp Gly Lys Arg Pro Phe His Leu Val Gly Thr Pro Val
225               230               235             240

Ala Ser Asp Pro Ala Asp Ala His Arg Ala Pro Lys Arg Arg Cys Thr
             245              250             255

Gly Arg Gly Glu Asp Gly Arg Gly Lys Cys Ala Thr Thr Gly Arg Cys
        260               265              270

His Cys Ser Lys Arg Lys Leu Arg Ile Lys Arg Ser Ile Arg Val
           275              280             285

Pro Ala Ile Ser Asn Lys Ile Ala Asp Ile Pro Pro Asp Glu Tyr Ser
290               295               300

Trp Arg Lys Tyr Gly Gln Lys Pro Ile Lys Gly Ser Pro His Pro Arg
305               310               315             320

Gly Tyr Tyr Lys Cys Ser Ser Val Arg Gly Cys Pro Ala Arg Lys His
             325              330             335

Val Glu Arg Cys Val Asp Asp Pro Ala Met Leu Ile Val Thr Tyr Glu
        340               345              350

Gly Glu His Ser His Thr Gln Leu Pro Ala Gln Pro Ala Gln Thr
           355              360             365

<210> SEQ ID NO 119
<211> LENGTH: 1104
<212> TYPE: DNA
<213> ORGANISM: Zea mays

<400> SEQUENCE: 119

```
atggaggagg tggaggtggc caacatggcc gcggtggaga gctgccaccg ggtgctggct    60
ctgctctcgc agcagcagga cccagccctg ctcaagagcg tagcttcaga gacggctgaa   120
gcctgcgcca gttcaggaa ggtagcggcc ctcctcggca gtgccagtgg cggaggtggc   180
tgtggccatg ctagaggcag gttctccaga cgagtccggc ctctgggct cgtcaaccag   240
aagagcccct ggggatcgc accggcagc ggcaacccgc tggagatgat gcccagcaca   300
gctgctgctg ctgggtctcc atctccacct cagtcgacta gctatgcgca aatgcgcgct   360
cggcttagca gtgcgccaga gtcctcacga gggctggatt tggcctgctc cagcagcagg   420
tgtagccctc atccatttgg agcccccaag ctggtccagc cactgtctgt gcagttccag   480
attgggagtg ttgcgcatag gtacccgttc accagcagc agtcgaggca gaagctgcag   540
gccgagatgt tcaggaggag caacagtggg atcagcctca gttcgatag ccctagcccc   600
agcggtggtg ctgctggcac catgtcgtct gcgagatcat tcatgtcgtc gttgagtata   660
gacaggagca tggcgagctt ggatgggaag cggccgttcc atttggtagg caccccggtg   720
```

-continued

```
gcgagcgacc cagcagatgc gcaccgtgcg cccaaacggc gatgcacggg tagaggggag    780
gatggaagag gcaagtgtgc caccactggc agatgccatt gctcaaagag aaggaaactg    840
cggattaaga ggtcgattag agtgccagcc attagcaaca aaatcgctga tatccctcct    900
gatgagtact cgtggcgcaa gtacgggcag aagccaatta agggttcccc acacccgagg    960
ggttactaca aatgcagcag cgtcagggc tgcccagcaa ggaagcacgt cgagcgatgt    1020
gtagacgacc cggcgatgct aatcgtgaca tacgaaggcg agcacagcca cacccagctg    1080
ccagcacagc ctgcccagac ctag                                            1104
```

<210> SEQ ID NO 120
<211> LENGTH: 369
<212> TYPE: PRT
<213> ORGANISM: Zea mays

<400> SEQUENCE: 120

```
Met Glu Glu Val Glu Glu Ala Asn Arg Glu Ala Val Glu Ser Cys Arg
1               5                   10                  15

Arg Val Leu Ala Leu Ser His Pro His Asp Pro Ala Gln Val Arg
            20                  25                  30

Ser Ile Ala Leu Gly Thr Asp Glu Ala Cys Thr Lys Phe Arg Lys Val
        35                  40                  45

Val Ser Leu Leu Ser Asn Gly Glu Val Gly Thr Gly Glu Ala Gly Pro
    50                  55                  60

Ser Gly Thr Ser Ala Ser Ala Ser His Pro Arg Ala Lys Leu Val Ser
65                  70                  75                  80

Arg Arg Gln Asn Pro Gly Phe Leu Thr Gln Lys Gly Phe Leu Asp Ser
                85                  90                  95

Asn Thr Pro Val Val Val Leu Asn Ser Ala Ala His Pro Ser Pro Thr
            100                 105                 110

Ser Ala Gln Val His Pro Arg Ala Gly Ala Leu Asp Thr Glu Gly Val
        115                 120                 125

His Pro Leu Gly Val Gly Gly Pro Pro Lys Leu Val Gln Pro Leu Ser
    130                 135                 140

Ala His Phe Gln Phe Gly Asn Val Ser Ser Arg Tyr Gln Gln Leu Pro
145                 150                 155                 160

Ser His His Arg His Gln Gln Gln Glu Lys Leu Gln Ala Ala Glu
                165                 170                 175

Met Phe Lys Arg Ser Asn Ser Gly Ile Asn Leu Lys Phe Glu Ser Ala
            180                 185                 190

Ser Gly Thr Gly Thr Met Ser Ser Ala Arg Ser Phe Leu Ser Ser Leu
        195                 200                 205

Ser Met Asp Gly Ser Val Val Ala Ser Leu Asp Gly Lys Leu Pro Ser
    210                 215                 220

Ser Ser Ser Ser Phe Arg Leu Ile Gly Ala Pro Ala Met Ser Asp Pro
225                 230                 235                 240

Ala Asn Ala Ala Gln Gln Ala Pro Arg Arg Cys Thr Gly Arg Gly
                245                 250                 255

Lys Asp Gly Thr Gly Lys Cys Ala Leu Ala Gly Arg Cys His Cys Ser
            260                 265                 270

Lys Arg Ser Lys Lys Leu Arg Val Lys Arg Ser Ile Lys Val Pro Ala
        275                 280                 285

Val Ser Asn Lys Ile Ala Asp Ile Pro Pro Asp Glu Tyr Ser Trp Arg
    290                 295                 300
```

```
Lys Tyr Gly Gln Lys Pro Ile Lys Gly Ser Pro His Pro Arg Gly Tyr
305                 310                 315                 320

Tyr Lys Cys Ser Ser Val Arg Gly Cys Pro Ala Arg Lys His Val Glu
            325                 330                 335

Arg Cys Val Asp Asp Ser Ala Met Leu Ile Val Thr Tyr Glu Gly Glu
        340                 345                 350

His Asn His Thr Gly Met Pro Ala Gln Ser Ala Ala Ala Ala Ala Gln
        355                 360                 365

Val

<210> SEQ ID NO 121
<211> LENGTH: 1110
<212> TYPE: DNA
<213> ORGANISM: Zea mays

<400> SEQUENCE: 121
atggaggaag tggaggaggc gaacagggaa gccgtggaga gctgccgcag ggtgctagcc      60
ttgctctccc atccgcatga ccccgcgcag gtcaggagca tagctctggg gacggacgaa     120
gcatgcacca agtttaggaa ggtggtctcc ctgctcagca atggagaagt aggaacagga     180
gaagccggac catcaggcac aagcgcaagc gcaagccatc ctagagctaa gcttgttagc     240
agaagacaga atccagggtt cttgactcag aaaggcttcc tggacagtaa caccccggtc     300
gtggtgctga cagcgccgc ccatccttct ccgacctccg cgcaggtgca tccaagagcc      360
ggagcattgg atacggaggg cgtgcacccc ctcggagttg aggacctcc caagctggtc      420 cagcctttgt ccgcgcattt tcagttcggc aatgtgtcgt cgaggtatca gcagttaccg     480
agtcatcatc atcgtcatca gcagcaggag aagctgcagg ccgccgagat gttcaagaga     540
agcaacagcg ggataaacct gaagttcgag agcgccagcg gcacgggtac aatgtcgtcg     600
gcgaggtcct tcctgtcgtc tctgagcatg gatggcagcg tggtggctag cctggatggc     660
aagctgccgt cgtcgtcgtc atcgttccgt ttgatcggtg cgcctgcaat gagcgatccg     720
gcgaacgccg cgcagcaggc cccgaggcgg cggtgcacgg ccgcgggaa ggacgggact      780 ggcaagtgcg ctttggcggg caggtgccat tgttcaaaga gaagtaagaa gttgcgggtg     840
aagaggtcga ttaaggttcc tgccgttagt aacaagatcg ctgatatacc tccggatgag     900
tactcgtgga ggaagtatgg gcagaagccg atcaagggtt cccctcatcc taggggctac     960
tacaaatgca gcagtgtgag gggctgtcca gctaggaagc acgtggaacg tgtgtgtggat   1020 gattcggcga tgctcatcgt gacatacgag ggcgagcaca accacaccgg aatgccagct   1080
cagtcagcag cagcagcagc acaggtgtag                                    1110

<210> SEQ ID NO 122
<211> LENGTH: 354
<212> TYPE: PRT
<213> ORGANISM: Zea mays

<400> SEQUENCE: 122

Met Glu Glu Val Glu Glu Ala Asn Arg Glu Ala Val Glu Ser Cys His
1               5                   10                  15

Arg Val Leu Ala Leu Leu Ser Gln Pro His Asp Pro Ala Gln Ala Arg
            20                  25                  30

Ser Ile Ala Leu Gly Thr Asp Glu Ala Cys Ala Arg Phe Arg Lys Val
        35                  40                  45

Val Ser Leu Leu Ser Asn Gly Gly Ala Gly Leu Gly Glu Ala Gly Pro
    50                  55                  60
```

```
Ser Cys Gly Ser Ala Ser Ala Ser Arg Pro Arg Ala Lys Leu Val Ser
 65                  70                  75                  80

Arg Arg Gln Asn Pro Gly Phe Leu Thr Gln Lys Gly Phe Leu Asp Ser
                 85                  90                  95

Asn Thr Pro Val Val Val Leu Asn Ser Ala His Pro Ser Thr Thr Ser
            100                 105                 110

Ala Gln Val Tyr Pro Arg Thr Gly Ala Leu Val Asp Ala Gln Ser Val
        115                 120                 125

His Pro Leu Gly Val Gly Pro Lys Leu Val Gln Pro Leu Ser
    130                 135             140

Ala His Phe Gln Phe Gly Ser Val Pro Ala Arg Tyr Gln Phe Pro Asn
145                 150                 155                 160

Gln Gln Gln Gln Lys Leu His Ala Glu Met Phe Lys Arg Ser Asn Ser
                165                 170                 175

Gly Val Asn Leu Lys Phe Glu Ser Ala Ser Gly Thr Ala Gly Thr Met
            180                 185                 190

Ser Ser Ala Arg Ser Phe Leu Ser Ser Leu Ser Met Asp Gly Ser Val
        195                 200                 205

Ala Ser Leu Asp Ala Lys Ser Ser Ser Phe His Leu Ile Gly Gly Pro
    210                 215                 220

Ala Met Ser Asp Pro Leu Asn Ala Gln Gln Pro Pro Arg Arg Cys
225                 230                 235                 240

Thr Gly Arg Gly Glu Asp Gly Thr Gly Lys Cys Ala Val Thr Gly Arg
                245                 250                 255

Cys His Cys Ser Lys Arg Ser Arg Lys Leu Arg Val Lys Arg Ser Ile
            260                 265                 270

Lys Val Pro Ala Ile Ser Asn Lys Ile Ala Asp Ile Pro Pro Asp Glu
        275                 280                 285

Tyr Ser Trp Arg Lys Tyr Gly Gln Lys Pro Ile Lys Gly Ser Pro His
    290                 295                 300

Pro Arg Gly Tyr Tyr Lys Cys Ser Ser Val Arg Gly Cys Pro Ala Arg
305                 310                 315                 320

Lys His Val Glu Arg Cys Val Asp Asp Ser Ala Met Leu Ile Val Thr
                325                 330                 335

Tyr Glu Gly Glu His Asn His Thr Arg Met Pro Thr Thr Gln Ser Ala
            340                 345                 350

Gln Val

<210> SEQ ID NO 123
<211> LENGTH: 1065
<212> TYPE: DNA
<213> ORGANISM: Zea mays

<400> SEQUENCE: 123
atggaggaag tggaggaagc gaacagggaa gccgtggaga gctgccacag ggtgctcgcc      60
ttgctctccc agccgcatga ccccgcgcag gccaggagca tagctctggg cacggacgaa     120
gcatgtgcca ggttcaggaa ggtggtctct ctactgagca atggaggagc ggggctagga     180
gaagccgggc cgtcatgcgg aagcgcaagc gcaagccgtc ctagagctaa gcttgttagc     240
agaagacaga atccagggtt cttgacccag aaaggcttcc tggacagcaa cacccccggtc    300 gtggtgttga acagcgccca tccttctact acctccgcgc aggtgtaccc tgaactgga     360 gctctcgtcg atgcacagag cgtgcacccc ctcggagtcg gaggacctcc caagctggtc     420
```

```
cagcccttgt ccgcgcactt tcagttcggc agtgtgccgg ctcggtatca gttcccgaat    480
cagcagcagc agaagttgca cgccgagatg ttcaagagaa gcaacagcgg ggttaacctg    540
aagttcgaga gcgccagtgg cactgctggg acgatgtcgt cggcgaggtc cttcttgtcg    600
tctctgagca tggacggtag cgtggctagc ctggacgcca agtcatcgtc gttccatttg    660
atcggtggac ctgcgatgag cgatccgctg aacgcgcagc agccccgag gaggcggtgc     720 acgggccgtg gggaggatgg gaccggcaag tgcgctgtta cagggaggtg ccactgttcg    780
aagagaagta ggaagttgcg ggtgaagagg tcgattaagg ttcctgccat tagtaacaag    840
attgccgata tacctccgga tgaatactcg tggaggaagt atgggcagaa gccaattaag    900
ggttcccctc atcctagggg ttactacaaa tgcagtagcg tgagggctg cccagccagg     960 aagcatgtgg aacggtgcgt agatgattcg gcgatgctca tcgtgacata tgagggcgag   1020
cacaaccaca ccagaatgcc aacaactcag tcagcacagg tgtaa                   1065
```

<210> SEQ ID NO 124
<211> LENGTH: 395
<212> TYPE: PRT
<213> ORGANISM: Zea mays

<400> SEQUENCE: 124

```
Met Glu Ala Met Glu Glu Ala Asn Arg Thr Ala Val Glu Ser Cys His
1               5                   10                  15

Arg Val Leu Ala Leu Leu Ser Asn Pro His Gly Gln Leu Val Pro Ser
            20                  25                  30

Arg Glu Leu Val Ala Thr Thr Gly Glu Ala Val Ala Arg Phe Gly Ser
        35                  40                  45

Leu Ala Ala Lys Leu Ser Ser Ser Asn Gly Asn Gly Leu Gln Gly His
    50                  55                  60

Ala Arg Val Arg Lys Thr Lys Lys Pro Leu Pro Ile Phe Tyr Ser Asn
65                  70                  75                  80

Leu Phe Leu Glu Ser Ser Ala Val Ala Ala Ala Thr Val Ala
                85                  90                  95

Lys Thr Pro Ser Pro Ser Pro Thr Thr Gly Leu Gln Leu Phe Pro Arg
            100                 105                 110

Tyr His Gln Met Glu Gly Ser Ser Cys Lys Asp Pro Val Arg Ile Pro
        115                 120                 125

Ala Gln Phe Pro Lys Arg Leu Leu Leu Glu Asn Leu Ala Ala Gly Leu
    130                 135                 140

Glu Gly Ser Ser Pro Pro Ala Pro Pro Val Arg Met Val Gln Pro Val
145                 150                 155                 160

Ser Val Ala Pro Pro Ala Gly Met Pro Thr Pro Ala Leu Pro Ala Ala
                165                 170                 175

His Leu His Phe Ile Gln Gln Gln Ser Tyr Gln Arg Phe Gln Leu
            180                 185                 190

Met Gln Gln Met Lys Ile Gln Ser Glu Met Val Lys Arg Ser Asn Leu
        195                 200                 205

Gly Glu Gln Gly Gly Ser Leu Ser Gly Gly Gly Gly Lys Gly
    210                 215                 220

Val Asn Leu Lys Phe Asp Ser Ser Asn Cys Thr Ala Ser Ser Ser Arg
225                 230                 235                 240

Ser Phe Leu Ser Ser Leu Ser Met Glu Gly Ser Leu Ala Ser Leu Asp
                245                 250                 255

Gly Ser Arg Ala Ser Arg Pro Phe Gln Leu Val Ser Gly Ser Gln Thr
```

|   |   |   | 260 |   |   |   | 265 |   |   |   | 270 |   |
|---|---|---|---|---|---|---|---|---|---|---|---|---|

Ser Ser Thr Pro Glu Leu Gly Leu Val Gln Arg Arg Cys Ala Gly
        275                 280                 285

Lys Glu Asp Gly Ser Gly Gln Cys Ala Thr Gly Ser Arg Cys His Cys
        290                 295                 300

Ser Lys Lys Arg Lys Leu Arg Ile Arg Arg Ser Ile Lys Val Pro Ala
305                 310                 315                 320

Val Ser Asn Lys Val Ala Asp Ile Pro Ala Asp Glu Phe Ser Trp Arg
                325                 330                 335

Lys Tyr Gly Gln Lys Pro Ile Lys Gly Ser Pro His Pro Arg Gly Tyr
            340                 345                 350

Tyr Lys Cys Ser Ser Val Arg Gly Cys Pro Ala Arg Lys His Val Glu
        355                 360                 365

Arg Cys Val Asp Asp Pro Ser Met Leu Ile Val Thr Tyr Glu Gly Asp
        370                 375                 380

His Asn His Ser Arg Val Leu Ala Gln Pro Ala
385                 390                 395

<210> SEQ ID NO 125
<211> LENGTH: 1188
<212> TYPE: DNA
<213> ORGANISM: Zea mays

<400> SEQUENCE: 125

| | | |
|---|---|---|
| atggaggcga tggaggaggc aacaggacg gcagtggaga gctgccaccg ggtgctggcg | 60 |
| ctcctctcca acccgcacgg ccagctcgtc cccagcaggg agctcgtggc caccaccggg | 120 |
| gaggccgtag ccaggttcgg ctccctggcg ccaagctct ccagctccaa cggcaatggc | 180 |
| ctgcagggcc acgctagggt caggaagacc aagaagcccc tgcccatctt ctacagcaac | 240 |
| ctcttcctcg agagcagctc tgcggtggcc gccgccgcga ctgtggccaa gacgcccagt | 300 |
| ccgagcccga ccactggcct ccagctgttc ccgaggtacc accagatgga gggctcgtcg | 360 |
| tgtaaggatc ctgtcaggat ccctgcgcag ttccccaaga ggttgctgct ggagaacctg | 420 |
| gctgccggtc tggaggggtc gtcgccgcct gcccctccgg tccggatggt gcagccggtg | 480 |
| tccgttgcgc ctcccgcagg gatgcccacc ccggcattgc ccgccgcaca cctccatttc | 540 |
| atccagcagc agcagagcta ccagaggttt cagctcatgc agcagatgaa gattcagagc | 600 |
| gagatggtta agaggagcaa tcttggtgag cagggtggta gcttaagtgg cggcggggc | 660 |
| ggtggtaagg gtgtgaacct caagtttgac agctccaatt gcacggcgtc atcgtctcgc | 720 |
| tcgttccttt cgtctctgag catggaagga agtcttgcga gcttggatgg aagccgggcc | 780 |
| agcaggccgt tccagctagt tagtggctct cagacatcta gcaccggga ctgggcctg | 840 |
| gtgcaaagga gaaggtgtgc tgggaaggag gatgggagtg gtcagtgcgc aaccgggagc | 900 |
| cggtgccatt gttcaaagaa aaggaagcta aggataagga ggtccatcaa gtccctgca | 960 |
| gtaagcaaca aggttgcaga catcccagct gatgagttct cgtggaggaa gtatgggcag | 1020 |
| aagccaatca agggatcccc acatcctagg ggttactaca gtgtagcag cgtgagaggc | 1080 |
| tgccccgcga ggaagcacgt cgagaggtgc gtggacgacc cttcgatgct gatcgttacc | 1140 |
| tacgagggtg accacaacca cagccgagtt ctagcccagc cagcctga | 1188 |

<210> SEQ ID NO 126
<211> LENGTH: 331
<212> TYPE: PRT
<213> ORGANISM: Zea mays

<400> SEQUENCE: 126

```
Met Thr Thr Leu Asp Leu Met Gly Gly Tyr Gly Arg Val Asp Glu Gln
1               5                   10                  15

Val Ala Ile Gln Glu Ala Ala Thr Ala Gly Leu Arg Gly Met Glu Arg
            20                  25                  30

Leu Ile Leu Gln Leu Ser Gln Ala Gly Thr Gly Glu Arg Ser Leu Ser
        35                  40                  45

Pro Pro Ala Val Gln Ala Arg Gln Gln Lys Gln Leu Glu Gln
    50                  55                  60

Ile Gln Gln Gln Val Asp Cys Arg Glu Leu Thr Asp Met Thr Val Ser
65              70                  75                  80

Lys Phe Lys Lys Val Ile Ser Ile Leu Asn Arg Thr Gly His Ala Arg
                85                  90                  95

Phe Arg Arg Gly Pro Val Ala Ala Arg Ser Gln Ser Gln Ser Gln Gly
            100                 105                 110

Pro Ala Ser Pro Glu Pro Ala Gln Ser Ala Pro Ala Ala Arg
        115                 120                 125

Pro Leu Thr Leu Asp Phe Thr Lys Ser Val Ser Gly Tyr Ser Arg Asp
    130                 135                 140

Ser Gly Phe Ser Val Ser Gly Ala Ser Ser Phe Leu Ser Ser Val
145                 150                 155                 160

Thr Thr Gly Asp Gly Ser Val Ser Asn Gly Arg Ala Gly Gly Ser Ser
                165                 170                 175

Phe Leu Met Phe Pro Ala Pro Gly Ala Ala Ser Cys Ala Lys Pro
            180                 185                 190

Pro Pro Ala Gly Ala Ala Gln Lys Arg Lys Cys His Asp His Ala His
    195                 200                 205

Ser Glu Asn Val Ala Gly Gly Lys Tyr Gly Ala Asn Gly Gly Arg Cys
210                 215                 220

His Cys Ser Lys Arg Arg Lys His Arg Val Lys Arg Thr Ile Arg Val
225                 230                 235                 240

Pro Ala Ile Ser Pro Lys Val Ala Asp Ile Pro Ala Asp Glu Tyr Ser
                245                 250                 255

Trp Arg Lys Tyr Gly Gln Lys Pro Ile Lys Gly Ser Pro Tyr Pro Arg
            260                 265                 270

Gly Tyr Tyr Lys Cys Ser Thr Val Arg Gly Cys Pro Ala Arg Lys His
        275                 280                 285

Val Glu Arg Asp Pro Ala Asp Pro Ser Met Leu Ile Val Thr Tyr Glu
    290                 295                 300

Gly Glu His Arg His Ser Pro Ala Ser Gly Gln Asp Pro Pro Pro
305                 310                 315                 320

Ser Leu Ala Pro Leu Pro Glu Leu Pro Ser His
                325                 330
```

<210> SEQ ID NO 127
<211> LENGTH: 996
<212> TYPE: DNA
<213> ORGANISM: Zea mays

<400> SEQUENCE: 127

```
atgacgaccc tcgatctgat gggagggtac gggcgggtgg acgagcaggt ggccatccag    60
gaggccgcca cggcgggggct gcgcgggatg gagcgtctca tcttgcagct ctcccaggct   120
ggcaccgggg agcggtcgtt gtccccaccg gcggtacagg cgcagcgcca gcagcagaag   180
```

-continued

```
cagctggagc agatccagca gcaggttgac tgccgggagc tcacggacat gacggtgtcc    240
aagttcaaga aggtgatctc catcctgaac cgcacgggc  acgcgcggtt ccggcgtggc    300
cccgtggcgg cgcggtcgca gtcgcagtcg cagggacctg cctcccccga gcccgcgcaa    360
tcggcgccgg ctcccgccgc gaggcccctg acgctggact tcaccaagtc ggtgtccggt    420
tacagcaggg actccgggtt cagcgtgtcc ggcgcgagct cgtcgttcct gtcgtcggtg    480
acgaccgggg acgggagcgt gtcgaacggg cgcgcgggag gctcgtcgtt cctcatgttc    540
ccaccggcgc cggcgcggc  cagctgcgcg aagccgccgc cgccggtgc  ggcgcagaag    600 cgcaagtgcc acgaccacgc gcactcggag aacgtcgccg gcggcaagta cggggctaac    660
ggcgggcgct gccactgctc gaagcgcagg aagcaccgtg tgaagcgcac gatccgcgtg    720
ccggcgatca gccccaaagt ggcggacatc cccgccgacg agtactcgtg gcgcaagtac    780
ggccagaaac ccatcaaggg gtcgccctac ccacgcggct actacaagtg cagcacggtg    840
cgcggctgcc ccgcccggaa gcatgtggag cgcgaccccg ccgacccgtc gatgctgatc    900
gtcacctacg agggcgagca ccgccacagc cccgcctccg gccaggaccc gccgccgccg    960
tcgctcgcgc cgctgccgga gctgcccagc cattga                              996
```

<210> SEQ ID NO 128
<211> LENGTH: 316
<212> TYPE: PRT
<213> ORGANISM: Zea mays

<400> SEQUENCE: 128

```
Met Ala Val Asp Leu Met Gly Cys Tyr Ala Pro Arg Arg Ala Asn Asp
1               5                   10                  15

Gln Leu Ala Ile Gln Glu Ala Ala Ala Gly Leu Arg Ser Leu Glu
            20                  25                  30

Leu Leu Val Ser Ser Leu Ser Thr Gln Ala Ala Pro His Arg Ala
        35                  40                  45

Ala Ala His Gln Leu Gln Lys Pro Pro Ser Gln Pro Pro Ile Gly Glu
    50                  55                  60

Ile Ala Asp Gln Ala Val Ser Arg Phe Arg Lys Val Ile Ser Ile Leu
65                  70                  75                  80

Asp Arg Thr Gly His Ala Arg Phe Arg Arg Gly Pro Val Val Glu Ala
                85                  90                  95

Pro Pro Val Pro Pro Ala Val Ser Ala Pro Ala Leu Pro Val
            100                 105                 110

Ala His Val Val Ala Pro Val Gly Ala Ala Gln Pro Gln Ser Leu Thr
        115                 120                 125

Leu Asp Phe Thr Lys Pro Asn Leu Ala Val Ser Gly Gly Ala Thr Ser
    130                 135                 140

Val Thr Ser Thr Ser Phe Phe Ser Ser Val Thr Ala Gly Glu Gly Ser
145                 150                 155                 160

Val Ser Lys Gly Arg Ser Leu Val Ser Ser Gly Lys Pro Pro Leu Ser
                165                 170                 175

Gly His Lys Arg Lys Pro Cys Ala Gly Ala His Ser Glu Ala Thr Thr
            180                 185                 190

Asn Gly Ser Arg Cys His Cys Ser Lys Arg Arg Lys Asn Arg Val Lys
        195                 200                 205

Arg Thr Ile Arg Val Pro Ala Ile Ser Ala Lys Ile Ala Asp Ile Pro
    210                 215                 220
```

Pro Asp Glu Tyr Ser Trp Arg Lys Tyr Gly Gln Lys Pro Ile Lys Gly
225                 230                 235                 240

Ser Pro Tyr Pro Arg Gly Tyr Tyr Lys Cys Ser Thr Val Arg Gly Cys
            245                 250                 255

Pro Ala Arg Lys His Val Glu Arg Ala Thr Asp Asp Pro Ala Met Leu
        260                 265                 270

Val Val Thr Tyr Glu Gly Glu His Arg His Thr Pro Gly Ala Pro Ala
    275                 280                 285

Pro Ala Pro Ser Pro Leu Ala Ala Ser Pro Val Pro Ala Ser Ala
    290                 295                 300

Ala Ala Ala Val Ser Ala Gly Asn Asn Gly Leu Val
305                 310                 315

<210> SEQ ID NO 129
<211> LENGTH: 951
<212> TYPE: DNA
<213> ORGANISM: Zea mays

<400> SEQUENCE: 129

```
atggccgtgg acctgatggg gtgctacgcc ccgcgccgcg ccaacgacca gctcgccatc      60
caggaggcgg cggcggcggg gctccgcagc ctggagctcc tcgtgtcgtc gctgtccacg     120
caggccgccg cgccgcacag ggccgcggct caccagctgc agaagccgcc ttcgcagccg     180
ccgatcggcg agatcgccga ccaggccgtc tccaggttcc gcaaggtcat ctccatcctg     240
gaccgcaccg gccacgcccg cttccggcgc gggcccgtgg tcgaggcgcc gccaccggtg     300
cctcctccgg ccgtctccgc tcccgctctc ccgtggcgc acgtggtggc tcccgtcggc      360
gcggcgcagc cccagagcct gaccctggac ttcacgaagc cgaacctggc cgtgtcgggc     420
ggcgccacgt ccgtcaccct cacgtccttc ttctcctcgg tcacggccgg cgagggcagc     480
gtgtccaagg ccgcagcct ggtgtcctcc ggcaagccgc cgctgtccgg ccacaagcgg      540
aagccctgcg ccggcgcgca ctccgaggcc accaccaacg cagccgctg ccactgctcc      600
aagagaagga aaaccgcgt gaagaggacc atcagagtgc cggcgatcag cgccaagatc      660
gcggacatcc cgccggacga gtactcgtgg aggaagtacg ccagaagcc catcaagggc      720
tcccctacc acggggcta ctacaagtgc agcaccgtgc gcgggtgccc ggcgaggaag       780
cacgtggagc gcgccaccga cgacccggcc atgctggtgg tgacgtacga gggcgagcac     840
cgccacacgc cgggcgcgcc cgcgcccgcg cccagccccc tggcggccgc gtcgccggtg     900
cccgcctccg ccgccgccgc cgtctccgcc ggcaacaacg gcttgtcta g               951
```

<210> SEQ ID NO 130
<211> LENGTH: 298
<212> TYPE: PRT
<213> ORGANISM: Zea mays

<400> SEQUENCE: 130

Met Ala Val Asp Leu Met Gly Cys Tyr Ala Pro Arg Arg Ala Asn Asp
1               5                   10                  15

Gln Leu Ala Ile Gln Glu Ala Ala Ala Ala Gly Leu Arg Asn Leu Glu
            20                  25                  30

Leu Leu Val Thr Ser Leu Ser Thr Gln Ala Ala Ala Pro His Arg Ala
        35                  40                  45

Ala Asp Gln Pro Phe Gly Glu Ile Ala Gly Gln Ala Val Ser Lys Phe
    50                  55                  60

Arg Lys Val Ile Ser Ile Leu Asp Arg Thr Gly His Ala Arg Phe Arg

```
                65                  70                  75                  80
Arg Gly Pro Val Glu Pro Pro Pro Thr Pro Pro Pro Pro Val
                    85                  90                  95

Val Pro Gly Pro Ala Pro Leu Ala Ala Val Ser Val Ala Gln Pro Pro
                100                 105                 110

Gln Ser Leu Thr Leu Asp Phe Thr Lys Pro Asn Leu Ala Val Ser Ala
            115                 120                 125

Ala Thr Ser Val Thr Ser Thr Ser Phe Phe Ser Ser Val Thr Ala Gly
        130                 135                 140

Glu Gly Ser Val Ser Lys Gly Arg Ser Leu Met Ser Ser Gly Lys Pro
145                 150                 155                 160

Pro Leu Ser Gly His Lys Arg Lys Pro Cys Ala Gly Ala His Ser Glu
                165                 170                 175

Ala Thr Thr Asn Gly Ser Arg Cys His Cys Ser Lys Arg Arg Lys Asn
            180                 185                 190

Arg Val Lys Arg Thr Ile Arg Val Pro Ala Ile Ser Ser Lys Val Ala
        195                 200                 205

Asp Ile Pro Ser Asp Glu Tyr Ser Trp Arg Lys Tyr Gly Gln Lys Pro
    210                 215                 220

Ile Lys Gly Ser Pro Tyr Pro Arg Gly Tyr Tyr Lys Cys Ser Thr Val
225                 230                 235                 240

Arg Gly Cys Pro Ala Arg Lys His Val Glu Arg Ala Thr Asp Asp Pro
                245                 250                 255

Ala Met Leu Val Val Thr Tyr Glu Gly Glu His Arg His Thr Pro Gly
            260                 265                 270

Ala Val Gln Gly Pro Ser Pro Leu Ala Thr Ala Ser Pro Val Pro Val
        275                 280                 285

Ala Val Ser Ala Gly Asn Gly Leu Val Val
    290                 295

<210> SEQ ID NO 131
<211> LENGTH: 897
<212> TYPE: DNA
<213> ORGANISM: Zea mays

<400> SEQUENCE: 131
atggccgtgg acctgatggg ctgctacgcc ccgcgccgcg ccaacgacca gctcgccatc        60
caggaggcgg cggcggccgg gctccgcaac ctggagctgc tggtgacgtc cctgtccacg       120
caggccgccg cgccgcacag agccgctgat cagccgttcg cgagatcgc cggccaggcc        180 gtctccaagt tccgcaaggt catctccatc ctcgaccgca cggggcacgc ccgcttccgc       240
cgcgggcccg tcgagccgcc gccgccgacg ccgccgccgc tcctgtcgt ccccggtcct        300 gcccccctgg cggccgtcag cgtggcgcag ccgccgcaga gcctgacgct ggacttcacg       360
aagccgaacc tggccgtgtc ggccgccacg tccgtcacct ccacgtcctt cttctcgtcg       420
gtcacggccg gcgagggcag cgtctccaag ggccggagcc tcatgtcctc cgggaagccg       480
ccgctgtccg gccacaagcg gaagccctgc gccggcgccc actccgaggc accaccaac        540 ggcagccgtt gccactgctc caagagaagg aagaaccgcg tgaagaggac catcagagtg       600
ccggcgatca gctcgaaggt cgccgacatc ccttcggacg agtactcgtg gaggaagtac       660
ggccagaagc ccatcaaggg ctccccttac ccacggggct actacaagtg cagcactgtg       720
```

```
cggggatgcc cggcgaggaa gcacgtggag cgggccaccg acgacccggc catgctggtg      780
gtgacgtacg agggcgagca ccgccacacg ccgggcgcgg tccaggggcc gagcccctg      840 gcgaccgcgt cgccggtgcc cgtcgccgtc tccgccggca acgggctcgt tgtctag        897
```

PLANTS WITH IMPROVED GROWTH

CROSS-REFERENCE TO RELATED APPLICATIONS

This is a U.S. National Phase of International Application No. PCT/SE2018/051245, filed Dec. 4, 2018, which claims priority to Swedish Application No. 1751493-6 filed Dec. 4, 2017.

FIELD OF THE INVENTION

The invention relates to the field of plants with improved growth and yield properties, and in particular to plants comprising heterologous nucleic acid constructs comprising improved combinations of growth improving genes and promoters influencing their expression in the plants.

BACKGROUND TO THE INVENTION

Plant growth is influenced by a large number of different growth influencing genes, where some are genes encodes for hormones, transcription regulators and other growth and development enhancing products. Some gene products are active throughout the plant life cycle, e.g. shoot elongation, the expansion and shape of leaves, flowering and seed germination other only for short periods. Several examples illustrating the importance of growth influencing genes can be found in the literature.

Plant Growth

It is known to a person skilled in the art that the phenotypical effect of any gene in the plant is highly dependent on gene regulation. For example, spatial and temporal expression patterns as well as stress induction of genes significantly influence the plant phenotype. Conversely, controlling gene regulation can be used in attempts to improve the plant phenotype, for example, increasing plant growth. Gene expression can be modified using promoters which spatially and temporally direct gene expression in specific tissues and to specific levels. Positive phenotypical traits conferred by a gene can be modified to improve growth by controlling gene expression. Similarly, controlling gene regulation can also be used to attempt to prevent negative phenotypical effects of a gene.

Growth of plants appear at apical meristems and results in the development of sets of primary tissues and in the lengthening of the stem and roots.

In addition to this primary growth, trees undergo secondary growth and produce secondary tissue "wood" from the cambium. This secondary growth increases the girth of stems and roots. There are several factors such as different gene products that might need to be altered in order to enhance biomass production in trees.

Growth in height, diameter, stem volume and wood density are important traits to observe for increased growth and biomass production. However, it is also known to a person skilled in the art that a specific spatial and temporal expression pattern of a gene may elicit different phenotypical effects under two distinctly different growth conditions, for example, the growth conditions to which the plants are exposed in the greenhouse compared to in a field trial environment.

Promoters

Promoters are regions of DNA involved in binding of RNA polymerase to initiate transcription of coding sequences. Promoters can comprise several regulatory elements, usually called cis elements, generally located within a few hundred nucleotides from the transcription initiation site but that may also be positioned as far upstream as several thousand nucleotides as well as in introns. Trans-acting proteins then usually bind to these cis elements and then regulate transcription. The cis regulatory elements are separated along the nucleotide sequence by nucleic acid stretches that have no known regulatory effect on their own, the spacing of the cis-elements could however be important for their function.

Promoters may be constitutive, tissue-specific, rhythmic, or inducible by certain stimuli.

Constitutive promoters induce expression of the coding sequence in most tissues of the plant, irrespective of developmental stage or environmental factors.

Tissue-specific promoters induce expression of the coding sequence in a specific tissue or region of the plant.

Rhythmic promoters is subjected to internal rhythms by an internal timer, these internal timers are for example influenced by light and temperature and their status influence long term expression patterns, for example yearly variations in gene expression.

Promoters can also have temporal variations in activity, for example could the activity of a promoter be reduced or increased during flower induction or dormancy related processes.

Inducible promoters are activated by chemical or physical factors, such as isopropyl β-D-1-thiogalactopyranoside (IPTG), light, or temperature.

The Cauliflower Mosaic Virus, CaMV, 35S promoter is the most frequently used promoter when studying effects of modified gene expression during development, since the studied genes are constitutively expressed when the promoter is operably linked to them. The use of the CaMV 35S promoter has generated a lot of data regarding gene function and effects of over-expression in laboratory tests. In some situation it can be useful to have access to a promoter that in combination with a gene is more specifically expressed in a certain plant tissue or plant part. Results from field tests have shown that plants genetically modified with a construct with the CaMV 35S promoter operably linked to a trait gene may be acceptable, but have also been shown to result in unimproved or adverse effects in the field.

Wood Production

Wood is used for paper production and for constructions. In many situations there is a need for improved properties and improved quality of the wood used. The main need is the quantity of wood. This can be achieved by cutting down more trees, or by using more land for tree production or by using trees which grow faster and have better growth properties. The later can be done by traditional breeding programs or by use of gene modification. Both strategies lead to a shorter rotation time, i.e. the time from planting to harvest. A major disadvantage with traditional tree breeding, especially for forest tree species, is the slow progress due to their long generation periods. Breeding programs are also dependent on the genetic variation present in a tree population. However, by taking advantage of recent developments in gene technology the time required to produce a new variety could be reduced significantly and the effect could be additive to effects produced by breeding.

Growth Improving Genes

The Gene G47

The gene called AtG47, Seq ID No.: 1, is expected to be an ERF/AP2 transcription factor, belonging to the CBF/DREB subfamily, very little is known about its function, some phylogenetic information can be found in the scientific literature.

Mendel Biotechnology Inc. have performed research on effects of over-expression of the G47 using the CaMV 35S promoter and that information can be found in a number of patent documents from Mendel Biotechnology, WO2004031349, WO2004076638, WO2005047516, WO2006069201, WO2006130156, and WO2014100289.

In WO2006130156 it is shown that seedlings of *Arabidopsis* over-expressing G47 under the CaMV 35S promoter have brighter green color leaves, more narrow bundles of xylem vessels, than wild type *Arabidopsis* plants. Further, the inflorescences from *Arabidopsis* over-expressing G47 plants appeared thick and fleshy, had reduced apical dominance, and exhibited reduced internode elongation leading to a short compact stature. Over-expressing G47 had an increase in the number of xylem vessels in stems, as well as increased lignin content.

In WO2004031349 and WO2006069201 *Arabidopsis* plants over-expressing overexpressing AP2 polypeptides under the control of the 35S promoter had increased stress tolerance but often grew at a reduced rate, were smaller, and may have experienced delayed flowering with respect to wild type plants.

In WO2005047516 it is shown that over-expression of G47 resulted in a variety of morphological and physiological phenotypic alterations. 35S: G47 plants showed enhanced tolerance to osmotic stress, enhanced survival and drought tolerance in a soil-based drought assay, delay in flowering time and caused a marked change in shoot architecture.

As a summary, over-expressing the gene G47 resulted in some positive and some negative growth effects when using the CaMV 35S-promoter linked to the gene G47.

In JP2016127811 the inventors have coupled an *Arabidopsis thaliana* promoter NST3 to a construct comprising the sequence of the gene SGF1 (100% sequence identity to G47) and the very strong VP16 transcription activator domain. This construct was then introduced into double NST1/NST3 mutant of *Arabidopsis thaliana*, which thus lack NST1 and NST3 proteins. When the construct proNST3: SGF1-VP16 was expressed in this double mutant *Arabidopsis thaliana* it showed enlarged flower stalks (flowering stems). JP2016127811 does not show how a wild-type perennial woody plants will grow in a greenhouse or in the field, when a promoter linked to the unmodified SGF1 gene, without VP16, is expressed in said woody plant.

The Gene TF0002

In WO2009084999 it is shown that a DNA sequence coding for a TF0002 polypeptide under the control of the CaMV 35S promoter inserted in a poplar genome results in increased growth compared to unmodified wild type trees when potted in soil and grown in the greenhouse. Similar results are presented in WO2011109661. However, the biological function of the TF0002 gene is not clearly defined.

In WO2002015675 it is shown that the overexpression of the *Arabidopsis* ortholog of TF0002 using the 35S promoter in *Arabidopsis* plants resulted in increased size of the plants.

The *Populus tremula* x *tremuloides* TF0002 gene, PttTF0002, Seq ID No.: 2 is a WRKY transcription factor, belonging to WRKY subfamily IId according to the WRKY gene classification presented in Eulgem et al. 2000. The WRKY domain, a 60 amino acid region defined by a conserved amino acid sequence (WRKYGQK) at its N-terminal end and a novel zinc-finger-like motif, has a sequence specific DNA-binding activity. Reviews of the current state of understanding on WRKY transcription factors can be found in, for example, Bakshi and Oelmüller (2014) and ☐lker and Somssich (2004). The WRKY subfamily IId transcription factors interact with calmodulin (CaM), which is a ubiquitous $Ca^{2+}$ binding protein known to regulate diverse cellular functions by modulating the activity of various target proteins. The CaM-binding domain (CaMBD) is a conserved structural motif (C-motif) found in subfamily IId of the WRKY protein family (Park et al. 2005). The WRKY transcription factor family subfamily IId genes in *Arabidopsis thaliana* are AtWRKY7, AtWRKY15, AtWRKY11, AtWRKY17, AtWRKY21 and AtWRKY39 (Eulgem et al. 2000). The putative ortholog to the PttTF0002 gene in *Arabidopsis thaliana* is AtWRKY7, accession number AT4G24240. The amino acid sequence identity between PttTF0002 and AtWRKY7 is 54%, determined using the 'Align Sequences Protein BLAST' tool at NCBI (https://www.ncbi.nlm.nih.gov/).

The biological function of the PttTF0002 gene has not been described in prior art.

The *Arabidopsis thaliana* WRKY7 gene (AtWRKY7) is induced by pathogen infection and salicylic acid (SA) treatment and may therefore play a role in plant defence responses. AtWRKY7 is localized in the nucleus, recognizes DNA molecules with the W-box (TTGAC) elements, and functions as a transcriptional repressor in plant cells. T-DNA insertion and RNAi mutant plants display enhanced resistance to a virulent strain of the bacterial pathogen *Pseudomonas syringae* as measured by significant decrease in both bacterial growth and symptom development as compared to those in wild type plants. The enhanced resistance in the loss-of-function mutants was associated with increased induction of SA-regulated Pathogenesis-Related 1 (PR1) gene expression by the bacterial pathogen. Transgenic plants that constitutively overexpress AtWRKY7 have altered leaf growth. AtWRKY7-overexpressing plants supported more growth of *P. syringae* and developed more severe disease symptoms than wild type plants. The enhanced susceptibility of the AtWRKY7-overexpressing plants correlates with reduced expression of defence-related genes, including PR1, but significantly increased accumulation of SA after pathogen infection, probably due to reduced negative feedback of SA synthesis. Thus, pathogen-induced AtWRKY7 transcription factor play a negative role in defence responses to *P. syringae* (Kim et al. 2006).

In summary, strong, constitutive over-expression of the TF0002 gene, using the CaMV 35S promoter may result in increased growth. However, no reports on the effect on plant growth of other promoters tested in combination with the TF0002 gene are available in prior art.

In conclusion, to anticipate the effect that a specific promoter-gene combination has on the plant is ingenious and nontrivial. Prior art does not provide information enough to foresee the effect that a specific combination of promoter and a TF0002 gene will have on the plant. Nor does prior art provide information enough to indicate which promoter should be used in combination with the TF0002 gene to improve plant growth or biomass production without the negative pleiotropic effects that strong constitutive 35S promoter expression may induce.

The Gene TF0097

In WO2009084999 it is shown that a DNA sequence coding for a TF0097 polypeptide under the control of the CaMV 35S promoter inserted in a poplar genome results in increased growth compared to unmodified wild type trees when potted in soil and grown in the greenhouse. However, the biological function of the TF0097 gene is not clearly defined.

The *Populus tremula* x *tremuloides* TF0097 gene, PttTF0097, Seq ID No.: 3 is a transcription factor belonging to the basic helix-loop-helix (bHLH) protein superfamily of transcription factors. There are three possible orthologs to the PttTF0097 gene in *Arabidopsis thaliana*, CIL2 (ACE3, AtbHLH077), CIB2 (AtbHLH078) and CIB3 (AtbHLH062), accession number AT3G23690, AT5G48560 and AT3G07340 respectively. In *Arabidopsis* the bHLH superfamily has approximately 160 predicted transcription factors with several subgroups, where the possible *Arabidopsis* orthologs CIL2, CIB2 and CIB3 all fall into subgroup XII, Pires and Dolan 2010. The amino acid sequence identity between PttTF0097 and CIL2 is approximately 50% over 76% of the polypeptide, determined using the 'Align Sequences Protein BLAST' tool at NCBI (https://www.ncbi.nlm.nih.gov/). The amino acid sequence identity between PttTF0097 and CIB2 is approximately 43% over 91% of the polypeptide and the amino acid sequence identity between PttTF0097 and CIB3 is approximately 46% over 100% of the polypeptide.

The biological function of the PttTF0097 gene has not been described in prior art. Some possible orthologues have been proposed and their function is discussed below.

Liu et al. (PLOS Genet 2013e1003861) studied the function of the possible *Arabidopsis* orthologs CIL2 (ACE3, AtbHLH077, AT3G23690), CIB2 (CRY2-interacting BHLH 2) (AtbHLH078, AT5G48560) and CIB3 (AtbHLH062, AT3G07340). *Arabidopsis thaliana* cryptochrome 2 (CRY2) mediates light control of flowering time. CIB1 (CRY2-interacting bHLH 1) specifically interacts with CRY2 in response to blue light to activate the transcription of FT (Flowering Locus T). CIB1 positively regulates floral initiation in a CRY2-dependent manner. Over-expression studies, using the 35S promoter, showed that when the genes CIB1 and CIB2 are over-expressed plants flowered significantly earlier than the wild type parents in long day condition, while transgenic plants over-expressing CIB3 or CIL2 showed no obvious flowering phenotype. The genetic analysis performed by Liu et al. show that CIB1, CIB2, CIB4, and CIB5 act redundantly to activate the transcription of FT and suggests that they are positive regulators of CRY2 mediated flowering. CIB proteins are involved in blue light signalling, they are specifically stabilized by blue light and are also blue light regulated. Similar to CIB1, the expression of CIB2, CIB4, and CIB5 proteins are regulated by blue light in a wavelength-specific manner.

In summary, constitutive over-expression of the TF0097 gene, using the CaMV 35S promoter may result in early flowering or increased growth. However, no reports are available in the prior art showing that promoters in combination with the TF0097 gene may have an effect on early flowering in plant.

In conclusion, to anticipate the effect that a specific promoter-gene combination has on a plant is ingenious and nontrivial. Prior art does not provide information enough to foresee the effect that a specific combination of promoter and a TF0097 gene will have on the plant. Nor does prior art provide information enough to indicate which promoter should be used in combination with the TF0097 gene to improve plant growth or biomass production without the negative pleiotropic effects that strong constitutive 35S promoter expression may induce.

The Gene TF0132

In WO2009084999 it is shown that a DNA sequence coding for a TF0132 polypeptide under the control of the CaMV 35S promoter inserted in a tree genome results in increased growth compared to unmodified wild type trees when potted in soil and grown in the greenhouse. However, the biological function of the TF0132 gene is not clearly defined.

The *Populus tremula* x *tremuloides* TF0132 gene, PttTF0132, Seq ID No.: 4, is a WRKY transcription factor, belonging to WRKY subfamily IId according to the WRKY gene classification presented in Eulgem et al. 2000. The WRKY domain, a 60 amino acid region defined by a conserved amino acid sequence, WRKYGQK, at its N-terminal end and a novel zinc-finger-like motif, has a sequence specific DNA-binding activity. Reviews of the current state of understanding on WRKY transcription factors can be found in, for example, Bakshi and Oelmüller (2014) and Iker and Somssich (2004). The WRKY subfamily IId transcription factors interact with calmodulin, CaM, which is a ubiquitous $Ca^{2+}$-binding protein known to regulate diverse cellular functions by modulating the activity of various target proteins. The CaM-binding domain, CaMBD, is a conserved structural motif, C-motif, found in subfamily IId of the WRKY protein family (Park et al. 2005). The WRKY transcription factor family subfamily IId genes in *Arabidopsis thaliana* are AtWRKY7, AtWRKY15, AtWRKY11, AtWRKY17, AtWRKY21 and AtWRKY39 Eulgem et al. (2000). The putative ortholog to the PttTF0132 gene in *Arabidopsis thaliana* is AtWRKY21, accession number AT2G30590. The amino acid sequence identity between PttTF0132 and AtWRKY21 is 58%, as determined using the 'Align Sequences Protein BLAST' tool at NCBI (https://www.ncbi.nlm.nih.gov/). Two AtWRKY21 homologs, AtWRKY39 and AtWRKY74, accession number AT3G04670 and AT5G28650 respectively, are also possible orthologs to PttTF0132. The amino acid sequence identity between PttTF0132 and AtWRKY39 is 52% and the amino acid sequence identity between PttTF0132 and AtWRKY74 is 50%, determined using the 'Align Sequences Protein BLAST' tool at NCBI (https://www.ncbi.nlm.nih.gov/).

The biological function of the PttTF0132 gene has not been described in prior art.

AtWRKY39 is induced by heat stress, salicylic acid (SA) and jasmonate. AtWRKY39 knock-down mutants have increased susceptibility to heat stress while over-expressors show enhanced thermotolerance and increased expression of the gene Pathogenesis-Related 1, PR1 (Li et al. 2010).

The ortholog to AtWRKY39 in cotton, GhWRKY39, is induced by infection or NaCl treatment. Constitutive over-expression of GhWRKY39 in *Nicotiana benthamiana* increased resistance to bacterial and fungal pathogen infections, as well as the expression of several pathogenesis-related genes. The transgenic plants also exhibited less hydrogen peroxide accumulation than wild type plants following pathogen infection. Moreover, GhWRKY39-overexpressing plants displayed enhanced tolerance to salt and oxidative stress, increased transcription of antioxidant enzyme genes, and improved activities of the antioxidant enzymes SOD, POD and CAT after pathogen infection and salt stress treatment. This suggests that GhWRKY39 may positively regulate the plant response against pathogen infection and salt stress (Shi et al. 2014).

In summary, strong, constitutive over-expression of the TF0132 gene, using the CaMV 35S promoter may result in increased growth. However, no reports on the effect on plant growth of other promoters tested in combination with the TF0132 gene are available in prior art.

In conclusion, to anticipate the effect that a specific promoter-gene combination has on the plant is ingenious and nontrivial. Prior art does not provide information enough to foresee the effect that a specific combination of promoter and a TF0132 gene will have on the plant. Nor does prior art provide information enough to indicate which promoter should be used in combination with the TF0132 gene to improve plant growth or biomass production without the negative pleiotropic effects that strong constitutive 35S promoter expression may induce.

The Gene TF0109

In WO2009084999 it is shown that a DNA sequence coding for a TF0109 polypeptide under the control of the 35S promoter inserted in a tree genome results in increased growth compared to unmodified wild type trees when potted in soil and grown in the greenhouse. However, the biological function of the TF0109 gene is not clearly defined.

The *Populus tremula* x *tremuloides* TF0109 gene, PttTF0109, Seq ID No.: 5, is a WRKY transcription factor, belonging to WRKY subfamily IId according to the WRKY gene classification presented in Eulgem et al. 2000. Reviews of the current state of understanding on WRKY transcription factors can be found in, for example, Bakshi and Oelmüller (2014) and Iker and Somssich (2004). The WRKY subfamily IId transcription factors interact with calmodulin (CaM), which is a ubiquitous $Ca^{2+}$-binding protein known to regulate diverse cellular functions by modulating the activity of various target proteins. The CaM-binding domain is a conserved structural motif found in subfamily IId of the WRKY protein family (Park et al. 2005). The WRKY transcription factor family subfamily IId genes in *Arabidopsis thaliana* are AtWRKY7, AtWRKY15, AtWRKY11, AtWRKY17, AtWRKY21 and AtWRKY39 (Eulgem et al. 2000). The putative ortholog to the PttTF0109 gene in *Arabidopsis thaliana* is either AtWRKY11 or AtWRKY17, accession numbers AT4G31550 and AT2G24570 respectively. The amino acid sequence identity between PttTF0109 and AtWRKY11 is 53% and the amino acid sequence identity between PttTF0109 and AtWRKY17 is 54%, determined using the 'Align Sequences Protein BLAST' tool at NCBI (https://www.ncbi.nlm.nih.gov/).

The biological function of the PttTF0109 gene has not been described in prior art.

Journot et al. (2006 The Plant Cell, 18, 3289-3302) analyzed the role of the WRKY subfamily IId transcription factors in the regulation of basal resistance to *Pseudomonas syringae* pv tomato (Pst). The levels of expression of AtWRKY7, AtWRKY11, AtWRKY15 and AtWRKY17 were induced after inoculation with avirulent and virulent strains of Pst, but not the other members of subfamily IId. Mutant analyses revealed that loss of WRKY11 function increased resistance toward avirulent and virulent Pst strains and that resistance was further enhanced in wrky11 wrky17 double mutant plants. This suggests that WRKY11 and WRKY17 act as negative regulators of basal resistance to Pst.

In summary, strong, constitutive over-expression of the TF0109 gene, using the CaMV 35S promoter may result in increased growth. However, no reports on the effect on plant growth of other promoters tested in combination with the TF0109 gene are available in prior art.

In conclusion, to anticipate the effect that a specific promoter-gene combination has on the plant is ingenious and nontrivial. Prior art does not provide information enough to foresee the effect that a specific combination of promoter and a TF0109 gene will have on the plant. Nor does prior art provide information enough to indicate which promoter should be used in combination with the TF0109 gene to improve plant growth or biomass production without the negative pleiotropic effects that strong constitutive 35S promoter expression may induce.

SUMMARY OF THE INVENTION

In some situations, it can be useful to have access to a promoter that in combination with a gene, is specifically expressed in a specific plant tissue or plant part. Thus there is a need for new combinations of new functional promoters in combination with genes that are well functional in field use, i.e. when the plant is grown under realistic outdoor conditions, such as in the real environment of the plant of interest. The present invention builds on the idea that an in average weak but specific promoter showing desired results on the wanted phenotype, when operably linked to a gene selected from G47, TF0002, TF0097, TF0132 and TF0109, ID No.: 1 to 5, will give either an increased desired effect or a less pleiotropic and possibly less negative effects in the field and in the mass production of a selected transgenic plant.

Thus there is a need for new combinations of functional promoters in combinations with genes that are well functional in field use, i.e. when the plant is grown under realistic outdoor conditions, such as in the real environment when growing the plant of interest.

In view of the need to provide plants capable of enhanced growth, yield and biomass in a range of different environmental conditions, as well as changing environmental conditions, there is a continual need to provide plants with different genetic traits, comprising different sets of promoters and active genes.

Furthermore, in view of the need to provide trees capable of enhanced growth and biomass production in a range of different environmental conditions, including areas where water is a limiting factor, as well as changing environmental conditions, there is a continual need to provide trees with different genetic traits, comprising different sets of promoters and active genes.

Thus, in a first aspect the invention relates to genetically modified woody plants comprising a heterologous nucleic acid construct comprising a promoter sequence operably linked to a coding sequence encoding a gene selected from G47 (SEQ ID No: 1), or TF0002 (SEQ ID No: 2), and to genetically modified plants comprising a heterologous nucleic acid construct comprising a promoter sequence operably linked to a coding sequence encoding a gene selected from TF0097, TF0132 and TF0109, ID No.: 3 to 5, respectively.

Thus, in one aspect the present invention relates to a genetically woody modified plant comprising a heterologous nucleic acid construct comprising a promoter sequence operably linked to a coding sequence encoding a gene product, wherein the gene product is selected from the group consisting of: G47 and TF0002, and the promoter sequence is selected from the group consisting of promoters preferentially or specifically expressed in phloem tissue of said plant; promoters preferentially or specifically expressed in meristematic tissue of said plant; promoters preferentially or specifically expressed in xylem tissue of said plant; promoters preferentially or specifically expressed in root tissue of said plant; and constitutively expressed promoters pECO1 and pECO2.

In a further aspect, the present invention relates to a genetically modified plant comprising a heterologous nucleic acid construct comprising a promoter sequence operably linked to a coding sequence encoding a gene product, wherein the gene product is selected from the group consisting of: TF0097; TF0132; and TF0109, and the promoter sequence is selected from the group consisting of promoters preferentially or specifically expressed in phloem tissue of said plant; promoters preferentially or specifically expressed in meristematic tissue of said plant; promoters preferentially or specifically expressed in xylem tissue of said plant; promoters preferentially or specifically expressed in root tissue of said plant; and constitutively expressed promoters pECO1 and pECO2.

In one embodiment, the promoter is selected from the group consisting of pLMP1 (SEQ ID No.: 13 or 33), pEC1 (SEQ ID No.: 12, 32 or 39), pEL1.1 (SEQ ID No.: 16, 34 or 40), pEA1 (SEQ ID No.: 8 or 28), pEA2 (SEQ ID No.: 9 or 29), pECO2 (SEQ ID No.: 7 or 27), pEA3 (SEQ ID No.: 10 or 30), pEA4 (SEQ ID No.: 11, 31 or 38), pLMX5 (SEQ ID No.: 14), pEX5 (SEQ ID No.: 15), pEL1.2 (SEQ ID No.: 17, 35 or 41), pER1 (SEQ ID No.: 18, 36 or 42), pER2 (SEQ ID No.: 19, 37 or 43), pECO1 (SEQ ID No.: 6 or 26), and promoters that have the same, or essentially the same, capability of initiating transcription of a coding sequence when operably linked to said coding sequence.

In one embodiment, the promoter preferentially or specifically expressed in meristematic tissue of said plant is preferentially or specifically expressed in at least one of cambium, vascular meristematic tissue, and shoot meristem tissue of said plant.

In one embodiment, the promoter is not significantly expressed in at least one of mature xylem, stem phloem, whole leaves, whole roots and bark of said plant.

In a further aspect, the invention relates to a genetically modified woody plant comprising a heterologous nucleic acid construct comprising a promoter sequence operably linked to a coding sequence encoding a gene product selected from the group consisting of G47; and TF0002, wherein the promoter is selected from the group consisting pLMP1 (SEQ ID No.: 13 or 33), pEC1 (SEQ ID No.: 12, 32 or 39), pEL1.1 (SEQ ID No.: 16, 34 or 40), pEA1 (SEQ ID No.: 8 or 28), pEA2 (SEQ ID No.: 9 or 29), pECO2 (SEQ ID No.: 7 or 27), pEA3 (SEQ ID No.: 10 or 30), pEA4 (SEQ ID No.: 11, 31 or 38), pLMX5 (SEQ ID No.: 14), pEX5 (SEQ ID No.: 15), pEL1.2 (SEQ ID No.: 17, 35 or 41), pER1 (SEQ ID No.: 18, 36 or 42), pER2 (SEQ ID No.: 19, 37 or 43), pECO1 (SEQ ID No.: 6 or 26), and promoters that have the same, or essentially the same, capability of initiating transcription of a coding sequence when operably linked to said coding sequence.

In a further aspect, the invention relates to a genetically modified plant comprising a heterologous nucleic acid construct comprising a promoter sequence operably linked to a coding sequence encoding a gene product selected from the group consisting of TF0097; TF0132; and TF0109, wherein the promoter is selected from the group consisting pLMP1 (SEQ ID No.: 13 or 33), pEC1 (SEQ ID No.: 12, 32 or 39), pEL1.1 (SEQ ID No.: 16, 34 or 40), pEA1 (SEQ ID No.: 8 or 28), pEA2 (SEQ ID No.: 9 or 29), pECO2 (SEQ ID No.: 7 or 27), pEA3 (SEQ ID No.: 10 or 30), pEA4 (SEQ ID No.: 11, 31 or 38), pLMX5 (SEQ ID No.: 14), pEX5 (SEQ ID No.: 15), pEL1.2 (SEQ ID No.: 17, 35 or 41), pER1 (SEQ ID No.: 18, 36 or 42), pER2 (SEQ ID No.: 19, 37 or 43), pECO1 (SEQ ID No.: 6 or 26), and promoters that have the same, or essentially the same, capability of initiating transcription of a coding sequence when operably linked to said coding sequence.

In one embodiment, the invention relates to a genetically modified plant according to the invention, wherein the gene product is a protein from *Eucalyptus grandis, Zea Mays, Populus trichocarpa*, or *Arabidopsis thaliana*.

It should be further noticed that the annual plant *Arabidopsis thaliana*, differ in many aspects from woody plants such as poplar and *eucalyptus*. In short, the differences can be summarized as in the table below,

| *Arabidopsis thaliana* | Woody plants |
|---|---|
| Determinate growth | Unterminated growth |
| Leaves are produced in a leaf rosette at the ground | Leaves are produced on the branches of trees and the growth pattern of the branches is important for yield in the field |
| No branches | Have branches |
| No stem, no wood formed | Stem with wood |
| Minute xylem tissue, only found flowering parts, such as flower stalks | Secondary xylem main tissue in woody plants |

There is little doubt, that *Arabidopsis* is an important model for trees, but it is also apparent that true woody plant systems are necessary to investigate some unique tree processes. One example is flowering time genes which will overlap between trees and annuals, but the effect flowering has on plant growth is completely different between *Arabidopsis* and trees. In *Arabidopsis* flowering ends the life cycle of the plant, whereas a woody plant continues to grow for many years after flowering.

Gene function is in many instances, partly similar between *Arabidopsis* and woody plants, but not all, such as *Eucalyptus* and *Populus*, however the effect the genes will have on growth and development will differ between species with such different life cycles and growth patterns as annuals such as *Arabidopsis* and perennial plants such as trees. The difference is extra clear when it comes to predict increased yield of tissues such as wood which is the main harvested and used tissue in woody plants trees. *Arabidopsis* have a growth cycle that is short and ends with producing seeds within a year, then the plant dies. The bulk of the biomass in *Arabidopsis* will be in the leaves and in the flower structures, very little will be in secondary xylem. In contrast a woody plant or a tree growth is indeterminately, flowering is usually after at least several years and the tree continue to live and grow after the first flowering have occurred. The main biomass of trees is also in the secondary xylem that make up the bulk of the root system and of the tree stem as well as the branches. The main goal in forestry is to produce trees with increased wood formation. Wood is produced by secondary growth, a growth phase clearly distinguished from elongation growth and production of leaves or flower structures.

In one embodiment, the invention relates to a genetically modified plant according to the invention having a modified trait as compared to a wild-type plant of the same species, wherein the modified trait is selected from plant yield, height, plant width, stem volume, stem dry weight, bark dry weight, wood density, leaf dry weight, average internode length, number of internodes, water use efficiency and drought tolerance.

In one embodiment, the invention relates to a genetically modified plant according to the invention, wherein the modified trait is increased as compared to a wild-type plant of the same species when said plants are grown under identical field conditions for a period of at least one year.

In one embodiment the plant is a woody plant, such as a hardwood plant.

In one embodiment the genetically modified plant is of the genus *Eucalyptus* or *Populus*.

In one embodiment the plant is a crop plant, preferably corn, soybeans or oil seed rape.

In one embodiment, the invention relates to a genetically modified woody plant according to the invention, wherein the coding sequence encodes the gene product G47 and the promoter sequence is selected from the group consisting of pLMP1 and pLMX5, and the modified trait is at least one of water use efficiency, plant yield, plant height, plant width, stem volume, stem dry weight, bark dry weight, water use efficiency and drought tolerance.

In one embodiment, the invention relates to a genetically modified woody plant according to the invention, wherein the coding sequence encodes the gene product TF0002 and the promoter sequence is selected from the group consisting of pLMP1 and pLMX5, and the modified trait is at least one of water use efficiency, plant yield, height, plant width, stem volume, stem dry weight, bark dry weight, and wood density.

In one embodiment, the invention relates to a genetically modified plant according to the invention, wherein the coding sequence encodes the gene product TF0097 and the promoter sequence is selected from the group consisting of pEC1, pEL1.1, pEA1, pEA3, pEX5, pER1, and the modified trait is at least one of water use efficiency, plant yield, height, plant width, stem volume, stem dry weight, bark dry weight, wood density, leaf dry weight.

In one embodiment, the invention relates to a genetically modified plant according to the invention, wherein the coding sequence encodes the gene product TF0132 and the promoter sequence is selected from the group consisting pEC1, pEA1, pEA4, pECO1, pECO2, and the modified trait is at least one of water use efficiency, plant yield, height, plant width, stem volume, stem dry weight, bark dry weight, wood density, leaf dry weight.

In one embodiment, the invention relates to a genetically modified plant according to the invention, wherein the coding sequence encodes the gene product TF0109 and the promoter sequence is selected from the group consisting pEA2, pEA1, pECO2, pEC1, pEX5, and the modified trait is at least one of water use efficiency, plant yield, height, plant width, stem volume, stem dry weight, bark dry weight, wood density, leaf dry weight.

In a further aspect, the invention relates to a method to make a genetically modified plant according to the invention, said method comprising the following steps;
 a) providing suitable part of a plant;
 b) providing a heterologous nucleic acid construct comprising a promoter sequence operably linked to a coding sequence encoding a gene product, wherein said coding sequence is selected from the group consisting of G47; TF0002, TF0097; TF0132; and TF0109, and wherein said promoter sequence is selected from the group consisting of promoters preferentially or specifically expressed in phloem tissue of said plant; promoters preferentially or specifically expressed in meristematic tissue of said plant; promoters preferentially or specifically expressed in xylem tissue of said plant; promoters preferentially or specifically expressed in root tissue of said plant; and constitutively expressed promoters pECO1 and pECO2.
 c) introducing the heterologous nucleic acid construct into said suitable part of the woody plant; and
 d) regenerating a genetically modified plant from said suitable part of the plant.

In a further aspect, the invention relates to a method to make a genetically modified plant according to the invention, said method comprising the following steps;
 a) providing suitable part of a plant;
 b) providing a heterologous nucleic acid construct comprising a promoter sequence operably linked to a coding sequence encoding a gene product, wherein said coding sequence is selected from the group consisting of G47; TF0002; TF0097; TF0132; and TF0109, and wherein said promoter is selected from the group consisting of pLMP1, pEC1, pEL1.1, pEA1, pEA2, pECO2, pEA3, pEA4, pLMX1, pEX5, pEL1.2, pER1, pER2, pECO1, and promoters that have the same, or essentially the same, capability of initiating transcription of a coding sequence when operably linked to said coding sequence;
 c) introducing the heterologous nucleic acid construct into said suitable part of the plant; and
 d) regenerating a genetically modified tree from said suitable part of the plant.

BRIEF DESCRIPTION OF THE DRAWINGS

In FIGS. 1, 2, 4, 5 and 6, H represent height, W represent width of the stem and S represent stem volume.

Definitions

Figure 1:
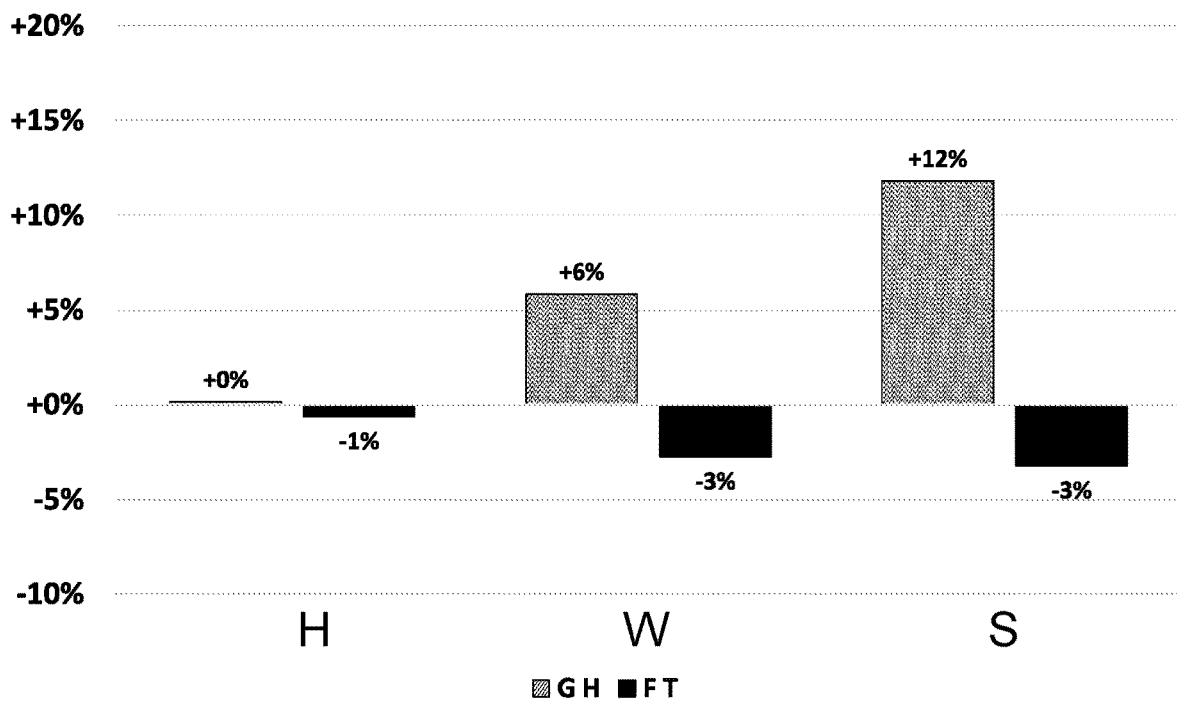
FIG. 1, shows greenhouse (G H) and field trial (F T) data for a prior art hybrid aspen, wherein a trait gene AtG47 is expressed under the constitutive 35S promoter. Percent numbers are compared to wild type reference plants.

All terms and words used in the present specification are intended to have the meaning generally given to them by the person skilled in the art of plant biotechnology. However, a few terms are explained in more detail below in order to avoid ambiguities.

The naming of genes presented in this disclosure originate from the inventors or others work. In brief, the first two or three letters denotes the plant name in Latin directly followed by the gene name, exemplified by the gene TF0097, from *Arabidopsis thaliana* it is denoted, AtTF0097. The same gene from *Eucalyptus grandis* is denoted EgTF0097. When an ortholog gene is know it will follow the name presented at the Phytozome Comparative Plant Genomics Portal (phytozome.jgi.doe.gov) using the latest version of Phytozome. At present the version 11.0 is used. Most ortholog gene names in the present disclosure are found in Phytozome.

A "p" in front of a gene denotes that this is the promoter of said gene, for example pRBCS is the promoter of the gene ribulose-1,5-bisphosphate carboxylase small subunit (RBCS).

If a promoter, when operably linked to a coding sequence, entails expression of the coding sequence in a certain tissue or region of the plant to a significantly larger extent than in another tissue or region, then that promoter is said to be "preferentially expressed" in that tissue or region. A promoter may be preferentially expressed in more than one tissue or region. Expression levels can be analysed as described herein.

If a promoter, when operably linked to a coding sequence, entails expression of the coding sequence in a single tissue or region of the plant to a significantly larger extent than in any other tissue or region, then that promoter is said to be "specifically expressed" in that tissue or region. Expression levels can be analysed as described herein.

By "ortholog" or "orthologous polypeptide" is meant a polypeptide expressed by evolutionarily related genes that have a similar nucleic acid sequence, where the polypeptide has similar functional properties. Orthologous genes are structurally related genes, from different species, derived by a speciation event from an ancestral gene. Related to orthologs are paralogs. Paralogous genes are structurally related genes within a single plant species most probably derived by a duplication of a gene. Several different methods are known by those of skill in the art for identifying and defining these functionally homologous sequences.

Orthologous genes from different organisms have highly conserved functions and can be used for identification of genes that could perform the invention in the same way as the genes presented here. Paralogous genes, which have diverged through gene duplication, may encode protein retaining similar functions. Orthologous genes are the product of speciation, the production of new species from a parental species, giving rise to two or more genes with common ancestry and with similar sequence and similar function. These genes, termed orthologous genes, often have an identical function within their host plants and are often interchangeable between species without losing function. Identification of an "ortholog" gene may be done by identifying polypeptides in public databases using the software tool BLAST with one of the polypeptides encoded by a gene. Subsequently additional software programs are used to align and analyze ancestry. The sequence identity between two orthologous genes may be low.

A promoter is said to be an "orthologous promoter" to a promoter in a different species when the respective promoters initiate transcription of orthologous genes in wild type plants of the respective species.

The term "plant" including "crop plants" as used herein encompasses whole plants, ancestors and progeny of the plants and plant parts, including seeds, shoots, stems, leaves, roots (including tubers), flowers, and tissues and organs, wherein each of the aforementioned comprise the gene/nucleic acid of interest. The term "plant" also encompasses plant cells, suspension cultures, callus tissue, embryos, meristematic regions, gametophytes, sporophytes, pollen and microspores, again wherein each of the aforementioned comprises the gene/nucleic acid of interest.

A "woody plant" is a plant that produces wood as a structural tissue.

The terms "substantially identical" or "sequence identity" may indicate a quantitative measure of the degree of identity between two amino acid sequences or two nucleic acids (DNA or RNA) of equal length. When the two sequences to be compared are not of equal length, they are aligned to give the best possible fit, by allowing the insertion of gaps or, alternatively, truncation at the ends of the polypeptide sequences or nucleotide sequences. The "sequence identity" may be presented as percent number, such as at least 40, 50%, 55,%, 60%, 65%, 70%, 75%, 80%, 81%, 82%, 83%, 84%, 85%, 86%, 87%, 88%, 89%, 90%, 91%, 92%, 93%, 94%, 95%, 96%, 97%, 98%, or at least 99% amino acid sequence identity of the entire length, when compared and aligned for maximum correspondence, as measured using a sequence comparison algorithm or by visual inspection.

The sequence identity of the polypeptides of the invention can be calculated as $(N_{ref}-N_{dif})\, 100/N_{ref}$, wherein $N_{dif}$ is the total number of non-identical residues in the two sequences when aligned and wherein $N_{ref}$ is the number of residues in one of the sequences. The sequence identity between one or more sequence may also be based on alignments using the Clustal W or Clustal X software. In one embodiment of the invention, alignment is performed with the sequence alignment method Clustal X version 2 with default parameters. The parameter set preferably used are for pairwise alignment: Gap open penalty: 10; Gap Extension Penalty: 0.1, for multiple alignment, Gap open penalty is 10 and Gap Extension Penalty is 0.2. Protein Weight matrix is set on Identity. Both Residue-specific and Hydrophobic Penalties are "ON", Gap separation distance is 4 and End Gap separation is "OFF", No Use negative matrix and finally the Delay Divergent Cut-off is set to 30%. The Version 2 of Clustal W and Clustal X is described in: Larkin et al. 2007, Clustal W and Clustal X version 2.0. Bioinformatics, 23:2947-2948. The identity between two sequence (protein or nucleic acids) can practically be determined by using different BLAST tools at NCBI (https://www.ncbi.nlm.nih.gov/).

Preferably, the numbers of substitutions, insertions, additions or deletions of one or more amino acid residues in the polypeptide as compared to its comparator polypeptide is limited, i.e. no more than 1, 2, 3, 4, 5, 6, 7, 8, 9, or 10 substitutions, no more than 1, 2, 3, 4, 5, 6, 7, 8, 9, or 10 insertions, no more than 1, 2, 3, 4, 5, 6, 7, 8, 9, or 10 additions, and no more than 1, 2, 3, 4, 5, 6, 7, 8, 9, or 10 deletions. Preferably the substitutions are conservative amino acid substitutions: limited to exchanges within members of group Glycine, Alanine, Valine, Leucine, Isoleucine; group Serine, Cysteine, Selenocysteine, Threonine, Methionine; group Proline; group Phenylalanine, Tyrosine, Tryptophan; Group Aspartate, Glutamate, Asparagine, and Glutamine.

In some aspects, the amino acid substantial identity exists over a polypeptide sequences length of 10, 15, 20, 25, 30, 35, 40, 45, 50, 55, 60, 65, 70, 75, 80, 85, 90, 95, 100, 110, 120, 130, 140, 150, 160, 170, 180, 190, 200, 250, 300, 350, 400, 450, 500, 600, 700 amino acids in the polypeptide with a "sequence identity" as defined above.

In certain aspects, substantial identity exists over a region of nucleic acid sequences of at least about 50 nucleic acid residues, such as at least about 100, 150, 200, 250, 300, 330, 360, 375, 400, 425, 450, 460, 480, 500, 600, 700, 800 such as at least about 900 nucleotides or such as at least about 1 kb, 2 kb, or such as at least about 3 kb.

A gene (nucleic acid molecule comprising a coding sequence) is "operably linked" to a promoter when its transcription is under the control of the promoter and where transcription results in a transcript whose subsequent translation yields the product encoded by the gene.

The term "increasing expression" is intended to encompass well known methods to increase the expression by regulatory sequences, such as promoters, or proteins, such as transcription factors. The terms "increasing expression", "enhanced expression" and "over-expression" can be used interchangeably in this text. Increased expression may lead to an increased amount of the over-expressed protein/enzyme, which may lead to an increased activity of the protein of interest that contributes to its high efficiency.

The term "yield" as used herein generally refers to a measurable product from a plant, particularly a crop. Yield and yield increase (in comparison to a non-transformed starting or wild-type plant) can be measured in a number of ways, and it is understood that a skilled person will be able to apply the correct meaning in view of the particular embodiments, the particular crop concerned and the specific purpose or application concerned. The terms "improved yield" or "increased yield" can be used interchangeable. As used herein, the term "improved yield" or the term "increased yield" means any improvement in the yield of any measured plant product, such as grain, fruit, leaf, root, cob or fibre. In accordance with the invention, changes in different phenotypic traits may improve yield. For example, and without limitation, parameters such as floral organ development, root initiation, root biomass, seed number, seed weight, harvest index, leaf formation, phototropism, apical dominance, and fruit development, are suitable measurements of improved yield. Increased yield includes higher fruit yields, higher seed yields, higher fresh matter production, and/or higher dry matter production. Any increase in yield is an improved yield in accordance with the invention. For example, the improvement in yield can comprise a 0.1%, 0.5%, 1%, 3%, 5%, 10%, 15%, 20%, 30%, 40%, 50%, 60%, 70%, 80%, 90% or greater increase in any measured parameter. For example, an increase in the bu/acre yield of soybeans or corn derived from a crop comprising plants which are transgenic for the chimeric genes of the invention, as compared with the bu/acre yield from untransformed soybeans or corn cultivated under the same conditions, is an improved yield in accordance with the invention. The increased or improved yield can be achieved in the absence or presence of stress conditions. For example, enhanced or increased "yield" refers to one or more yield parameters selected from the group consisting of biomass yield, dry biomass yield, aerial dry biomass yield, underground dry biomass yield, fresh-weight biomass yield, aerial fresh-weight biomass yield, underground fresh-weight biomass yield; enhanced yield of harvestable parts, either dry or fresh-weight or both, either aerial or underground or both; enhanced yield of crop fruit, either dry or fresh-weight or both, either aerial or underground or both; and enhanced yield of seeds, either dry or fresh-weight or both, either aerial or underground or both. "Crop yield" is defined herein as the number of bushels of relevant agricultural product (such as grain, forage, or seed) harvested per acre. Crop yield is impacted by abiotic stresses, such as drought, heat, salinity, and cold stress, and by the size (biomass) of the plant. The yield of a plant can depend on the specific plant/crop of interest as well as its intended application (such as food production, feed production, processed food production, biofuel, biogas or alcohol production, or the like) of interest in each particular case. Thus, in one embodiment, yield can be calculated as harvest index (expressed as a ratio of the weight of the respective harvestable parts divided by the total biomass), harvestable parts weight per area (acre, square meter, or the like); and the like. The harvest index is the ratio of yield biomass to the total cumulative biomass at harvest. Harvest index is relatively stable under many environmental conditions, and so a robust correlation between plant size and grain yield is possible. Measurements of plant size in early development, under standardized conditions in a growth chamber or greenhouse, are standard practices to measure potential yield advantages conferred by the presence of a transgene. Accordingly, the yield of a plant can be increased by improving one or more of the yield-related phenotypes or traits. Such yield-related phenotypes or traits of a plant the improvement of which results in increased yield comprise, without limitation, the increase of the intrinsic yield capacity of a plant, improved nutrient use efficiency, and/or increased stress tolerance. For example, yield refers to biomass yield, e.g. to dry weight biomass yield and/or fresh-weight biomass yield. Biomass yield refers to the aerial or underground parts of a plant, depending on the specific circumstances (test conditions, specific crop of interest, application of interest, and the like). In one embodiment, biomass yield refers to the aerial and underground parts. Biomass yield may be calculated as fresh-weight, dry weight or a moisture adjusted basis. Biomass yield may be calculated on a per plant basis or in relation to a specific area (e.g. biomass yield per acre/square meter/or the like). "Yield" can also refer to seed yield which can be measured by one or more of the following parameters: number of seeds or number of filled seeds (per plant or per area (acre/square meter/or the like)); seed filling rate (ratio between number of filled seeds and total number of seeds); number of flowers per plant; seed biomass or total seeds weight (per plant or per area (acre/square meter/or the like); thousand kernel weight (TKW; extrapolated from the number of filled seeds counted and their total weight; an increase in TKW may be caused by an increased seed size, an increased seed weight, an increased embryo size, and/or an increased endosperm). Other parameters allowing to measure seed yield are also known in the art. Seed yield may be determined on a dry weight or on a fresh weight basis, or typically on a moisture adjusted basis, e.g. percent moisture. For example, the term "increased yield" means that a plant, exhibits an increased growth rate, e.g. in the absence or presence of abiotic environmental stress, compared to the corresponding wild-type plant. An increased growth rate may be reflected inter alia by or confers an increased biomass production of the whole plant, or an increased biomass production of the aerial parts of a plant, or by an increased biomass production of the underground parts of a plant, or by an increased biomass production of parts of a plant, like stems, leaves, blossoms, fruits, and/or 3 seeds. A prolonged growth comprises survival and/or continued growth of the plant, at the moment when the non-transformed wild type organism shows visual symptoms of deficiency and/or death. When the plant of the invention is a corn plant, increased yield for corn plants means, for example, increased seed yield, in particular for corn varieties used for feed or food. Increased seed yield of corn refers to an increased kernel size or weight, an increased kernel per ear, or increased ears per plant. Alternatively or in addition the cob yield may be increased, or the length or size of the cob is increased, or the kernel per cob ratio is improved. When the plant of the invention is a soy plant, increased yield for soy plants means increased seed yield, in particular for soy varieties used for feed or food. Increased seed yield of soy refers for example to an increased kernel size or weight, an increased kernel per pod, or increased pods per plant. When the plant of the invention is an oil seed rape (OSR) plant, increased yield for OSR plants means increased seed yield, in particular for OSR varieties used for feed or food. Increased seed yield of OSR refers to an increased seed size or weight, an increased seed number per silique, or increased siliques per plant. When the plant of the invention is a cotton plant, increased yield for cotton plants means increased lint yield. Increased lint yield of cotton refers in one embodiment to an increased length of lint. When the plant is a plant belonging to grasses an increased leaf can mean an increased leaf biomass. Said increased yield can typically be achieved by enhancing or improving, one or more yield related traits of the plant. Such yield-related traits of a plant comprise, without limitation, the increase of the intrinsic yield capacity of a plant, improved nutrient use efficiency, and/or increased stress tolerance, in particular increased abiotic stress tolerance. Intrinsic yield capacity of a plant can be, for example, manifested by improving the specific (intrinsic) seed yield (e.g. in terms of increased seed/grain size, increased ear number, increased seed number per ear, improvement of seed filling, improvement of seed composition, embryo and/or endosperm improvements, or the like); modification and improvement of inherent growth and development mechanisms of a plant (such as plant height, plant growth rate, pod number, pod position on the plant, number of internodes, incidence of pod shatter, efficiency of nodulation and nitrogen fixation, efficiency of carbon assimilation, improvement of seedling vigour/early vigour, enhanced efficiency of germination (under stressed or non-stressed conditions), improvement in plant architecture, cell cycle modifications, photosynthesis modifications, various signalling pathway modifications, modification of transcriptional regulation, modification of translational regulation, modification of enzyme activities, and the like); and/or the like.

The term "water use efficiency" (WUE) has been defined in various ways in the literature, but is commonly known as a simple measure for the water productivity of a plant. An increase in water use efficiency is commonly cited as a response mechanism of plants to moderate to severe soil water deficits, and has been the focus of many programs that seek to increase crop tolerance of drought. Different plant species has different inherent water use efficiency.

Water use efficiency is preferably measured by the carbon isotope discrimination analysis for improved drought tolerance. It is known that carbon isotope discrimination is highly correlated with water use efficiency in C3 plants. The isotopic ratio of $^{13}C$ to $^{12}C$ ($\delta^{13}C$) in plant tissue is less than the isotopic ratio of $^{13}C$ to $^{12}C$ in the atmosphere, indicating that plants discriminate against $^{13}C$ during photosynthesis. The isotopic ratio $\delta^{13}C$ varies mainly due to discrimination during diffusion of $CO_2$ across the stomatal pore, where diffusion of $^{13}CO_2$ is lower than that of $^{12}CO_2$, and an additional effect caused by the preference of ribulose bisphosphate carboxylase for $^{12}CO_2$ over $^{13}CO_2$. Both processes discriminate against the heavier isotope, $^{13}C$, Farquhar, G. D., J. R. Ehleringer, and K. T. Hubick. 1989. Carbon isotope discrimination and photosynthesis. Ann. Rev. Plant Physiol. 40:503-537.

Specific plants have been genetically modified to better withstand drought and/or to improve their water use efficiency. For example, US 2016/0,272,990 describes a plant cell having a recombinant DNA construct which provides for an enhanced trait as compared to control plants. The said enhanced trait may e.g. be enhanced water use efficiency, enhanced cold tolerance, increased yield, enhanced nitrogen use efficiency, enhanced seed protein, or enhanced seed oil.

The terms "increase", "improve" or "enhance" are interchangeable and shall mean in the sense of the application at least a 3%, 4%, 5%, 6%, 7%, 8%, 9% or 10%, preferably at least 15% or 20%, more preferably 25%, 30%, 35%, 40%, 50%, 60%, 70%, 80%, 90%, 95% or more yield and/or growth in comparison to control plants as defined herein.

DETAILED DESCRIPTION OF THE INVENTION

On a general level, the present invention relates to controlling gene regulation in order to retain or further improve positive phenotypical traits provided by a trait gene when growth conditions change. Controlled gene regulation is used to tailor the expression pattern of the trait gene to the growth condition under which the plant is to be grown.

The present inventors have found that constitutive overexpression of a trait gene that provide improved growth under greenhouse conditions may not provide similar improved growth under field conditions, and may in fact lead to impaired growth, see Example 1.

These unexpected results led the inventors to test other combinations of promoters and genes. It is evident from the results disclosed in Example 1 that having a strong constitutive expression of a trait gene can, as with the CaMV 35S promoter construct, have disadvantageous effects under some field trial conditions. Furthermore, these results demonstrate the need for new promoters and new promoter-gene combinations to tailor the expression pattern of the trait gene to the specific growth condition and to retain or further improve the positive phenotypical traits provided by the gene when growth conditions change.

Consequently, the invention consists of combinations of promoters, in particular pECO1, pECO2, pEA1, pEA2, pEA3, pEA4, pEC1, pLMP1, pLMX5, pEX5, pEL1.1, pEL1.2, pER1 and pER2 promoters, and one of the following genes, G47, TF0002, TF0097, TF0132 and TF0109 that confer improved plant traits in field use.

Novel Promoter-Gene Combinations

This invention discloses novel combinations of promoters and trait genes, selected from G47, TF0002, TF0097, TF0132 and TF0109. When any of these combinations are expressed in a tree a number of improved phenotypical effects might be noted, such as plant height, plant biomass, stem diameter, stem volume, wood density, stem dry weight, bark dry weight, average internode length, number of internodes.

The combinations of promoters and genes were designed based on scientific information about the function and expression pattern of the trait gene and the promoter established by the inventors and supported by information available in the prior art. Such information provides concepts where to direct expression as well as where to avert gene expression. However, it is known to a person skilled in the art that anticipating the effect that a specific promoter-gene combination has on the plant is ingenious and nontrivial.

The novel combinations of a promoter and a biological functional polypeptide selected from the genes G47, TF0002, TF0097, TF0132 and TF0109, as defined by their polypeptide sequence ID No.: 1 to 5, respectively, when it is introduced into the plant by use of a recombinant DNA construct, as explained herein.

Crop Plants.

Crop plants that are useful in the methods of the invention include in particular monocotyledonous and dicotyledonous plants including fodder or forage legumes, ornamental plants, food crops, trees or shrubs selected from the list comprising *Acer* spp., *Actinidia* spp., *Abelmoschus* spp., *Agave sisalana*, *Agropyron* spp., *Agrostis stolonifera*, *Allium* spp., *Amaranthus* spp., *Ammophila arenaria*, *Ananas comosus*, Annona spp., *Apium graveolens*, *Arachis* spp, *Artocarpus* spp., *Asparagus officinalis*, *Avena* spp. (e.g. *Avena sativa*, *Avena fatua*, *Avena byzantina*, *Avena fatua* var. *sativa*, *Avena hybrida*), *Averrhoa carambola*, *Bambusa* sp., *Benincasa hispida*, *Bertholletia excelsea*, *Beta vulgaris*, *Brassica* spp. (e.g. *Brassica napus*, *Brassica rapa* ssp. [canola, oilseed rape, turnip rape]), *Cadaba farinosa*, *Camellia sinensis*, *Canna indica*, *Cannabis sativa*, *Capsicum* spp., *Carex elata*, *Carica papaya*, *Carissa macrocarpa*,

*Carya* spp., *Carthamus tinctorius, Castanea* spp., *Ceiba pentandra, Cichorium endivia, Cinnamomum* spp., *Citrullus lanatus, Citrus* spp., *Cocos* spp., *Coffea* spp., *Colocasia esculenta, Cola* spp., *Corchorus* sp., *Coriandrum sativum, Corylus* spp., *Crataegus* spp., *Crocus sativus, Cucurbita* spp., *Cucumis* spp., *Cynara* spp., *Daucus carota, Desmodium* spp., *Dimocarpus longan, Dioscorea* spp., *Diospyros* spp., *Echinochloa* spp., *Elaeis* (e.g. *Elaeis guineensis, Elaeis oleifera), Eleusine coracana, Eragrostis tef, Erianthus* sp., *Eriobotrya japonica, Eucalyptus* sp., *Eugenia uniflora, Fagopyrum* spp., *Fagus* spp., *Festuca* 30 *arundinacea, Ficus carica, Fortunella* spp., *Fragaria* spp., *Ginkgo biloba, Glycine* spp. (e.g. *Glycine max, Soja hispida* or *Soja* max), *Gossypium hirsutum, Helianthus* spp. (e.g. *Helianthus annuus), Hemerocallis fulva, Hibiscus* spp., *Hordeum* spp. (e.g. *Hordeum vulgare), Ipomoea batatas, Juglans* spp., *Lactuca sativa, Lathyrus* spp., *Lens culinaris, Linum usitatissimum, Litchi chinensis, Lotus* spp., *Luffa acutangula, Lupinus* spp., *Luzula sylvatica, Lycopersicon* spp. (e.g. *Lycopersicon esculentum, Lycopersicon lycopersicum, Lycopersicon pyriforme), Macrotyloma* spp., *Malus* spp., *Malpighia emarginata, Mammea americana, Mangifera indica, Manihot* spp., *Manilkara zapota, Medicago sativa, Melilotus* spp., *Mentha* spp., *Miscanthus sinensis, Momordica* spp., *Morus nigra, Musa* spp., *Nicotiana* spp., *Olea* spp., *Opuntia* spp., *Ornithopus* spp., *Oryza* spp. (e.g. *Oryza sativa, Oryza latifolia), Panicum miliaceum, Panicum virgatum, Passiflora edulis, Pastinaca sativa, Pennisetum* sp., *Persea* spp., *Petroselinum crispum, Phalaris arundinacea, Phaseolus* spp., *Phleum pratense, Phoenix* spp., *Phragmites australis, Physalis* spp., *Pinus* spp., *Pistacia vera, Pisum* spp., *Poa* spp., *Populus* spp., *Prosopis* spp., *Prunus* spp., *Psidium* spp., *Punica granatum, Pyrus communis, Quercus* spp., *Raphanus sativus, Rheum rhabarbarum, Ribes* spp., *Ricinus communis, Rubus* spp., *Saccharum* spp., *Salix* sp., *Sambucus* spp., *Secale cereale, Sesamum* spp., *Sinapis* sp., *Solanum* spp. (e.g. *Solanum tuberosum, Solanum integrifolium* or *Solanum lycopersicum), Sorghum bicolor, Spinacia* spp., *Syzygium* spp., *Tagetes* spp., *Tamarindus indica, Theobroma cacao, Trifolium* spp., *Tripsacum dactyloides, Triticosecale rimpaui, Triticum* spp. (e.g. *Triticum aestivum, Triticum durum, Triticum turgidum, Triticum hybernum, Triticum macha, Triticum sativum, Triticum monococcum* or *Triticum vulgare), Tropaeolum minus, Tropaeolum majus, Vaccinium* spp., *Vicia* spp., *Vigna* spp., *Viola odorata, Vitis* spp., *Zea mays, Zizania palustris, Ziziphus* spp., amongst others.

Woody Plants

The present invention further relates to genetically modified woody plants, such as genetically modified angiosperms, dicotyledonous woody plants, preferably trees.

The invention further relates to genetically modified woody plants from gymnosperms, such as conifer trees.

The woody plant may be a hardwood plant e.g. selected from the group consisting of *acacia, eucalyptus*, hornbeam, beech, mahogany, walnut, oak, ash, willow, hickory, birch, chestnut, poplar, alder, maple, sycamore, *ginkgo*, a palm tree and sweet gum. Hardwood plants, such as *eucalyptus* and plants from the Salicaceae family, such as willow, poplar and aspen including variants thereof, are of particular interest, as these groups include fast-growing species of tree or woody shrub which are grown specifically to provide timber for building material, raw material for pulping, bio-fuels and/or bio chemicals.

In further embodiments, the genetically modified tree is a conifer tree, such as a member of the order Pinales, with members of the family Cupressaceae, such as *Cupressus* spp., *Juniperus* spp., *Sequoia* spp., *Sequoiadendron* spp.; with members of the family Taxaceae (*Taxus* spp.) and with members of the family Pinaceae, such as the genera *Abies* spp., *Cedrus* spp., *Larix* spp., *Picea* spp., *Pinus* spp., *Pseudotsuga* spp., *Tsuga* spp.

Alternatively, the woody plants which may be selected from the group consisting of cotton, bamboo and rubber plants.

In another embodiment, the genetically modified tree is a deciduous tree including hybrids, and cultivars such as acacia (*Acacia* spp.), alder (*Alnus* spp.), birch (*Betula* spp.), hornbeam (*Carpinus* spp.), hickory (*Carya* spp.), chestnut (*Castanea* spp.), beech (*Fagus* spp.), walnut (*Juglans* spp.), oak (*Quercus* spp.), ash (*Fraxinus* spp.), poplar (*Populus* spp.), aspen (*Populus* spp.), willow (*Salix* spp.), eucalyptus (*Eucalyptus* spp.), sycamore (*Platanus* spp.), maple (*Acer* spp.), mahogany (*Swietenia* spp.), sweet gum (*Liquidambar* spp.). Genetically modified trees of the families Salicaceae and Myrtaceae are preferred, most preferred are genetically modified tree from the genus *Eucalyptus* and *Populus*.

In yet another embodiment, the genetically modified tree is a fruit bearing plant, including hybrids, and cultivars such as, apple (*Malus* spp.), plum (*Prunus* spp.), pear (*Pyrus* spp.), orange (*Citrus* spp.), lemon (*Citrus* spp.), kiwi fruit (*Actinidia* spp.), cherry (*Prunus* spp.), grapevine (*Vitis* spp.), and fig (*Ficus* spp.).

In a specific embodiment, the genetically modified tree is a woody plant whose leaves can be eaten as leaf vegetables include *Adansonia, Aralia, Moringa, Morus*, and *Toona* species.

Promoters

A general method for identification of ortholog plants promoters, preferably tissue-specific promoter.

The following set of criteria may be used to identify plant promoters. Some of these criteria are:

Establishment of expression pattern:
  Select the plant of interest and identify promoters that corresponds to tested and verified promoters of plants similar to the selected plant.
  Identify promoters with a well-established expression pattern, preferably confirmed by extensive analysis from a plant similar to the selected plant.
  Selection of should preferably be based on expression pattern analysis performed in plant similar to the selected plant, for example, microarray or expressed RNA sequence analysis.

Identification of an ortholog promoter.
  Once a desired expression pattern is identified a phylogenetic analysis of the corresponding gene and closely related genes from another plant species similar to the selected plant can be done.
  Identification of an ortholog gene might be performed using publicly available genome database resources, such as the Phytozome database.
  The region upstream the coding sequence of the identified orthologues gene is selected and a putative promoter is chosen. The length of the putative promoter may be determined by using available scientific information together with homology analyses of promoter regions of orthologous genes from multiple plant species.

The identified ortholog promoter might be verified by different expression methods, such as GUS-expression.

Identification of *Eucalyptus* Promoters

A set of criteria has been used to identify *Eucalyptus* promoters. Some of these criteria are:
  *Eucalyptus* promoters that corresponds to tested and verified *Populus* promoters.
  *Eucalyptus* promoters that corresponds to promoters with a well-established expression pattern confirmed by extensive analysis.

Selection of *Eucalyptus* promoters based on expression pattern analysis performed in *Eucalyptus*, for example, microarray or RNAseq analysis.

Selection of *Eucalyptus* promoters based on expression pattern analysis performed in *Populus* and/or *Arabidopsis*, for example, microarray or RNAseq analysis.

Once a desired expression pattern was identified a phylogenetic analysis of the corresponding gene and closely related genes from *Eucalyptus grandis, Populus trichocarpa* and *Arabidopsis thaliana* was performed using publicly available genome database resources. Mostly the Phytozome database was used for searches. Thus, orthology and homology within and between species was determined and a *Eucalyptus* gene with a putative expression pattern similar to the desired expression pattern was identified.

The region upstream the coding sequence of the identified *Eucalyptus* gene was examined and a putative promoter region length was determined using available scientific information together with homology analyses of promoter regions of orthologous genes from multiple plant species, such as *Eucalyptus, Populus* and *Arabidopsis*.

Identification of Novel *Eucalyptus* Tissue-Specific Promoters

This invention has established a number of novel *Eucalyptus* tissue-specific promoters such as, such as apex active promoters, stem/cambium active promoters, root active promoters and promoters active in leaves. These promoters offer invaluable instruments to specifically control the expression of trait genes in a plant, more specifically in a tree and even more specifically in *Eucalyptus*.

The novel *Eucalyptus* promoters were identified by using scientific information available from multiple plant species, such as *Eucalyptus, Populus* and *Arabidopsis*, from gene expression analyses, expression of known promoters and the expression and function of the corresponding genes and of identified orthologous/homologous genes.

In order to identify the *Eucalyptus* promoters a strategy was formulated involving two steps, first identification of a set of promoters and secondly verifying that the identified promoter is functional.

Fourteen *Eucalyptus* promoters were selected for combination with the five trait genes. Two promoters from hybrid aspen were also included, see below for details. The constitutive Cauliflower Mosaic Virus 35S promoter, p35S was used in combination with all genes for comparison. For details about cloning of the genes, see the examples.

The above identified nucleic acid sequences constitute promoter regions. As known in the art, promoter regions comprise a number of cis-regulatory elements, to which proteins involved in transcription bind. These regulatory elements are primarily located within a few hundred nucleotides upstream the start codon.

Thus, in one aspect the methods and products of the invention make use of the promoter regions in the plants and methods according to the invention.

In further aspects, the methods and products of the invention make use of the regulatory elements comprised in the promoter regions, i.e. polynucleotides that have the same, or essentially the same, capability of initiating transcription of a coding sequence when operably linked to said coding sequence, as compared to the promoter regions disclosed in Table 1.

In one aspect, the methods and products of the invention make use of the part of the promoter region that is located between start codon and 3000, 2500, 2000, 1800, 1600, 1400, 1200, 1000, 900, 800, 700, 600, 500, 400, 300, 250, 200, 175, 150, or 125 nucleotides upstream, or nucleic acid stretches that are at least 40%, 50%, 55,%, 60%, 65%, 70%, 75%, 80%, 81%, 82%, 83%, 84%, 85%, 86%, 87%, 88%, 89%, 90%, 91%, 92%, 93%, 94%, 95%, 96%, 97%, 98%, or at least 99% identical to said part of the promoter region and that have the same, or essentially the same, capability of initiating transcription of a coding sequence when operably linked to said coding sequence, as compared to the promoter regions disclosed in Table 1.

In one aspect, the methods and products of the invention make use of promoters that are orthologous to the promoters disclosed in Table 1, i.e. promoters from different species that initiate transcription of orthologous genes in wild type woody plants of the respective species. Also such orthologous promoters should have the same, or essentially the same, capability of initiating transcription of a coding sequence when operably linked to said coding sequence, as compared to the promoter regions disclosed in Table 1.

Assessment of whether a nucleic acid has the same, or essentially the same, capability of initiating transcription of a coding sequence when operably linked to said coding sequence, can be done in a number of ways known to the skilled person. One way is to study expression patterns by histological studies of plants harbouring a promoter-β-glu-

TABLE 1

*Eucalyptus* and hybrid aspen promoters and the CaMV 35S promoter.

| | Promoters | | | Examples of orthologous promoters | | | | |
|---|---|---|---|---|---|---|---|---|
| Promoter name | Sequence ID No. | Promoter region length (nt) | Promoter name | Sequence ID No. | Promoter region length (nt) | Promoter name | Sequence ID No. | Promoter region length (nt) |
| pECO1 | 6 | 1084 | pECO1-ort poplar | 26 | 1802 | | | |
| pECO2 | 7 | 2000 | pECO2-ort poplar | 27 | 2000 | | | |
| pEA1 | 8 | 2000 | pEA1-ort poplar | 28 | 2000 | | | |
| pEA2 | 9 | 2500 | pEA2-ort poplar | 29 | 2500 | | | |
| pEA3 | 10 | 2700 | pEA3-ort poplar | 30 | 2700 | | | |
| pEA4 | 11 | 2500 | pEA4-ort poplar | 31 | 2500 | pEA4-para poplar | 38 | 2500 |
| pEC1 | 12 | 2101 | pEC1-ort poplar | 32 | 2101 | pEC1-para poplar | 39 | 2101 |
| pLMP1 | 13 | 1487 | pEP1 | 33 | 1801 | | | |
| pLMX5 | 14 | 1780 | pEX5 | 15 | 2001 | | | |
| pEL1.1 | 16 | 600 | pEL1.1-ort poplar | 34 | 600 | pEL1.1-para poplar | 40 | 600 |
| pEL1.2 | 17 | 1800 | pEL1.2-ort poplar | 35 | 1800 | pEL1.2-para poplar | 41 | 1800 |
| pER1 | 18 | 2000 | pER1-ort poplar | 36 | 2000 | pER1-para poplar | 42 | 2000 |
| pER2 | 19 | 2000 | pER2-ort poplar | 37 | 2000 | pER2-para poplar | 43 | 2000 |
| p35S | 20 | 942 | | | | | | | curonidase (GUS) construct, as detailed in Example 1 and 2. The nucleic acid's activity as a promoter is then assayed using the established histochemical GUS staining technique, and compared to one or more constructs harbouring one or more of the promoter regions of the present disclosure.

Promoters from *Eucalyptus* and Hybrid Aspen

The Promoter pECO1

The dynamin protein, a GTPase that is responsible for endocytosis in the eukaryotic cell, was identified as a highly and constitutively expressed gene by studying expression data from hybrid aspen microarray experiments.

To clone the *Eucalyptus* pECO1 promoter, the amino acid sequence from *Populus trichocarpa* dynamin protein gene, accession number Potri.001G090600, was used in a blast search followed by a phylogenetic analysis of the identified putative homologous and orthologous genes. The identified *E. grandis* ortholog, accession number Eucgr. E00053, has an 86.7% polypeptide sequence identity to the *Populus* gene product. The sequence immediately upstream of, but not including, the start codon of the gene Eucgr. E00053 was used for synthesis of the pECO1 promoter, Seq ID No.: 6. A putative orthologous promoter to the pECO1 promoter is the *Populus tremula* x *tremuloides* promoter pECO1-ort poplar, Seq ID No.: 26.

The promoter pECO1 has been established and used as a constitutive promoter in the patent application SE1651431-7.

The Promoter pECO2

A constitutively expressed gene encoding a housekeeping protein, glyceraldehyde 3-phosphate dehydrogenase, GAPDH, was identified as a constitutively expressed gene suitable as a stable reference for RT-qPCR analysis by Czechowski et al. Plant Physiology 2005, Vol. 139, 5-17. GAPDH catalyses a step in glycolysis and serves to break down glucose for energy and carbon molecules.

The GAPDH gene from *A. thaliana*, accession number AT1G13440, was used in a blast search followed by a phylogenetic analysis of the identified putative homologous and orthologous genes. The identified *Eucalyptus grandis* ortholog, accession number Eucgr. H04673, has a 93.1% polypeptide sequence identity to AT1G13440. Avoiding to include the coding region of an adjacent gene, a 1084 base pair long promoter fragment immediately upstream of, but not including, the start codon of gene Eucgr. H04673 was used for synthesis of the pECO2 promoter, Seq ID No.: 7. A putative orthologous promoter to the pECO2 promoter is the promoter region, pECO2-ort poplar, Seq ID No.: 27, of the *Populus trichocarpa* gene with accession number Potri.010G055400.

The promoter pECO2 has been established and used as a constitutive promoter in the patent application SE1651431-7.

The Promoter pEA1

The gene *ERECTA* (ER) from *A. thaliana* (accession number AT2G26330) was selected based on publications regarding its known function and expression in shoot apex. The ER gene is homologous to receptor protein kinases and involved in specification of organs originating from the shoot apical meristem. The ER polypeptide contains a cytoplasmic protein kinase catalytic domain, a transmembrane region, and an extracellular leucine-rich repeat. ER has further been identified as a quantitative trait locus for transpiration efficiency by influencing epidermal and mesophyll development, stomatal density and porosity of leaves. ER has also been implicated in resistance to bacteria and to necrotrophic fungus. ER governs, together with ERL1 and ERL2, the initial decision of protodermal cells to either divide proliferatively to produce pavement cells or divide asymmetrically to generate stomatal complexes, Yokoyama et al. 1998, The Plant Journal, 15(3), 301-310.

The AT2G26330 polypeptide was used in a blast search followed by a phylogenetic analysis of the identified putative homologous and orthologous genes. This identified the *E. grandis* ortholog, accession number Eucgr. C00732. The orthologous gene of *Populus trichocarpa* is Potri.006G220100. Since the length of the promoter is unknown, a 2000 base pair long promoter fragment immediately upstream of, but not including, the start codon of gene Eucgr. C00732 was selected for synthesis of the pEA1 promoter, Seq ID No.: 8. A putative orthologous promoter to the pEA1 promoter is the promoter region, pEA1-ort poplar, Seq ID No.: 28, of the *Populus trichocarpa* gene with accession number Potri.006G220100.

The promoter pEA1 has been established and used as a tissue specific promoter in the patent application SE1651431-7.

The Promoter pEA2

The gene AINTEGUMENTA (ANT) from *A. thaliana* (accession number AT4G37750) was selected for its known function in cell proliferation and as a positive regulator of cell division and for its known expression in actively dividing cells. Loss-of-function *Arabidopsis* mutants lacking ANT have reduced cell division and cell number leading to reduced size of all lateral organs while over-expression increases cell number and thus organ size, Mizukami and Fischer (2000) PNAS, 97(2): 942-947.

The AT4G37750 polypeptide was used in a blast search followed by a phylogenetic analysis of the identified putative homologous and orthologous genes. This identified the *E. grandis* ortholog, accession number Eucgr.F02223. The putative orthologous gene in *Populus trichocarpa* is Potri.002g114800. Since the length of the promoter is unknown, a 2500 base pair long promoter fragment immediately upstream of, but not including, the start codon of gene Eucgr. F02223 was selected for synthesis of the pEA2 promoter, Seq ID No.: 9. A putative orthologous promoter to the pEA2 promoter is the promoter region, pEA2-ort poplar, Seq ID No.: 29, of the *Populus trichocarpa* gene with accession number Potri.002g114800.

The promoter pEA2 has been established and used as a tissue specific promoter in the patent application SE1651431-7.

The Promoter pEA3

The promoter of the Asymmetric leaves1 (AS1) gene, accession number AT2G37630, drives gene expression in the apical region of the plant, specifically in the leaf forming tissues of the leaf primordia. The AS1 promoter was selected based on its known specific expression pattern and the function of AS1 in leaf primordia, Byrne et al. 2000, Nature, 408(6815) 967-971.

The AT2G37630 polypeptide was used in a blast search followed by a phylogenetic analysis of the identified putative homologous and orthologous genes. The putative orthologous gene in *Populus trichocarpa* is Potri.006G085900. The identified *Eucalyptus grandis* ortholog, accession number Eucgr. K03130, has a polypeptide sequence identity of 67% to AT2G37630 over 98% of the *E. grandis* sequence. Promoter analysis in *Arabidopsis* has shown that the promoter is approximately 2.7 kb. The promoter, in both *Arabidopsis* and *Eucalyptus*, contains a large intron in the predicted 5' UTR. A 2700 base pair long promoter fragment immediately upstream of, but not including, the start codon of gene Eucgr. K03130 was selected for synthesis of the pEA3 promoter, Seq ID No.: 10. Orthologous to the pEA3 promoter is the promoter region, pEA3-ort poplar, Seq ID No.: 30, of the *Populus trichocarpa* gene with accession number Potri.006G085900.

The promoter pEA3 has been established and used as a tissue specific promoter in the patent application SE1651431-7.

The Promoter pEA4

The *A. thaliana* gene AT5G67260 (AtCYCD3:2) encode CYCD3;2, a CYCD3 D-type cyclin, which is important for determining cell number in developing lateral organs and mediating cytokinin effects in apical growth and development. CYCD3 function contributes to the control of cell number in developing leaves by regulating the duration of the mitotic phase and timing of the transition to endocycles. CYCD3;1 expression is restricted to the shoot apical meristem (SAM), very young primordia, and young hydathodes, whereas CYCD3;2 and CYCD3;3 reporters are also active in older leaf primordia, with CYCD3;2 expression persisting longest in young leaves. The phytohormone cytokinin regulates cell division in the shoot meristem and developing leaves and induces CYCD3 expression. Loss of CYCD3 impairs shoot meristem function and leads to reduced cytokinin responses, Dewitte et al., 2007 PNAS, 104(36) 14537-14542.

The AT5G67260 polypeptide was used in a blast search followed by a phylogenetic analysis of the identified putative homologous and orthologous genes. The identified *Eucalyptus grandis* ortholog, accession number Eucgr. 100802, has a polypeptide sequence identity of 51% to AT5G67260 over 94% of the *E. grandis* sequence. In *Populus trichocarpa* two putative orthologous genes are identified, Potri.007G048300 and Potri.005G141900; these two genes are considered paralogous genes. Promoter analysis in *Arabidopsis* has shown that the promoter fragment is approximately 2.5 kb. Therefore, a 2500 base pair long promoter fragment immediately upstream of, but not including, the start codon of gene Eucgr. 100802 was selected for synthesis of the pEA4 promoter, Seq ID No.: 11. A putative orthologous promoter to the pEA4 promoter is the *Populus trichocarpa* promoter regions, pEA4-ort poplar, Seq ID No.: 31, and pEA4-para poplar, Seq ID No.: 38.

The promoter pEA4 has been established and used as a tissue specific promoter in the patent application SE1651431-7.

The Promoter pEC1

The WOX4 gene in *A. thaliana* is preferentially expressed in the procambial/cambial stem cells and is a regulator of vascular stem cell proliferation, Mizukami and Fischer (2000) PNAS, 97(2): 942-947. The expression pattern of the hybrid aspen ortholog (HB3/WOX4) was first identified in a high resolution expression profile over the vascular cambium, Schrader et al. 2004, The Plant Cell 16(9) 2278-2292, subsequently using more precise methods such as promoter:GUS analysis, real-time PCR and in-situ hybridization Nilsson, Doctoral thesis 2010:29, Faculty of Forest Sciences, Umeå. These studies combined show that WOX4/HB3 is a cambium specific promoter well suited for tissue specific expression of chosen trait genes.

The *Eucalyptus* gene Eucgr. F02320 forms a phylogenetic group with the *Arabidopsis* WOX4 (AT1G46480) and two *P. trichocarpa* homologs Potri.014G025300 and Potri.002G124100. Alignment of 4 kb fragments upstream of the coding sequence of the hybrid aspen transcripts with 4 kb upstream of the Eucgr. F02320 gene reveals major similarities of approximately 2.1 kb. This region was selected for synthesis of the stem/cambium specific promoter pEC1, Seq ID No.: 12. Putative orthologous promoters to the pEC1 promoter are the *Populus trichocarpa* promoter regions, pEC1-ort poplar, Seq ID No.: 32, and pEC1-para poplar, Seq ID No.: 39.

The promoter pEC1 has been established and used as a tissue specific promoter in the patent application SE1651431-7

The Hybrid Aspen Promoter pLMP1

The pLMP1 promoter, Seq ID No.: 13, from hybrid aspen has been established and used as a phloem-specific promoter, WO2004097024. The gene immediately downstream of the pLMP1 promoter was found to be preferentially expressed in the cambium and developing phloem by studying expression data from hybrid aspen microarray experiments. The phloem-specific expression pattern of the pLMP1 promoter was further verified in GUS expression assays, studying stem sections of transgenic hybrid aspen trees harbouring a recombinant DNA construct with the pLMP1 promoter and the beta-glucuronidase (GUS) reporter gene. The gene immediately downstream of the pLMP1 promoter in hybrid aspen is orthologous to the *Populus trichocarpa* gene with accession number Potri.013G127900.

Identification of an ortholog promoter to pLMP1. The amino acid sequence from the *Populus trichocarpa* gene Potri.013G127900 was used in a blast search followed by a phylogenetic analysis of the identified putative homologous and orthologous genes.

The identified *E. grandis* ortholog, accession number Eucgr. B01456, has a 64% polypeptide sequence identity to the *Populus* gene product. The length of the hybrid aspen pLMP1 promoter is 1487 base pair. To allow for some interspecies variation, an 1.8 kb long promoter fragment immediately upstream of, but not including, the start codon of the gene Eucgr. B01456 was used for synthesis of the pEP1 promoter, Seq ID No.: 33. The pEP1 and pLMP1 are orthologous promoters.

The Promoter pLMX5

The pLMX5 promoter, Seq ID No.: 14, from hybrid aspen has been established and used as a xylem-specific promoter earlier and is presented in WO2004097024. The gene immediately downstream of the pLMX5 promoter was found to be preferentially expressed in the developing xylem by studying expression data from hybrid aspen microarray experiments. The xylem-specific expression pattern of the pLMX5 promoter was further verified in GUS expression assays, studying stem sections of transgenic hybrid aspen trees harbouring a recombinant DNA construct with the pLMX5 promoter and the beta-glucuronidase (GUS) reporter gene. The gene immediately downstream of the pLMX5 promoter in hybrid aspen is orthologous to the *Populus trichocarpa* gene with accession number Potri.002G101200.

The Promoter pEX5

To clone the *Eucalyptus* pEX5 promoter, the amino acid sequence from the *Populus trichocarpa* gene Potri.002G101200 was used in a blast search followed by a phylogenetic analysis of the identified putative homologous and orthologous genes. The identified *E. grandis* ortholog, accession number Eucgr. B00045, has a 55% polypeptide sequence identity to the *Populus* gene product. The length of the hybrid aspen pLMX5 promoter is 1.8 kb. To allow for some interspecies variation, a 2001 base pair long promoter fragment immediately upstream of, but not including, the start codon of the gene Eucgr. B00045 was used for synthesis of the pEX5 promoter, Seq ID No.: 15. The pEX5 and pLMX5 are orthologous promoters.

The pEL1.1 and pEL1.2 Promoters

The pEL1.1 and pEL1.2 promoters originate from the one of the best characterized light-inducible genes in leaves, the small subunit of ribulose-1,5-bisphosphate carboxylase (RuBisCo or RBCS) gene promoter. The Rubisco small subunit, RBCS, is a multigene family in *Arabidopsis thaliana* and consists of four genes; RBCS1A (At1g67090), RBCS1B (At5g38430), RBCS2B (At5g38420), and RBCS3B (At5g38410).

It has been found that the promoter from RBCS genes contain an intricate assortment of positive and negative regulatory elements that are able to confer light-inducible and tissue-specific expression in transgenic plants (Gilmartin and Chua 1990, Mol Cell Biol, 10(10) 5565-5568). Anisimov et al. 2007, Mol Breeding, 19, 241-253, describes that the level of expression conferred by the pRBCS promoter differ depending on the length of the used promoter fragment. A longer promoter of 1.6 kb has an expression level that is four times higher than a short promoter fragment of 300-600 bp.

The four polypeptides of the RBCS multigene family from *Arabidopsis thaliana* were used in a blast search followed by a phylogenetic analysis of the identified putative homologous and orthologous genes.

The three identified loci, Eucgr. B03013, Eucgr. J01502, and Eucgr. K02223, were found to have 70-80% amino acid identity to query sequence. The highest scoring, Eucgr.B03013, has 79.7%, 80.2%, 80.2% and 79.1% identity, respectively, to the above-mentioned *Arabidopsis thaliana* genes. In the phylogenetic analysis the Eucgr. K02223 gene was identified as the closest homologue to *Arabidopsis thaliana* RBCS, from which the *Eucalyptus* promotor were cloned. In *Populus trichocarpa* two putative orthologous genes are identified, Potri.017G114600 and Potri.004G100000; these two genes are considered paralogous genes.

Based on the findings of Anisimov, et al. 2007, Mol Breeding, 19, 241-253, two promoter fragments of different lengths from *Eucalyptus grandis* were selected for synthesis; pEL1.1, Seq ID No.: 16, has a short promoter sequence of 600 bp, while pEL1.2, Seq ID No.: 17, has a longer promoter sequence of 1800 bp.

The putative orthologous and paralogous promoters to the pEL1.1 promoter are the *Populus trichocarpa* promoter regions, pEL1.1-ort poplar, Seq ID No.: 34, and pEL1.1-para poplar, Seq ID No.: 40, respectively.

The putative orthologous and paralogous promoters to the pEL1.2 promoter are the *Populus trichocarpa* promoter regions, pEL1.2-ort poplar, Seq ID No.: 35, and pEL1.2-para poplar, Seq ID No.: 41, respectively.

The pEL1.1 and pEL1.2 promoters have been established and used as a tissue specific promoter in the patent application SE1651431-7.

The Promoter pER1

The *Eucalyptus camaldulensis* EcPT2 gene, Genbank accession number AB242817, was found to be specifically expressed in the root by Koyama et al. 2006, Plant Biotechnology, 23, 215-218. The EcPT2 gene encodes an inorganic phosphate (Pi) transporter protein. Phosphate is one of the most important nutrients for plant growth and it is likely that Pi transporters in roots play a major role in inorganic phosphate uptake from the soil.

The EcPT2 nucleotide sequence was used in a blast search followed by a phylogenetic analysis of the identified putative homologous and orthologous genes. The *E. grandis* gene with accession number Eucgr. H00165 was identified as the ortholog to the EcPT2 gene. Putative orthologous genes in *Populus trichocarpa* are Potri.005G175700, Potri.005G175500, Potri.015G022800 and Potri.019G061900.

Since the length of the promoter is unknown, a 2000 base pair long promoter fragment immediately upstream of, but not including, the start codon of gene Eucgr. H00165 was selected for synthesis of the pER1 promoter, Seq ID No.: 18.

Putative orthologous and paralogous promoters to the pER1 promoter are the *Populus trichocarpa* promoter regions, pER1-ort poplar, Seq ID No.: 36, PER1-para poplar1, Seq ID No.: 42 and pER1-para poplar2, Seq ID No.: 44, respectively.

The Promoter pER2

The *Eucalyptus grandis* TIP2 gene, EgTIP2, accession number Eucgr. D02090, has a root specific expression pattern as presented in Rodrigues et al. 2013, Plant Science, 213, 106-113 and Vicentini et al. 2005, Genetics and Molecular Biology, 28, 487-495. Tonoplast intrinsic proteins (TIPs) are plant aquaporins. Aquaporins are integral membrane proteins, facilitating water transport and have been implicated in multiple physiological processes, including adaptation to certain abiotic stresses. TIP proteins are involved in the regulation of cell elongation and turgor homeostasis by mediating the transport of water and small molecules across the vacuolar membrane.

The EgTIP2 nucleotide sequence was used in a blast search followed by a phylogenetic analysis of the identified putative homologous and orthologous genes. Putative orthologous genes in *Populus trichocarpa* are Potri.001G157000 and Potri.003G077800.

A short, 900 nucleotides long, EgTIP2 promoter drives expression in all vascular tissue in transformed tobacco seedlings, including but not limited to root and root tip (Rodrigues et al, 2013). Since a 900 nucleotide fragment is insufficient for root specific expression, at least in tobacco, and the promoter length is unknown, a 2000 base pair long promoter fragment immediately upstream of, but not including, the start codon of gene Eucgr. D02090 was selected for synthesis of the pER2 promoter, Seq ID No.: 19.

The putative orthologous and paralogous promoters to the pER2 promoter are the *Populus trichocarpa* promoter regions, pER2-ort poplar, Seq ID No.: 37, and pER2-para poplar, Seq ID No.: 43, respectively.

Functional Tests of the Identified Promoters.

In order to verify that all newly identified *Eucalyptus* promoters including the two variants of the leaf specific promoter were functional in trees, transgenic hybrid aspen with the different recombinant promoter-GUS constructs were created and studied. The DNA sequence of the identified promoter regions of the genomic sequence were manufactured by DNA synthesis, creating identical copies of the identified promoter regions of the genomic sequence of *Eucalyptus grandis*.

The synthetic promoters were cloned into an expression vector, positioned in front of the beta-glucuronidase (GUS) reporter gene. The recombinant promoter-GUS constructs were used in *Agrobacterium*-mediated transformation of hybrid aspen.

The promoter expression pattern was determined by histological studies of transgenic hybrid aspen plants harbouring the promoter-GUS construct, where the expression of the GUS gene was monitored using the established histochemical GUS staining technique. Details for these experiments are found in Example 1 and 2.

*Eucalyptus* promoters having a desired expression pattern could subsequently be used for controlling gene expression, to specifically direct the expression of a trait gene in planta.

Trait Genes

All trail genes below might by expressed in any cell type or specific tissue. The specificity of the above-mentioned promoters may make them ideal for affecting actively growing cells while minimizing side effects on cells not actively involved in growth in the plant.

As known there is a variation in the observed level of phenotypical effect of the genetic modification between the different independent transgenic lines. This variation is anticipated for a person skilled in the art, since plants are living, multicellular organisms impossible to grow completely uniformly and since the point of integration of the recombinant DNA construct in the plant genome to a large extent is random and are known to affect the expression of an inserted trait gene.

Trait Gene G47

The gene called G47, Seq ID No.: 1, is as earlier mentioned expected to be an ERF/AP2 transcription factor, belonging to the CBF/DREB subfamily. The gene G47 can also be named SGF1 as in JP2016127811. Ortholog genes to the G47 are probably, in poplar, Potri.019G073300.1 or Potri.013G100300.1, in *Eucalyptus*, Eucgr.F02967.1 and in corn GRMZM2G307152 or GRMZM2G481668.

The G47 gene used in the present invention is a nucleic acid encoding a G47 gene product that preferably has an amino acid sequence of at least 50%, such as 60%, 70%, 75%, 80%, 85%, 90%, 95%, 99% or 100% identical to an amino acid sequence having the amino acid sequence according to Seq ID No.: 1 (AtG47, AT1G22810). A summary of orthologous G47 genes and their peptide percent identities are found the Table 2, below.

TABLE 2a

| Gene name or Organism | Ortholog accession number: | Amino acid sequence Seq ID No: | Number of amino acids | Nucleotide sequence Seq ID No: | Number of nucleotides |
|---|---|---|---|---|---|
| AtG47 | AT1G22810 | 1 | 144 | 21 | 435 |
|  | Potri.019G073300 | 50 | 186 | 51 | 561 |
|  | Potri.013G100300 | 52 | 168 | 53 | 507 |
|  | Eucgr.F02967 | 54 | 155 | 55 | 468 |
| *Zea mays* | GRMZM2G307152 | 100 | 178 | 101 | 537 |
|  | GRMZM2G481668 | 102 | 186 | 103 | 561 |

TABLE 2b

Peptide percent Identity Matrix - created by Clustal 2.1.

|  | Seq_ID_No_1_ AtG47 | Seq_ID_No_50_ Potri.019G073300 | Seq_ID_No_52_ Potri.013G100300 | Seq_ID_No_54_ Eucgr.F02967 | Seq_ID_No_100_ GRMZM2G307152 | Seq_ID_No_102_ GRMZM2G481668 |
|---|---|---|---|---|---|---|
| Seq_ID_No_1_ AtG47 | 100 | 50 | 47 | 49 | 41 | 40 |
| Seq_ID_No_50_ Potri.019G073300 | 50 | 100 | 82 | 54 | 41 | 39 |
| Seq_ID_No_52_ Potri.013G100300 | 47 | 82 | 100 | 52 | 43 | 40 |
| Seq_ID_No_54_ Eucgr.F02967 | 49 | 54 | 52 | 100 | 50 | 47 |
| Seq_ID_No_100_ GRMZM2G307152 | 41 | 41 | 43 | 50 | 100 | 62 |
| Seq_ID_No_102_ GRMZM2G481668 | 40 | 39 | 40 | 47 | 62 | 100 |

Trait Gene TF0002

A TF0002 gene useful in the present invention is a nucleic acid encoding a TF0002 gene product that and preferably has an amino acid sequence at least 50%, such as 60%, 70%, 75%, 80%, 85%, 90%, 95%, 99% or 100% identical to an amino acid sequence having the amino acid sequence according to Seq ID No.: 1 (PttTF0002). A summary of orthologous TF0002 genes and their peptide percent identities are found the Table 3, below.

TABLE 3a

| Gene name or Organism | Ortholog accession number: | Amino acid sequence Seq ID No: | Number of amino acids | Nucleotide sequence Seq ID No: | Number of nucleotides |
|---|---|---|---|---|---|
| PttTF0002 | | 2 | 361 | 22 | 1086 |
| | Potri.014G024200 | 56 | 388 | 57 | 1167 |
| | Potri.002G123300 | 58 | 358 | 59 | 1077 |
| | Eucgr.F00187 | 60 | 437 | 61 | 1314 |
| AtWRKY7 | AT4G24240 | 62 | 353 | 63 | 1062 |
| Zea mays | GRMZM2G091331 | 104 | 316 | 105 | 951 |
| | GRMZM2G102583 | 106 | 331 | 107 | 996 |

TABLE 3b

Peptide percent Identity Matrix - created by Clustal 2.1

| | Seq_ID_No_2_ PttTF0002 | Seq_ID_No_56_ Potri.014G024200 | Seq_ID_No_58_ Potri.002G123300 | Seq_ID_No_60_ Eucgr.F00187 | Seq_ID_No_62_ AT4G24240 | Seq_ID_No_104_ GRMZM2G091331 | Seq_ID_No_106_ GRMZM2G102583 |
|---|---|---|---|---|---|---|---|
| Seq_ID_No_2_ PttTF0002 | 100 | 97 | 88 | 66 | 59 | 8 | 46 |
| Seq_ID_No_56_ Potri.014G024200 | 97 | 100 | 89 | 62 | 59 | 47 | 46 |
| Seq_ID_No_58_ Potri.002G123300 | 88 | 89 | 100 | 67 | 58 | 46 | 45 |
| Seq_ID_No_60_ Eucgr.F00187 | 66 | 62 | 67 | 100 | 57 | 46 | 44 |
| Seq_ID_No_62_ AT4G24240 | 59 | 59 | 58 | 57 | 100 | 47 | 46 |
| Seq_ID_No_104_ GRMZM2G091331 | 48 | 47 | 46 | 46 | 47 | 100 | 61 |
| Seq_ID_No_106_ GRMZM2G102583 | 46 | 46 | 45 | 44 | 46 | 61 | 100 |

Trait Gene TF0097

As mentioned above the *Populus tremula* x *tremuloides* TF0097 gene, PttTF0097, is a transcription factor belonging to the basic helix-loop-helix (bHLH) protein superfamily of transcription factors. In the present disclosure a TF0097 gene is a nucleic acid encoding a TF0097 gene product that preferably has an amino acid sequence at least 50%, such as 60%, 70%, 75%, 80%, 85%, 90%, 95%, 99% or 100% identical to an amino acid sequence having the amino acid sequence according to Seq ID No.: 3 (PttTF0097). A summary of orthologous TF0097 genes and their peptide percent identities are found the Table 4, below.

The TF0097 gene product, Seq ID No: 3 is orthologous to two *Populus trichocarpa* UPA20-like polypeptides presented in WO2012117330. The amino acid sequence identity between PttTF0097 and the sequences is 97% and 96% respectively. However, WO2012117330 does not provide a description of the function or a phenotypical effect of a modified expression of the TF0097 gene or any genes closely related to TF0097.

TABLE 4a

| Gene name or Organism | Ortholog accession number: | Amino acid sequence Seq ID No: | Number of amino acids | Nucleotide sequence Seq ID No: | Number of nucleotides |
|---|---|---|---|---|---|
| PttTF0097 | | 3 | 568 | 23 | 1707 |
| | Potri.014G148900 | 64 | 572 | 65 | 1719 |
| | Potri.002G235400 | 66 | 567 | 67 | 1704 |

TABLE 4a-continued

| Gene name or Organism | Ortholog accession number: | Amino acid sequence Seq ID No: | Number of amino acids | Nucleotide sequence Seq ID No: | Number of nucleotides |
|---|---|---|---|---|---|
| EucTF0097 | Eucgr.H02628 | 68 | 531 | 69 | 1596 |
| | AT5G48560 | 70 | 498 | 71 | 1497 |
| | AT3G07340 | 72 | 456 | 73 | 1371 |
| Zea mays | GRMZM2G083504 | 108 | 350 | 109 | 1056 |
| | GRMZM2G180406 | 110 | 460 | 111 | 1383 |
| | GRMZM5G828396 | 112 | 1218 | 113 | 404 |

TABLE 4b

Peptide percent Identity Matrix - created by Clustal 2.1

| | Seq_ID_No_3_ PttTF0097 | Seq_ID_No_64_ Potri.014G148900 | Seq_ID_No_66_ Potri.002G235400 | Seq_ID_No_68_ Eucgr.H02628 | Seq_ID_No_70_ AT5G48560 |
|---|---|---|---|---|---|
| Seq_ID_No_3_ PttTF0097 | 100 | 91 | 86 | 56 | 46 |
| Seq_ID_No_64_ Potri.014G148900 | 91 | 100 | 81 | 52 | 43 |
| Seq_ID_No_66_ Potri.002G235400 | 86 | 81 | 100 | 55 | 44 |
| Seq_ID_No_68_ Eucgr.H02628 | 56 | 52 | 55 | 100 | 41 |
| Seq_ID_No_70_ AT5G48560 | 46 | 43 | 44 | 41 | 100 |
| Seq_ID_No_72_ AT3G07340 | 46 | 43 | 45 | 42 | 65 |
| Seq_ID_No_108_ GRMZM2G083504 | 35 | 34 | 35 | 34 | 31 |
| Seq_ID_No_110_ GRMZM2G180406 | 38 | 36 | 39 | 34 | 33 |
| Seq_ID_No_112_ GRMZM5G828396 | 36 | 35 | 37 | 32 | 32 |

| | Seq_ID_No_72_ AT3G07340 | Seq_ID_No_108_ GRMZM2G083504 | Seq_ID_No_110_ GRMZM2G180406 | Seq_ID_No_112_ GRMZM5G828396 |
|---|---|---|---|---|
| Seq_ID_No_3_ PttTF0097 | 46 | 35 | 38 | 36 |
| Seq_ID_No_64_ Potri.014G148900 | 43 | 34 | 36 | 35 |
| Seq_ID_No_66_ Potri.002G235400 | 45 | 35 | 39 | 37 |
| Seq_ID_No_68_ Eucgr.H02628 | 42 | 34 | 34 | 32 |
| Seq_ID_No_70_ AT5G48560 | 65 | 31 | 33 | 32 |
| Seq_ID_No_72_ AT3G07340 | 100 | 35 | 36 | 35 |
| Seq_ID_No_108_ GRMZM2G083504 | 35 | 100 | 48 | 60 |
| Seq_ID_No_110_ GRMZM2G180406 | 36 | 48 | 100 | 49 |
| Seq_ID_No_112_ GRMZM5G828396 | 35 | 60 | 49 | 100 |

Trait Gene TF0132

The TF0132 gene is a WRKY transcription factor, belonging to WRKY subfamily IId according to the WRKY gene classification presented above. In the present disclosure a TF0132 gene is a nucleic acid encoding a TF0132 gene product that preferably has an amino acid sequence at least 50%, such as 60%, 70%, 75%, 80%, 85%, 90%, 95%, 99% or 100% identical to an amino acid sequence having the amino acid sequence according to Seq ID No.: 5(PttTF0132). A summary of orthologous TF0132 genes and their peptide percent identities are found the Table 5, below.

TABLE 5a

| Gene name: | Ortholog accession number: | Amino acid sequence Seq ID No: | Number of amino acids | Nucleotide sequence Seq ID No: | Number of nucleotides |
|---|---|---|---|---|---|
| PttTF0132 | | 4 | 347 | 24 | 1044 |
| | Potri.005G219500 | 84 | 347 | 85 | 1044 |
| | Potri.002G043500 | 86 | 351 | 87 | 1056 |
| | Eucgr.B01503 | 88 | 343 | 89 | 1032 |
| AtWRKY21 | AT2G30590 | 90 | 380 | 91 | 1143 |
| Zea mays | GRMZM2G018487 | 114 | 397 | 115 | 1194 |
| | GRMZM2G130374 | 116 | 374 | 117 | 1125 |
| | GRMZM2G173680 | 118 | 367 | 119 | 1104 |
| | GRMZM5G880069 | 120 | 369 | 121 | 1110 |
| | GRMZM2G070211 | 122 | 354 | 123 | 1065 |
| | GRMZM2G147880 | 124 | 395 | 125 | 1188 |

TABLE 5b

Peptide percent Identity Matrix - created by Clustal 2.1

| | Seq_ID_No_4_ PttTF0132 | Seq_ID_No_84_ Potri.005G219500 | Seq_ID_No_86_ Potri.002G043500 | Seq_ID_No_88_ Eucgr.B01503 | Seq_ID_No_90_ AT2G30590 | Seq_ID_No_114_ GRMZM2G018487 |
|---|---|---|---|---|---|---|
| Seq_IDNo_4_ PttTF0132 | 100 | 97 | 93 | 80 | 65 | 51 |
| Seq_ID_No_84_ Potri.005G219500 | 97 | 100 | 95 | 82 | 65 | 51 |
| Seq_ID_No_86_ Potri.002G043500 | 93 | 95 | 100 | 81 | 64 | 53 |
| Seq_ID_No_88_ Eucgr.B01503 | 80 | 82 | 81 | 100 | 65 | 50 |
| Seq_ID_No_90_ AT2G30590 | 65 | 65 | 64 | 65 | 100 | 47 |
| Seq_ID_No_114_ GRMZM2G018487 | 51 | 51 | 53 | 50 | 47 | 100 |
| Seq_ID_No_116_ GRMZM2G130374 | 49 | 50 | 51 | 50 | 47 | 46 |
| Seq_ID_No_118_ GRMZM2G173680 | 51 | 51 | 51 | 51 | 48 | 47 |
| Seq_ID_No_120_ GRMZM5G880069 | 51 | 51 | 51 | 50 | 44 | 47 |
| Seq_ID_No_122_ GRMZM2G070211 | 51 | 51 | 51 | 52 | 45 | 49 |
| Seq_ID_No_124_ GRMZM2G147880 | 50 | 50 | 51 | 50 | 48 | 90 |

| | Seq_ID_No_116_ GRMZM2G130374 | Seq_ID_No_118_ GRMZM2G173680 | Seq_ID_No_120_ GRMZM5G880069 | Seq_ID_No_122_ GRMZM2G070211 | Seq_ID_No_124_ GRMZM2G147880 |
|---|---|---|---|---|---|
| Seq_IDNo_4_ PttTF0132 | 49 | 51 | 51 | 51 | 50 |
| Seq_ID_No_84_ Potri.005G219500 | 50 | 51 | 51 | 51 | 50 |
| Seq_ID_No_86_ Potri.002G043500 | 51 | 51 | 51 | 51 | 51 |
| Seq_ID_No_88_ Eucgr.B01503 | 50 | 51 | 50 | 52 | 50 |
| Seq_ID_No_90_ AT2G30590 | 47 | 48 | 44 | 45 | 48 |
| Seq_ID_No_114_ GRMZM2G018487 | 46 | 47 | 47 | 49 | 90 |
| Seq_ID_No_116_ GRMZM2G130374 | 100 | 86 | 60 | 61 | 46 |
| Seq_ID_No_118_ GRMZM2G173680 | 86 | 100 | 60 | 62 | 47 |
| Seq_ID_No_120_ GRMZM5G880069 | 60 | 60 | 100 | 87 | 47 |
| Seq_ID_No_122_ GRMZM2G070211 | 61 | 62 | 87 | 100 | 48 |
| Seq_ID_No_124_ GRMZM2G147880 | 46 | 47 | 47 | 48 | 100 |

Trait Gene TF0109

The TF0109 gene is a WRKY transcription factor, belonging to WRKY subfamily IId according to the WRKY gene classification presented above. In the present disclosure a TF0109 gene is a nucleic acid encoding a TF0109 gene product that preferably has an amino acid sequence at least 50%, such as 60%, 70%, 75%, 80%, 85%, 90%, 95%, 99% or 100% identical to an amino acid sequence having the amino acid sequence according to Seq ID No.: 4(PttTF0109). A summary of orthologous TF0109 genes and their peptide percent identities are found the Table 6, below.

TABLE 6

| Gene name or Organism | Ortholog accession number: | Amino acid sequence Seq ID No: | Number of amino acids | Nucleotide sequence Seq ID No: | Number of nucleotides |
|---|---|---|---|---|---|
| PttTF0109 | | 5 | 301 | 25 | 906 |
| | Potri.006G072400 | 74 | 301 | 75 | 906 |
| | Potri.018G139300 | 76 | 300 | 77 | 903 |
| | Eucgr.C04011 | 78 | 343 | 79 | 1032 |
| AtWRKY11 | AT4G31550 | 80 | 325 | 81 | 978 |
| AtWRKY17 | AT2G24570 | 82 | 321 | 83 | 966 |
| Zea mays | GRMZM2G102583 | 126 | 331 | 127 | 996 |
| | GRMZM2G091331 | 128 | 316 | 129 | 951 |
| | GRMZM2G071907 | 130 | 298 | 131 | 897 |

TABLE 6b

Peptide percent Identity Matrix - created by Clustal 2.1

| | Seq_ID_No_5_ PttTF0109 | Seq_ID_No_74_ Potri.006G072400 | Seq_ID_No_76_ Potri.018G139300 | Seq_ID_No_78_ Eucgr.C04011 | Seq_ID_No_80_ AT4G31550 |
|---|---|---|---|---|---|
| Seq_ID_No_5_ PttTF0109 | 100 | 98 | 87 | 59 | 57 |
| Seq_ID_No_74_ Potri.006G072400 | 98 | 100 | 87 | 59 | 57 |
| Seq_ID_No_76_ Potri.018G139300 | 87 | 87 | 100 | 58 | 58 |
| Seq_ID_No_78_ Eucgr.C04011 | 59 | 59 | 58 | 100 | 63 |
| Seq_ID_No_80_ AT4G31550 | 57 | 57 | 58 | 63 | 100 |
| Seq_ID_No_82_ AT2G24570 | 59 | 59 | 57 | 66 | 76 |
| Seq_ID_No_126_ GRMZM2G102583 | 55 | 55 | 57 | 55 | 57 |
| Seq_ID_No_128_ GRMZM2G091331 | 57 | 58 | 58 | 52 | 56 |
| Seq_ID_No_130_ GRMZM2G071907 | 57 | 58 | 60 | 53 | 56 |

| | Seq_ID_No_82_ AT2G24570 | Seq_ID_No_126_ GRMZM2G102583 | Seq_ID_No_128_ GRMZM2G091331 | Seq_ID_No_130_ GRMZM2G071907 |
|---|---|---|---|---|
| Seq_ID_No_5_ PttTF0109 | 59 | 55 | 57 | 57 |
| Seq_ID_No_74_ Potri.006G072400 | 59 | 55 | 58 | 58 |
| Seq_ID_No_76_ Potri.018G139300 | 57 | 57 | 58 | 60 |
| Seq_ID_No_78_ Eucgr.C04011 | 66 | 55 | 52 | 53 |
| Seq_ID_No_80_ AT4G31550 | 76 | 57 | 56 | 56 |
| Seq_ID_No_82_ AT2G24570 | 100 | 55 | 57 | 56 |
| Seq_ID_No_126_ GRMZM2G102583 | 55 | 100 | 61 | 62 |
| Seq_ID_No_128_ GRMZM2G091331 | 57 | 61 | 100 | 90 |
| Seq_ID_No_130_ GRMZM2G071907 | 56 | 62 | 90 | 100 |

Plant Transformation

DNA constructs were transformed into *Agrobacterium* and subsequently into hybrid aspen, where *Populus tremula* x *tremuloides* clone T89, also called "poplar" in this application, was transformed and regenerated. Typically, 8 independent lines were generated for each construct. One such group of transgenic trees produced using the same DNA construct is hereafter called a "construction group", that is different transgenic trees emanating from one construct.

Each transgenic line within each construction group derives from a different transformation event and has most probably the recombinant DNA inserted into a unique location in the plant genome. This makes the different transgenic lines within one construction group partly different. For example it is known that different transformation events will produce plants with different expression levels of the gene product. It is also known that different levels of expression of a gene will result in different levels of phenotypic effects.

Maize transformation can be performed according to Coussens et al., 2012 and WO2014195287.

Plant Growth

The transgenic hybrid aspen lines were grown together with wild type control trees, in a greenhouse under a photoperiod of 18 h and a temperature of 22° C./15° C. (day/night). All transgenic lines were grown in three clonal replicates. The plants were grown for 8-9 weeks before harvest and fertilized weekly. During this time height and diameter were measured weekly. Wild type (typically 35-45 trees) and transgenic trees were grown in parallel in the greenhouse under the same conditions. All comparisons between wild type trees and the transgenic trees with a specific promoter-gene combination are made within the cultivation group.

Maize and *Arabidopsis* plants might be tested for biomass, leaf length width and yield, more details according to the following examples and in WO2014195287.

Growth Analyses

To identify construction groups showing a significant difference compared to the wild type population, data from each construction group was subjected to a number of growth data analyses of growth/biomass and wood density measurements.

After 8 to 9 weeks growth in the greenhouse the trees were harvested and sampled. Two principal types of harvests were used; either a general setup designed for e.g. chemical analysis, wood morphology analysis, gene expression analysis, wood density analysis and metabolomics analysis, or a second setup designed for dry weight measurements of bark, wood, leaves and roots.

Measurements of plant height and diameter were recorded one to two times per week during the cultivation and before harvest of the plants. Final height and diameter measurements were subsequently used to identify construction groups with altered growth characteristics.

The volume of the stem of each individual plant was approximated from final height and final diameter measurements using the formula for volume of a cone.

Stem volume approximation:

$$V = \frac{\pi * r^2 * h}{3}$$

where: V=Volume; h=height (Final height), r=radius (Final diameter/2)

Average final volumes of each construction group population and corresponding wild type population were subsequently calculated.

Wood Density Analyses

Wood density is an important trait for increasing biomass production. An increase in wood density increases the energy content per cubic metre reduces the volume of a fixed amount of biomass and hence, e.g. the volume required to transport a fixed amount of biomass. Correspondingly, more biomass can be transported per volume. Therefore increased density is of interest, even if total biomass is not increased. Increased density could also be of benefit coupled to pulp and paper production.

A 5 cm long stem segment, sampled between 36 and 41 cm from the soil from each harvested plant and stored in a freezer after harvest, was used for density measurements. Samples to be analysed were thawed followed by removal of bark and pith. The weight (w) was measured using a balance and the volume (V) was determined using the principle of Archimedes, where wood samples were submerged (using a needle) into a beaker (placed on a balance) with water. The recorded increase in weight is equivalent to the weight of the water displaced by the wood sample. Since the density of water is 1 g/cm3 at ambient room temperature the recorded increase is also equivalent to the volume of the wood sample. The samples were subsequently dried in oven for >48 h at 60° C.

The dry weights (dw) were measured and the density (d) was calculated according to:

$$d = \frac{dw}{V}$$

Samples from each construction group were compared to wild type samples from the same cultivation.

Analysis of Expression Levels

Real-time RT-PCR was used to compare construct gene expression levels of the construction group with corresponding wild type group. The expression level of 26S proteasome regulatory subunit S2 was used as a reference to which construct gene expression was normalized. The comparative CT method was used for calculation of relative construct gene expression level, where the ratio between construction and reference gene expression level is described by $(1+E_{target})-CT_{target}/(1+E_{reference})-CT_{reference}$, where $E_{target}$ and $E_{reference}$ are the efficiencies of construct and reference gene PCR amplification respectively and $CT_{target}$ and $CT_{reference}$ are the threshold cycles as calculated for construct and reference gene amplification respectively.

Obtaining Plants

The present invention extends to any plant cell of the above genetically modified, or transgenic plants obtained by the methods described herein, and to all plant parts, including harvestable parts of a plant, seeds, somatic embryos and propagules thereof, and plant explant or plant tissue. The present invention also encompasses a plant, a part thereof, a plant cell or a plant progeny comprising a DNA construct according to the invention. The present invention extends further to encompass the progeny of a primary transformed or transfected cell, tissue, organ or whole plant that has been produced by any of the aforementioned methods, the only requirement being that progeny exhibit the same genotypic and/or phenotypic characteristic(s) as those produced in the parent by the methods according to the invention. It should be noted that embodiments and features described in the context of one of the aspects of the present invention also apply to the other aspects of the invention. Thus, definitions of one embodiment regard mutatis mutandis to all other embodiments comprising or relating to the one embodiment. When for example definitions are made regarding DNA constructs or sequences, such definitions also apply with respect to methods for producing a plant, vectors, plant cells, plants comprising the DNA construct and vice versa. A DNA construct described in relation to a plant also regards all other embodiments. Details about obtaining maize, soya and *Arabidopsis* can be found in WO2014195287, hereby included by reference.

Methods for Enhancing the Productivity of a Plant by Genetic Modification

One or more of the constructs according to the invention may be introduced into a plant cell by transformation.

Transformation of Plant Cells

In accordance with the present invention, the method comprises transforming regenerable cells of a plant with a nucleic acid construct or recombinant DNA construct and regenerating a transgenic plant from said transformed cell. Production of stable, fertile transgenic plants is now a routine method.

Various methods are known for transporting the construct into a cell to be transformed. *Agrobacterium*-mediated transformation is widely used by those skilled in the art to transform tree species, in particular hardwood species such as poplar and *Eucalyptus*. Other methods, such as microprojectile or particle bombardment, electroporation, microinjection, direct DNA uptake, liposome mediated DNA uptake, or the vortexing method may be used where *Agrobacterium* transformation is inefficient or ineffective, for example in some gymnosperm species.

A person of skill in the art will realize that a wide variety of host cells may be employed as recipients for the DNA constructs and vectors according to the invention. Non-limiting examples of host cells include cells in embryonic tissue, callus tissue type I, II, and III, hypocotyls, meristem, root tissue, tissues for expression in phloem, leaf discs, petioles and stem internodes. Once the DNA construct or vector is within the cell, integration into the endogenous genome can occur.

Selection of Transformed Plant Cells and Regeneration of Plant or Woody Plants

Following transformation, transgenic plants are preferably selected using a dominant selectable marker incorporated into the transformation vector. Typically, such a marker will confer antibiotic or herbicide resistance on the transformed plants and selection of transformants can be accomplished by exposing the plants to appropriate concentrations of the antibiotic or herbicide. A selection marker using the D-form of amino acids and based on the fact that plants can only tolerate the L-form offers a fast, efficient and environmentally friendly selection system.

Subsequently, a plant may be regenerated, e.g. from single cells, callus tissue or leaf discs, as is standard in the art. Almost any plant can be entirely regenerated from cells, tissues and organs of the plant. After transformed plants are selected and they are grown to maturity and those plants showing altered growth properties phenotype are identified.

The promotors of genes G47, TF0002, TF0097, TF0132 and TF109 or their corresponding ortholog might be mutated using the methods for site-directed mutagenesis such as TALENs or CRISPR/Cas9 to modify the expression of these genes.

Methods for Detecting Modified Expression of a Gene Encoding a Polypeptide in a Plant or Woody Plant of the Invention Real-time RT-PCR can be used to compare gene expression, i.e. the mRNA expression levels, in a genetically modified (GM) plant or woody plant with the corresponding non-GM plant or woody plant. The amount of the polynucleotides disclosed herein can be determined using Northern blots, sequencing, RT-PCR or microarrays.

Western blots with immune detection or gel shift assays can be used to measure the expression levels or amounts of a polypeptide expressed in a GM plant or woody plant of the invention. Antibodies raised to the respective polypeptide may be used for specific immune-detection of the expressed polypeptide in tissue derived from a woody plant.

*Eucalyptus* plants are generated in a similar way, through transformation, regeneration and growth analysis.

The invention is further illustrated below by way of examples. The examples are not intended to restrict the scope of the invention, which is that of the appended claims.

EXAMPLES

Example 1 Cloning of Promoters

Cloning of *Eucalyptus* Promoters:

The identification of novel *Eucalyptus* promoters is described in the detailed description above. All *Eucalyptus* promoters were cloned in the same way. The promoter DNA fragments were manufactured by DNA synthesis, using the DNA sequences of the identified promoter regions of the publically available *Eucalyptus grandis* genome as a template, thus creating identical copies of the corresponding *Eucalyptus grandis* promoter regions. The synthesized promoter fragments were flanked by Gateway recombination sites for sub-cloning purposes. All promoter fragments were sub-cloned using Gateway recombination into the pK7m24GW.3 vector (VIB, Rijvisschestraat 120, B-9052 Zwijnaarde, Belgium), where they were placed upstream of and thus controlling the expression of a trait gene. The novel combinations of promoters and genes are further described in Example 3, below.

The promoters were also cloned in front of the beta-glucuronidase (GUS) reporter gene, in order to verify their correct expression as further described in Example 2.

1.1 the Constitutive Promoter pECO1

The DNA sequence upstream of the *Eucalyptus grandis* gene with accession Eucgr. E00053 was thoroughly investigated as described (in the detailed description) above. A fragment of 1084 nucleotides immediately upstream, but not including, the start codon was selected to define the pECO1 promoter, Seq ID No: 6.

1.2 the Constitutive Promoter pECO2

The DNA sequence upstream of the *Eucalyptus grandis* gene with accession Eucgr.H04673 was thoroughly investigated as described (in the detailed description) above. A fragment of 2000 nucleotides immediately upstream, but not including, the start codon was selected to define the pECO2 promoter, Seq ID No: 7.

1.3 the Tissue-Specific Promoter pEA1

The DNA sequence upstream of the *Eucalyptus grandis* gene with accession Eucgr. C00732 was thoroughly investigated as described (in the detailed description) above. A fragment of 2000 nucleotides immediately upstream, but not including, the start codon was selected to define the pEA1 promoter, Seq ID No: 8.

1.4 the Tissue-Specific Promoter pEA2

The DNA sequence upstream of the *Eucalyptus grandis* gene with accession Eucgr. F02223 was thoroughly investigated as described (in the detailed description) above. A fragment of 2500 nucleotides immediately upstream, but not including, the start codon was selected to define the pEA2 promoter, Seq ID No: 9.

1.5 the Tissue-Specific Promoter pEA3

The DNA sequence upstream of the *Eucalyptus grandis* gene with accession Eucgr. K03130 was thoroughly investigated as described (in the detailed description) above. A fragment of 2700 nucleotides immediately upstream, but not including, the start codon was selected to define the pEA3 promoter, Seq ID No: 10.

1.6 the Tissue-Specific Promoter pEA4

The DNA sequence upstream of the *Eucalyptus grandis* gene with accession Eucgr. 100802 was thoroughly investigated as described (in the detailed description) above. A fragment of 2500 nucleotides immediately upstream, but not including, the start codon was selected to define the pEA4 promoter, Seq ID No: 11.

1.7 the Tissue-Specific Promoter pEC1

The DNA sequence upstream of the *Eucalyptus grandis* gene with accession Eucgr.F02320 was thoroughly investigated as described (in the detailed description) above. A fragment of 2101 nucleotides immediately upstream, but not including, the start codon was selected to define the pEC1 promoter, Seq ID No: 12.

1.8 Cloning of the Tissue-Specific Hybrid Aspen Promoter pLMP1

The pLMP1 promoter was cloned as described in WO2004097024. The promoter was placed in a pPCV812 binary plasmid in front/upstream of a Gateway® cassette, consisting of a ccdB gene flanked by attR recombination sites to facilitate Gateway® recombination cloning. The pLMP1 promoter, similar to Genbank accession number DJ416318, consists of a 1486 base pair long fragment excluding the restriction sites used for cloning, Seq ID No: 13.

1.9 Cloning of the Tissue-Specific Hybrid Aspen Promoter pLMX5

The pLMX5 promoter was cloned as described in WO2004097024. The promoter was placed in a pPCV812 binary plasmid in front/upstream of a Gateway® cassette, consisting of a ccdB gene flanked by attR recombination sites to facilitate Gateway® recombination cloning. The pLMX5 promoter, similar to Genbank accession number DJ416317, consists of a 1780 base pair long fragment excluding the restriction sites used for cloning, Seq ID No: 14.

1.10 the Tissue-Specific Promoter pEX5

The DNA sequence upstream of the *Eucalyptus grandis* gene with accession Eucgr. B00045 was thoroughly investigated as described (in the detailed description) above. A fragment of 2001 nucleotides immediately upstream, but not including, the start codon was selected to define the pEX5 promoter, Seq ID No: 15.

1.11 the Tissue-Specific Promoters, pEL1.1 and pEL1.2

The DNA sequence upstream of the *Eucalyptus grandis* gene with accession Eucgr. K02223 was thoroughly investigated as described (in the detailed description) above. Based on these studies two promoter variants were selected; a shorter and a longer promoter fragment. Fragments of 600 and 1800 nucleotides immediately upstream, but not including, the start codon were selected to define the shorter pEL1.1 (Seq ID No: 16) and longer pEL1.2 (Seq ID No: 17) promoter variants respectively.

1.12 the Tissue-Specific Promoter pER1

The DNA sequence upstream of the *Eucalyptus grandis* gene with accession Eucgr.H00165 was thoroughly investigated as described (in the detailed description) above. A fragment of 2000 nucleotides immediately upstream, but not including, the start codon was selected to define the pER1 promoter, Seq ID No: 18.

1.13 the Tissue-Specific Promoter pER2

The DNA sequence upstream of the *Eucalyptus grandis* gene with accession Eucgr. D02090 was thoroughly investigated as described (in the detailed description) above. A fragment of 2000 nucleotides immediately upstream, but not including, the start codon was selected to define the pER2 promoter, Seq ID No: 19.

Example 2 Verification of Expression Pattern of the *Eucalyptus* Promoters

The expression patterns of the *Eucalyptus* promoters were determined by histological studies of transgenic hybrid aspen plants harbouring the promoter-GUS construct. Promoter activity was assayed using the established histochemical GUS staining technique.

Samples were collected from young transgenic plants. Five to eight transgenic lines from each promoter-GUS construct were sampled and the following eight parts of the plant were stained for GUS expression; 1) Apex with leaf primordia and small young leaf; 2) Part of young leaf; 3) Young stem section, close to apex; 4) Part of petiole; 5) Axillary bud; 6) Part of old leaf; 7) Longitudinal stem section of old stem and 8) Root. The stained plant tissues were carefully studied under a light microscope.

Results

The resolution of the GUS assay is sufficient to distinguish the tissue regions from which the product of GUS enzyme activity emanates, but not high enough to distinguish the specific cells from which the product of GUS enzyme activity emanates.

pECO1: Constitutive expression was confirmed in early stages of transgenic tissue formation. Faint expression observed in older plant tissues.

pECO2: Strong constitutive expression was confirmed.

pEA1: Tissue-specific expression in the regions of the meristematic tissue responsible for primary growth in the apex, axillary buds and in leaf primordia was confirmed.

pEA2: Tissue-specific expression in the regions of the actively dividing cells of the apex, in axillary buds and in the vascular tissues of young and older stem was confirmed.

pEA3: Very faint tissue-specific expression in the regions of the meristematic tissues responsible for primary growth in the apex and axillary buds was confirmed.

pEA4: Weak tissue-specific expression in the regions of meristematic tissues responsible for primary and secondary growth in the apex, cambium and root was confirmed.

pEC1: Low resolution GUS analysis confirmed expression in the vascular region, thus indicating the expected expression in the cambial region.

pLMP1: Expression is found in the cambium with the strongest expression in the phloem, Article 3 in Björklund, Doctoral thesis 2007:81, Faculty of Forest Sciences, Umeå, Sweden.

pLMX5: Expression is found in the cambium with the strongest expression in the vascular cambium and early xylem, Article 3 in Björklund, Doctoral thesis 2007:81, Faculty of Forest Sciences, Umeå, Sweden.

pEX5: Expression in the vascular tissues of young stem, older stem, root and leaf was confirmed. However, the resolution of the GUS assay is not high enough to distinguish the specific cells of the vascular tissue from which the product of GUS enzyme activity emanates.

pEL1.1: Strong green-tissue-specific expression, also in light-exposed root tissues was confirmed.

pER1: Tissue-specific expression in the root was confirmed, with strong expression in young root, root hairs and root tip. Expression in the regions of the meristematic tissues responsible for primary growth in the root as well as in the apex was also observed.

pER2: Tissue-specific expression in the root was confirmed, with strong expression in young root and root hairs. No expression was observed in root tip.

Example 3 Construction of Novel Promoter-Gene Combinations

As described in Example 1 the *Eucalyptus* promoter DNA fragments were manufactured by DNA synthesis and flanked by Gateway recombination sites for sub-cloning purposes. All *Eucalyptus* promoter fragments were sub-cloned using Gateway recombination into the pK7m24GW,3 vector, where they were placed upstream of and thus controlling the expression of the gene of interest as described below.

3.1 Constructs with the gene G47

Construct Gro4

The G47 gene from *Arabidopsis thaliana*, AtG47, Seq ID No: 1, was operably linked with the 35S promoter, Seq ID No: 20, to create the recombinant DNA construct Gro4, p35S-AtG47. A construct comprising this promoter might be used to increase the level of ATG47 gene product in all tissues of the plant.

Construct Gro5

The G47 gene from *Arabidopsis thaliana*, AtG47, Seq ID No: 1, was operably linked with the tissue-specific vascular promoter pLMX5, Seq ID No: 14 to create the recombinant DNA construct, Gro5, pLMX5-AtG47. A construct comprising this promoter might be used to increase the level of G47 gene product specifically in the vascular tissue.

Construct Gro6

The G47 gene from *Arabidopsis thaliana*, AtG47, Seq ID No: 1, was operably linked with the tissue-specific vascular promoter pLMP1, Seq ID No: 13 to create the recombinant DNA construct, Gro6, pLMP1-AtG47. A construct comprising this promoter might be used to increase the level of G47 gene product specifically in the vascular tissue.

3.2 Constructs with the Gene TF0002

Construct TF0002F1

The TF0002 gene from *Populus tremula* x *tremuloides*, PttTF0002, Seq ID No: 2, was operably linked with the 35S promoter, Seq ID No: 20, to create the recombinant DNA construct TF0002F1, p35S-PttTF0002. A construct comprising this promoter might be used to increase the level of TF0002 gene product specifically in all tissues of the plant.

Construct LMX5-008

The TF0002 gene from *Populus tremula* x *tremuloides*, PttTF0002, Seq ID No: 2, was operably linked with the LMX5 promoter, Seq ID No: 14, to create the recombinant DNA construct LMX5-008, pLMX5-PttTF0002. A construct comprising this promoter might be used to increase the level of TF0002 gene product specifically in the vascular tissue.

Construct pLMP1-PttTF0002

The TF0002 gene from *Populus tremula* x *tremuloides*, PttTF0002, Seq ID No: 2, was operably linked with the LMP1 promoter, Seq ID No: 13, to create the recombinant DNA construct pLMP1-PttTF0002. A construct comprising this promoter might be used to increase the level of TF0002 gene product specifically in the vascular tissue.

3.3 Constructs with the Gene TF0097

Construct F101

The PttTF0097 gene from *Populus tremula* x *tremuloides*, Seq ID No: 3, was operably linked with the 35S promoter, Seq ID No: 20, to create the recombinant DNA construct F101, 35S-PttTF0097. A construct comprising this promoter might be used to increase the level of TF0097 gene product in all tissues of the plant.

Construct F102

The PttTF0097 gene from *Populus tremula* x *tremuloides*, Seq ID No: 3, was operably linked with the pECO1 promoter, Seq ID No: 6, to create the recombinant DNA construct F102, pECO1-PttTF0097. A construct comprising this promoter might be used to increase the level of TF0097 gene product specifically in all tissues of the plant.

Construct F103

The PttTF0097 gene from *Populus tremula* x *tremuloides*, Seq ID No: 3, was operably linked with the pECO2 promoter, Seq ID No: 7, to create the recombinant DNA construct F103, pECO2-PttTF0097. A construct comprising this promoter might be used to increase the level of TF0097 gene product specifically in all tissues of the plant.

Construct F104

The PttTF0097 gene from *Populus tremula* x *tremuloides*, Seq ID No: 3, was operably linked with the pEA1 promoter, Seq ID No: 8, to create the recombinant DNA construct F104, pEA1-PttTF0097. A construct comprising this promoter might be used to increase the level of TF0097 gene product specifically in the shoot apical meristem and organ primordia.

Construct F105

The PttTF0097 gene from *Populus tremula* x *tremuloides*, Seq ID No: 3, was operably linked with the pEA3 promoter, Seq ID No: 10, to create the recombinant DNA construct F105, pEA3-PttTF0097. A construct comprising this promoter might be used to increase the level of TF0097 gene product specifically in the leaf primordia.

Construct F106

The PttTF0097 gene from *Populus tremula* x *tremuloides*, Seq ID No: 3, was operably linked with the pEC1 promoter, Seq ID No: 12, to create the recombinant DNA construct F106, pEC1-PttTF0097. A construct comprising this promoter might be used to increase the level of TF0097 gene product specifically in the procambial/cambial stem cells.

Construct F107

The PttTF0097 gene from *Populus tremula* x *tremuloides*, Seq ID No: 3, was operably linked with the pEX5 promoter, Seq ID No: 15, to create the recombinant DNA construct F107, pEX5-PttTF0097. A construct comprising this promoter might be used to increase the level of TF0097 gene product specifically in the vascular xylem tissue.

Construct F108

The PttTF0097 gene from *Populus tremula* x *tremuloides*, Seq ID No: 3, was operably linked with the pEL1.1 promoter, Seq ID No: 16, to create the recombinant DNA construct F108, pEL1.1-PttTF0097. A construct comprising this promoter might be used to increase the level of TF0097 gene product specifically in all green tissues of the plant.

Construct F109

The PttTF0097 gene from *Populus tremula* x *tremuloides*, Seq ID No: 3, was operably linked with the pER1 promoter, Seq ID No: 18, to create the recombinant DNA construct F109, pER1-PttTF0097. A construct comprising this promoter might be used to increase the level of TF0097 gene product specifically in the root, root tip and root hairs.

Construct F110

The PttTF0097 gene from *Populus tremula* x *tremuloides*, Seq ID No: 3, was operably linked with the pER2 promoter, Seq ID No: 19, to create the recombinant DNA construct F110, pER2-PttTF0097. A construct comprising this promoter might be used to increase the level of TF0097 gene product specifically in the root and root hairs.

3.4 Constructs with the Gene TF0132

Construct F111

The PttTF0132 gene from *Populus tremula* x *tremuloides*, Seq ID No: 4, was operably linked with the 35S promoter, Seq ID No: 20, to create the recombinant DNA construct F111, 35S-PttTF0132. A construct comprising this promoter might be used to increase the level of TF0132 gene product in all tissues of the plant.

Construct F112

The PttTF0132 gene from *Populus tremula* x *tremuloides*, Seq ID No: 3, was operably linked with the pECO1 promoter, Seq ID No: 6, to create the recombinant DNA construct F112, pECO1-PttTF0132. A construct comprising this promoter might be used to increase the level of TF0132 gene product specifically in all tissues of the plant.

Construct F113

The PttTF0132 gene from *Populus tremula* x *tremuloides*, Seq ID No: 4, was operably linked with the pECO2 promoter, Seq ID No: 7, to create the recombinant DNA construct F113, pECO2-PttTF0132. A construct comprising this promoter might be used to increase the level of TF0132 gene product specifically in all tissues of the plant.

Construct F114

The PttTF0132 gene from *Populus tremula* x *tremuloides*, Seq ID No: 4, was operably linked with the pEA1 promoter, Seq ID No: 8, to create the recombinant DNA construct F114, pEA1-PttTF0132. A construct comprising this promoter might be used to increase the level of TF0132 gene product specifically in the shoot apical meristem and organ primordia.

Construct F115

The PttTF0132 gene from *Populus tremula* x *tremuloides*, Seq ID No: 4, was operably linked with the pEA2 promoter, Seq ID No: 9, to create the recombinant DNA construct F115, pEA2-PttTF0132. A construct comprising this promoter might be used to increase the level of TF0132 gene product specifically in the actively dividing cells in the cambial region of the stem and the shoot apical meristem.

Construct F116

The PttTF0132 gene from *Populus tremula* x *tremuloides*, Seq ID No: 4, was operably linked with the pEA3 promoter, Seq ID No: 10, to create the recombinant DNA construct F116, pEA3-PttTF0132. A construct comprising this promoter might be used to increase the level of TF0132 gene product specifically in the leaf forming tissues of the leaf primordia.

Construct F117

The PttTF0132 gene from *Populus tremula* x *tremuloides*, Seq ID No: 4, was operably linked with the pEA4 promoter, Seq ID No: 11, to create the recombinant DNA construct F117, pEA4-PttTF0132. A construct comprising this promoter might be used to increase the level of TF0132 gene product specifically in the shoot apical meristem, leaf primordia and to some extent in younger leaves.

Construct F118

The PttTF0132 gene from *Populus tremula* x *tremuloides*, Seq ID No: 4, was operably linked with the pEC1 promoter, Seq ID No: 12, to create the recombinant DNA construct F118, pEC1-PttTF0132. A construct comprising this promoter might be used to increase the level of TF0132 gene product specifically in the procambial/cambial stem cells.

Construct F119

The PttTF0132 gene from *Populus tremula* x *tremuloides*, Seq ID No: 4, was operably linked with the pEL1.1 promoter, Seq ID No: 16, to create the recombinant DNA construct F119, pEL1.1-PttTF0132. A construct comprising this promoter might be used to increase the level of TF0132 gene product specifically in all green tissues of the plant.

3.5 Constructs with the Gene TF0109

Construct F120

The PttTF0109 gene from *Populus tremula* x *tremuloides*, Seq ID No: 5, was operably linked with the 35S promoter, Seq ID No: 20, to create the recombinant DNA construct F120, 35S-PttTF0109. A construct comprising this promoter might be used to increase the level of TF0109 gene product specifically in all tissues of the plant.

Construct F121

The PttTF0109 gene from *Populus tremula* x *tremuloides*, Seq ID No: 5, was operably linked with the pECO1 promoter, Seq ID No: 6, to create the recombinant DNA construct F121, pECO1-PttTF0109. A construct comprising this promoter might be used to increase the level of TF0109 gene product specifically in all tissues of the plant.

Construct F122

The PttTF0109 gene from *Populus tremula* x *tremuloides*, Seq ID No: 5, was operably linked with the pECO2 promoter, Seq ID No: 7, to create the recombinant DNA construct F122, pECO2-PttTF0109. A construct comprising this promoter might be used to increase the level of TF0109 gene product specifically in all tissues of the plant.

Construct F123

The PttTF0109 gene from *Populus tremula* x *tremuloides*, Seq ID No: 5, was operably linked with the pEA1 promoter, Seq ID No: 8, to create the recombinant DNA construct F123, pEA1-PttTF0109. A construct comprising this promoter might be used to increase the level of TF0109 gene product specifically in the shoot apical meristem and organ primordia.

Construct F124

The PttTF0109 gene from *Populus tremula* x *tremuloides*, Seq ID No: 5, was operably linked with the pEA2 promoter, Seq ID No: 9, to create the recombinant DNA construct F124, pEA2-PttTF0109. A construct comprising this promoter might be used to increase the level of TF0109 gene product specifically in the actively dividing cells in the cambial region of the stem and the shoot apical meristem.

Construct F125

The PttTF0109 gene from *Populus tremula* x *tremuloides*, Seq ID No: 5, was operably linked with the pEA3 promoter, Seq ID No: 10, to create the recombinant DNA construct F125, pEA3-PttTF0109. A construct comprising this promoter might be used to increase the level of TF0109 gene product specifically in the leaf forming tissues of the leaf primordia.

Construct F126

The PttTF0109 gene from *Populus tremula* x *tremuloides*, Seq ID No: 5, was operably linked with the pEX5 promoter, Seq ID No: 15, to create the recombinant DNA construct F126, pEX5-PttTF0109. A construct comprising this promoter might be used to increase the level of TF0109 gene product specifically in the vascular xylem tissue.

Example 4 Transformation of Hybrid Aspen

The DNA constructs described in Example 3 were transformed into hybrid aspen (*Populus tremula* x *Populus tremuloides* Michx., clone T89) by *Agrobacterium*-mediated transformation. The transformation and regeneration of transgenic plants were performed as described in the experimental part of WO2016108750. Typically, 8 independent transgenic lines were generated for each construct.

Example 5 Growth Experiments and Analyses 5.1 Hybrid Aspen Greenhouse Experiments and Growth Analysis For each promoter-gene construct, three transgenic hybrid aspen lines in three clonal replicates each were grown together with wild type reference trees in the greenhouse, as described in the experimental part of WO2016108750 and in the detailed description above.

After 8 weeks of growing in the greenhouse the hybrid aspen trees were measured, harvested and sampled for the following traits, plant height, width, stem volume, average internode length and wood density. For some trees the dry weight of stem and bark was measured.

5.2 Hybrid Aspen Field Trial Experiments and Growth Analysis

The same transgenic hybrid aspen lines that were studied in the greenhouse experiments were again propagated from tissue culture material for field trial experiments. In some filed trials a selection of transgenic hybrid aspen lines made before propagation. Wild type reference plants were propagated in parallel and treated exactly as the transgenic plants throughout the experiments. Plants were grown in vitro until ready for planting in soil. The plants were hardened during a period of five weeks; the first two weeks to establish rooting in soil in the greenhouse and then another three weeks in outdoor growth conditions. After this the plants were transported to the field site and kept in pots in outdoor conditions for 5 weeks before planting into the field. The height of the plants were measured at planting and in the end of the growing season, which was used for statistical analysis. Further measurements was done and will continue to be done during the field trail.

5.3 Statistical Analysis of Results from Greenhouse and in Field Grown Trees

Statistical analysis was used to determine phenotypical differences between transgenic and wild type trees. Firstly, the population of transgenic trees from each promoter-gene combination was compared to the wild type population of trees with the Student s t-test and a stringent p-value cut off of 0.01. Second, the population of transgenic trees from each promoter-gene combination was compared to the wild type population of trees using the established Dunnett's multiple comparison of means method and a stringent p-value cutoff of 0.01. Similarly, to identify the best performing transgenic lines, the population of trees from each transgenic line, that is, the three replicates, was compared to the wild type population of trees with the same statistical test and settings. The results of the statistical analyses are presented in the results tables as the percentage differences between averages of the compared populations of transgenic and wild type trees, wild type being the reference point. Percentage differences that are statistically significant according to the statistical criteria specified above are marked with an asterisk (*) in the results tables.

Example 6 Promoter and Gene G47 Combinations 6.1 Greenhouse and Field Trial Experiments with the Promoter-Gene Construct p35S-G47 for Growth Improvements and/or Improved Water Stress Properties Such as Improved Water Use Efficiency.

Over-expression of a gene may elicit different phenotypical effects under two distinctly different growth conditions. With the recombinant DNA construct p35S-AtG47 the G47 gene from *Arabidopsis thaliana*, AtG47, Seq ID: 1, was constitutively over-expressed in hybrid aspen trees using the CaMV 35S promoter. This modification in the transgenic trees resulted in an average stem volume growth increase of 12% compared to wild type reference trees when grown in the greenhouse.

The same hybrid aspen trees were subsequently planted in an open field trial in the south of Sweden. However, it was discovered that the transgenic trees harbouring the promoter-gene construct p35S-AtG47 did not perform as well as expected in these field growth tests. The observed average stem volume increase of 12% in greenhouse tests was contrasted with a reduction of stem volume growth of 3% compared to the wild type reference trees grown at the same test site location, FIG. 1.

6.2 Greenhouse and Field Trial Experiments with the Promoter-Gene Construct pLMP1:G47 for Growth Improvements and/or Improved Water Stress Properties Such as Improved Water Use Efficiency.

Figure 2:
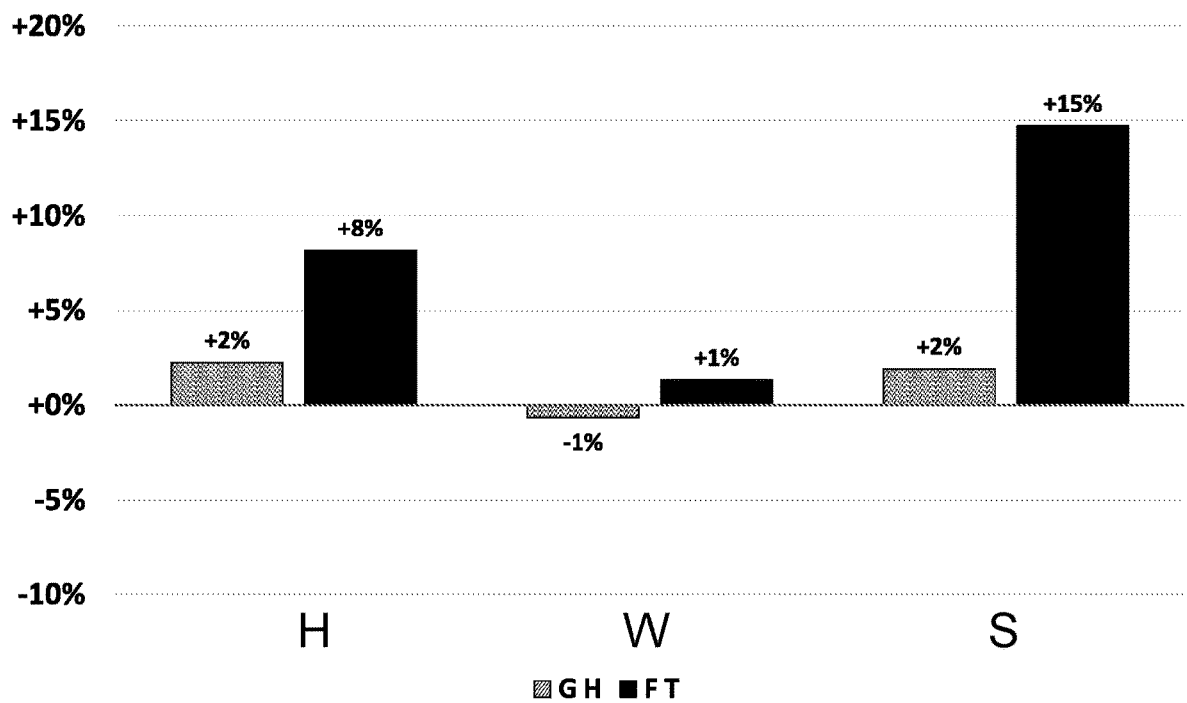
FIG. 2, shows greenhouse (G H) and field trial (F T) data from a hybrid aspen, wherein a trait gene AtG47 is expressed using the phloem-specific promoter, pLMP1. Percent numbers are compared to wild type reference plants.

When the AtG47 gene is specifically over-expressed by the pLMP1 promoter no considerable increase in plant growth is observed in the greenhouse. However, unlike the results of the constitutive p35S-G47 promoter-gene construct, a considerable significant increase in plant growth is observed when the transgenic pLMP1-G47 trees are grown in the field, under similar field trial conditions and on the same location as used for the p35S-G47 over-expressing trees. An average stem volume increase of the transgenic pLMP1-G47 trees of 15% compared to the wild type reference was observed in the field. Plant height also increased 8% in the field in the transgenic pLMP1-G47 trees compared to the wild type reference, FIG. 2. In the field the trees will be in conditions that includes reduced availability to water. The pLMP1-G47 trees have improved phenotypic properties coupled to drought response and water use efficiency which could be the reason for the improved growth in the pLMP1-G47 trees.

It is evident and unexpected from these results, that having a strong, constitutive expression of the G47 trait gene, as with the 35S-G47 promoter-gene construct, can have disadvantageous effects under some field trial conditions, whilst having a more specific expression pattern under the same conditions, as with the pLMP1-G47 promoter-gene construct, results in improved growth and improved drought response properties compared to wild type.

These results demonstrate the beneficial and inventive use of specific combinations of promoters and genes to tailor the expression pattern of the gene to the specific tissue and/or to the specific growth condition and to retain or further improve the positive phenotypical traits provided by the gene when growth conditions change.

6.3 Greenhouse Experiments with the Promoter-Gene Construct pLMX5-G47 for Growth Improvements When the AtG47 gene is specifically over-expressed by the vascular cambium/early xylem pLMX5 promoter no considerable increase in plant growth is observed in the greenhouse. No field trail data is available for this promoter-gene combination.

6.4 Greenhouse Experiments with the Promoter-Gene G47 Constructs for Improved Drought Tolerance.

Transgenic hybrid aspen trees with the p35S-AtG47, pLMX5-AtG47 and pLMP1-AtG47 constructs were grown together with wild type reference trees in the greenhouse. The wild type and the transgenic plants were subjected to a period of limited water supply and the effects of drought stress on plant vigour and health were monitored.

Healthy plant cells are turgid and plants rely on turgidity to maintain rigidity. Turgor pressure pushes the plasma membrane against the cell wall of plant cells by osmotic flow of water from outside the cell into the cell s vacuole. Turgor pressure also plays a key role in plant cell growth where the cell wall undergoes irreversible expansion due to the force of turgor pressure.

When water supply is reduced to test plant drought tolerance, 71% of wild type trees lose turgor pressure, which halts plant growth and causes the leaves to wilt. However, when the AtG47 gene is constitutively over-expressed by the 35S promoter a reduction in turgor loss of 44% compared to wild type trees is observed, as only 40% of the transgenic plants lose their turgor pressure, FIG. 3.

Figure 3:
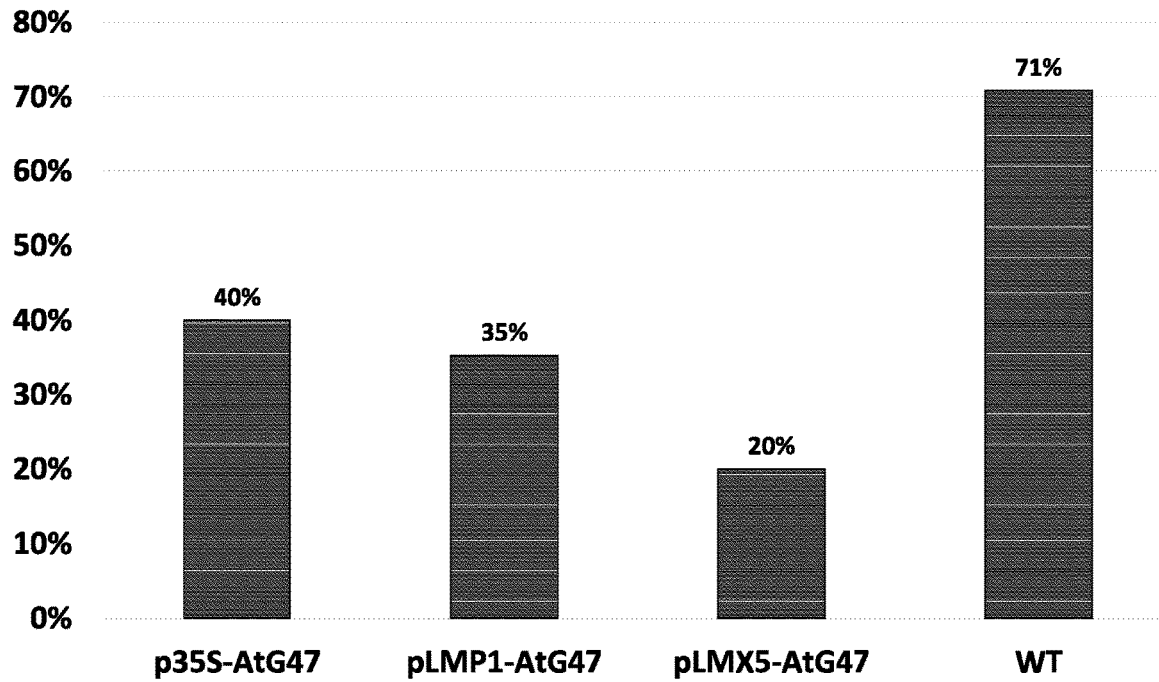
FIG. 3, shows improved drought stress tolerance analysis in green house experiments of the tree different constructs pLMX5:AtGA47, pLMP1:AtGA47 and p35S:AtGA47 compared to wild type plants. Y-axis, shows the percent of plants suffering of turgor loss during water shortage.

Furthermore, the pLMP1-AtG47 constructs, surprisingly showed an even more notable reduction in turgor loss of 50% compared to wild type trees is observed, as only 35% of the transgenic plants lose their turgor pressure, FIG. 3.

Moreover, the pLMX5-AtG47 construct showed a 72% reduction in turgor loss compared to wild type trees, as only 20% of the transgenic plants lose their turgor pressure, FIG. 3.

6.5 Water Use Efficiency (WUE)

A set of transgenic hybrid aspen trees grown in greenhouse containing constructs p35S-AtG47, pLMX5-AtG47 and pLMP1-AtG47 were tested according to the method presented in Farquhar, G. D., J. R. Ehleringer, and K. T. Hubick. 1989. Carbon isotope discrimination and photosynthesis. Ann. Rev. Plant Physiol. 40:503-537.

The $^{13}C$ discrimination data from greenhouse experiments for constructs p35S-AtG47, pLMX5-AtG47 and pLMP1-AtG47 all showed reduced $^{13}C$ discrimination and increased water use efficiency. One of the lines plant with the contruct pLMP1-AtG47 from showed a reduced $^{13}C$ discrimination of about 1 unit which is highly significant.

6.6 Conclusion: Promoter Gene G47 Combinations

As a summary the promoter-gene combinations pLMP1-G47 and pLMX5-G47 or these promoters in combinations with orthologues of the gene G47 can be used to tailor the expression pattern of the gene G47 or orthologues thereof to the specific growth condition for transgenic plants and trees harbouring such construct, resulting in an improved phenotypical effect such as plant height, width, stem volume, stem dry weight, bark dry weight, water use efficiency and improved drought tolerance compared to wild type plants and trees.

Example 7 Promoter and Gene TF0002 Combinations 7.1 Greenhouse and Field Trial Experiments with the Promoter-Gene Construct p35S-PttTF0002

Over-expression of a gene may elicit different phenotypical effects under two distinctly different growth conditions. In WO2009084999, the recombinant DNA construct TF0002 was used to constitutively over-express the *Populus tremula* x *tremuloides* gene PttTF0002, Seq ID: 2, in hybrid aspen trees using the CaMV 35S promoter. This modification in the transgenic trees resulted in an average stem volume growth increase of 36% compared to wild type reference trees when grown in the greenhouse.

Figure 4:
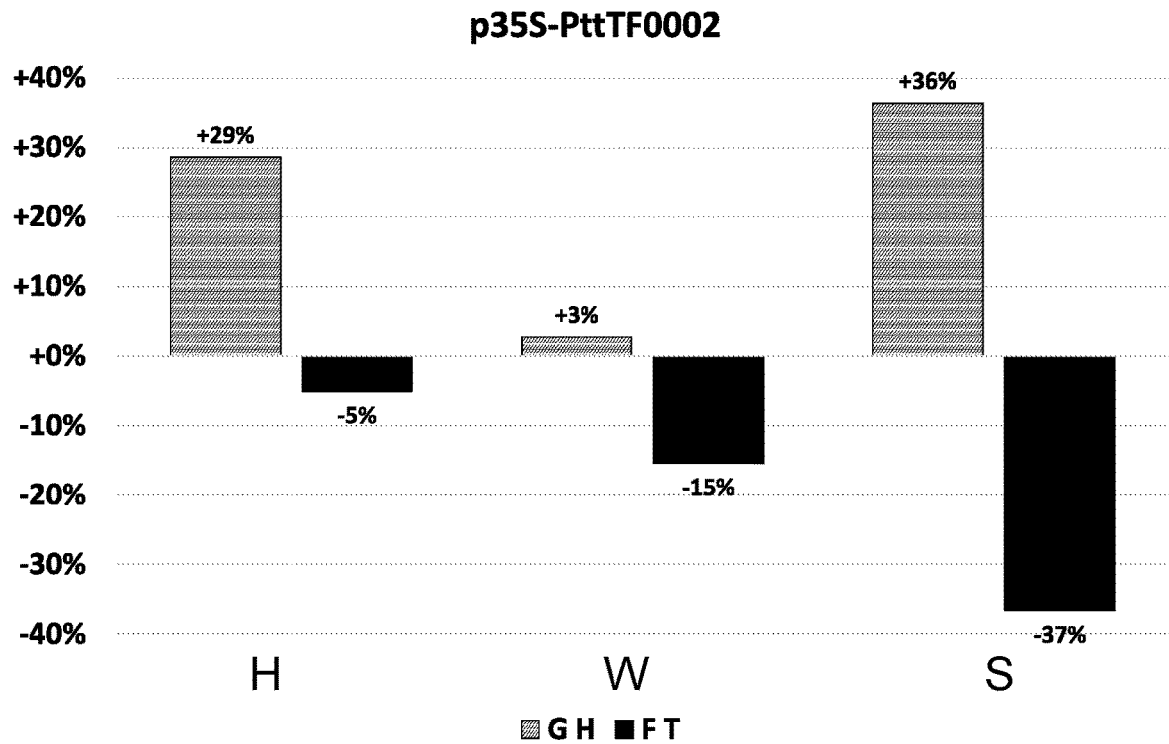
FIG. 4, shows greenhouse (G H) and field trial (F T) data from transgenic hybrid aspen plants with the promoter-gene construct p35S-PttTF0002. Percent numbers are compared to wild type reference plants.

The same hybrid aspen trees were subsequently planted in an open field trial in the south of Sweden. After three years in the field the hybrid aspen trees were measured. It was discovered that the transgenic trees harbouring the promoter-gene construct p35S-PttTF0002 did not perform as well as expected in these field growth tests. The observed average stem volume increase of 36% in greenhouse tests was contrasted with a considerable reduction of stem volume growth of 37% compared to the wild type reference trees grown at the same test site location, FIG. 4. This result was much unexpected, since the CaMV 35S promoter construct consistently worked very well under greenhouse conditions. Constitutive over-expression may have disadvantageous effects on plant growth under field trial conditions.

7.2 Greenhouse and Field Trial Experiments with the Promoter-Gene Construct pLMX5-PttTF0002

The transgenic hybrid aspen trees with the promoter-gene construct pLMX5-PttTF0002 were grown in the greenhouse as well as in an open field trial in the south of Sweden.

Figure 5:
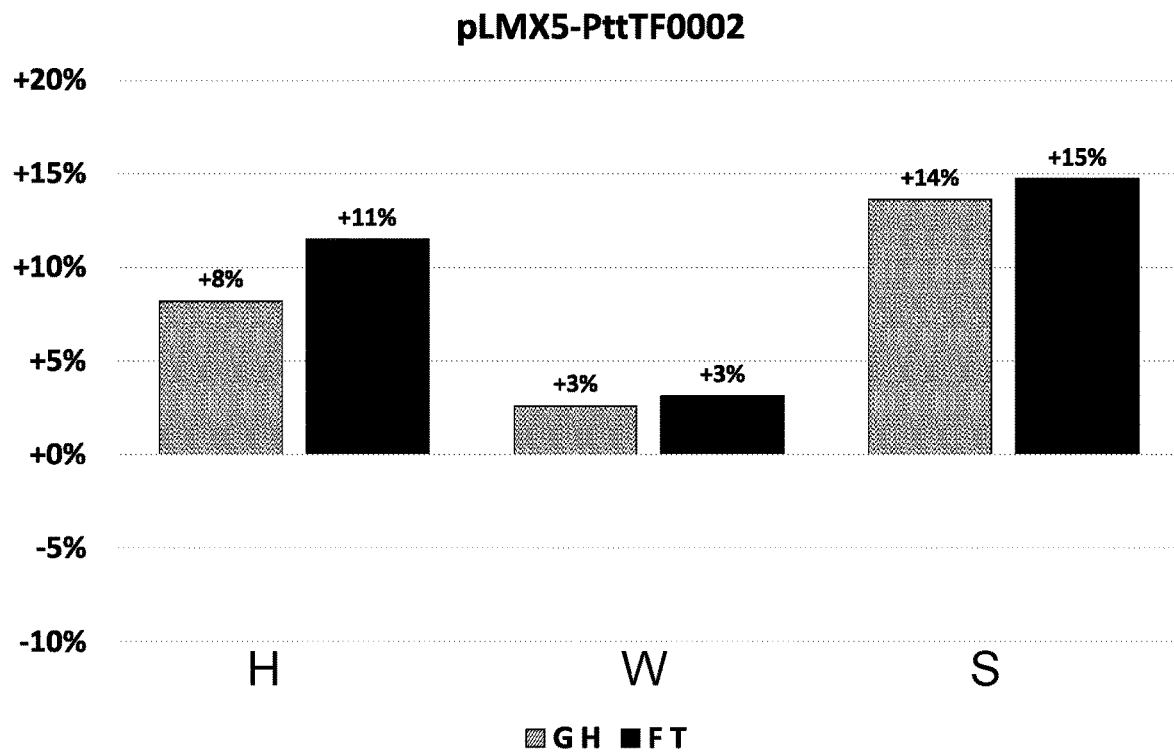
FIG. 5, shows greenhouse (G H) and field trial (F T) data from transgenic hybrid aspen plants with the vascular/xylem specific promoter-gene construct pLMX5-PttTF0002. Percent numbers are compared to wild type reference plants.

Surprisingly, transgenic hybrid aspen trees with the vascular/xylem specific promoter-gene construct pLMX5-PttTF0002 showed a considerable increase in plant growth both in the greenhouse and in the field, under similar field trial conditions and on the same location as used for the 35S over-expressing trees. Average stem volume increases of 14% and 15% compared to the wild type reference were observed in the greenhouse and the field respectively. Average plant height also increase 8% in the greenhouse and 11% the field in the transgenic trees, FIG. 5.

It is evident from these results, that having a strong, constitutive expression of a trait gene, as with the 35S promoter construct, can have disadvantageous effects under some field trial conditions, whilst having a more specific expression pattern under the same conditions still results in improved growth compared to wild type. These results demonstrate the beneficial and inventive use of specific combinations of promoters and genes to tailor the expression pattern to the specific growth condition and to retain or further improve the positive phenotypical traits provided by the gene when growth conditions change.

7.3 Greenhouse Experiments with the Promoter-Gene Construct pLMP1-PttTF0002

Figure 6:
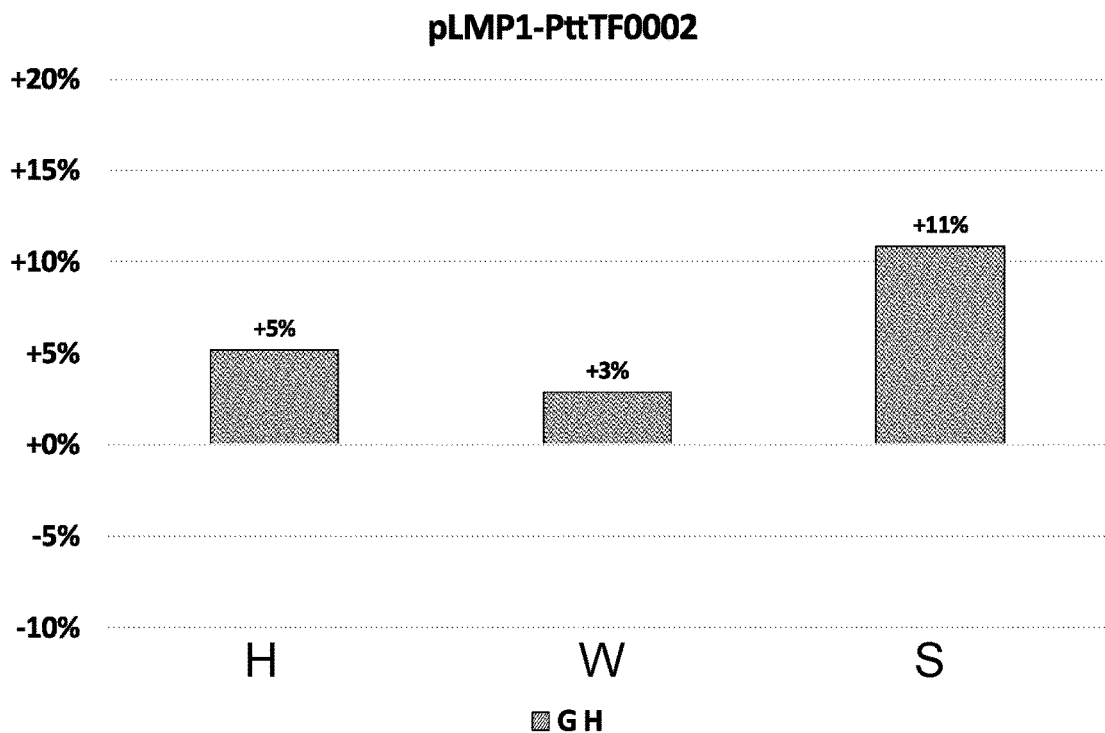
FIG. 6, shows greenhouse (G H) data from transgenic hybrid aspen plants with the phloem-specific promoter-gene construct pLMP1-PttTF0002. Percent numbers are compared to wild type reference plants.

The PttTF0002 gene was over-expressed by the vascular/phloem specific pLMP1 promoter hybrid aspen trees, it was surprisingly noticed that plants grown in the greenhouse had an increase in an average stem volume increase of 11% compared to the wild type reference, FIG. 6. Albeit no field trail data is available for the pLMP-PttTF0002 promoter-gene combination, it is obvious that specifically expressing the TF0002 trait gene with different promoters have different phenotypical effects and can be used to tailor the expression pattern of the gene to the specific growth condition at hand.

7.4 Conclusion: Promoter Gene TF0002 Combinations

As a summary the promoter-gene combinations based on the promoter pLMP1 can be used to tailor the expression pattern of the gene TF0002 or orthologues of the gene TF0002 to the specific growth condition for transgenic plants or trees harbouring this construct, resulting in an improved phenotypical effect such as plant height, plant width, stem volume, stem dry weight, bark dry weight, wood density, and drought tolerance compared to wild type.

Example 8 Promoter and Gene TF0097 Combinations 8.1 TF0097 Greenhouse Experiments Eleven different novel promoter-gene constructs were tested in the greenhouse. A construct where the 35S promoter was used to drive TF0097 expression was included as a reference. These constructs were made as disclosed in Example 3 and plant material was transformed and trees generated as described in Example 4. Finally, transgenic tree growth experiments, measurements and statistics were performed as described in Example 5.

The growth characteristics of the transgenic trees of the different constructs in greenhouse, relative to the wild type reference trees, are summarized in Table 7 A, 7B, 7C, 7D and 7E, below.

TABLE 7A

Significant differences (p < 0.01) compared to wild type marked with an asterisk (*).

| Construct | Gene | Promoter | Height | Width | Stem volume | Wood density |
|---|---|---|---|---|---|---|
| TF0097 | PttTF0097 | p35S | +33% * | +11% * | +68% * | +11% * |
| LMP1-003 | PttTF0097 | pLMP1 | +5% | −14% * | −17% | +4% |
| LMX5-003 | PttTF0097 | pLMX5 | −1% | −1% | −2% | |

TABLE 7B

Significant differences (p < 0.01) compared to wild type marked with an asterisk (*).

| Construct | Gene | Promoter | Height | Width | Stem volume | Stem dry weight | Bark dry weight | Internode length | Wood density | Leaf dry weight |
|---|---|---|---|---|---|---|---|---|---|---|
| F104 | PttTF0097 | pEA1 | +4% | +5% | +15% | +25% * | +13% | −2% | +3% | +24% * |
| F105 | PttTF0097 | pEA3 | +5% | +8% * | +23% * | +29% * | +15% * | +1% | +2% | +28% * |
| F106 | PttTF0097 | pEC1 | +6% * | +7% | +23% * | +26% * | +15% | +3% | −2% | +23% * |
| F107 | PttTF0097 | pEX5 | +2% | +9% * | +21% * | +31% * | +16% * | −5% | −2% | +35% * |
| F108 | PttTF0097 | pEL1.1 | +1% | +6% | +15% | +16% | +10% | −4% | −2% | +25% * |
| F109 | PttTF0097 | pER1 | +0% | +3% | +9% | +8% | −3% | −6% | +6% * | +11% |
| F110 | PttTF0097 | pER2 | −11% * | −5% | −19% * | −26% * | −22% * | −20% * | −4% | −21% * |
| F102 | PttTF0097 | pECO1 | +1% | +3% | +8% | +11% | +7% | −2% | −0% | +15% |
| F103 | PttTF0097 | pECO2 | −1% | +2% | +3% | +5% | +7% | −4% | +1% | +10% |

TABLE 7C

The results from each transgenic line presented individually. Significant differences (p < 0.01) compared to wild type marked with an asterisk (*).

| Construct | Gene | Promoter | Height | Width | Stem volume | Stem dry weight | Bark dry weight | Internode length | Wood density | Leaf dry weight |
|---|---|---|---|---|---|---|---|---|---|---|
| F104-Line1 | PttTF0097 | pEA1 | +8% | +4% | +16% | +30% * | +14% | +3% | +0% | +25% * |
| F104-Line2 | | | +4% | +5% | +13% | +18% | +17% | −5% | +2% | +17% |
| F104-Line3 | | | +0% | +8% | +15% | +26% * | +7% | −4% | +8% * | +29% * |
| F105-Line1 | PttTF0097 | pEA3 | +4% | +3% | +9% | +19% | +9% | −0% | +1% | +13% |
| F105-Line2 | | | +6% | +14% * | +38% * | +50% * | +27% * | −3% | +2% | +51% * |
| F105-Line3 | | | +5% | +7% | +21% | +20% | +8% | +5% | +2% | +19% |
| F106-Line1 | PttTF0097 | pEC1 | +5% | +12% * | +32% * | +44% * | +30% * | +4% | −2% | +31% * |
| F106-Line2 | | | +3% | +2% | +9% | +9% | +8% | +1% | +1% | +14% |
| F106-Line3 | | | +8% | +8% | +26% | +23% | +7% | +5% | −4% | +23% |
| F107-Line1 | PttTF0097 | pEX5 | +5% | +11% | +28% * | +46% * | +30% * | −5% | −2% | +43% * |
| F107-Line2 | | | +2% | +9% | +21% | +17% | +5% | −4% | −6% | +27% * |
| F107-Line3 | | | −1% | +8% | +15% | +31% * | +15% | −5% | +2% | +36% * |
| F108-Line1 | PttTF0097 | pEL1.1 | −1% | −1% | +0% | −4% | −7% | −6% | +1% | +1% |
| F108-Line2 | | | +1% | +10% | +21% | +22% | +10% | −6% | −3% | +36% * |
| F108-Line3 | | | +4% | +9% | +23% | +32% * | +27% * | +0% | −3% | +37% * |
| F109-Line1 | PttTF0097 | pER1 | −2% | −5% | −4% | −5% | −6% | −5% | +9% * | −4% |
| F109-Line2 | | | +7% | +13% * | +38% * | +32% * | +5% | −3% | +2% | +37% * |
| F109-Line3 | | | −4% | −1% | −7% | −4% | −8% | −9% | +8% * | −1% |
| F110-Line1 | PttTF0097 | pER2 | −2% | −4% | −10% | −21% | −12% | −21% * | +4% | −18% |
| F110-Line2 | | | −28% * | −6% | −36% * | −40% * | −41% * | −31% * | −15% * | −40% * |
| F110-Line3 | | | −2% | −5% | −12% | −18% | −14% | −9% * | −1% | −5% |
| F102-Line1 | PttTF0097 | pECO1 | +2% | −1% | +1% | −4% | −4% | −4% | −8% * | +1% |
| F102-Line2 | | | −4% | +3% | +5% | +11% | +10% | −3% | +6% | +20% |
| F102-Line3 | | | +5% | +5% | +16% | +20% | +11% | −0% | −0% | +20% |
| F103-Line1 | PttTF0097 | pECO2 | −1% | +6% | +10% | +1% | +2% | −7% | −0% | +5% |
| F103-Line2 | | | −1% | +0% | −0% | +12% | +11% | −1% | −4% | +16% |
| F103-Line3 | | | +0% | +1% | +1% | +1% | +8% | −3% | +6% | +9% |

TABLE 7D

Significant differences (p < 0.01) compared to wild type marked with an asterisk (*).

| Construct | Gene | Promoter | Height | Width | Stem volume | Stem dry weight | Bark dry weight | Internode length | Wood density | Leaf dry weight |
|---|---|---|---|---|---|---|---|---|---|---|
| F101 | PttTF0097 | p35S | +19% * | +4% | +31% * | +26% * | +26% * | +12% * | +4% | −2% |

TABLE 7E

The results from each transgenic line presented individually. Significant differences (p < 0.01) compared to wild type marked with an asterisk (*).

| Construct | Gene | Promoter | Height | Width | Stem volume | Stem dry weight | Bark dry weight | Internode length | Wood density | Leaf dry weight |
|---|---|---|---|---|---|---|---|---|---|---|
| F101-Line1 | PttTF0097 | p35S | +28% * | +7% | +48% * | +27% | +25% * | +11% * | +3% | −3% |
| F101-Line2 | | | +6% | +1% | +8% | −0% | +11% | +5% | +8% * | −10% |
| F101-Line3 | | | +24% * | +5% | +35% * | +51%* | +42% * | +19% * | +2% | +8% |

8.2 TF0097 Field Trial Experiments

The transgenic hybrid aspen lines of six novel promoter-gene constructs, with the most improved growth characteristics in greenhouse compared to wild type, were selected for field trial testing. Transgenic hybrid aspen lines with the 35S promoter driving TF0097 gene expression was included as a reference. Trees were again propagated from tissue culture material for a field trial experiment, according to Example 5. Wild type reference plants were propagated in parallel and treated exactly as the transgenic plants throughout the experiment.

The growth characteristics of the transgenic trees of the different constructs in field, relative to the wild type reference trees, are summarized in Table 8A, 8B and 8C, below.

TABLE 8A

Significant differences (p < 0.05) compared to wild type marked with an asterisk (*).

| Construct | Gene | Promoter | Height | Width | Stem volume |
|---|---|---|---|---|---|
| TF0097 | PttTF0097 | p35S | −22% * | −22% | −54% |

TABLE 8B

Significant differences according to Dunnett's test compared to wild type (p < 0.05) marked with an asterisk (*).

| Construct | Gene | Promoter | Height |
|---|---|---|---|
| F101 | PttTF0097 | p35S | −12% |
| F104 | PttTF0097 | pEA1 | +1% |
| F105 | PttTF0097 | pEA3 | +8% |
| F106 | PttTF0097 | pEC1 | +17% |
| F107 | PttTF0097 | pEX5 | −0% |
| F108 | PttTF0097 | pEL1.1 | +17% * |
| F109 | PttTF0097 | pER1 | +3% |

TABLE 8C

The results from each transgenic line presented individually. Significant differences according to Dunnett's test compared to wild type (p < 0.05) marked with an asterisk (*).

| Construct | Gene | Promoter | Height |
|---|---|---|---|
| F101-5A | PttTF0097 | p35S | −6% |
| F101-6B | | | −24% |
| F104-3A | PttTF0097 | pEA1 | +0% |
| F104-3B | | | +3% |
| F104-5B | | | +0% |
| F105-3B | PttTF0097 | pEA3 | +8% |
| F106-5A | PttTF0097 | pEC1 | +17% |
| F107-1A | PttTF0097 | pEX5 | −6% |
| F107-4A | | | −4% |
| F107-4B | | | +10% |
| F108-1A | PttTF0097 | pEL1.1 | +7% |
| F108-1B | | | +18% |
| F108-3B | | | +25% |
| F109-6B | PttTF0097 | pER1 | +3% |

8.3 CaMV 35S Over-Expression of TF0097

Although known to potentially increase the risk of gene silencing, constitutive over-expression was used to demonstrate the strong positive effect that TF0097 over-expression can have on plant growth under controlled greenhouse conditions. Transgenic hybrid aspen trees harbouring a recombinant DNA construct, wherewith the TF0097 gene from *Populus tremula* x *tremuloides* is over-expressed using the strong constitutive 35S promoter, grow significantly faster, becoming taller and wider as well as having an increased stem volume and dry weight compared to wild type trees, Table 8A, 8D and 8E. Average internode length and wood density are also positively affected by the modification.

A negative pleiotropic effect was observed in the 35S over-expressors. The trees grew tall but consistently had a spindly and slightly curved phenotype of the stem.

However, in the field trial experiment conducted with transgenic trees over-expressing the TF0097 gene using the 35S promoter, strong constitutive over-expression results in severely reduced growth, in contrast to the greenhouse results. These results demonstrate the need for new combinations of a promoter and a trait gene, such as TF0097, or like methods to modify the expression pattern of the trait gene, to achieve an increase in plant growth or biomass production under a given growth condition.

8.4 Tissue-Specific Over-Expression of TF0097

By using a number of tissue-specific promoters to control the expression of the TF0097 gene, the inventors are able to demonstrate that specific over-expression of TF0097 gene product does not necessarily lead to an increase in plant growth, Table 7A, 7B and 7C. Conversely, specific over-expression of TF0097 gene product will not generally have a significant effect on plant growth. This demonstrates the non-obvious and inventive use of the specific combinations of promoters and genes disclosed herein to increase plant growth.

Strong, constitutive over-expression of TF0097 is known to potentially have negative effects on growth, for example as described in section 8.2, Table 8A, and may also increase the risk of gene silencing. This risk of adverse effects can be reduced by using for example tissue-specific promoters, such as pEC1 or pEL1.1 to over-express the TF0097 gene.

When the constitutive 35S promoter is used to over-express the TF0097 gene product, leaf dry weight is not significantly affected while the dry weight of other plant parts increase compared to wild type. However, in several instances where a tissue-specific promoter is used to over-express the TF0097 gene product, both leaf dry weight and the dry weight of other plant parts are significantly increased compared to wild type. This again suggests a potentially negative pleotropic effect of strong, constitutive over-expression using the 35S promoter When the pEA1 promoter is used to over-express the TF0097 gene product growth is significantly improved compared to wild type; looking at the average of all tested transgenic lines, including the three replicates of each, stem dry weight is increased by 25% and the total dry weight of all leaves is increased by 24%. If instead each transgenic line, including its three replicates, is compared to the wild type reference, increases in stem dry weight and total dry weight of all leaves by 30% and 25% respectively are observed in the most improved transgenic line; in the second most improved transgenic line increases in stem dry weight and total dry weight of all leaves by 26% and 29% respectively are observed, as well as an increase in wood density of 8%. Dry weight results confirm that the increase in growth also includes a considerable increase in biomass production in the transgenic trees compared to wild type. No adverse phenotypical effects of tissue-specific over-expression of the TF0097 gene using the pEA1 promoter, are observed.

When the pEA3 promoter is used to over-express the TF0097 gene product growth is significantly improved compared to wild type; looking at the average of all tested transgenic lines, including the three replicates of each, stem diameter is increased by 8% and stem volume is increased by 23%. Further, substantial increases in stem and bark dry weights as well as total dry weight of all leaves of in average 29%, 15% and 28% respectively, are observed. If instead each transgenic line, including its three replicates, is compared to the wild type reference, increases in stem and bark dry weight as well as total dry weight of all leaves by 50%, 27% and 51% respectively are observed in the most improved transgenic line; stem diameter and stem volume are increased by 14% and 38% respectively in the same line. Dry weight results confirm that the increase in growth also includes a considerable increase in biomass production in the transgenic trees compared to wild type. No adverse phenotypical effects of tissue-specific over-expression of the TF0097 gene using the pEA3 promoter, are observed.

When the pEC1 promoter is used to over-express the TF0097 gene product growth is significantly improved compared to wild type; looking at the average of all tested transgenic lines, including the three replicates of each, plant height is increased by 6% and stem volume is increased by 23%. Further, substantial increases in stem dry weight and total dry weight of all leaves of in average 26% and 23% respectively, are observed. If instead each transgenic line, including its three replicates, is compared to the wild type reference, increases in stem and bark dry weight as well as total dry weight of all leaves by 44%, 30% and 31% respectively are observed in the most improved transgenic line; stem diameter and stem volume are increased by 12% and 32% respectively in the same line. Dry weight results confirm that the increase in growth also includes a considerable increase in biomass production in the transgenic trees compared to wild type. No adverse phenotypical effects of tissue-specific over-expression of the TF0097 gene using the pEC1 promoter, are observed.

When the pEX5 promoter is used to over-express the TF0097 gene product growth is significantly improved When the pEL1.1 promoter is used to over-express the TF0097 gene product growth is significantly improved compared to wild type; looking at the average of all tested transgenic lines, including the three replicates of each, the total dry weight of all leaves is increased by 25%. If instead each transgenic line, including its three replicates, is compared to the wild type reference, increases in stem and bark dry weight as well as total dry weight of all leaves by 32%, 27% and 37% respectively are observed in the most improved transgenic line; in the second most improved transgenic line an increase in total dry weight of all leaves by 36% is observed. Dry weight results confirm that the increase in growth also includes a considerable increase in biomass production in the transgenic trees compared to wild type. No adverse phenotypical effects of tissue-specific over-expression of the TF0097 gene using the pEL1.1 promoter, are observed. The strong promoter pEL1.1 has an expression level and a broad pattern of expression in all green tissues of the plant that make it, in some ways, comparable to the 35S promoter.

When the pER1 promoter is used to over-express the TF0097 gene product growth is significantly improved compared to wild type; looking at the average of all tested transgenic lines, including the three replicates of each, wood density is increased by 6%. If instead each transgenic line, including its three replicates, is compared to the wild type reference, increases in stem and bark dry weight as well as total dry weight of all leaves by 38%, 32% and 37% respectively are observed in the most improved transgenic line; stem diameter and stem volume are increased by 13% and 38% respectively in the same line. Dry weight results confirm that the increase in growth also includes a considerable increase in biomass production in the transgenic trees compared to wild type. No adverse phenotypical effects of tissue-specific over-expression of the TF0097 gene using the pER1 promoter, are observed.

When the pER2 promoter is used to over-express the TF0097 gene product growth is significantly reduced compared to wild type; looking at the average of all tested transgenic lines, including the three replicates of each, plant height, stem volume as well as the dry weight of stem, bark and leaves are significantly reduced. Furthermore, this construct showed narrower leaves in the transgenes compared to wild type leaves was also observed.

8.5 Constitutive Over-Expression of TF0097

No statistically significant positive phenotypical effect is observed in the greenhouse when over-expressing the TF0097 using the pECO1 or the pECO2 promoter. The constitutive promoters pECO1 and pECO2 are both weaker than the 35S promoter. The levels of gene over-expression conferred by the pECO1 or pECO2 promoters are too weak to significantly change the growth of the trees in this experiment, Table 7B. Wood density is slightly reduced in one of the transgenic lines when using pECO1 to drive the expression of the TF0097 gene, Table 7C. The risk of adverse effects of strong constitutive expression can be reduced by using weaker constitutive promoters, such as pECO1 or pECO2, to over-express the TF0097 gene.

8.3 Conclusions Promoter Gene TF0097 Combinations

Overexpressing the TF0097 gene with different tissue-specific promoters have different phenotypical effects which can be used to tailor the expression pattern of the gene to the specific growth condition at hand and to retain or further improve the positive phenotypical traits provided by the gene when growth conditions change.

Tissue-specific over-expression of the TF0097 gene product provides a more efficient use of resources for the tree compared to constitutive over-expression. When the TF0097 gene is strongly over-expressed in the majority of cells throughout the plant using, for example, the 35S promoter constructs, large quantities of TF0097 gene product are produced also in cells and tissues where there is little or no need of the TF0097 gene product. The impact on plant growth relative to the total amount of TF0097 gene product produced is therefore much higher in transgenic plants with a tissue-specific TF0097 gene over-expression driven by, for example, the pEC1, pEL1.1, pEA1, pEA3, pLMP1, pLMX5, pEX5 or pER1 promoter than in the 35S over-expressing plants. At the same time, specific over-expression will reduce the risk of adverse effects, such as those observed in the field trial described in section 8.2, Table 8A, where the TF0097 gene product was constitutively over-expressed at high levels. It is important to note that different specific promoters function differently and may minimize the risk for negatively growth effects.

It is obvious that specifically expressing the TF0097 gene with different promoters have different phenotypical effects and can be used to tailor the expression pattern of the gene to the specific growth condition at hand. Similarly, it is also obvious that transgenic trees harbouring the 35S promoter construct might still perform optimally for another set of field growth conditions, resulting in an improved phenotypical effect compared to wild type.

In an article by Noh et al 2015, "The poplar basic helix-loop-helix transcription factor BEE3-Like gene affects biomass production by enhancing proliferation of xylem cells in poplar" it is shown that a bHLH transcription factor has positive effect on biomass production. This bHLH protein have 39% identity when compared to Seq ID No.: 3.

Example 9 Promoter and Gene TF0109 Combinations 9.1 TF0109 Greenhouse Experiments Eight different novel promoter-gene constructs were tested in the greenhouse. A construct where the 35S promoter was used to drive TF0109 expression was included as a reference. These constructs were made as disclosed in Example 3 and plant material was transformed and trees generated as described in Example 4. Finally, transgenic tree growth experiments, measurements and statistics were performed as described in Example 5.

The growth characteristics of the transgenic trees relative to the wild type reference trees in greenhouse of the different constructs are summarized in Table 9A, 9B, 9C, 9D and 9E, below.

TABLE 9A

Significant differences (p < 0.01) compared to wild type marked with an asterisk (*).

| Construct | Gene | Promoter | Height | Width | Stem volume | Wood density |
|---|---|---|---|---|---|---|
| TF0109 | PttTF0109 | p35S | +22% * | +15% * | +58% * | +1% |
| LMP1-004 | PttTF0109 | pLMP1 | +5% | −9% | −16% | +1% |
| LMX5-004 | PttTF0109 | pLMX5 | +4% | +1% | +8% | |

TABLE 9B

Significant differences (p < 0.01) compared to wild type marked with an asterisk *.

| Construct | Gene | Promoter | Height | Width | Stem volume | Stem dry weight | Bark dry weight | Internode length | Wood density | Leaf dry weight |
|---|---|---|---|---|---|---|---|---|---|---|
| F123 | PttTF0109 | pEA1 | +6% * | +4% | +15% * | +16% | +9% | −2% | +1% | +9% |
| F124 | PttTF0109 | pEA2 | +7% * | +7% * | +22% * | +22% * | +17% * | −4% | +3% | +15% * |
| F125 | PttTF0109 | pEA3 | +1% | +1% | +4% | +1% | −0% | −2% | −3% | −2% |
| F126 | PttTF0109 | pEX5 | −1% | −4% | −9% | −11% | −9% | +4% | +4% | −9% |
| F121 | PttTF0109 | pECO1 | +1% | +1% | +4% | +1% | −3% | +0% | +3% | −2% |
| F122 | PttTF0109 | pECO2 | +4% | +6% | +16% * | +20% * | +6% | −1% | +4% | +10% |

TABLE 9C

The results from each transgenic line presented individually. Significant differences (p < 0.01) compared to wild type marked with an asterisk (*).

| Construct | Gene | Promoter | Height | Width | Stem volume | Stem dry weight | Bark dry weight | Internode length | Wood density | Leaf dry weight |
|---|---|---|---|---|---|---|---|---|---|---|
| F123-2A | PttTF0109 | pEA1 | +4% | +9% | +24% * | +23% | +12% | −2% | +3% | +7% |
| F123-2B | | | +6% | +2% | +11% | +15% | +13% | −6% | −0% | +15% |
| F123-3A | | | +7% | +1% | +10% | +10% | +2% | +1% | −1% | +4% |
| F124-2B | PttTF0109 | pEA2 | +7% | +10% | +29% * | +30% * | +18% | −6% | +7% | +18% |
| F124-3B | | | +7% | +1% | +10% | +12% | +12% | −1% | +1% | +10% |
| F124-6A | | | +5% | +10% | +28% * | +23% | +21% | −5% | +1% | +18% |
| F125-2A | PttTF0109 | pEA3 | +3% | −0% | +2% | +1% | +1% | −3% | −1% | −5% |
| F125-4A | | | +1% | +0% | +1% | −2% | −7% | −1% | −3% | −3% |
| F125-4B | | | −1% | +4% | +8% | +6% | +5% | −2% | −4% | +2% |
| F126-4B | PttTF0109 | pEX5 | +4% | −4% | −4% | −7% | −9% | +3% | −2% | −7% |
| F126-5A | | | −5% | −4% | −14% | −23% | −18% | +14% * | −2% | −19% |
| F126-7B | | | −2% | −5% | −9% | −5% | +1% | −5% | +17% * | −3% |
| F121-2B | PttTF0109 | pECO1 | +3 | +0 | +4% | +1% | −5% | +3% | −2% | −3% |
| F121-3A | | | −1% | +2% | +2% | −2% | −4% | −5% | +5% | −5% |
| F121-3B | | | +1% | +2% | +5% | +4% | −2% | +3% | +7% | +2% |
| F122-2A | PttTF0109 | pECO2 | +4% | +3% | +10% | +11% | +4% | +0% | +4% | +2% |
| F122-3A | | | +2% | +6% | +15% | +17% | +8% | +2% | +3% | +9% |
| F122-4A | | | +6% | +7% | +23% | +31% * | +6% | −6% | +4% | +18% |

TABLE 9D

Significant differences (p < 0.01) compared to wild type marked with an asterisk *.

| Construct | Gene | Promoter | Height | Width | Stem volume | Stem dry weight | Bark dry weight | Internode length | Wood density | Leaf dry weight |
|---|---|---|---|---|---|---|---|---|---|---|
| F120 | PttTF0109 | p35S | +14% * | −5% | +2% | +10% | +0% | +7% * | +11% * | −18% * |

TABLE 9E

The results from each transgenic line presented individually. Significant differences (p < 0.01) compared to wild type marked with an asterisk (*).

| Construct | Gene | Promoter | Height | Width | Stem volume | Stem dry weight | Bark dry weight | Internode length | Wood density | Leaf dry weight |
|---|---|---|---|---|---|---|---|---|---|---|
| F120-1A | PttTF0109 | p35S | +16% * | −4% | +6% | +13% | +1% | +6% | +11% * | −28% * |
| F120-2A | | | +7% | −2% | +3% | +2% | +3% | −0% | +4% | +6% |
| F120-2B | | | +18% * | −9% | −1% | +15% | −3% | +16% * | +17% * | −33% * |

9.2 TF0109 Field Trial Experiments

The transgenic hybrid aspen lines of three novel promoter-gene constructs, with the most improved growth characteristics in greenhouse compared to wild type, were selected for field trial testing. Transgenic hybrid aspen lines with the 35S promoter driving TF0109 gene expression was included as a reference. Trees were again propagated from tissue culture material for a field trial experiment, according to Example 5. Wild type reference plants were propagated in parallel and treated exactly as the transgenic plants throughout the experiment.

The growth characteristics of the transgenic trees of the different constructs in field, relative to the wild type reference trees, are summarized in Table 9F and 9G, below.

TABLE 9F

Significant differences according to Dunnett's test compared to wild type (p < 0.05) marked with an asterisk (*).

| Construct | Gene | Promoter | Height |
|---|---|---|---|
| F120 | PttTF0109 | p35S | −14% |
| F123 | PttTF0109 | pEA1 | −3% |
| F122 | PttTF0109 | pECO2 | +9% |

TABLE 9G

The results from each transgenic line presented individually. Significant differences according to Dunnett's test compared to wild type (p < 0.05) marked with an asterisk (*).

| Construct | Gene | Promoter | Height |
|---|---|---|---|
| F120-1A | PttTF0109 | p35S | −28% |
| F120-2B | | | −9% |

TABLE 9G-continued

The results from each transgenic line presented individually.
Significant differences according to Dunnett's test compared
to wild type (p < 0.05) marked with an asterisk (*).

| Construct | Gene | Promoter | Height |
|---|---|---|---|
| F123-2A | PttTF0109 | pEA1 | −3% |
| F122-2A | PttTF0109 | pECO2 | +6% |
| F122-3A | | | +7% |
| F122-4A | | | +13% |

There is a variation in the observed level of phenotypical effect of the genetic modification between the different independent transgenic lines. This variation is anticipated for a person skilled in the art, since plants are living, multicellular organisms impossible to grow completely uniformly and since the point of integration of the recombinant DNA construct in the plant genome to a large extent is random and may affect the expression of the inserted genes.

9.3 CaMV 35S Over-Expression of TF0109

Although known to potentially increase the risk of gene silencing, constitutive over-expression was used to demonstrate the strong positive effect that TF0109 over-expression can have on plant growth under controlled greenhouse conditions. Transgenic hybrid aspen trees harbouring a recombinant DNA construct, wherewith the TF0109 gene from *Populus tremula* x *tremuloides* is over-expressed using the strong constitutive 35S promoter, grow significantly faster, becoming taller and wider with an increased stem volume as well as having an increased wood density and leaf dry weight compared to wild type trees, Table 9A, 9D and 9E. Average internode length can also be positively affected by the modification.

9.4 Tissue-Specific Over-Expression of TF0109

By using a number of tissue-specific promoters to control the expression of the TF0109 gene, the inventors are able to demonstrate that specific over-expression of TF0109 gene product does not necessarily lead to an increase in plant growth, Table 9A, 9B and 9C. Conversely, specific over-expression of TF0109 gene product will not generally have a significant effect on plant growth. This demonstrates the non-obvious and inventive use of the specific combinations of promoters and genes disclosed herein to increase plant growth.

Strong, constitutive over-expression of TF0109 is known to potentially have negative effects on growth and may also increase the risk of gene silencing. This risk of adverse effects can be reduced by using for example tissue-specific promoters, such as pEA1, pEA2 and pEC2 to over-express the TF0109 gene.

When the constitutive 35S promoter is used to over-express the TF0109 gene product, leaf dry weight is significantly reduced while the dry weight of other plant parts are not significantly affected compared to wild type. However, in other instances where a tissue-specific promoter is used to over-express the TF0109 gene product, leaf dry weight is not negatively affected while the dry weight of other plant parts are significantly increased compared to wild type. This again suggests a potentially negative pleotropic effect of strong, constitutive over-expression using the 35S promoter.

When the pEA1 promoter is used to over-express the TF0109 gene product growth is significantly improved compared to wild type; looking at the average of all tested transgenic lines, including the three replicates of each, plant height is increased by 6% and stem volume is increased by 15%. If instead each transgenic line, including its three replicates, is compared to the wild type reference, an increase in stem volume by 24% is observed in the most improved transgenic line. No adverse phenotypical effects of tissue-specific over-expression of the TF0109 gene using the pEA1 promoter, are observed.

When the pEA2 promoter is used to over-express the TF0109 gene product growth is significantly improved compared to wild type; looking at the average of all tested transgenic lines, including the three replicates of each, plant height and stem diameter increase by 7% each and stem volume increase by and 22%. Further, substantial increases in stem and bark dry weights as well as total dry weight of all leaves of in average 22%, 17% and 15% respectively, are observed. If instead each transgenic line, including its three replicates, is compared to the wild type reference, increases in stem volume and dry weight by 29% and 30% respectively are observed in the most improved transgenic line. Dry weight results confirm that the increase in growth also includes a considerable increase in biomass production in the transgenic trees compared to wild type. No adverse phenotypical effects of tissue-specific over-expression of the TF0109 gene using the pEA2 promoter, are observed.

No statistically significant positive phenotypical effect is observed in the greenhouse when over-expressing the TF0109 using the pEA3 promoter. No adverse phenotypical effects of tissue-specific over-expression of the TF0109 gene using the pEA3 promoter, are observed.

No statistically significant positive phenotypical effect is observed in the greenhouse when over-expressing the TF0109 using the pLMP1 promoter. No adverse phenotypical effects of tissue-specific over-expression of the TF0109 gene using the pLMP1 promoter, are observed.

The pEX5 and pLMX5 are orthologous promoters, as described in the detailed description of the invention. When the pEX5 promoter is used to over-express the TF0109 gene product wood density is significantly improved compared to wild type; if each transgenic line, including its three replicates, is compared to the wild type reference, an increase in wood density by 17% is observed in the most improved transgenic line. No statistically significant positive phenotypical effect is observed in the greenhouse when over-expressing the TF0109 using the pLMX5 promoter. Wood density was not measured in these transgenic trees. No adverse phenotypical effects of tissue-specific over-expression of the TF0109 gene using the either the pEX5 or the pLMX5 promoter, are observed.

9.5 Constitutive Over-Expression of TF0109

No statistically significant positive phenotypical effect is observed in the greenhouse when over-expressing the TF0109 using the pECO1 promoter. The constitutive promoters pECO1 and pECO2 are both weaker than the 35S promoter. The levels of gene over-expression conferred by the pECO1 promoter is too weak to significantly change the growth of the trees in this experiment, Table B. When the pECO2 promoter is used to over-express the TF0109 gene product growth is significantly improved compared to wild type; looking at the average of all tested transgenic lines, including the three replicates of each, stem volume and stem dry weight are increased by 16% and 20% respectively. If instead each transgenic line, including its three replicates, is compared to the wild type reference, an increase in stem dry weight by 31% is observed in the most improved transgenic line. Dry weight results confirm that the increase in growth also includes a considerable increase in biomass production in the transgenic trees compared to wild type. No adverse phenotypical effects of constitutive over-expression of the TF0109 gene using the either the pECO1 or the pECO2 promoter, are observed. The risk of adverse effects of strong constitutive expression might be reduced by using weaker constitutive promoters, such as pECO1 or pECO2, to overexpress the TF0109 gene.

9.6 Conclusions Promoter Gene TF0109 Combinations

Overexpressing the TF0109 gene with different tissue-specific promoters have different phenotypical effects which can be used to tailor the expression pattern of the gene to the specific growth condition at hand and to retain or further improve the positive phenotypical traits provided by the gene when growth conditions change.

Tissue-specific over-expression of the TF0109 gene product provides a more efficient use of resources for the tree compared to constitutive over-expression. When the TF0109 gene is strongly over-expressed in the majority of cells throughout the plant using, for example, the 35S promoter constructs, large quantities of TF0109 gene product are produced also in cells and tissues where there is little or no substrate to process. The impact on plant growth relative to the total amount of TF0109 gene product produced is therefore much higher in transgenic plants with a tissue-specific TF0109 gene over-expression driven by, for example, the pEA1, pEA2, or pEC2 promoter than in the 35S over-expressing plants. At the same time, specific over-expression will reduce the risk of adverse effects, such as those observed in the field trial.

It is obvious that specifically expressing the TF0109 gene with different promoters have different phenotypical effects and can be used to tailor the expression pattern of the gene to the specific growth condition at hand. Similarly, it is also obvious that transgenic trees harbouring the 35S promoter construct might still perform optimally for another set of field growth conditions, resulting in an improved phenotypical effect compared to wild type.

Example 10 Promoter and Gene TF0132 Combinations 10.1 TF0132 Greenhouse Experiments Ten different novel promoter-gene constructs were tested in the greenhouse. A construct where the 35S promoter was used to drive TF0132 expression was included as a reference. These constructs were made as disclosed in Example 3 and plant material was transformed and trees generated as described in Example 4. Finally, transgenic tree growth experiments, measurements and statistics were performed as described in Example 5.

The growth characteristics of the transgenic trees relative to the wild type reference trees in greenhouse of the different constructs are summarized in Table 10A, B, C, D and E, below.

TABLE 10A

Significant differences ($p < 0.01$) compared to wild type marked with an asterisk (*).

| Construct | Gene | Promoter | Height | Width | Stem volume | Wood density |
|---|---|---|---|---|---|---|
| TF0132 | PttTF0132 | p35S | +27% * | +12% * | +65% * | +7% |
| LMP1-005 | PttTF0132 | pLMP1 | +6% | +5% | +17% | −1% |
| LMX5-005 | PttTF0132 | pLMX5 | +3% | −5% | −7% | |

TABLE 10B

Significant differences ($p < 0.01$) compared to wild type marked with an asterisk *.

| Construct | Gene | Promoter | Height | Width | Stem volume | Stem dry weight | Bark dry weight | Internode length | Wood density | Leaf dry weight |
|---|---|---|---|---|---|---|---|---|---|---|
| F114 | PttTF0132 | pEA1 | +6% * | +2% | +11% | +12% | +9% | +3% | +3% | +4% |
| F115 | PttTF0132 | pEA2 | +1% | +1% | +3% | +10% | +5% | −5% | +5% | −0% |
| F116 | PttTF0132 | pEA3 | +1% | +1% | +4% | +12% | +8% | −3% | +2% | +9% |
| F117 | PttTF0132 | pEA4 | +1% | +1% | +3% | +9% | +8% | +0% | +2% | +7% |
| F118 | PttTF0132 | pEC1 | +8% * | +4% | +15% * | +22% * | +20% * | +0% | +3% | +16% * |
| F119 | PttTF0132 | pEL1.1 | −3% | −4% | −10% | −6% | −7% | +2% | −2% | −5% |
| F112 | PttTF0132 | pECO1 | +2% | +5% | +13% | +21% * | +18% * | −1% | +8% * | +12% |
| F113 | PttTF0132 | pECO2 | +2% | +2% | +5% | +16% * | +13% | +3% | +9% * | +12% |

TABLE 10C

The results from each transgenic line presented individually. Significant differences ($p < 0.01$) compared to wild type marked with an asterisk (*).

| Construct | Gene | Promoter | Height | Width | Stem volume | Stem dry weight | Bark dry weight | Internode length | Wood density | Leaf dry weight |
|---|---|---|---|---|---|---|---|---|---|---|
| F114-1A | PttTF0132 | pEA1 | +4% | −5% | −6% | −4% | −5% | +4% | +2% | −12% |
| F114-3B | | | +11% * | +7% | +26% * | +26% * | +19% | +8% | +7% | +11% |
| F114-4A | | | +2% | +5% | +13% | +14% | +13% | −3% | +0% | +13% |
| F115-3A | PttTF0132 | pEA2 | +4% | +3% | +10% | +18% | +8% | −1% | +5% | +8% |
| F115-4A | | | −3% | −0% | −3% | −3% | −7% | −11% | +1% | −8% |

TABLE 10C-continued

The results from each transgenic line presented individually. Significant differences (p < 0.01) compared to wild type marked with an asterisk (*).

| Construct | Gene | Promoter | Height | Width | Stem volume | Stem dry weight | Bark dry weight | Internode length | Wood density | Leaf dry weight |
|---|---|---|---|---|---|---|---|---|---|---|
| F115-4B | | | +1% | −0% | +1% | +15% | +13% | −3% | +9% | −1% |
| F116-2B | PttTF0132 | pEA3 | +2% | +4% | +10% | +18% | +6% | +2% | +2% | +17% |
| F116-3A | | | −1% | +3% | +4% | +11% | +13% | −11% | +3% | +11% |
| F116-4A | | | +3% | −3% | −3% | +5% | +5% | +1% | +1% | −3% |
| F117-2B | PttTF0132 | pEA4 | −9% * | +1% | −7% | −12% | −12% | +2% | +1% | −1% |
| F117-4B | | | +8% * | +0% | +9% | +20% | +18% | +2% | +3% | +10% |
| F117-5B | | | +4% | +2% | +7% | +21% * | +19% | −5% | +2% | +12% |
| F118-1A | PttTF0132 | pEC1 | +13% * | +8% | +31% * | +33% * | +23% | +2% | −0% | +19% |
| F118-2A | | | +7% | −1% | +5% | +20% | +23% * | +5% | +5% | +12% |
| F118-3A | | | +4% | +5% | +15% | +18% | +14% | −5% | +3% | +18% |
| F119-1B | PttTF0132 | pEL1.1 | −0% | −0% | −1% | +14% | +12% | −5% | +4% | +10% |
| F119-2A | | | −14% * | −5% | −23% * | −32% * | −31% * | +12% | −9% | −21% * |
| F119-3A | | | +6% | −5% | −5% | +1% | −1% | −0% | −1% | −5% |
| F112-1A | PttTF0132 | pECO1 | −5% | −0% | −5% | −5% | +1% | +7% | +10% * | −6% |
| F112-3B | | | +5% | +7% | +20% | +35% * | +25% * | −7% | +5% | +20% * |
| F112-6B | | | +7% | +8% | +24% * | +33% * | +27% * | −0% | +8% | +22% * |
| F113-1A | PttTF0132 | pECO2 | +1% | +9% | +21% | +31% * | +23% * | +1% | +11% * | +25% * |
| F113-2A | | | +4% | −2% | −0% | +14% | +10% | +4% | +6% | +12% |
| F113-2B | | | −0% | −3% | −5% | +3% | +5% | +5% | +10% * | −2% |

TABLE 10D

Significant differences (p < 0.01) compared to wild type marked with an asterisk *.

| Construct | Gene | Promoter | Height | Width | Stem volume | Stem dry weight | Bark dry weight | Internode length | Wood density | Leaf dry weight |
|---|---|---|---|---|---|---|---|---|---|---|
| F111 | PttTF0132 | p35S | +30% * | −0% | +28% * | +46% * | +30% * | +19% * | +14% * | +8% |

TABLE 10E

The results from each transgenic line presented individually. Significant differences (p < 0.01) compared to wild type marked with an asterisk (*).

| Construct | Gene | Promoter | Height | Width | Stem volume | Stem dry weight | Bark dry weight | Internode length | Wood density | Leaf dry weight |
|---|---|---|---|---|---|---|---|---|---|---|
| F111-2A | PttTF0132 | p35S | +31% * | −3% | +22% * | +47% * | +33% * | +18% * | +23% * | +5% |
| F111-3A | | | +41% * | −3% | +33% * | +65% * | +47% * | +20% * | +22% * | +18% |
| F111-4A | | | +18% * | −3% | +29% * | +26% * | +12% | +20% * | −2% | +3% |

10.2 TF0132 Field Trial Experiments

The transgenic hybrid aspen lines of four novel promoter-gene constructs, with the most improved growth characteristics in greenhouse compared to wild type, were selected for field trial testing. Transgenic hybrid aspen lines with the 35S promoter driving TF0132 gene expression was included as a reference. Trees were again propagated from tissue culture material for a field trial experiment, according to Example 5. Wild type reference plants were propagated in parallel and treated exactly as the transgenic plants throughout the experiment.

The growth characteristics of the transgenic trees of the different constructs in field, relative to the wild type reference trees, are summarized in Table 10F, 10G and 10H, below.

TABLE 10F

Significant differences (p < 0.05) compared to wild type marked with an asterisk (*).

| Construct | Gene | Promoter | Height | Width | Stem volume |
|---|---|---|---|---|---|
| TF0132 | PttTF0132 | p35S | +4% | −14% | −21% |

TABLE 10G

Significant differences according to Dunnett's test compared to wild type (p < 0.05) marked with an asterisk (*).

| Construct | Gene | Promoter | Height |
|---|---|---|---|
| F111 | PttTF0132 | p35S | −14% |
| F114 | PttTF0132 | pEA1 | −4% |
| F118 | PttTF0132 | pEC1 | +3% |
| F112 | PttTF0132 | pECO1 | −3% |
| F113 | PttTF0132 | pECO2 | +3% |

TABLE 10H

The results from each transgenic line presented individually.
Significant differences according to Dunnett's test compared
to wild type ($p < 0.05$) marked with an asterisk (*).

| Construct | Gene | Promoter | Height |
|---|---|---|---|
| F111-2A | PttTF0132 | p35S | −21% |
| F111-3A | | | −10% |
| F111-4A | | | −11% |
| F114-3B | PttTF0132 | pEA1 | −4% |
| F118-1A | PttTF0132 | pEC1 | +6% |
| F118-2A | | | +12% |
| F118-3A | | | −10% |
| F112-1A | PttTF0132 | pECO1 | −9% |
| F112-3B | | | −1% |
| F112-6B | | | +4% |
| F113-1A | PttTF0132 | pECO2 | +3% |

10.3 Tissue-Specific Over-Expression of TF0132

By using a number of tissue-specific promoters to control the expression of the TF0132 gene, the inventors are able to demonstrate that specific over-expression of TF0132 gene product does not necessarily lead to an increase in plant growth, Table 10A, B and C. Conversely, specific over-expression of TF0132 gene product will not generally have a significant effect on plant growth. This demonstrates the non-obvious and inventive use of the specific combinations of promoters and genes disclosed herein to increase plant growth.

10.4 CaMV 35S Over-Expression of TF0132

Although known to potentially increase the risk of gene silencing, constitutive over-expression was used to demonstrate the strong positive effect that TF0132 over-expression can have on plant growth under controlled greenhouse conditions. Transgenic hybrid aspen trees harbouring a recombinant DNA construct, wherewith the TF0132 gene from *Populus tremula* x *tremuloides* is over-expressed using the strong constitutive 35S promoter, grow significantly faster, becoming taller and wider with an increased stem volume and dry weight as well as having an increased wood density and average internode length compared to wild type trees, Table 10 A, D and E.

However, in the field trial experiment conducted with transgenic trees over-expressing the TF0132 gene using the 35S promoter, strong constitutive over-expression does not result in significantly increased growth, in contrast to the greenhouse results. These results demonstrate the need for new combinations of a promoter and a trait gene, such as TF0132, or like methods to modify the expression pattern of the trait gene, to achieve an increase in plant growth or biomass production under a given growth condition.

Strong, constitutive over-expression of TF0132 is known to potentially have negative effects on growth and may also increase the risk of gene silencing. This risk of adverse effects can be reduced by using for example tissue-specific promoters, such as pEC1 and/or pEA1, to over-express the TF0132 gene.

When the pEA1 promoter is used to over-express the TF0132 gene product growth is significantly improved compared to wild type; looking at the average of all tested transgenic lines, including the three replicates of each, plant height is increased by 6%. If instead each transgenic line, including its three replicates, is compared to the wild type reference, increases in plant height by 11% and in stem volume and dry weight by 26% each are observed in the most improved transgenic line. Dry weight results confirm that the increase in growth also includes a considerable increase in biomass production in the transgenic trees compared to wild type. No adverse phenotypical effects of tissue-specific over-expression of the TF0132 gene using the pEA1 promoter, are observed.

No statistically significant positive phenotypical effect is observed in the greenhouse when over-expressing the TF0132 using the pEA2 promoter. No adverse phenotypical effects of tissue-specific over-expression of the TF0132 gene using the pEA2 promoter, are observed.

No statistically significant positive phenotypical effect is observed in the greenhouse when over-expressing the TF0132 using the pEA3 promoter. No adverse phenotypical effects of tissue-specific over-expression of the TF0132 gene using the pEA3 promoter, are observed.

When the pEA4 promoter is used to over-express the TF0132 gene product growth is significantly improved compared to wild type; if each transgenic line, including its three replicates, is compared to the wild type reference, an increase in stem dry weight by 21% is observed in the most improved transgenic line. No adverse phenotypical effects of tissue-specific over-expression of the TF0132 gene using the pEA4 promoter, are observed.

When the pEC1 promoter is used to over-express the TF0132 gene product growth is significantly improved compared to wild type; looking at the average of all tested transgenic lines, including the three replicates of each, plant height is increased by 8% and stem volume is increased by 15%. Further, substantial increases in stem and bark dry weight as well as total dry weight of all leaves of in average 22%, 20% and 16% respectively, are observed. If instead each transgenic line, including its three replicates, is compared to the wild type reference, an increase in stem dry weight by 33% is observed in the most improved transgenic line; plant height and stem volume are increased by 13% and 31% respectively in the same line. Dry weight results confirm that the increase in growth also includes a considerable increase in biomass production in the transgenic trees compared to wild type. No adverse phenotypical effects of tissue-specific over-expression of the TF0132 gene using the pEC1 promoter, are observed.

No statistically significant positive phenotypical effect is observed in the greenhouse when over-expressing the TF0132 using the pLMP1 promoter. No adverse phenotypical effects of tissue-specific over-expression of the TF0132 gene using the pLMP1 promoter, are observed.

No statistically significant positive phenotypical effect is observed in the greenhouse when over-expressing the TF0132 using the pLMX5 promoter. No adverse phenotypical effects of tissue-specific over-expression of the TF0132 gene using the pLMX5 promoter, are observed.

When the pEL1.1 promoter is used to over-express the TF0132 gene product growth is significantly reduced compared to wild type; if each transgenic line, including its three replicates, is compared to the wild type reference, a reduction in plant height by 14% is observed in one of the transgenic lines; stem volume is reduced by 23% in the same line. Further, substantial reductions in stem and bark dry weight as well as total dry weight of all leaves of 32%, 31% and 21% respectively, are observed in this transgenic line.

10.5 Constitutive Over-Expression of TF0132

The constitutive promoters pECO1 and pECO2 are both weaker than the 35S promoter. When the pECO1 promoter is used to over-express the TF0132 gene product growth is significantly improved compared to wild type; looking at the average of all tested transgenic lines, including the three replicates of each, stem and bark dry weight are increased by 21% and 18% respectively and an increase in wood density of 8% is observed. If instead each transgenic line, including its three replicates, is compared to the wild type reference, stem and bark dry weight as well as total dry weight of all leaves increase by 33%, 27% and 22% respectively, in the most improved transgenic line. Stem volume is increased by 24% in the same line. When the pECO2 promoter is used to over-express the TF0132 gene product growth is significantly improved compared to wild type; looking at the average of all tested transgenic lines, including the three replicates of each, stem dry weight is increased by 16% and an increase in wood density of 9% is observed. If instead each transgenic line, including its three replicates, is compared to the wild type reference, stem and bark dry weight as well as total dry weight of all leaves increase by 31%, 23% and 25% respectively, in the most improved transgenic line. Wood density is increased by 11% in the same line. Dry weight results confirm that the increase in growth also includes a considerable increase in biomass production in the transgenic trees compared to wild type. No adverse phenotypical effects of constitutive over-expression of the TF0132 gene using the either the pECO1 or the pECO2 promoter, are observed. The risk of adverse effects of strong constitutive expression can be reduced by using weaker constitutive promoters, such as pECO1 or pECO2, to over-express the TF0132 gene.

10.6 Conclusions Promoter Gene TF0132 Combinations

Overexpressing the TF0132 gene with different tissue-specific promoters have different phenotypical effects which can be used to tailor the expression pattern of the gene to the specific growth condition at hand and to retain or further improve the positive phenotypical traits provided by the gene when growth conditions change.

Tissue-specific over-expression of the TF0132 gene product provides a more efficient use of resources for the tree compared to constitutive over-expression. When the TF0132 gene is strongly over-expressed in the majority of cells throughout the plant using, for example, the 35S promoter constructs, large quantities of TF0132 gene product are produced also in cells and tissues where there is little or no substrate to process. The impact on plant growth relative to the total amount of TF0132 gene product produced is therefore much higher in transgenic plants with a tissue-specific TF0132 gene over-expression driven by, for example, the pEA1, pEA2, pEA3, pEA4, pEC1, pLMP1, pLMX5 or pEL1.1 promoter than in the 35S over-expressing plants. The most preferred promoters are pEC1 and pEA1. At the same time, specific over-expression will reduce the risk of adverse effects, such as those observed in the field trial described in section 8.2, Table F, where the TF0097 gene product was constitutively over-expressed at high levels.

It is obvious that specifically expressing the TF0132 gene with different promoters have different phenotypical effects and can be used to tailor the expression pattern of the gene to the specific growth condition at hand. Similarly, it is also obvious that transgenic trees harbouring the 35S promoter construct might still perform optimally for another set of field growth conditions, resulting in an improved phenotypical effect compared to wild type.

Example 11 Construction of Novel Promoter-Gene Combinations for Expression in *Eucalyptus*

As described in Example 1 the *Eucalyptus* promoter DNA fragments were manufactured by DNA synthesis and flanked by Gateway recombination sites for sub-cloning purposes. All *Eucalyptus* promoter fragments were cloned upstream of the gene of interest using the pSTT0111 vector or modification of it, and thus controlling the expression of the gene of interest as described below.

11.1 Constructs with the Gene G47

Construct E0011

The promoter pLMP1, Seq ID No: 13, with expression in the cambium and in the phloem was combined with the *Arabidopsis thaliana*, AtG47 gene, Seq ID No: 1, in the pSTT0111 vector to create the recombinant DNA construct E0011, pLPM1-AtG47. The construct is used to produce transgenic *Eucalyptus* trees.

11.2 Constructs with the Gene TF0097

Construct E0012

In this construct the stem/cambium specific promoter pEC1, Seq ID No: 12, was combined with the *Populus tremula* x *tremuloides*, PttTF0097 gene, Seq ID No: 23, in the pSTT0118 vector to create the recombinant DNA construct E0012, pEC1-PttTF0097. This construct is used to produce transgenic *Eucalyptus* trees.

Construct E0017

The strong constitutive promoter p35S, Seq ID No: 20, was combined with the *Populus tremula* x *tremuloides*, PttTF0097 gene, Seq ID No: 23, in the pSTT0117 vector to create the recombinant DNA construct E0017, p35S-PttTF0097. The construct is used to produce transgenic *Eucalyptus* trees.

Construct E0018

The strong constitutive promoter p35S, Seq ID No: 20, was combined with the *Eucalyptus grandis* x *urophylla*, EucTF0097 gene, Seq ID No: 55, in the pSTT0117 vector to create the recombinant DNA construct E0018, p35S-EucTF0097. The construct is used to produce transgenic *Eucalyptus* trees.

Construct E0019

The root and the meristematic tissues promoter pER1, Seq ID No: 18, was combined with the *Eucalyptus grandis* x *urophylla*, EucTF0097 gene, Seq ID No: 55, in the pSTT0117 vector to create the recombinant DNA construct E0019, pER1-EucTF0132. The construct is used to produce transgenic *Eucalyptus* trees.

11.3 Constructs with the Gene TF0132

Construct E0025

The strong constitutive promoter p35S, Seq ID No: 20, was combined with the *Populus tremula* x *tremuloides*, PttTF0132 gene, Seq ID No: 24 in the pSTT0117 vector to create the recombinant DNA construct E0025, p35S-PttTF0132. The construct is used to produce transgenic *Eucalyptus* trees.

Construct E0026

The constitutive promoter pECO1, Seq ID No: 6, was combined with the *Populus tremula* x *tremuloides*, PttTF0132 gene, Seq ID No: 24 in the pSTT0117 vector to create the recombinant DNA construct E0026, pECO1-PttTF0132. The construct is used to produce transgenic *Eucalyptus* trees.

Construct E0027

The constitutive promoter pEC1, Seq ID No: 12, was combined with the *Populus tremula* x *tremuloides*, PttTF0132 gene, Seq ID No: 24 in the pSTT0117 vector to create the recombinant DNA construct E0027, pEC1-PttTF0132. The construct is used to produce transgenic *Eucalyptus* trees.

Construct E0028

The constitutive promoter pEA1, Seq ID No: 8, was combined with the *Populus tremula* x *tremuloides*, PttTF0132 gene, Seq ID No: 24 in the pSTT0117 vector to create the recombinant DNA construct E0028, pEA1-PttTF0132. The construct is used to produce transgenic *Eucalyptus* trees.

Example 12 *Eucalyptus* Transformation

A new transformation vector is constructed for expression of a trait gene in *Eucalyptus*. The vector backbone is based on the established plasmid-PZP (pPZP) vector system, a small, versatile pPZP family of *Agrobacterium* binary vectors for plant transformation, Hajdukiewicz et al. 1994, Plant Mol. Biol. 25 (6), 989-994. The T-DNA cassette is designed to contain the desired genetic elements, a selectable marker cassette and a trait gene expression cassette. The genetic elements are separated by linker sequences containing unique restriction sites to facilitate cloning. The selectable marker is kanamycin for both bacterial selection (plasmid selection) and selection of transgenic plants during the transformation process. The method of transformation of *Eucalyptus* may be *Agrobacterium* mediated transformation using a standard protocol and kanamycin selection essentially as described by Tournier et al. Transgenic Research, 2003, Volume 12, Issue 4, pp 403-411, or by Ho et al., Plant Cell Reports, 1998, Volume 17, Issue 9, pp 675-680.

Example 13 Regeneration and Growth of *Eucalyptus* Plants

The transformed tissue generated in Example 12 is further treated under conditions for plant formation and root formation to get a transgenic *Eucalyptus* plant. The regeneration may be essentially done according to the protocol presented by Tournier et al. Transgenic Research, 2003, Volume 12, Issue 4, pp 403-411, or by Ho et al., Plant Cell Reports, 1998, Volume 17, Issue 9, pp 675-680.

The invention claimed is:

1. A genetically modified woody plant comprising a heterologous nucleic acid construct comprising a promoter sequence operably linked to a coding sequence encoding a G47 gene comprising
   (i) a nucleotide sequence as set forth in SEQ ID NO: 21, 51, 53, 55, 101, or 103, or an ortholog thereof, or
   (ii) a nucleotide sequence encoding a polypeptide comprising an amino acid sequence as set forth in SEQ ID NO: 1, 50, 52, 54, 100 or 102, or an ortholog thereof, wherein the promoter sequence is selected from the group consisting of:
   (a) a pLMP1 promoter sequence comprising the nucleotide sequence as set forth in SEQ ID NO: 13 or 33,
   (b) a pEC1 promoter sequence comprising the nucleotide sequence as set forth in SEQ ID NO: 12, 32 or 39, and
   (c) a pEA2 promoter sequence comprising the nucleotide sequence as set forth in SEQ ID NO: 9 or 29.

2. The genetically modified plant according to claim 1, wherein the promoter sequence is preferentially or specifically expressed in at least one of cambium, vascular meristematic tissue, and shoot meristem tissue of said plant.

3. The genetically modified plant according to claim 2, wherein the promoter sequence is not significantly expressed in at least one of mature xylem, stem phloem, whole leaves, whole roots, and bark of said plant.

4. The genetically modified plant according to claim 1, wherein the G47 gene is from *Eucalyptus grandis, Zea Mays, Populus trichocarpa*, or *Arabidopsis thaliana*.

5. The genetically modified plant according to claim 1, having a modified trait as compared to a wild-type plant of the same species, wherein the modified trait is selected from one or more traits in the group of water use efficiency, plant yield, plant height, plant width, stem volume, stem dry weight, bark dry weight, wood density, leaf dry weight, average internode length, number of internodes, and drought tolerance.

6. The genetically modified plant according to claim 5, wherein the modified trait is increased as compared to a wild-type plant of the same species when said plants are grown under identical field conditions for a period of at least one year.

7. The genetically modified plant according to claim 1, wherein the plant is a hardwood plant.

8. The genetically modified plant according to claim 1, which is of the genus *Eucalyptus* or *Populus*.

9. The genetically modified woody plant according to claim 1, wherein the promoter sequence is pLMP1, and the modified trait is at least drought tolerance.

10. A method of making a genetically modified plant according to claim 1, said method comprising:
    providing a suitable part of a plant;
    providing a heterologous nucleic acid construct comprising a promoter sequence operably linked to a coding sequence encoding the G47 gene, wherein said promoter sequence is selected from the group consisting of pLMP1, pEC1, and pEA2;
    introducing the heterologous nucleic acid construct into said suitable part of the plant; and
    generating the genetically modified plant from said suitable part of the plant.

11. The genetically modified plant according to claim 2, wherein the G47 gene is from *Eucalyptus grandis, Zea Mays, Populus trichocarpa*, or *Arabidopsis thaliana*.

12. The genetically modified plant according to claim 1, wherein the G47 gene is from *Eucalyptus grandis, Zea Mays, Populus trichocarpa*, or *Arabidopsis thaliana*.

13. The genetically modified plant according to claim 2, having a modified trait as compared to a wild-type plant of the same species, wherein the modified trait is selected from one or more traits in the group of water use efficiency, plant yield, plant height, plant width, stem volume, stem dry weight, bark dry weight, wood density, leaf dry weight, average internode length, number of internodes, and drought tolerance.

14. The genetically modified plant according to claim 3, having a modified trait as compared to a wild-type plant of the same species, wherein the modified trait is selected from one or more traits in the group of water use efficiency, plant yield, plant height, plant width, stem volume, stem dry weight, bark dry weight, wood density, leaf dry weight, average internode length, number of internodes, and drought tolerance.

15. The genetically modified plant according to claim 4, having a modified trait as compared to a wild-type plant of the same species, wherein the modified trait is selected from one or more traits in the group of water use efficiency, plant yield, plant height, plant width, stem volume, stem dry weight, bark dry weight, wood density, leaf dry weight, average internode length, number of internodes, and drought tolerance.

16. The genetically modified plant according to claim 2, wherein the plant is a hardwood plant.

17. The genetically modified plant according to claim 3, wherein the plant is a hardwood plant.

18. The genetically modified plant according to claim 4, wherein the plant is a hardwood plant.

19. The genetically modified plant according to claim 5, wherein the plant is a hardwood plant.

20. A genetically modified woody plant comprising a heterologous nucleic acid construct comprising a promoter sequence operably linked to a coding sequence encoding a G47 gene comprising
    (i) a nucleotide sequence as set forth in SEQ ID NO: 21, 51, 53, 55, 101, or 103, or an ortholog thereof, or
    (ii) a nucleotide sequence encoding a polypeptide comprising an amino acid sequence as set forth in SEQ ID NO: 1, 50, 52, 54, 100 or 102, or an ortholog thereof, wherein the promoter sequence is selected from the group consisting of:
    (a) a pLMP1 promoter sequence comprising the nucleotide sequence as set forth in SEQ ID NO: 13 or 33,
    (b) a pEC1 promoter sequence comprising the nucleotide sequence as set forth in SEQ ID NO: 12, 32 or 39, and (c) a pEA2 promoter sequence comprising the nucleotide sequence as set forth in SEQ ID NO: 9 or 29, wherein the promoter sequence is preferentially or specifically expressed in at least one of cambium, vascular meristematic tissue, and shoot meristem tissue of said plant, wherein the modified plant has a modified trait as compared to a wild-type plant of the same species, wherein the modified trait is selected from one or more traits in the group of water use efficiency, plant yield, plant height, plant width, stem volume, stem dry weight, bark dry weight, wood density, leaf dry weight, average internode length, number of internodes, and drought tolerance, and wherein the modified trait is increased as compared to a wild-type plant of the same species when said plants are grown under identical field conditions for a period of at least one year.

* * * * *